(12) United States Patent
Marshall et al.

(10) Patent No.: US 12,064,439 B2
(45) Date of Patent: *Aug. 20, 2024

(54) PHENOTHIAZINE DIAMINIUM SALTS AND THEIR USE

(71) Applicant: WisTa Laboratories Ltd., Singapore (SG)

(72) Inventors: Colin Marshall, Old Aberdeen (GB); Scott Clunas, Aberdeenshire (GB); John Mervyn David Storey, Aberdeenshire (GB); James Peter Sinclair, Aberdeenshire (GB); Thomas Craven Baddeley, Old Aberdeen (GB); Ahtsham Ishaq, Aberdeenshire (GB); Michael Simpson, Aberdeenshire (GB); Craig Williamson, Guildford (GB); Barry Alan Wood, Aberdeenshire (GB); Claude Michel Wischik, Aberdeen (GB); Charles Robert Harrington, Aberdeenshire (GB); Janet Elizabeth Rickard, Aberdeenshire (GB); David Horsley, Aberdeenshire (GB); Yin Sze Loh, Singapore (SG); Karrar Ahmad Khan, West Bridgeford (GB); Christopher Paul Larch, Aberdeenshire (GB)

(73) Assignee: WisTa Laboratories Ltd., Singapore (SG)

( * ) Notice: Subject to any disclaimer, the term of this patent is extended or adjusted under 35 U.S.C. 154(b) by 44 days.
This patent is subject to a terminal disclaimer.

(21) Appl. No.: 17/499,498

(22) Filed: Oct. 12, 2021

(65) Prior Publication Data
US 2022/0098161 A1     Mar. 31, 2022

Related U.S. Application Data

(60) Continuation of application No. 16/751,811, filed on Jan. 24, 2020, now Pat. No. 11,180,464, which is a
(Continued)

(30) Foreign Application Priority Data

Feb. 11, 2011    (SG)  .............................. 201101060-0

(51) Int. Cl.
*A61K 31/5415*     (2006.01)
*A61K 9/00*     (2006.01)
(Continued)

(52) U.S. Cl.
CPC ........ *A61K 31/5415* (2013.01); *A61K 9/0053* (2013.01); *A61K 9/2095* (2013.01);
(Continued)

(58) Field of Classification Search
None
See application file for complete search history.

(56) References Cited

U.S. PATENT DOCUMENTS

| 2,928,767 A | 3/1960 | Gulesich et al. |
|---|---|---|
| 4,309,255 A | 1/1982 | Gendler et al. |

(Continued)

FOREIGN PATENT DOCUMENTS

| DE | 4 430 091 A1 | 8/1994 |
|---|---|---|
| EP | 0 457 295 A3 | 11/1991 |

(Continued)

OTHER PUBLICATIONS

International Preliminary Report on Patentability for PCT/GB2011/001221 dated Aug. 22, 2013 (6 pages).
(Continued)

*Primary Examiner* — Bethany P Barham
*Assistant Examiner* — Barbara S Frazier
(74) *Attorney, Agent, or Firm* — Wolf, Greenfield & Sacks, P.C.

(57) ABSTRACT

Disclosed are compounds of general formula (I):

(I)

(Continued)

and pharmaceutically acceptable salts thereof, formulations, methods and uses in, for example, the treatment of disease.

18 Claims, 22 Drawing Sheets

Related U.S. Application Data division of application No. 15/912,166, filed on Mar. 5, 2018, now Pat. No. 10,864,216, which is a division of application No. 15/056,610, filed on Feb. 29, 2016, now Pat. No. 9,907,804, which is a division of application No. 13/984,841, filed as application No. PCT/GB2011/001221 on Aug. 15, 2011, now Pat. No. 9,283,230.

(60) Provisional application No. 61/485,880, filed on May 13, 2011.

(51) Int. Cl.
| | |
|---|---|
| *A61K 9/20* | (2006.01) |
| *A61P 31/04* | (2006.01) |
| *A61P 31/12* | (2006.01) |
| *A61P 31/14* | (2006.01) |
| *A61P 31/18* | (2006.01) |
| *A61P 33/02* | (2006.01) |
| *A61P 33/06* | (2006.01) |
| *A61P 35/00* | (2006.01) |
| *C07D 279/20* | (2006.01) |
| *A61K 9/28* | (2006.01) |
| *A61L 2/00* | (2006.01) |
| *C07C 303/32* | (2006.01) |
| *C07C 309/04* | (2006.01) |
| *C07C 309/05* | (2006.01) |
| *C07C 309/30* | (2006.01) |
| *C07C 309/35* | (2006.01) |

(52) U.S. Cl.
CPC .............. *A61P 31/04* (2018.01); *A61P 31/12* (2018.01); *A61P 31/14* (2018.01); *A61P 31/18* (2018.01); *A61P 33/02* (2018.01); *A61P 33/06* (2018.01); *A61P 35/00* (2018.01); *C07D 279/20* (2013.01); *A61K 9/2893* (2013.01); *A61L 2/0052* (2013.01); *C07C 303/32* (2013.01); *C07C 309/04* (2013.01); *C07C 309/05* (2013.01); *C07C 309/30* (2013.01); *C07C 309/35* (2013.01); *Y02A 50/30* (2018.01)

(56) References Cited

U.S. PATENT DOCUMENTS

| | | | |
|---|---|---|---|
| 4,622,395 | A | 11/1986 | Bellus et al. |
| 4,647,525 | A | 3/1987 | Miller |
| 5,095,011 | A | 3/1992 | Kaplan et al. |
| 5,220,009 | A | 6/1993 | Mazur et al. |
| 5,693,638 | A | 12/1997 | Myers |
| 5,827,644 | A | 10/1998 | Floyd et al. |
| 6,068,854 | A | 5/2000 | Wunderlich et al. |
| 6,376,205 | B1 | 4/2002 | Wischik et al. |
| 6,953,794 | B2 | 10/2005 | Wischik et al. |
| 6,953,974 | B2 | 10/2005 | Rathfelder et al. |
| 7,737,138 | B2 | 6/2010 | Wischik et al. |
| 7,888,350 | B2 | 2/2011 | Wischik et al. |
| 8,263,589 | B2 | 9/2012 | Wischik et al. |
| 8,710,051 | B2 | 4/2014 | Wischik et al. |
| 9,149,481 | B2 | 10/2015 | Wischik et al. |
| 9,174,954 | B2 | 11/2015 | Wischik et al. |
| 9,211,294 | B2 | 12/2015 | Wischik et al. |
| 10,188,658 | B2 | 1/2019 | Wischik et al. |
| 10,864,216 | B2 | 12/2020 | Marshall et al. |
| 11,180,464 | B2 | 11/2021 | Marshall et al. |
| 11,344,558 | B2 | 5/2022 | Wischik et al. |
| 2002/0103189 | A1 | 8/2002 | Miyamoto et al. |
| 2002/0168687 | A1 | 11/2002 | Wischik et al. |
| 2002/0197258 | A1 | 12/2002 | Ghanbari et al. |
| 2003/0181389 | A1 | 9/2003 | Wülfert et al. |
| 2004/0078835 | A1 | 4/2004 | Wishik et al. |
| 2005/0136110 | A1 | 6/2005 | Bartholomaeus et al. |
| 2006/0014216 | A1 | 1/2006 | Wishik et al. |
| 2006/0287523 | A1 | 12/2006 | Wishik et al. |
| 2007/0116757 | A1 | 5/2007 | Rariy et al. |
| 2007/0191352 | A1 | 8/2007 | Wischik et al. |
| 2016/0051559 | A1 | 2/2016 | Wischik et al. |
| 2019/0046537 | A1 | 2/2019 | Marshall et al. |
| 2020/0246350 | A1 | 8/2020 | Marshall et al. |
| 2022/0152038 | A1 | 5/2022 | Wischik et al. |

FOREIGN PATENT DOCUMENTS

| | | |
|---|---|---|
| EP | 0 909 814 A2 | 4/1999 |
| EP | 0 911 390 A2 | 4/1999 |
| EP | 0 911 398 A2 | 4/1999 |
| EP | 0 618 968 B1 | 10/1999 |
| EP | 1 067 386 A2 | 10/2001 |
| EP | 0 737 671 B1 | 12/2001 |
| FR | 2788436 | 7/2000 |
| JP | 06-289015 | 10/1994 |
| WO | WO 89/03993 | 5/1989 |
| WO | WO 93/03177 | 2/1993 |
| WO | WO 93/03369 | 2/1993 |
| WO | WO 93/11231 | 6/1993 |
| WO | WO 95/05466 | 2/1995 |
| WO | WO 95/05601 | 2/1995 |
| WO | WO 96/04915 | 2/1996 |
| WO | WO 96/05837 | 2/1996 |
| WO | WO 96/30766 A1 | 10/1996 |
| WO | WO 98/31219 | 7/1998 |
| WO | WO 99/62548 | 12/1999 |
| WO | WO 01/53340 | 7/2001 |
| WO | WO 02/03972 | 1/2002 |
| WO | WO 02/04025 | 1/2002 |
| WO | WO 02/055720 A2 | 7/2002 |
| WO | WO 02/059150 A2 | 8/2002 |
| WO | WO 02/075318 A2 | 9/2002 |
| WO | WO 03/007933 A1 | 1/2003 |
| WO | WO 2005/030676 A1 | 4/2005 |
| WO | WO 2005/054217 A1 | 6/2005 |
| WO | WO 2006/032879 A2 | 3/2006 |
| WO | WO 2006/091728 A2 | 8/2006 |
| WO | WO 2007/110627 A2 | 10/2007 |
| WO | WO 2007/110629 A1 | 10/2007 |
| WO | WO 2008/007074 A2 | 1/2008 |
| WO | WO 2008/155533 A2 | 12/2008 |
| WO | WO 2009/044127 A1 | 4/2009 |

OTHER PUBLICATIONS

International Search Report for PCT/GB2007/001103 dated Aug. 30, 2007 (4 pages.).
International Search Report of the corresponding application PCT/GB2008/003315, dated Jan. 22, 2009.
International Search Report and Written Opinion issue in related International patent Application No. PCT/GB2011/001221, mailed Nov. 3, 2011.
Examination Report for Application No. BR112013020539-3, mailed Jul. 12, 2021.
Indian Hearing Notice for Application No. 7375/DELNP/2013, issued Feb. 9, 2021.
Argentinian Office Action for Application No. 20110102969, dated Sep. 16, 2019.
Argentinian Office Action for Application No. 20110102969, dated Aug. 5, 2020.
Non-Final Office Action mailed May 27, 2010 in U.S. Appl. No. 12/294,599, 14 pages.
Non-Final Office Action issued in U.S. Appl. No. 16/248,746 dated Mar. 20, 2019.

(56) References Cited

OTHER PUBLICATIONS

Non-Final Office Action issued in U.S. Appl. No. 15/056,610 dated Feb. 2, 2017 (14 pages).
Non-Final Office Action issued in U.S. Appl. No. 13/011,797 dated Sep. 27, 2012.
Non-Final Office Action issued in U.S. Appl. No. 14/248,730 dated Sep. 18, 2014.
Non-Final Office Action issued in U.S. Appl. No. 14/929,111 dated May 16, 2016.
US Office Action on 088736-0121 Dtd May 27, 2010.
US Office Action on U.S. Appl. No. 96/000,137 dated Mar. 1, 2016.
Final Office Action issued in U.S. Appl. No. 13/011,797 dated May 21, 2013.
Final Office Action issued in U.S. Appl. No. 14/866,035 dated Dec. 13, 2016 (12 pages).
Final Office Action issued in U.S. Appl. No. 16/248,746 dated Sep. 19, 2019.
Notice of Allowance issued in U.S. Appl. No. 13/011,797 dated Dec. 12, 2013.
Notice of Allowance issued in U.S. Appl. No. 14/248,730 dated Mar. 25, 2015.
Notice of Allowance mailed Oct. 19, 2010 in U.S. Appl. No. 12/294,599, 4 pages.
Aizawa et al., "Microtubule-binding domain of tau proteins," Journal of Biological Chemistry, 1988, vol. 263, pp. 7703-7707.
Allen et al., "Further clinical experience with toluidine blue and protamine sulfate", Abnormal Bleeding II, 1949, vol. 89, No. 6, pp. 692-703.
Andersen, "Amyotrophic Lateral Sclerosis Associated with Mutations in the CuZn Superoxide Dismutase Gene", Current Neurology and Neuroscience Reports, 2006, vol. 6, pp. 37-46.
Anderton et al., "Dendritic Changes in Alzheimer's Disease and Factors That May Underlie these Changes," Prog. Neurobiol., Aug. 1998., pp. 595-609, vol. 55, No. 6.
Arai et al., "Phosphorylated and cleaved TDP-43 in ALS, FTLD and other neurodegenerative disorders and in cellular models of TDP-43 proteinopathy", Neuropathology, 2010, vol. 30, pp. 170-181, doi:10.1111/j.1440-1789.2009.01089.x.
Askanas et al., "Inclusion Body Myositis: A Degenerative Muscle Disease Associated with Intra-Muscle Fiber Multi-Protein Aggregates, Proteasome Inhibition, Endoplasmic Reticulum Stress and Decreased Lysosomal Degradation", Brain Pathology, 2009, vol. 19, pp. 493-506.
Avila et al., Assorted Proteins, Harwood Aend Publishers, Amsterdam, 1997.
Bancher et al., "Accumulation of abnormally phosphorylated T precedes the formation of neurofibrillary tangles in Alzheimer's disease," Brain Research, 1989, vol. 477, pp. 90-99.
Barmada et al., "Cytoplasmic Mislocalization of TDP-43 is Toxic to Neurons and Enhanced by a Mutation Associated with Familial Amyotrophic Lateral Sclerosis", J. Neurosci., Jan. 13, 2010, vol. 30, No. 2, pp. 639-649.
Baxmann et al., "Effect of Vitamin C Supplements on Urinary Oxalate and pH in Calcium Stone-forming Patients," Kidney International (2003), 63, No. 3, 1066-1071.
Berge et al., "Pharmaceutical Salts", Journal of Pharmaceutical Sciences, 66(1):1-19 (Jan. 1977).
Biernat et al., "The switch of tau protein to an Alzheimer-like state includes the phosphorylation of two serine-proline motifs upstream of the microtubule binding region," EMBO Journal 11, 1992, pp. 1593-1597.
Blair et al., "FUS mutations in amyotrophic lateral sclerosis: clinical, pathological, neurophysiological and genetic analysis", J Neurol Neurosurg Psychiatry, doi:10.1136/jnnp.2009.194399, 2010, vol. 81, pp. 639-645.
Bondareff et al., "Immunohistochemical staging of neurofibrillary degeneration in Alzheimer's disease", Journal of Neuropathology and Experimental Neurology (Mar. 1994), vol. 53, No. 2, pp. 158-164.
Braak et al., "Alzheimer's Disease: Transiently Developing Dendritic Changes in Pyramidal Cells of Sector CA1 of the Ammon's Horn," Acta Neuropathol., 1997, pp. 323-325, vol. 93.
Brandt, "Cytoskeletal Mechanisms of Axon Outgrowth and Pathfinding," Cell Tissue Res., 1998, pp. 181-189, vol. 292.
Brion et al., "Characterization of a Partial cDNA Specific for the High Molecular Weight Microtubule-Associated Protein MAP2 That Encodes Epitopes Shared with Paired Helical Filaments of Alzheimer's Disease," Dementia, 1990, pp. 304-315, vol. 1.
Byrne et al., "Rate of familial amyotrophic lateral sclerosis: a systematic review and meta-analysis", J Neurol Neurosurg Psychiatry, doi:10.1136/jnnp.2010.224501, Nov. 3, 2010, pp. 1-5.
Callaway et al., "Methylene blue restores spatial memory retention impaired by an inhibitor of cytochrome oxidase in rats". Neuroscience Letters. 2002. vol. 332, pp. 83-86.
Caputo et al., "Amyloid-like properties of a synthetic peptide corresponding to the carboxy terminus of β-amyloid protein precursor," Archives of Biochemistry and Biophysics, 1992, vol. 292, No. 1, pp. 199-205.
Caputo et al., "The amyloid proteins of Alzheimer's disease as potential targets for drug therapy," Neurobiology of Aging, Feb. 21, 1989, vol. 10, pp. 451-461.
Cecil Textbook of Medicine (20th Edition, vol. 2, 1996, pp. 1739-1747).
Cavaliere et al., "Binding of methylene blue to a surface cleft inhibits the oligomerization and brillization of prion protein", Biochimica Biophysica Acta, vol. 1832, pp. 20-28 (2013).
Chemical Abstracts Service, XP002661598. Database Accession No. 1236208-20-0, 1 page (2010).
Chen-Plotkin et al., "TAR DNA-binding protein 4'3 in neurodegenerative disease", Nature Reviews Neurology, Apr. 2010, vol. 6, pp. 211-220.
Condamines et al., "New immunoassay for the mapping of neurofibrillary degeneration in Alzheimer's disease using two monoclonal antibodies against human paired helical filament tau proteins," Neuroscience Letters, Jun. 9, 1995, vol. 192, No. 2, pp. 81-84.
Contineanu et al., "Radiolysis of Methylene Blue Studied by ESR", Radiochem. Radioanal. Letters. 1983, vol. 57, No. 1, pp. 9-22.
Cox et al., "Mutations in CHMP2B in Lower Motor Neuron Predominant Amyotrophic Lateral Sclerosis (ALS)", PLoS ONE, Mar. 2010, vol. 5, No. 3, e9872, pp. 1-16.
Cudd et al., "Pharmacokinetics and toxicity of tolonium chloride in sheep", Vet Human Toxicol, vol. 38, No. 5, Oct. 1996, pp. 329-334.
Day R., "How to Write and Publish a Scientific Paper," 1983, pp. 124-127, ISI Press, Philadelphia, PA.
De Ancos et al., "Differences in Microtubule Binding and Self-association Abilities of Bovine Brain Tau Isoforms", Journal of Biological Chemistry, 1993, pp. 7976-7982, vol. 268(11).
DeTure et al., "In vitro assembly of Alzheimer-like filaments. How a small cluster of charged residues in tau and MAP2 controls filament morphology," Journal of Biological Chemistry, 2002, vol. 277, pp. 34755-34759.
Drew et al., "Derivatives of Methylene-blue", Journal of the Chemical Society, 1933, pp. 248-253.
Elden et al., "Ataxin-2 intermediate-length polyglutamine expansions are associated with increased risk for ALS", Nature, doi:10.1038/nature09320, Aug. 26, 2010, vol. 466, pp. 1069-1075.
Epstein et al., "The utility of toluidine blue application as a diagnostic aid in patients previously treated for upper oropharyngeal carcinoma", Oral medicine, (1997), pp. 537-547, vol. 83, No. 5.
Fasulo et al., "Overexpression of Alzheimer's PHF core tau fragments: implications for the tau truncation hypothesis," Rapid Science Publishers, Alzheimer's Research, vol. 2, No. 5, pp. 195-200, Oct. 1996.
Finsterer, "Mitochondrial disorders, cognitive impairment and dementia", Journal of the Neurological Sciences, 2009, vol. 283, pp. 143-148, doi:10.1016/j.jns.2009.02.347.
Friedhoff et al., "Rapid Assembly of Alzheimer-like Paired Helical Filaments from Microtubule-Associated Protein Tau Monitored by Fluorescence in Solution", Biochemistry, 1998, pp. 10223-10230, vol. 37.
Friedhoff et al., "A nucleated assembly mechanism of Alzheimer paired helical filaments", PNAS, 1998, pp. 15712-15717, vol. 95.

(56) References Cited

OTHER PUBLICATIONS

Garcini et al., "In Vitro Conditions for the Self-Polymerization of the Microtubule-Associated Protein, Tau Factor," J. Biochem., 1987, pp. 1415-1421, vol. 102, No. 6.

Garcini et al., Self Assembly of Microtubule Associated Protein TAU into Filaments Resembling those found in Alzheimer Disease, Biochemical and Biophysical Research Communications, 1988, pp. 790-797.

Garcini et al., FEBS Letters, "Tau Factor Polymers are Similar to Paired Helical Filaments of Alzheimer's Disease," 1988, vol. 236, No. 1, pp. 150-154, Elsevier Science Publishers B.V.

Gavezzotti, "Are Crystal Structures Predictable?" Accounts of Chemical Research, vol. 27, pp. 309-314 (1994).

Gendron et al., Review: Transactive response DNA-binding protein 43 (TDP-43): mechanisms of neurodegeneration, Neuropathology and Applied Neurobiology, 2010, vol. 36, pp. 97-112, doi:10.1111/j.1365-2990.2009.01060.x.

Gertz et al., "Examination of the validity of the hierarchical model of neuropathological staging in normal aging and Alzheimer's disease", Aeta Neuropathol (1998), vol. 95, pp. 154-158.

Gertz et al., "The relationship between clinical dementia and neuropathological staging (Braak) in a very elderly community sample", Eur Arch Psychiatry Clin Neurosci (1996) vol. 246, pp. 132-136.

Geser et al., "Amyotrophic lateral sclerosis and frontotemporal lobar degeneration: A spectrum of TDP-43 proteinopathies", Neuropathology, 2010, vol. 30, 103-112.

Giannetti et al., "Fibers of tau fragments, but not full length tau, exhibit a cross (β-structure: implications for the formation of paired helical filaments," Protain Science, 2000, vol. 9, pp. 2427-2435.

Gitcho et al., "TDP-43 A315T Mutation in Familial Motor Neuron Disease", Ann Neurol, 2008, vol. 63, pp. 535-538.

Goedert et al., "Tau Proteins of Alzheimer Paired Helical Filaments: Abnormal Phosphorylation of All Six Brain Isoforms," Neuron, Jan. 1992, pp. 159-168, vol. 8.

Goedert et al., "Cloning and sequencing of the cDNA encoding a core protein of the paired helical filament of Alzheimer disease: Identification as the microtubule-associated protein tau," Proc. Natl. Acad. Sci. USA, Jun. 1988, vol. 85, pp. 4051-4055.

Götz et al., "Tau filaments formation in transgenic mice expressing P301L tau," J. Biol. Chem., Jan. 5, 2001, vol. 276(1), pp. 529-534.

Grover et al., "5' Splice Site Mutations in Tau Associated with the Inherited Dementia FTDP-17 Affect a Stem-Loop Structure That Regulates Alternative Splicing of Exon 10*," The Journal of Biological Chemistry, May 21, 1999 Issue, pp. 15134-15143, vol. 274, No. 21.

Grundke-Iqbal et al., "Abnormal phosphorylation of microtubule-associated protein T (tau) in Alzheimer cytoskeletal pathology," Proc. Natl. Acad. Sci. USA 83(13): 4913-4917 (1986).

Hagestedt et al., "Tau protein becomes long and stiff upon phosphorylation: correlation between paracrystalline structure and degree of phosphorylation," The Journal of cell biology, 1989, vol. 109, pp. 1643-1651.

Harada et al., "Altered Microtubule Organization In Small-Calibre Axons of Mice Lacking Tau Protein," Letters to Nature, Jun. 9, 1994, vol. 369, pp. 488-489.

Harrington et al., "Cellular Models of Aggregation-dependent Template-directed Proteolysis to Characterize Tau Aggregation Inhibitors for Treatment of Alzheimer Disease", The Journal of Biological Chemistry, vol. 290, No. 17, pp. 10862-10875 (2015).

Harrington et al., "Competitive ELISA for the Measurement of Tau Protein in Alzheimer's Disease," Journal of Immunological Methods, 1990, pp. 261-271, vol. 134.

Harrington et al., "Measurement of Distinct Immunochemical Presentations of Tau Protein in Alzheimer Disease," Proc. Natl. Acad. Sci., Jul. 1991, pp. 5842-5846, vol. 88.

Higashi et al., "TDP-43 physically interacts with amyotrophic lateral sclerosis-linked mutant CuZn superoxide dismutase", Neurochemistry International, 2010, vol. 57, pp. 906-913.

Higson et al., "Iron Enhancement of Ascorbate Toxicity," Free Rad. Res. Comms. (1988) 5(2): 107-115.

Hochgräfe et al., "Preventive methylene blue treatment preserves cognition in mice expressing full-length pro-aggregant human Tau", Acta Neuropathologica Communications, 3:25 (2015).

Holoubek et al., "Toluidine blue in bleeding associated with thrombopenia", J.A.M.A., Jan. 22, 1949, vol. 139, No. 4, pp. 214-216.

Hosokawa, "Methylene Blue Reduced Abnormal Tau Accumulation in P3011 Tau Transgenic Mice", PLoS ONE, vol. 7, No. 12, e52389 (2012).

Hutton et al., "Association of Missense and 5'-splice-site Mutations in Tau With the Inherited Dementia FTDP-17," Nature, Jun. 18, 1998, pp. 702-705, vol. 393.

Igaz et al., "Expression of TDP-43 C-terminal Fragments in Vitro Recapitulates Pathological Features of TDP-43 Proteinopathies", The Journal of Biological Chemistry, Mar. 27, 2009, vol. 284, No. 13, pp. 8516-8524.

Ishiguro et al., "A novel tubulin-dependent protein kinase forming a paired helical filament epitope on tau," J. Biochem, 1988, vol. 104, pp. 319-321.

Ishiguro et al., "A serine/threonine proline kinase activity is included in the tau protein kinase fraction forming a paired helical filament epitope," Neuroscience Letters, 1991, vol. 128, pp. 195-198.

Ishiguro et al., "Phosphorylation sites on tau by tau protein kinase I, a bovine derived kinase generating an epitope of paired helical filaments," Neuroscience Letters, 1992, vol. 148, pp. 202-206.

Ishiguro et al., "Tau protein kinase I converts normal tau protein into A68-like component of paired helical filaments," Journal of Biological Chemistry, 1992, vol. 267, pp. 10897-10901.

Ishihara et al., "Age-Dependent Emergence and Progression of a Tauopathy in Transgenic Mice Overexpressing the Shortest Human Tau Isoform," Neuron, Nov. 1999, pp. 751-762, vol. 24.

Ito et al., "Enhancing effect of ascorbate on toluidine blue-photosensitization of yeast cells" Photochemistry and Photobiology, (1982), pp. 501-505, vol. 35.

Jakes et al., "Identification of 3- and 4-repeat Tau Isoforms within the PHF in Alzheimer's Disease," The EMBO Journal, 1991, pp. 2725-2729, vol. 10, No. 10.

Janciauskiene et al., "In vitro amyloid fibril formulation from ($\alpha_1$-antitrypsin," Bio Chem, 1995, vol. 375, pp. 103-109.

Jinwal et al., "Chemical Manipulation of Hsp70 ATPase Activity Regulates Tau Stability", J. Neurosci., Sep. 30, 2009, vol. 29, No. 39, pp. 12079-12088.

Johnson et al., "A yeast TDP-43 proteinopathy model: Exploring the molecular determinants of TDP-43 aggregation and cellular toxicity", PNAS, Apr. 29, 2008, vol. 105, No. 17, pp. 6439-6444.

Johnson et al., "TDP-43 is Intrinsically Aggregation-prone, and Amyotrophic Lateral Sclerosis-linked Mutations Accelerate Aggregation and Increase Toxicity", The Journal of Biological Chemistry, Jul. 24, 2009, vol. 284, No. 30, pp. 20329-20339.

Johnson et al., "Exome Sequencing Reveals VCP Mutations as a Cause of Familial ALS", Neuron, Dec. 9, 2010, vol. 68, pp. 857-864.

Kabashi et al., "Gain and loss of function of ALS-related mutations of TARDBP (TDP-43) cause motor deficits in vivo", Human Molecular Genetics, 2010, vol. 19, No. 4, pp. 671-683, doi:10.1093/hmg/ddp534.

Kabashi et al., "TARDBP mutations in individuals with sporadic and familial amyotrophic lateral sclerosis", Nature Genetics, May 2008, vol. 40, No. 5, pp. 572-574.

Kaech et al., "Cytoskeletal Plasticity in Cells Expressing Neuronal Microtubule-Associated Proteins," Neuron, Dec. 1996, pp. 1189-1199, vol. 17.

Kiese et al., "Comparative studies on the effects of toluidine blue and methylene blue on the reduction of ferrihaemoglobin in man and dog" , Europ. J. Clin. Pharmacol., 1972, vol. 4, pp. 115-118.

Klymkowsky, "Weaving a tangled web: the interconnected cytoskeleton", Nature Cell Biology (1999) vol. 1, No. 5, pg E121.

Kohler, "Toluidinblau," Drug Information, Alsbach, Germany. Jul. 1997.

Koryta, "Ions, Electrodes and Membranes", Institute of Physiology, Second Edition, John Wiley & Sons (1991).

(56) References Cited

OTHER PUBLICATIONS

Ksiezak-Reding et al., "Mass and Physical Dimensions of Two Distinct Populations of Paired Helical Filaments," Neurobiology of Aging, 1993, pp. 11-18, vol. 15, No. 1.
Ksiezak-Reding et al., "Structural Stability of Paired Helical Filaments Requires Microtubule-Binding Domains of Tau: A Model for Self-Association," Neuron, 1991, pp. 717-728, vol. 6.
Ksiezak-Reding et al., Assembled tau filaments differ from native paired helical filaments as determined by scanning transmission electron microscopy (STEM), Brain Research (1998), vol. 814, pp. 86-98.
Lai et al., "Examination of Phosphorylated Tau Protein as a PHF-Precursor at Early State Alzheimer's Disease," Neurobiology of Aging, May-Jun. 1995, pp. 433-445, vol. 16, No. 3.
Lai, "The Role of Abnormal Phosphorylation of Tau Protein in the Development of Neurofibrillary Pathology in Alzheimer's Disease"—Submitted for the Degree of Doctor of Philosophy at the University of Cambridge, Christ's College, 1994, pp. 1-243.
Ledesma et al., "Implication of brain cdc2 and MAP2 kinases in the phosphorylation of tau protein in Alzheimer's disease," FEBS, 1992, vol. 308, No. 2, pp. 218-224.
Lee et al., "Tau Proteins and their significance in the Pathobiology of Alzheimer's Disease," Pathobiology of Alzheimer's Disease, 1995, ISBN 0-12-286965-5, pp. 41-58.
Lee et al., untitled, Science, 1992., vol. 251.
Lee et al., "A68: A Major Subunit of Paired Helical Filaments and Derivatized Forms of Normal Tau," Science, 1991, pp. 675-678, vol. 251.
Lewis et al., "Microtubule-Associated Protein MAP2 Shares a Microtubule Binding Motif with Tau Protein", Science(Nov. 11, 1988) vol. 242, pp. 936-939.
Lichtenberg-Kraag et al., "Alzheimer-Type Phosphorylation of Microtubule-Associated Protein Tau In Vitro", 1991/92.
Lichtenberg-Kraag et al., "Phosphorylation-dependent epitopes of neurofilament antibodies on tau protein and relationship with Alzheimer tau", Proc. Natl. Acad. Sci (Jun. 1992) vol. 89, pp. 5384-5388.
Ling et al., "ALS-associated mutations in TDP-43 increase its stability and promote TDP-43 complexes with FUS/TLS", PNAS, Jul. 27, 2010, vol. 107, No. 30, pp. 13318-13323.
Link, "Targeting Melanoma with 211 At/131I-Methylene Blue: Preclinical and Clinical Experience", Hybridoma (Nov. 1, 1999), vol. 18, No. 1, pp. 77-82.
Lomas et al., "The mechanism of Z alpha1-antitrypsin accumulation in the liver", Letters of Nature (Jun. 18, 1992), vol. 357, pp. 605-607.
Love et al, "Neurofibrillary tangles in Niemann-Pick disease type C", Brain, 1995, vol. 118, pp. 119-129.
MacKenzie I.R.A., et al, "Pathological TDP-43 Distinguishes Sporadic Amyotrophic Lateral Sclerosis from Amyotrophic Lateral Sclerosis with SOD1 Mutations", Ann Neurol, 2007, vol. 61, pp. 427-434.
MacKenzie et al,, "TDP-43 and FUS in amyotrophic lateral sclerosis and frontotemporal dementia", Lancet Neurol, Oct. 2010, vol. 9, pp. 995-1007.
Mukaetova-Ladinska et al., "Staging of cytoskeletal and beta-amyloid changes in human isocortex reveals biphasic synaptic protein response during progression of Alzheimer's disease", American Journal of Pathology (Aug. 2000) vol. 157, No. 2, pp. 623-636.
Martinez et al., "Methylene blue alters retention of inhibitory avoidance responses", Physiol. Psychol., 1978, vol. 6, No. 3, pp. 387-390.
Mashberg, "Tolonium (Toluidine blue) rinse—a screening method for recognition of squanous carcinoma—continuing study of oral-cancer 4," Jama-Journal of the American Medical Association, Jun. 19, 1981, vol. 245 No. 23, pp. 2408-2410.
Masuda et al., Small molecule inhibitors of ($\alpha$-synuclein filament assembly. Biochemistry, (2006), pp. 6085-6094, 45.
May et al., "Reduction and uptake of methylene blue by human erythrocytes", Am J Physiol Cell Physiol, 286, 2004, pp. C1390-C1398.
Mayo Clinic; "Alzheimer's prevention: Does it exist?" Retrieved from http://www.mayoclinic.com/health/alzheimers-prevention/AN02099/METHOD=print on Sep. 25, 2012.
Melis et al., "Effects of oxidised and reduced forms of Methylthioninium in two transgenic mouse tauopathy models", Behavioural Pharmacology, vol. 26, No. 4, pp. 353-368 (2015).
Mena et al., "A Progressive Deposition of Paired Helical Filaments (PHF) in the Brain Characterizes the Evolution of Dementia in Alzheimer's Disease," Journal of Neuropathology and Experimental Neurology, 1991, pp. 474-490.
Mena et al., "Monitoring Pathological Assembly of tau and ($\beta$-Amyloid Proteins in Alzheimer's Disease," Acta Neuropathol., 1994, pp. 50-56.
Mena et al., "Staging the Pathological Assembly of Truncated tau Protein into Paired Helical Filaments in Alzheimer's Disease," Acta Neuropathol, 1996, pp. 633-641.
Mohideen et al., "Nontoxic singlet oxygen generator as a therapeutic candidate for treating tauopathies", Scientific Reports, 5:10821 | DOi:10.1038/srep10821, pp. 1-14 (2015).
Müller, "Light-microscopic demonstration of methylene blue accumulation sites in mouse brain after supravital staining", Acta Anat., 1992, vol. 144, pp. 39-44.
Murthy et al., "Cyclic-voltametric studies of some phenothiazine dyes," J. Chem. Soc., Faraday Trans., 1984, vol. 80, pp. 2745-2750.
Neary et al., "Frontotemporal lobar degeneration—A consensus on clinical diagnostic criteria", Neurology, 1998, vol. 51, pp. 1546-1554.
Neumann, "Molecular Neuropathology of TDP-43 Proteinopathies", Int. J. Mol. Sci., 2009, vol. 10, pp. 232-246, doi:10.3390/ijms10010232.
Neumann et al., "Ubiquitinated TDP-43 in Frontotemporal Lobar Degeneration and Amyotrophic Lateral Sclerosis", Science, Oct. 6, 2006, vol. 314, pp. 130-133.
Nonaka et al., "Truncation and pathogenic mutations facilitate the formation of intracellular aggregates of TDP-43", Human Molecular Genetics, 2009, vol. 18, No. 18, pp. 3353-3364, doi:10.1093/hmg/ddp275.
Novak et al., "Molecular Characterization of the Minimal Protease Resistant Tau Unit of the Alzheimer's Disease Paired Helical Filament," The EMBO Journal, 1993, pp. 365-370, vol. 12, No. 1.
Ohmi et al., "Sanfilippo syndrome type B, a lysosomal storage disease, is also a tauopathy", PNAS, May 19, 2009, vol. 106, No. 20, 8332-8337.
Orr et al., "Trinucleotide Repeat Disorders", Annu. Rev. Neurosci., vol. 30, pp. 575-621 (2007).
Pedrotti et al., "Interactions of Microtubule-Associated Protein MAP2 with Unpolymerized and Polymerized Tubulin and Actin Using a 96-Well Microtiter Plate Solid-Phase Immunoassay"; Biochemistry 1994 33:8798-8806.
Perez et al., "In vitro assembly of tau protein: Mapping the regions involved in filament formation," Biochemistry, 2001, vol. 40, 5983-5991.
Perez-Tur et al., "Neurodegenerative disease of Guam: Analysis of TAU," American Academy of Neurology, 1999, vol. 53, pp. 411-412.
Pickhardt et al., "Anthraquinones inhibit tau aggregation and dissolve Alzheimer paired helical filaments in vitro and in cells," Journal of Biological Chemistry, 2005, vol. 280, pp. 3628-3635.
Poulter et al., "Locations and immunoreactivities of phosphorylation sites on bovine and porcine tau proteins and a PHF-tau fragment," The Journal of Biological Chemistry, 1993, vol. 268, No. 13, pp. 9636-9644.
Rumbolz et al., "Use of protamine sulfate and toluidine blue for abnormal uterine bleeding," Am. J. Obst. & Gynec., May 1952, vol. 63, No. 5, pp. 1029-1037.
Ryoakira et al., Chapter 4 Drug Crystallization Method excerpted from Handbook of Principles and Know-how of Organic Compound Crystallization; Jul. 2008; pp. 57-84; Maruzen Co., Ltd., Japan.
Sato-Harada et al., "Microtubule-associated Proteins Regulate Microtubule Function as the Track for Intracellular Membrane Organelle Transports," Cell Structure and Function, 1996, pp. 283-295, vol. 21.

(56) References Cited

OTHER PUBLICATIONS

Schneider et al., "Phosphorylation that detaches tau protein from microtubules (Ser262, Ser214) also protects it against aggregation into Alzheimer paired helical filaments," Biochemistry, 1999, vol. 38, pp. 3549-3558.
Seetharaman et al., "Immature Copper-Zinc Superoxide Dismutase and Familial Amyotrophic Lateral Sclerosis", Exp Biol Med (Maywood), Oct. 2009, vol. 234, No. 10, pp. 1140-1154, doi:10.3181/0903-MR-104.
Seilhean et al., "Accumulation of TDP-43 and $\alpha$-actin in an amyotrophic lateral sclerosis patient with the K17I ANG mutation", Acta Neuropathol, 2009, vol. 118, pp. 561-573, doi:10.1007/s00401-009-0545-9.
Shojania et al., "The effect of toluidine blue and methylene blue in immunochemical reactions in vitro", Clinical Immunology and Immunopathology, (1987), pp. 223-228, 43.
Sigma Biosciences, "In vitro toxicology assay kit lactate dehydrogenase based," Cell Viability (2009).
Smith et al., "The molecular pathology of Alzheimer's disease: are we any closer to understanding the neurodegenerative process?," Neuropathology and Applied Neurobiology, 1994, pp. 322 338, vol. 20, XP002002176.
Solomons, T.W. Graham, Organic Chemistry, 3rd Edition, pp. 6 and 850; 1984.
Sontag et al., "Methylene Blue Modulates Huntingtin Aggregation Intermediates and Is Protective in Huntington's Disease Models", The Journal of Neuroscience, vol. 32, No. 32, pp. 11109-11119 (2012).
Sreedharan et al., "TDP-43 Mutations in Familial and Sporadic Amyotrophic Lateral Sclerosis", Science, Mar. 21, 2008, vol. 319, pp. 1668-1672, doi:10.1126/science.1154584.
Taniguchi et al., "Inhibition of heparin-induced tau filament formation by phenothiazines, polyphenols, and porphyrins." JBC Papers in Press, 2004, Manuscript M408714200.
Tint et al., "Acute Inactivation of Tau Has No Effect on Dynamics of Microtubules in Growing Axons of Cultured Sympathetic Neurons," The Journal of Neuroscience, Nov. 1, 1998, pp. 8661-8673, vol. 18, No. 21.
Van Bebber et al., "Methylene blue fails to inhibit Tau and polyglutamine protein dependent toxicity in zebrafish", Neurobiology of Disease, vol. 39, pp. 265-271 (2010).
Van Rossum et al., "Cytoskeletal Dynamics in Dendritic Spines: Direct Modulation By Glutamate Receptors?," Trends Neurosci., 1992, pp. 290-295, vol. 22.
Vance et al., "Mutations in FUS, an RNA Processing Protein, Cause Familial Amyotrophic Lateral Sclerosis Type 6", Science, Feb. 27, 2009, vol. 323, pp. 1208-1211.
Varani et al., "Structure of tau exon 10 splicing regulatory element RNA and destabilization by mutations of frontotemporal dementia and parkinsonism linked to chromosome 17," Proc. Natl. Acad. Sci. USA, 1999, vol. 96, pp. 8229-8234.
Vippagunta et al., Crystalline Solids, Advance Drug Delivery Reviews (2001), 48:3-26.
Von Bergen et al., "Assembly of tau protein into Alzheimer's paired helical filaments depends on a local sequence motif forming ($^{306}$VQIVYK$^{311}$) beta structure," Proceedings of the National Academy of Sciences of USA, National Academy of Science, May 9, 2000, vol. 97, No. 10, pp. 5129-5134.
Wijesekera et al., "Amyotrophic lateral sclerosis", Feb. 3, 2009, Orphanet Journal of Rare Diseases, 2009, vol. 4, No. 3, pp. 1-22.
Wille et al., Alzheimer-like paired helical filaments and antiparallel dimars formed from microtubule-associated protein tau in vitro, J. Cell Biol., 1992, pp. 573-584, vol. 118.
Wischik, Dissertation by Claude Wischik. May 19, 1989. pp. 182, 189, 233 and 234.
Wischik C., "Molecular Neuropathology of Alzheimer's Disease," 1989, pp. 44-70.
Wischik C., "Molecular neuropathology of Alzheimer's disease," John Libbey & Co., 1991, pp. 239-250.

Wischik et al., "Quantitative Analysis of Tau Protein in Paired Helical Filament Preparations: Implications for the Role of Tau Protein Phosphorylation in PHF Assembly in Alzheimer's Disease," Neurobiology of Aging, 1995, pp. 409-431, vol. 16, No. 3.
Wischik et al., "Author's Response to Commentaries," Neurobiology of Aging, 1995, vol. 16, No. 3, pp. 423-431.
Wischik et al., "Isolation of a Fragment of Tau Derived From the Core of the Paired Helical Filament of Alzheimer Disease," Proc. Natl. Acad. Sol. USA, Jun. 1998, pp. 4506-4510, vol. 85.
Wischik et al., "Modelling Prior-like Processing of Tau Protein in Alzheimer's disease for Pharmaceutical Development," Harwood Acad. Publishers, 1997, pp. 185-241.
Wischik et al., "Selective inhibition of Alzheimer disease-like tau aggregation by phenothiazines," Proc. Natl. Acad. Sci. USA, 1996, pp. 11213-11218, vol. 93.
Wischik et al., "Structural Characterization of the Core of the Paired Helical Filament of Alzheimer Disease," Proc. Natl. Acad. Sci. USA, Jul. 1998, pp. 4884 4888, vol. 85.
Wischik et al., "Structure, Biochemistry and Molecular Pathogenesis of Paired Helical Filaments in Alzheimer's Disease," Pathobiology of Alzheimer's Disease, 1995, pp. 10-39.
Wischik et al., "Subunit Structure of Paired Helical Filaments in Alzheimer's Disease," The Journal of Cell Biology, 1985, vol. 100, pp. 1905-1912.
Wischik et al., "The molecular basis of tau protein pathology in Alzheimer's disease and related neurodegenerative dementias," In Neurobiology of Alzheimer's Disease (Eds. D. Dawbarn & S.J. Allen) Oxford University Press, 2001, Oxford, pp. 103-206.
Wischik, Thesis, "The Structure and Biochemisty of Paired Helical Filaments in Alzheimer's Disease", Part I and II, Cambridge University, May 19, 1989, pp. 182, 189, 232-234.
Wischik, Thesis. "The Structure and Biochemistry of Paired Helical Filaments in Alzheimer's Disease", Part I and II, Cambridge University, May 1989, pp. 1-455.
Wischik, "Cell biology of the Alzheimer tangle," Current Opinion in Cell Biology, 1989, vol. 1, pp. 115-122.
Wischik et al., "Tau Aggregation Inhibitor Therapy: An Exploratory Phase 2 Study in Mild or Moderate Alzheimer's Disease", Journal of Alzheimer's Disease, vol. 44, pp. 705-720 (2015).
Wischik et al., "The role of tau protein in the neurodegenerative dementias", Dementia 2nd Edition (2000), Hodder Arnold Published, pp. 461-492.
Yamashita et al., "Methylene blue and dimebon inhibit aggregation of TDP-43 in cellular models", FEBS Letters, 2009, vol. 583, pp. 2419-2424.
Yen, et al., "Alzheimer's Neurofibrillary Tangles Contain Unique Epitopes and Epitopes in Common With the Heat-Stable Microtubule Associated Proteins Tau and MAP2," AJP, Jan. 1987, vol. 126, pp. 81-91.
Zhang, et al, "Aberrant cleavage of TDP-43 enhances aggregation and cellular toxicity", PNAS, May 5, 2009, vol. 106, No. 18, pp. 7607-7612.
Zhang et al., "Methylene Blue Prevents Neurodegeneration Caused by Rotenone in the Retina", Neurotoxicity Research, vol. 9, No. 1, 2006, pp. 47-57.
Gaudette et al., Determination of methylene blue and leucomethylene blue in male and female Fischer 344 rat urine and B6C3F1 mouse urine. J. Anal. Toxicol. Jan.-Feb. 2005;29(1):28-33. doi: 10.1093/jat/29.1.28.
Swarbrick, Encyclopedia of Pharmaceutical Technology. Third Edition. vol. 1. 2007. Informa Healthcare USA, Inc., eds. pp. 3003 and 3178.
International Preliminary Report on Patentability for Application No. PCT/GB2007/001103, mailed Jul. 31, 2008.
International Preliminary Report on Patentability for Application No. PCT/GB2008/003315 mailed Apr. 7, 2010.
Non-Final Office Action for U.S. Appl. No. 16/248,746 mailed Mar. 20, 2019.
Notification of Reexamination for CN Application No. 201510002365.2, mailed Dec. 19, 2019.
Decision of Final Rejection for CN Application No. 201510002365.2, mailed Dec. 18, 2018.

(56) References Cited

OTHER PUBLICATIONS

US Final Office Action issued in U.S. Appl. No. 14/929,111 dated Mar. 16, 2021.
US Non-Final Office Action issued in U.S. Appl. No. 14/929,111 dated Sep. 14, 2020.
[No Author Listed] FDA Orange Book, available at https://www.fda.gov/drugs/development-approval-process-drugs/orange-book-preface. Last accessed May 13, 2020. 27 pages.
Bernthsen, Studies in the methylene blue group. In: Justus Liebig's Annalen der Chemie. Band 230. Apr. 16, 1885. Kopp et al., Eds.:137-211. German, (partial translation).
Bernthsen, Studies in the methylene blue group. In: Justus Liebig's Annalen der Chemie. Band 230. Jul. 7, 1885. Kopp et al., Eds.:73-136. German, (partial translation).
Bernthsen, Studies in the methylene blue group. In: Justus Liebig's Annalen der Chemie. Band 251. Nov. 1, 1889. Kopp et al., Eds.:1-97. German, (partial translation).
Black et al., Structure, Solubility, Screening, and Synthesis of Molecular Salts. J Pharm Sci. May 2007;96(5):1053-68. doi: 10.1002/jps.20927.
Bondareff et al., Immunohistochemical staging of neurofibrillary degeneration in Alzheimer's disease. J Neuropathol Exp Neurol. Mar. 1994;53(2):158-64. doi: 10.1097/00005072-199403000-00007.
Butterfield et al., Brain protein oxidation in age-related neurodegenerative disorders that are associated with aggregated proteins. Mech Ageing Dev. Jul. 15, 2001;122(9):945-62. doi: 10.1016/s0047-6374(01)00249-4.
Declaration Under 37 C. F. R. § 1.132 by Professor Claude Wischik, filed on Feb. 9, 2018.
Declaration Under 37 C. F. R. § 1.132 by Professor John Storey, filed on Feb. 9, 2018.
Declaration Under 37 C.F.R. § 1.132 by Dr. Stephen Hilton, filed on Jul. 14, 2020.
Giorgini et al., Connecting the dots in Huntington's disease with protein interaction networks. Genome Biol. 2005;6(3):210. doi: 10.1186/GB-2005-6-3-210. Epub Feb. 28, 2005.
Goedert et al., Cloning and sequencing of the cDNA encoding a core protein of the paired helical filament of Alzheimer disease: identification as the microtubule-associated protein tau. Proc Natl Acad Sci U S A. Jun. 1988;85(11):4051-5. doi: 10.1073/pnas.85.11.4051.
Han et al., Medicament Manufacture Technology. Mar. 2000. First Edition. Chapter 1. Science and Technology Literature Press, Eds. pp. 215-216.
Jellinger, Interaction between α-synuclein and other proteins in neurodegenerative disorders. Scientific WorldJournal. 2011;11:1893-907. doi: 10.1100/2011/371893. Epub Oct. 24, 2011.
Raust et al., Stability studies of ionised and non-ionised 3,4-diaminopyridine: Hypothesis of degradation pathways and chemical structure of degradation products. Journal of Pharmaceutical and Biomedical Analysis. 2007;43:83-88.
Ross et al., Opinion: What is the role of protein aggregation in neurodegeneration? Nat Rev Mol Cell Biol. Nov. 2005;6(11):891-8. doi: 10.1038/nrm1742.
Schwab et al, A Protein Aggregation Inhibitor, Leuco-Methylthioninium Bis(Hydromethanesulfonate), Decreases α-Synuclein Inclusions in a Transgenic Mouse Model of Synucleinopathy. Frontiers in Molecular Neuroscience. Jan. 2018; 10(447):1-15.
Shiyu, Synthetic drugs and intermediates Manual. 2003. Chapter 4. Beijing Chemical Industry Press, Eds. p. 285.
Shumin, Medicinal Chemistry. 2014. Shandong People's Publishing House, Eds. pp. 113-116.
Sigfridsson et al., A case study where pharmaceutical salts were used to address the issue of low in vivo exposure. Drug Development and Industrial Pharmacy. 2019;45(2):202-211. DOI 10.1080/03639045.2018.1529184.
Wirths et al., α-Synuclein, Aβ and Alzheimer's disease. Prog Neuropsychopharmacol Biol Psychiatry. Feb. 2003;27(1):103-8. doi: 10.1016/S0278-5846(02)00339-1.
Wood et al., Protein aggregation in motor neurone disorders. Neuropathology and Applied Neurobiology. 2003;29:529-545.
Yale et al., 4-{3-[10-(2-Trifluoromethyl)-phenothiazinyl]-propyl}-1-piperazine-ethanol1 and Related Compounds. Squibb Institute for Medical Research. Apr. 20, 1960;82: 2039-2042.

Figure 15a:
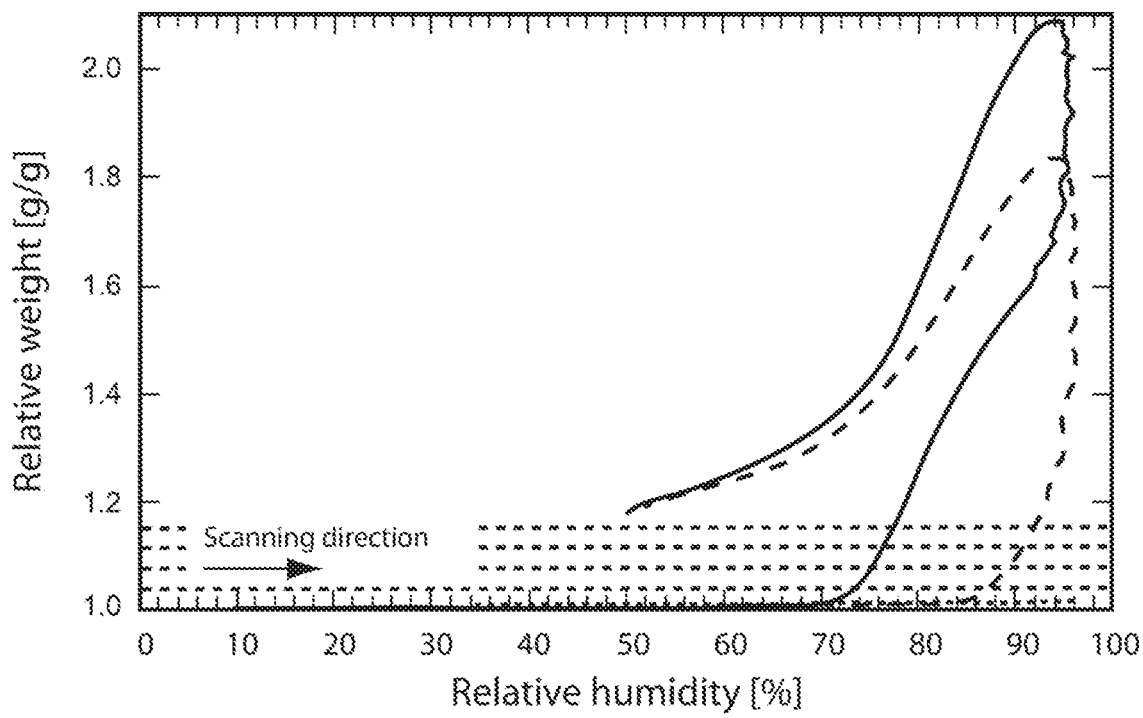
Figure 15b – expanded view:
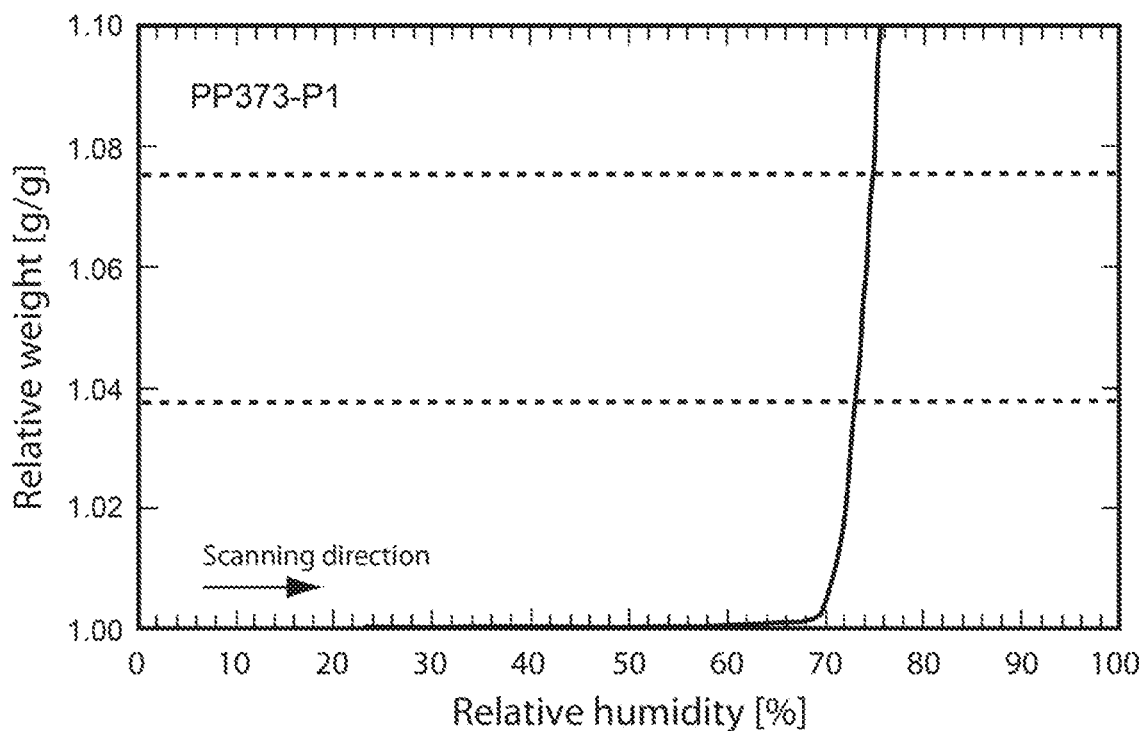

X-ray structure (unit cell) of LMTEs

X-ray structure (unit cell) of LMT.EDSA

X-ray structure (unit cell) of LMTM

PHENOTHIAZINE DIAMINIUM SALTS AND THEIR USE

CROSS REFERENCE TO RELATED APPLICATIONS

This application is a continuation of U.S. application Ser. No. 16/751,811, filed Jan. 24, 2020, which issued on Nov. 23, 2021 as U.S. Pat. No. 11,180,464, which is a divisional of U.S. application Ser. No. 15/912,166, filed Mar. 5, 2018, which issued on Dec. 15, 2020, as U.S. Pat. No. 10,864,216; which is a divisional of U.S. application Ser. No. 15/056,610, filed Feb. 29, 2016, which issued on Mar 6, 2018, as U.S. Pat. No. 9,907,804; which is a divisional of U.S. application Ser. No. 13/984,841, filed Aug. 9, 2013, which issued on Mar. 15, 2016, as U.S. Pat. No. 9,283,230; which entered U.S. National Phase on Aug. 9, 2013, from International Application No. PCT/GB2011/001221, filed Aug. 15, 2011, and which was published in English on Aug. 16, 2012 as WO 2012/107706. The foregoing claim priority to U.S. Provisional Patent Application No. 61/485,880, filed May 13, 2011, and Singapore Patent Application No. 2011-01060-0, filed Feb. 11, 2011. The foregoing are incorporated by reference in their entireties.

TECHNICAL FIELD

This invention pertains generally to the field of phenothiazine compounds, in particular certain phenothiazine diaminium salts, including uses and formulations thereof. In some embodiments the invention relates to bis(sulfonic acid) salts of diaminophenothiazine compounds such as N,N,N',N'-tetramethyl-10H-phenothiazine-3,7-diamine. The compounds of the invention are useful, for example, in the treatment of tauopathies such as Alzheimer's disease (AD).

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

Conditions of dementia are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska, E. B. et al., 2000, Am. J. Pathol., Vol. 157, No. 2, pp. 623-636).

In Alzheimer's disease, both neuritic plaques and NFTs contain paired helical filaments (PHFs), of which a major constituent is the microtubule-associated protein tau (see, e.g., Wischik et al., 1988, PNAS USA, Vol. 85, pp. 4506-4510). Plaques also contain extracellular β-amyloid fibrils derived from the abnormal processing of amyloid precursor protein (APP) (see, e.g., Kang et al., 1987, Nature, Vol. 325, p. 733). An article by Wischik et al. (in 'Neurobiology of Alzheimer's Disease', 2nd Edition, 2000, Eds. Dawbarn, D. and Allen, S. J., The Molecular and Cellular Neurobiology Series, Bios Scientific Publishers, Oxford) discusses in detail the putative role of tau protein in the pathogenesis of neurodegenerative dementias. Loss of the normal form of tau, accumulation of pathological PHFs, and loss of synapses in the mid-frontal cortex all correlate with associated cognitive impairment. Furthermore, loss of synapses and loss of pyramidal cells both correlate with morphometric measures of tau-reactive neurofibrillary pathology, which parallels, at a molecular level, an almost total redistribution of the tau protein pool from a soluble to a polymerised form (i.e., PHFs) in Alzheimer's disease.

Tau exists in alternatively-spliced isoforms, which contain three or four copies of a repeat sequence corresponding to the microtubule-binding domain (see, e.g., Goedert, M., et al., 1989, EMBO J., Vol. 8, pp. 393-399; Goedert, M., et al., 1989, Neuron, Vol. 3, pp. 519-526). Tau in PHFs is proteolytically processed to a core domain (see, e.g., Wischik, C. M., et al., 1988, PNAS USA, Vol. 85, pp. 4884-4888; Wischik et al., 1988, PNAS USA, Vol. 85, pp. 4506-4510; Novak, M., et al., 1993, EMBO J., Vol. 12, pp. 365-370) which is composed of a phase-shifted version of the repeat domain; only three repeats are involved in the stable tau-tau interaction (see, e.g., Jakes, R., et al., 1991, EMBO J., Vol. 10, pp. 2725-2729). Once formed, PHF-like tau aggregates act as seeds for the further capture and provide a template for proteolytic processing of full-length tau protein (see, e.g., Wischik et al., 1996, PNAS USA, Vol. 93, pp. 11213-11218).

The phase shift which is observed in the repeat domain of tau incorporated into PHFs suggests that the repeat domain undergoes an induced conformational change during incorporation into the filament. During the onset of AD, it is envisaged that this conformational change could be initiated by the binding of tau to a pathological substrate, such as damaged or mutated membrane proteins (see, e.g., Wischik, C. M., et al., 1997, in "Microtubule-associated proteins: modifications in disease", Eds. Avila, J., Brandt, R. and Kosik, K. S. (Harwood Academic Publishers, Amsterdam) pp. 185-241).

In the course of their formation and accumulation, PHFs first assemble to form amorphous aggregates within the cytoplasm, probably from early tau oligomers which become truncated prior to, or in the course of, PHF assembly (see, e.g., Mena, R., et al., 1995, Acta Neuropathol., Vol. 89, pp. 50-56; Mena, R., et al., 1996, Acta Neuropathol., Vol. 91, pp. 633-641). These filaments then go on to form classical intracellular NFTs. In this state, the PHFs consist of a core of truncated tau and a fuzzy outer coat containing full-length tau (see, e.g., Wischik et al., 1996, PNAS USA, Vol. 93, pp. 11213-11218). The assembly process is exponential, consuming the cellular pool of normal functional tau and inducing new tau synthesis to make up the deficit (see, e.g., Lai, R. Y. K., et al., 1995, Neurobiology of Ageing, Vol. 16, No. 3, pp. 433-445). Eventually, functional impairment of the neurone progresses to the point of cell death, leaving behind an extracellular NFT. Cell death is highly correlated with the number of extracellular NFTs (see, e.g., Wischik et al., in 'Neurobiology of Alzheimer's Disease', 2nd Edition, 2000, Eds. Dawbarn, D. and Allen, S. J., The Molecular and Cellular Neurobiology Series, Bios Scientific Publishers, Oxford). As tangles are extruded into the extracellular space, there is progressive loss of the fuzzy outer coat of the neurone with corresponding loss of N-terminal tau immunoreactivity, but preservation of tau immunoreactivity associated with the PHF core (see, e.g., Bondareff, W. et al., 1994, J. Neuropath. Exper. Neurol., Vol. 53, No. 2, pp. 158-164).

Diaminophenothiazine Compounds

Methythioninium Chloride (MTC) (also known as Methylene blue (MB); methylthionine chloride; tetramethylthionine chloride; 3,7-bis(dimethylamino) phenothiazin-5-ium chloride; C. I. Basic Blue 9; tetramethylthionine chloride; 3,7-bis(dimethylamino) phenazathionium chloride; Swiss blue; C. I. 52015; C. I. Solvent Blue 8; aniline violet; and Urolene Blue®) is a low molecular weight (319.86), water soluble, tricyclic organic compound of the following formula:

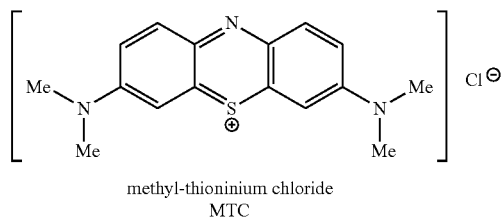

methyl-thioninium chloride
MTC

Methythioninium Chloride (MTC) is a well known phenothiazine dye and redox indicator and has also been used as an optical probe of biophysical systems, as an intercalator in nanoporous materials, as a redox mediator, and in photoelectrochromic imaging.

Methythioninium chloride (MTC) and other diaminophenothiazines have been described as inhibitors of protein aggregation in diseases in which proteins aggregate pathologically.

In particular, diaminopenothiazines including MTC have been shown to inhibit tau protein aggregation and to disrupt the structure of PHFs, and reverse the proteolytic stability of the PHF core (see, e.g., WO 96/30766, Hofmann-La Roche). Such compounds were disclosed for use in the treatment or prophylaxis of various diseases, including Alzheimer's disease.

WO2007/110630 (WisTa Laboratories Ltd) also discloses certain specific diaminophenothiazine compounds related to MTC, including ETC, DEMTC, DMETC, DEETC, MTZ, ETZ, MTI, MTILHI, ETI, ETLHI, MTN, and ETN, which are useful as drugs, for example in the treatment of Alzheimer's disease.

Additionally, WO 2005/030676 (The University Court of the University of Aberdeen) discusses radiolabelled phenothiazines, and their use in diagnosis and therapy, for example, of tauopathies.

Methythioninium chloride (MTC) has also been disclosed for other medical uses. For example it is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria, either singly (see, e.g., Guttmann, P. and Ehrlich, P., 1891, "Uber die wirkung des methylenblau bei malaria," Berl. Klin. Woschenr., Vol. 28, pp. 953-956) or in combination with chloroquine (see, e.g., Schirmer, H., et al., 2003, "Methylene blue as an antimalarial agent," Redox Report, Vol. 8, pp. 272-275; Rengelshausen, J., et al., 2004, "Pharmacokinetic interaction of chloroquine and methylene blue combination against malaria," European Journal of Clinical Pharmacology, Vol. 60, pp. 709-715).

MTC (under the name Virostat®, from Bioenvision Inc., New York) has also shown potent viricidal activity in vitro. Specifically Virostat® is effective against viruses such as HIV and West Nile Virus in laboratory tests. Virostat® is also currently in clinical trials for the treatment of chronic Hepatitis C, a viral infection of the liver. The virus, HCV, is a major cause of acute hepatitis and chronic liver disease, including cirrhosis and liver cancer.

MTC, when combined with light, can also prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compound then binds to the nucleic acid of the viral or bacterial pathogen, preventing replication of the DNA or RNA. Because MTC can inactivate pathogens, it has the potential to reduce the risk of transmission of pathogens that would remain undetected by testing.

Oral and parenteral formulations of MTC have been commercially available in the United States, usually under the name Urolene Blue®.

Reduced ('Leuco') Forms

MTC, a phenothiazin-5-ium salt, may be considered to be an "oxidized form" in relation to the corresponding 10H-phenothiazine compound, N,N,N',N'-tetramethyl-10H-phenothiazine-3,7-diamine, which may be considered to be a "reduced form":

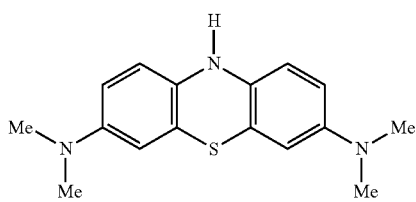

reduced form oxidation
(-H$_2$ + HCl)

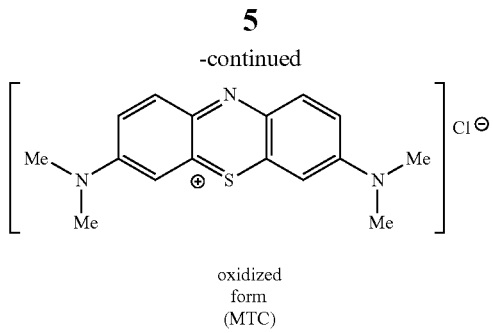

oxidized
form
(MTC)

The "reduced form" (or "leuco form") is known to be unstable and can be readily and rapidly oxidized to give the corresponding "oxidized" form.

May et al. (Am J Physiol Cell Physiol, 2004, Vol. 286, pp. C1390-C1398) have shown that human erythrocytes sequentially reduce and take up MTC; that MTC itself is not taken up by the cells; that it is the reduced form of MTC that crosses the cell membrane; that the rate of uptake is enzyme dependent; and that both MTC and reduced MTC are concentrated in cells (reduced MTC re-equilibrates once inside the cell to form MTC).

MTC and similar drugs are taken up in the gut and enter the bloodstream. Unabsorbed drug percolates down the alimentary canal, to the distal gut. One important undesired side-effect is the effect of the unabsorbed drug in the distal gut, for example, sensitisation of the distal gut and/or antimicrobial effects of the unabsorbed drug on flora in the distal gut, both leading to diarrhoea. Therefore, it is desirable to minimize the amount of drug that percolates to the distal gut. By increasing the drug's uptake in the gut (i.e., by increasing the drug's bioavailability), dosage may be reduced, and the undesired side-effects, such as diarrhoea, may be ameliorated.

Since it is the reduced form of MTC that is taken up by cells, it may be desirable to administer the reduced form to patients. This may also reduce reliance on the rate limiting step of enzymatic reduction.

WO 02/055720 (The University Court of the University of Aberdeen) discloses the use of reduced forms of certain diaminophenothiazines for the treatment of protein aggregating diseases, primarily tauopathies.

WO2007/110627 (WisTa Laboratories Ltd) disclosed certain 3,7-diamino-10H-phenothiazinium salts, effective as drugs or pro-drugs for the treatment of diseases including Alzheimer's disease. These compounds are also in the "reduced" or "leuco" form when considered in respect of MTC. These included the following salts:

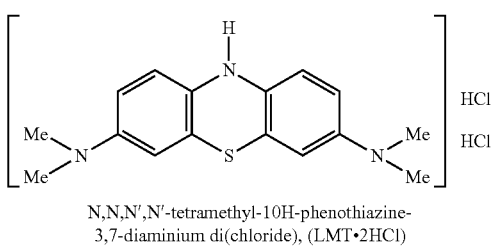

N,N,N',N'-tetramethyl-10H-phenothiazine-
3,7-diaminium di(chloride), (LMT·2HCl)

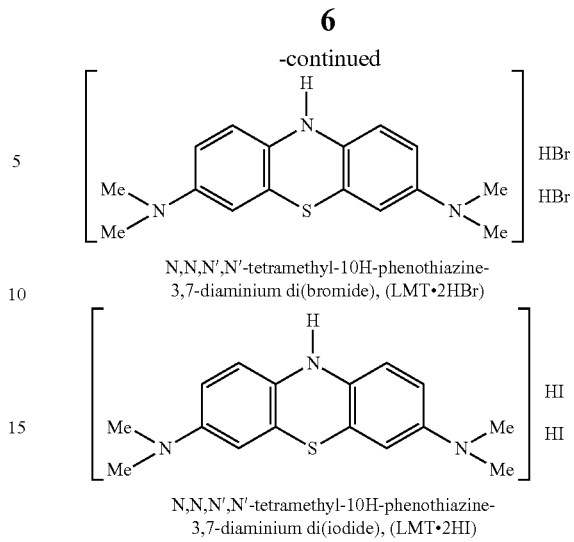

N,N,N',N'-tetramethyl-10H-phenothiazine-
3,7-diaminium di(bromide), (LMT·2HBr)

N,N,N',N'-tetramethyl-10H-phenothiazine-
3,7-diaminium di(iodide), (LMT·2HI)

Although providing certain advantages over the use of MTC, the synthesis of LMT.2HCl under certain conditions may result in $CH_3Cl$ being trapped within the crystal. This then needs to be removed since $CH_3Cl$ is toxic and levels need to be kept below safety levels.

Furthermore LMT.2HBr contains bromide ions. This is in principle less desirable since bromide is toxic either at high levels or with chronic dosing and, at lower levels, can causes side effects such as confusion in patients.

Therefore it can be seen the provision of further salts of methylthioninium compounds, having one or more desirable properties over those already known, would be a contribution to the art.

Furthermore the provision of novel formulations of methylthioninium compounds which enhance stability, absorption, and\or otherwise improve their effectiveness as therapeutics would be a contribution to the art.

SUMMARY OF THE INVENTION

The present inventors have now identified a new class of stable phenothiazine diaminium compounds which have improved properties as compared to previously disclosed diaminophenothiazine compounds and salts.

The properties of the compounds are described hereinafter, whereby it can be seen that in preferred embodiments the invention can provide one or more of improved physical, pharmacokinetic, biochemical or other beneficial properties.

In other aspects the present inventors also provide novel formulations of 3,7-diamino-10H-phenothiazinium salts.

In one aspect the present invention provides certain compounds, specifically, certain phenothiazine diaminium compounds, as described herein.

The compound may be selected from compounds of general formula (I):

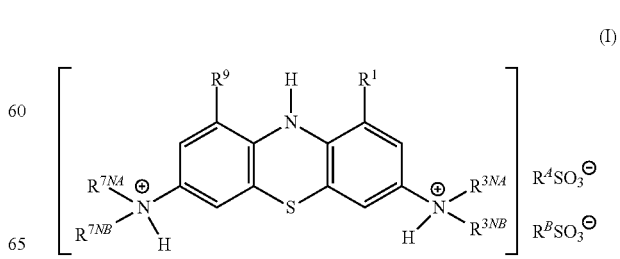

(I)

wherein:

each of $R^1$ and $R^9$ is independently selected from: —H, $C_{1-4}$alkyl, $C_{2-4}$alkenyl, and halogenated $C_{1-4}$alkyl;

each of $R^{3NA}$ and $R^{3NB}$ is independently selected from: —H, $C_{1-4}$alkyl, $C_{2-4}$alkenyl, and halogenated $C_{1-4}$alkyl;

each of $R^{7NA}$ and $R^{7NB}$ is independently selected from: —H, $C_{1-4}$alkyl, $C_{2-4}$alkenyl, and halogenated $C_{1-4}$alkyl;

and wherein:

each of $R^A$ and $R^B$ is independently selected from: $C_{1-4}$alkyl, halogenated $C_{1-4}$alkyl, and $C_{6-10}$ aryl;

or $R^A$ and $R^B$ are linked to form a group $R^{AB}$, wherein $R^{AB}$ is selected from:

$C_{1-6}$ alkylene and $C_{6-10}$ arylene;

and pharmaceutically acceptable salts thereof.

Another aspect of the invention pertains to processes for synthesizing a compound as described above.

Another aspect of the invention pertains to a pharmaceutical composition comprising a compound as described herein and a pharmaceutically acceptable carrier or diluent.

Another aspect of the invention pertains to a method of preparing a pharmaceutical composition comprising admixing a compound as described herein and a pharmaceutically acceptable carrier or diluent.

Another aspect of the invention pertains to a pharmaceutical composition in solid dosage form, comprising a compound as described herein and further comprising at least one diluent suitable for dry compression, and optionally one or more other excipients.

Another aspect of the invention pertains to a process for the manufacture of a pharmaceutical composition by a dry compression method, said composition being a solid dosage form comprising a compound as described herein, at least one diluent suitable for dry compression, and optionally one or more other excipients.

Another aspect of the invention pertains to a free-flowing, cohesive powder, comprising a compound as described herein and at least one diluent suitable for dry compression, and optionally one or more other excipients, said powder being capable of being compressed into a solid dosage form.

Another aspect of the present invention pertains to a method of reversing and/or inhibiting the aggregation of a protein (e.g., a tau protein, a synuclein, etc.), for example, aggregation of a protein associated with a neurodegenerative disease and/or clinical dementia, comprising contacting the protein with an effective amount of a compound or composition as described herein. Such a method may be performed in vitro, or in vivo.

Another aspect of the present invention pertains to a method of treatment or prophylaxis of a disease condition in a subject comprising administering to said subject a prophylactically or therapeutically effective amount of a compound as described herein, preferably in the form of a pharmaceutical composition, preferably a pharmaceutical composition in solid dosage form, as further described herein.

Another aspect of the present invention pertains to a compound or composition as described herein for use in a method of treatment or prophylaxis (e.g., of a disease condition) of the human or animal body by therapy.

Another aspect of the present invention pertains to use of a compound or composition as described herein, in the manufacture of a medicament for use in the treatment or prophylaxis of a disease condition.

In some embodiments, the disease condition is a disease of protein aggregation.

In some embodiments, the disease condition is a tauopathy, e.g., a neurodegenerative tauopathy, e.g., Alzheimer's disease or other disease described hereinafter.

In some embodiments, the disease condition is skin cancer, e.g., melanoma.

In some embodiments, the disease condition is a viral, bacterial or protozoal disease condition, e.g., Hepatitis C, HIV, West Nile Virus (WNV), or malaria.

Another aspect of the present invention pertains to a method of inactivating a pathogen in a sample (for example a blood or plasma sample), comprising the steps of introducing a compound or composition as described herein, into the sample, and then exposing the sample to light.

Another aspect of the present invention pertains to a kit comprising (a) a compound as described herein, preferably provided as a pharmaceutical composition and in a suitable container and/or with suitable packaging; and (b) instructions for use, for example, written instructions on how to administer the compound or composition.

As will be appreciated by one of skill in the art, features and preferred embodiments of one aspect of the invention will also pertain to other aspects of the invention.

Figure 15C:
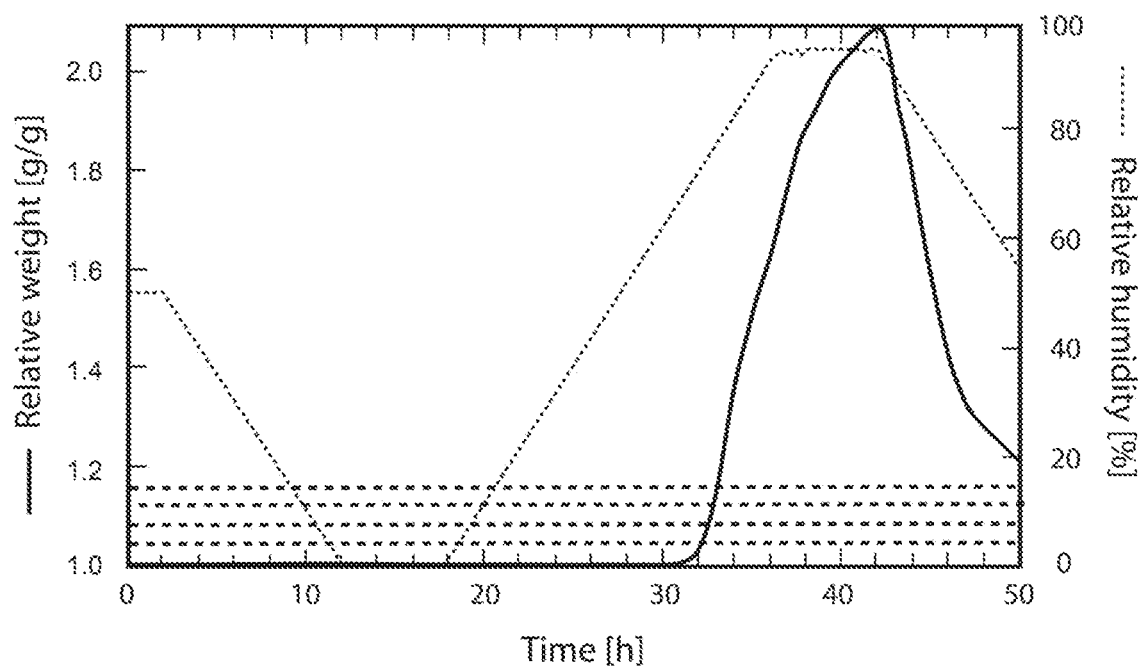
FIGS. 15a and 15b show the dynamic vapour sorption (DVS) curve for crystalline LMT.2MsOH measured at 25° C. with 5%/h scanning rate. The horizontal dashed lines indicate steps of water uptake of one equivalent. A stable weight of the sample (less than 0.5% weight change) was observed in the relative humidity (r.h.) range between 0% and 70%. Above this r.h., the water uptake increased rapidly, and the sample ultimately deliquesced. Upon drying, the water content decreased again to approximately 4 equiv. at 50% r.h. The DVS curve of the crystalline dihydrochloride salt (LMT.2HCl) is shown for comparison as a dashed line, the DVS curve of the dihydrobromide salt (LMT.2HBr) as a dotted line.

FIG. 15c shows the dynamic vapour sorption (DVS) curve for crystalline LMT.2MsOH as a function of time. The relative humidity is also indicated (right axis). The horizontal dashed lines indicate steps of one equivalent water uptake.

Figure 16:
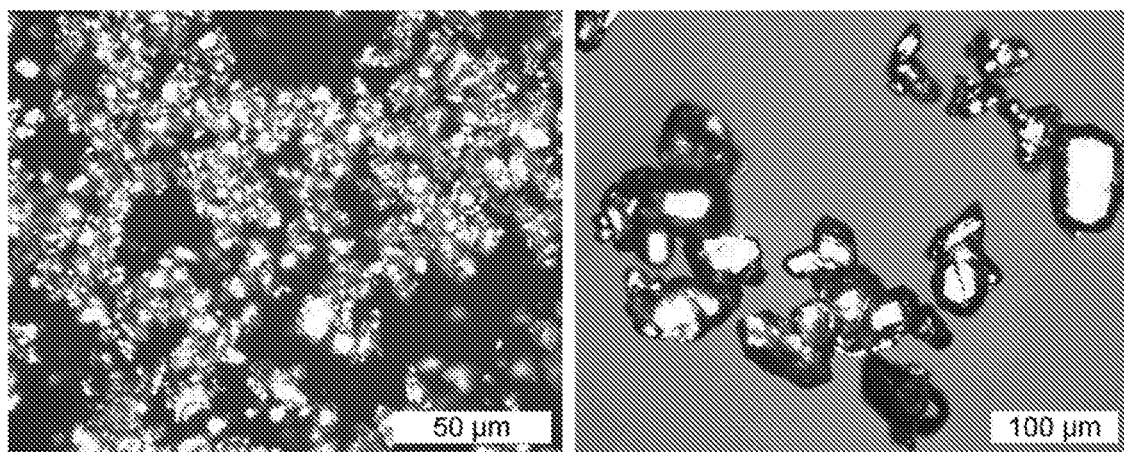

FIG. 16 shows polarizing microscopy pictures of the LMT.2MsOH (left) and recrystallized LMT.2MsOH (right). Crystals of up to 100 µm in size were obtained by recrystallization from 2-PrOH/water. Crystals are irregularly shaped.

Figure 17A:
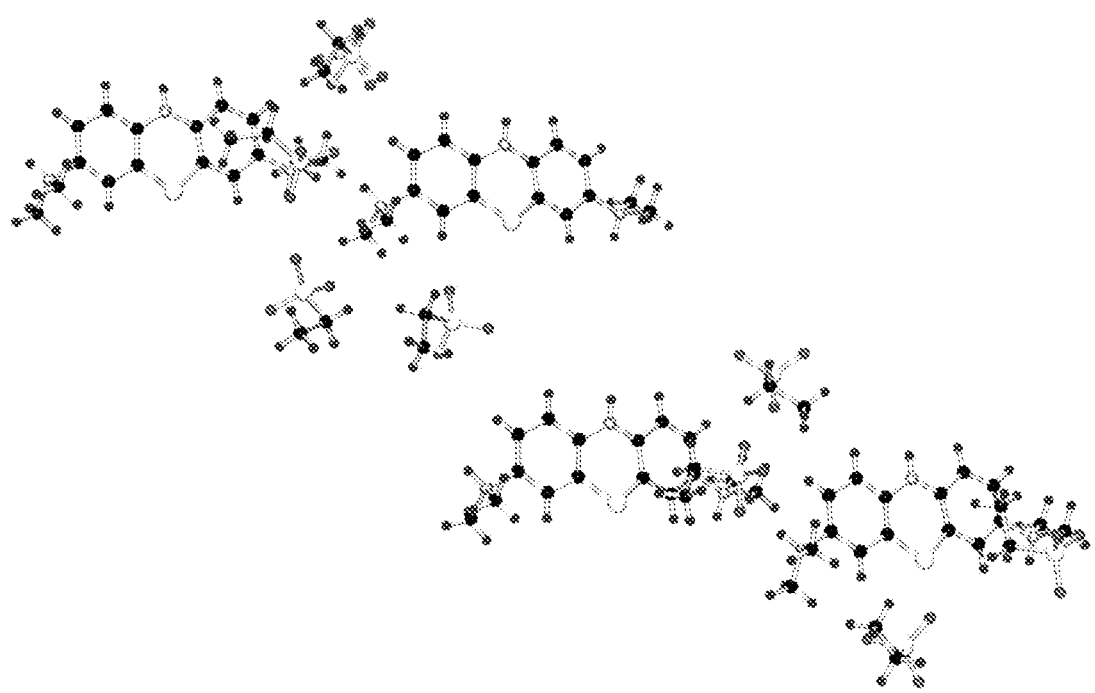
Figure 17B:
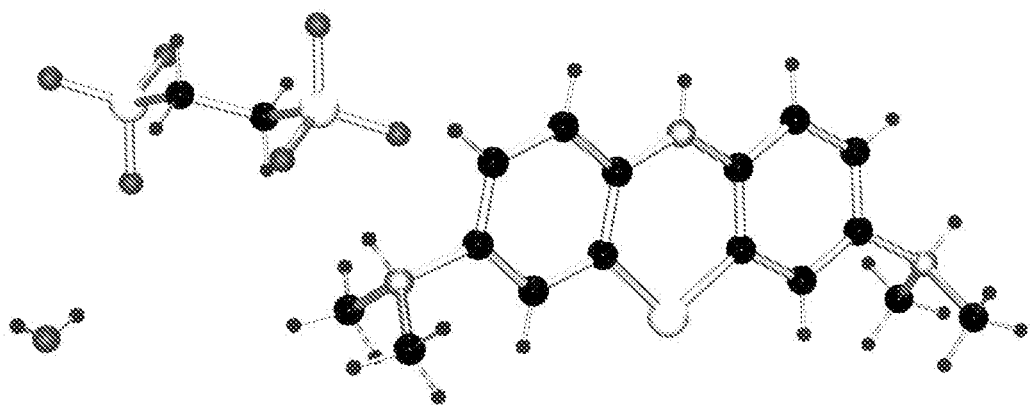
Figure 17C:
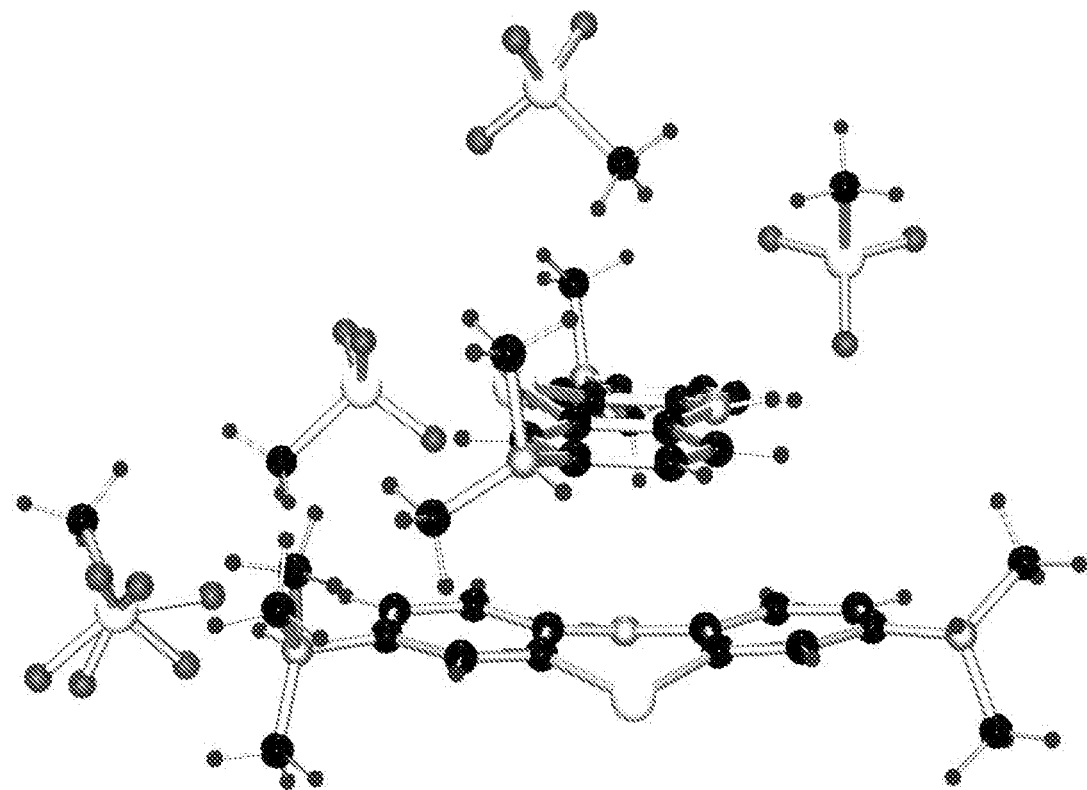
Figure 18:
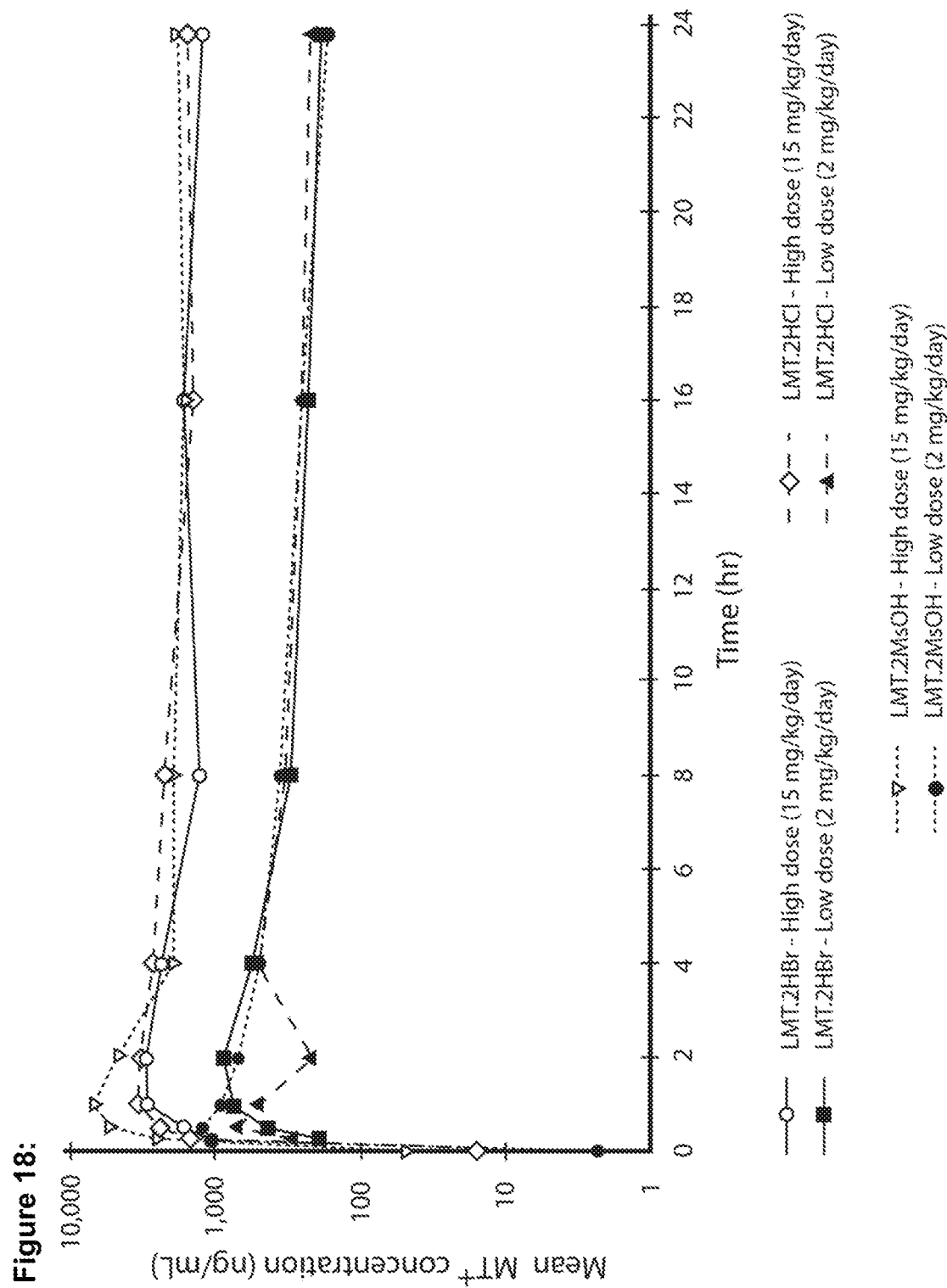

FIGS. 17a-17c shows the X-ray crystal structures of LMTEsOH, LMT.EDSA. and LMT.2MsOH FIG. 18 shows a comparison of the plasma concentration in pig of the MT moiety over time following dosing of LMT.2HBr, LMT.2HCl and LMT.2MsOH.

Figure 19:
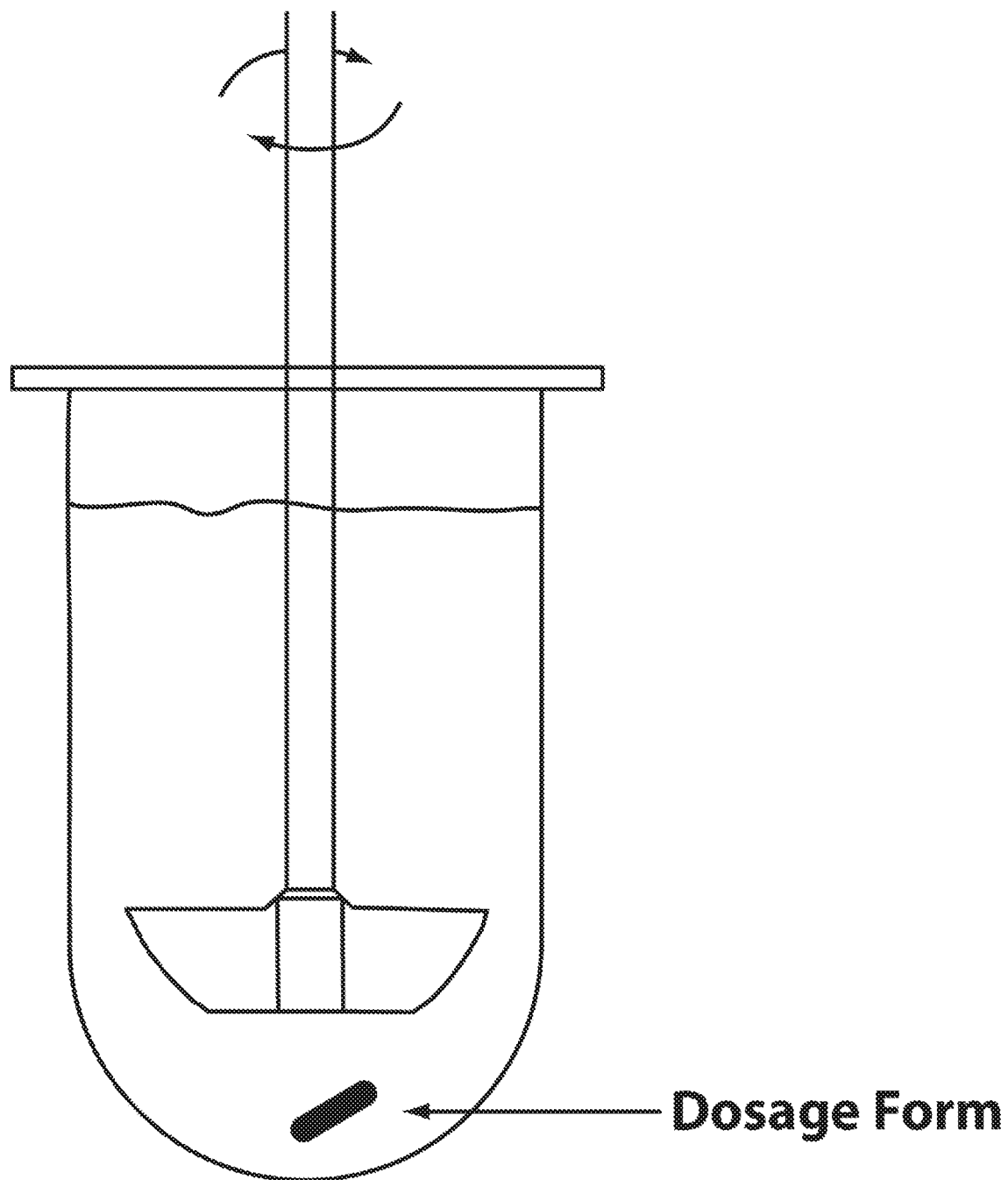

FIG. 19 is a diagram of the apparatus used in the dissolution studies (see Formulation Example 12).

DETAILED DESCRIPTION OF THE INVENTION

The present inventors have identified a new class of phenothiazine diaminium compounds which have desirable physical or other properties and\or surprisingly improved activity as compared to previously disclosed diaminophenothiazine compounds and salts.

In other aspects they have additionally provided novel formulations of phenothiazine diaminium compounds, including (but not limited to) the class above.

The Compounds

In general terms, unless context demands otherwise, the compounds of the invention may be described as bis(sulfonate) salts (or bis(sulfonic acid) salts) of 3,7-diamino-10H-phenothiazine compounds. In other words, the compounds are salts of the corresponding 3,7-diamino-10H-phenothiazine compounds with organic sulfonic acids.

More specifically, a compound of the invention is a bis(sulfonate) salt of a compound of general formula:

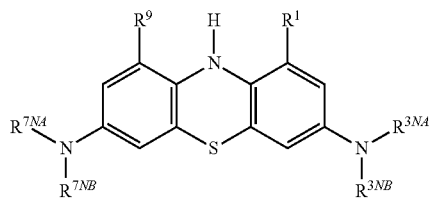

wherein $R^1$, $R^9$, $R^{3NA}$, $R^{3NB}$, $R^{7NA}$ and $R^{7NB}$ are as defined above.

In some embodiments, the salt is a bis(alkylsulfonate) salt or a bis(arylsulfonate) salt.

In some embodiments, the salt is selected from a bis(methanesulfonate) salt, a bis(ethanesulfonate) salt, a bis(p-toluenesulfonate) salt, a bis(benzenesulfonate) salt, an ethanedisulfonate salt, a propanedisulfonate salt, or a naphthalenedisulfonate salt.

In some embodiments, the salt is a bis(methanesulfonate) salt (which may also be called a bis(mesylate) salt).

In some embodiments, the salt is a bis(ethanesulfonate) salt (which may also be called a bis(esylate) salt).

In some embodiments, the salt is a bis(p-toluenesulfonate) salt (which may also be called a bis(tosylate) salt).

In some embodiments, the salt is a bis(benzenesulfonate) salt.

In some embodiments, the salt is an ethanedisulfonate salt.

In some embodiments, the salt is a propanedisulfonate salt.

In some embodiments, the salt is a naphthalenedisulfonate salt, preferably a naphthalene-1,5-disulfonate salt.

In other words, the compounds of the invention can be considered to be products obtainable from the reaction of a 3,7-diamino-10H-phenothiazine compound, for example as set out above, with two organic sulfonic acid moieties ($R^A SO_3 H$ and $R^B O_3 H$). The two organic sulfonic acid moieties may optionally be present on the same molecule, i.e. where $R^A$ and $R^B$ are linked.

In some embodiments, compounds of the invention are selected from compounds of general formula (I):

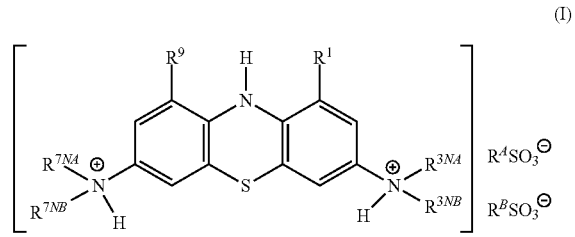

wherein:

each of $R^1$ and $R^9$ is independently selected from: —H, $C_{1-4}$alkyl, $C_{2-4}$alkenyl, and halogenated $C_{1-4}$alkyl;

each of $R^{3NA}$ and $R^{3NB}$ is independently selected from: —H, $C_{1-4}$alkyl, $C_{2-4}$alkenyl, and halogenated $C_{1-4}$alkyl;

each of $R^{7NA}$ and $R^{7NB}$ is independently selected from: —H, $C_{1-4}$alkyl, $C_{2-4}$alkenyl, and halogenated $C_{1-4}$alkyl;

and wherein:

each of $R^A$ and $R^B$ is independently selected from:

$C_{1-4}$alkyl, halogenated $C_{1-4}$alkyl, and $C_{6-10}$aryl;

or $R^A$ and $R^B$ are linked to form a group $R^{AB}$, wherein $R^{AB}$ is selected from:

$C_{1-6}$ alkylene and $C_{6-10}$ arylene;

and pharmaceutically acceptable salts, solvates, and hydrates thereof.

Compounds of the invention are represented herein by a general formula showing the structure of the 3,7-diamino-10H-phenothiazine compound, with the 3,7-diamino groups being in protonated form.

The resultant doubly positively-charged species is associated with two sulfonate counterion moieties (which may optionally be present on the same molecule, i.e. where $R^A$ and $R^B$ are linked):

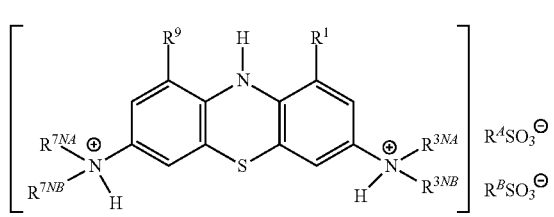

However, as will be understood by one skilled in the art, the same salt could equally be represented in other ways, such as, for example:

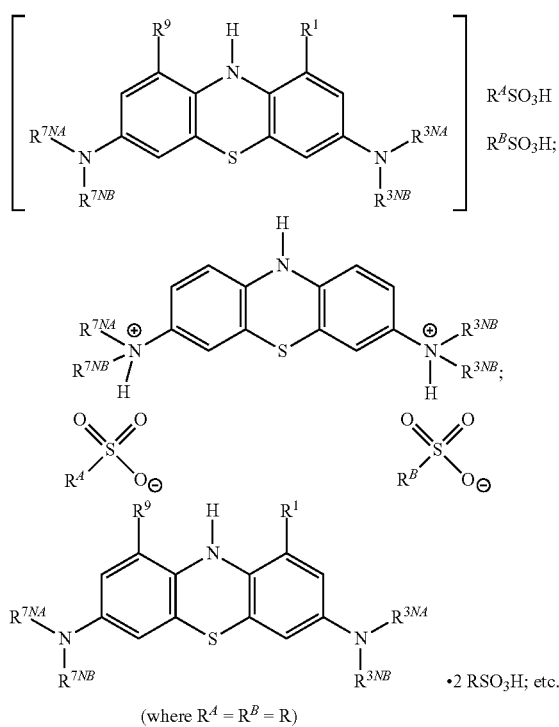

(where $R^A = R^B = R$)

Further Definitions and Preferences

The term "$C_{1-4}$ alkyl", as used herein, pertains to a monovalent moiety obtained by removing a hydrogen atom from a hydrocarbon compound having from 1 to 4 carbon atoms, which may be aliphatic or alicyclic, or a combination thereof.

Similarly, the term "$C_{2-4}$ alkenyl" pertains to a monovalent moiety obtained by removing a hydrogen atom from a $C_{2-4}$ alkene compound (i.e. a hydrocarbon compound containing at least one double bond and from 2 to 4 carbon atoms).

The term "$C_{1-6}$ alkylene", as used herein, pertains to a bidentate moiety obtained by removing two hydrogen atoms, either both from the same carbon atom, or one from each of two different carbon atoms, of an aliphatic linear hydrocarbon compound having from 1 to 6 carbon atoms.

In some embodiments, $C_{1-4}$alkyl groups may be selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In some embodiments, $C_{2-4}$alkenyl groups may be selected from linear $C_{1-4}$alkenyl groups, such as —CH=CH$_2$ (vinyl) and —CH$_2$—CH=CH$_2$ (allyl).

In some embodiments, halogenated $C_{1-4}$alkyl groups may be selected from: —CF$_3$, —CH$_2$CF$_3$, and —CF$_2$CF$_3$.

The term "$C_{6-10}$ aryl", as used herein, pertains to a monovalent moiety obtained by removing a hydrogen atom from an aromatic ring atom of a $C_{6-10}$ aromatic compound, said compound having one ring, or two or more rings (e.g., fused), and having from 6 to 10 ring atoms, and wherein at least one of said ring(s) is an aromatic ring.

The term "$C_{6-10}$ arylene", as used herein, pertains to a bidentate moiety obtained by removing two hydrogen atoms from an aromatic compound having from 6 to 10 carbon atoms.

In some embodiments, $C_{6-10}$ aryl groups may be selected from $C_{6-10}$ carboaryl groups such as phenyl, and naphthyl.

In some embodiments, $C_{6-10}$ arylene groups may be selected from phenylene and naphthylene.

Said $C_{1-4}$ alkyl and $C_{1-6}$ alkylene groups may be unsubstituted or may optionally be substituted, for example with one or more groups selected from halo (e.g. F, Cl, Br, or I), amino (e.g. —NH$_2$, —NHR, or —NR$_2$, wherein each R is independently $C_{1-4}$alkyl), hydroxy (—OH), alkoxy (—OR, wherein R is independently $C_{1-4}$alkyl), nitro (—NO$_2$), etc.

Said $C_{6-10}$ aryl and $C_{6-10}$ arylene groups may be unsubstituted or may optionally be substituted, for example with one or more groups selected from $C_{1-4}$ alkyl, for example -Me, halogenated $C_{1-4}$alkyl, for example —CF$_3$, halo (e.g. F, Cl, Br, or 1), amino (e.g. —NH$_2$, —NHR, or —NR$_2$, wherein each R is independently $C_{1-4}$alkyl), hydroxy (—OH), alkoxy (—OR, wherein R is independently $C_{1-4}$alkyl), nitro (—NO$_2$), etc.

Groups $R^A$ and $R^B$

Each of $R^A$ and $R^B$ is independently selected from:

$C_{1-4}$alkyl, halogenated $C_{1-4}$alkyl, and $C_{6-10}$aryl;

or $R^A$ and $R^B$ are linked to form a group $R^{AB}$, wherein $R^{AB}$ is selected from:

$C_{1-6}$ alkylene and $C_{6-10}$ arylene;

In some embodiments, each of $R^A$ and $R^B$ is independently selected from: $C_{1-4}$alkyl, halogenated $C_{1-4}$alkyl, and $C_{6-10}$aryl.

In some embodiments, each of $R^A$ and $R^B$ is independently $C_{1-4}$ alkyl.

In some embodiments, each of $R^A$ and $R^B$ is independently selected from Me, Et, nPr, Pr, nBu, iBu, tBu.

In some embodiments, each of $R^A$ and $R^B$ is independently selected from Me and Et.

In some embodiments, each of $R^A$ and $R^B$ is independently $C_{6-10}$aryl.

In some embodiments, each of $R^A$ and $R^B$ is independently selected from benzene, 1-naphthalene, 2-naphthalene and p-toluene.

In some embodiments, each of $R^A$ and $R^B$ is independently selected from Me, Et, benzene and p-toluene.

In some embodiments, $R^A$ and $R^B$ are the same.

In some embodiments, $R^A$ and $R^B$ are different.

In some embodiments, $R^A$ and $R^B$ are the same and are independently Me. The compound may then be referred to as a diaminophenothiazine bis(methanesulfonate) salt which is of general formula (Ia):

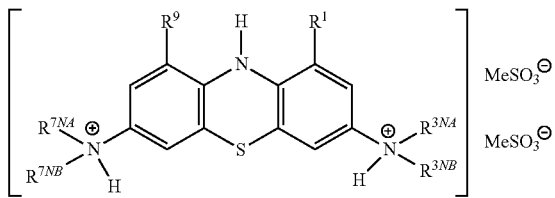

(Ia)

In some embodiments, $R^A$ and $R^B$ are linked to form a group $R^{AB}$.

In these embodiments, the compounds of the invention may alternately be represented by general formula Ib:

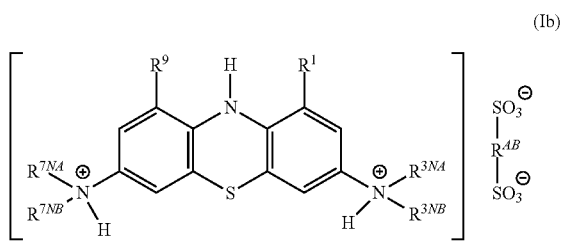

(Ib)

wherein $R^{AB}$ is selected from $C_{1-6}$ alkylene and $C_{6-10}$ arylene.

In some embodiments, $R^{AB}$ is a $C_{1-6}$ alkylene group.

In some embodiments, $R^{AB}$ is a $C_{1-6}$ alkylene group selected from —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$—.

In some embodiments, $R^{AB}$ is a $C_{1-6}$ alkylene group selected from methylene (—CH$_2$—), ethylene (—CH$_2$CH$_2$—) and propylene (—CH$_2$CH$_2$CH$_2$—).

In some embodiments, $R^{AB}$ is ethylene.

In some embodiments, $R^{AB}$ is a $C_{6-10}$ arylene group.

In some embodiments, $R^{AB}$ is a $C_{6-10}$ arylene group selected from phenylene and naphthylene.

In some embodiments, $R^{AB}$ is phenylene.

In some embodiments, $R^{AB}$ is selected from 1,2-phenylene, 1,3-phenylene, and 1,4-phenylene.

In some embodiments, $R^{AB}$ is phenylene optionally substituted with one or more substituents, for example selected from $C_{1-4}$ alkyl, halogenated $C_{1-4}$alkyl, and halo.

In some embodiments, $R^{AB}$ is naphthylene.

In some embodiments, $R^{AB}$ is selected from 1,2-naphthylene, 1,3-naphthylene, 1,4-naphthylene, 1,5-naphthylene, 1,6-naphthylene, 1,7-naphthylene and 1,8-naphthylene.

In some embodiments, $R^{AB}$ is selected from: 1,5-naphthylene i.e.

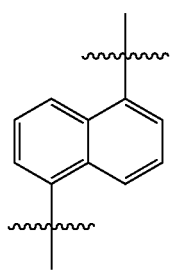 [SMILES: *c1cccc2c(*)cccc12]

and 1,8-naphthylene. i.e.

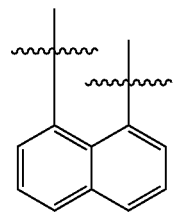 [SMILES: *c1cccc2cccc(*)c12]

In some embodiments, $R^{AB}$ is naphthylene optionally substituted with one or more substituents, for example selected from $C_{1-4}$ alkyl, halogenated $C_{1-4}$alkyl, and halo.

Groups $R^1$ and $R^9$

In some embodiments, each of $R^1$ and $R^9$ is independently —H, -Me, -Et, or —CF$_3$.

In some embodiments, each of $R^1$ and $R^9$ is independently —H, -Me, or -Et.

In some embodiments, $R^1$ and $R^9$ are the same.

In some embodiments, $R^1$ and $R^9$ are different.

In some embodiments, each of $R^1$ and $R^9$ is independently —H.

In some embodiments, each of $R^1$ and $R^9$ is independently -Me.

In some embodiments, each of $R^1$ and $R^9$ is independently -Et.

Groups $R^{3NA}$ and $R^{3NB}$

Each of $R^{3NA}$ and $R^{3NB}$ is independently selected from: —H, $C_{1-4}$alkyl, $C_{2-4}$alkenyl, and halogenated $C_{1-4}$alkyl.

In some embodiments, each of $R^{3NA}$ and $R^{3NB}$ is independently selected from: $C_{1-4}$alkyl, $C_{2-4}$alkenyl, and halogenated $C_{1-4}$alkyl.

In some embodiments, each of $R^{3NA}$ and $R^{3NB}$ is independently -Me, -Et, -nPr, -nBu, —CH$_2$—CH═CH$_2$, or —CF$_3$.

In some embodiments, each of $R^{3NA}$ and $R^{3NB}$ is independently -Me, -nPr, -nBu, —CH$_2$—CH═CH$_2$, or —CF$_3$.

In some embodiments, each of $R^{3NA}$ and $R^{3NB}$ is independently -Me or -Et.

In some embodiments, $R^{3NA}$ and $R^{3NB}$ are the same.

In some embodiments, $R^{3NA}$ and $R^{3NB}$ are different.

In some embodiments, each of $R^{3NA}$ and $R^{3NB}$ is independently -Me.

Groups $R^{7NA}$ and $R^{7NB}$

Each of $R^{7NA}$ and $R^{7NB}$ is independently selected from: —H, $C_{1-4}$alkyl, $C_{2-4}$alkenyl, and halogenated $C_{1-4}$alkyl.

In some embodiments, each of $R^{7NA}$ and $R^{7NB}$ is independently selected from: $C_{1-4}$alkyl, $C_{2-4}$alkenyl, and halogenated $C_{1-4}$alkyl.

In some embodiments, each of $R^{7NA}$ and $R^{7NB}$ is independently -Me, -Et, -nPr, -nBu, —CH$_2$—CH═CH$_2$, or —CF$_3$.

In some embodiments, each of $R^{7NA}$ and $R^{7NB}$ is independently -Me, -nPr, -nBu, —CH$_2$—CH═CH$_2$, or —CF$_3$.

In some embodiments, each of $R^{7NA}$ and $R^{7NB}$ is independently -Me or -Et.

In some embodiments, $R^{7NA}$ and $R^{7NB}$ are the same.

In some embodiments, $R^{7NA}$ and $R^{7NB}$ are different.

In some embodiments, each of $R^{7NA}$ and $R^{7NB}$ is independently -Me.

Groups $R^{3NA}$, $R^{3NB}$, $R^{7NA}$ and $R^{7NB}$

In some embodiments:
each of $R^{3NA}$ and $R^{3NB}$ is independently $C_{1-4}$alkyl, $C_{2-4}$alkenyl, or halogenated $C_{1-4}$alkyl;

each of $R^{7NA}$ and $R^{7NB}$ is independently $C_{1-4}$alkyl, $C_{2-4}$alkenyl, or halogenated $C_{1-4}$alkyl.

In some embodiments:
each of $R^{3NA}$ and $R^{3NB}$ is independently -Me, -Et, -nPr, -nBu, —$CH_2$—CH=$CH_2$, or —$CF_3$;
each of $R^{7NA}$ and $R^{7NB}$ is independently -Me, -Et, -nPr, -nBu, —$CH_2$—CH=$CH_2$, or —$CF_3$.

In some embodiments:
each of $R^{3NA}$ and $R^{3NB}$ is independently -Me or -Et;
each of $R^{7NA}$ and $R^{7NB}$ is independently -Me or -Et.

In some embodiments, $R^{3NA}$ and $R^{3NB}$ and $R^{7NA}$ and $R^{7NB}$ are all the same.

In some embodiments, $R^{3NA}$ and $R^{3NB}$ and $R^{7NA}$ and $R^{7NB}$ are the same and are all -Me or all -Et.

In some embodiments, $R^{3NA}$ and $R^{3NB}$ and $R^{7NA}$ and $R^{7NB}$ are the same and are all -Me.

Salts and Solvates

Although the compounds described herein are themselves salts, they may also be provided in the form of a mixed salt (i.e., the compound of the invention in combination with another salt). Such mixed salts are intended to be encompassed by the term "and pharmaceutically acceptable salts thereof". Unless otherwise specified, a reference to a particular compound also includes salts thereof.

The compounds of the invention may also be provided in the form of a solvate or hydrate. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc. Unless otherwise specified, any reference to a compound also includes solvate and hydrate forms thereof.

Naturally, solvates or hydrates of salts of the compounds are also encompassed by the present invention.

Isotopic Variation

In some embodiments, one or more carbon atoms of the compound is $^{11}C$, $^{13}C$ or $^{14}C$.

In some embodiments, one or more carbon atoms of the compound is $^{11}C$.

In some embodiments, one or more carbon atoms of the compound is $^{13}C$.

In some embodiments, one or more carbon atoms of the compound is $^{14}C$.

In some embodiments, one or more nitrogen atoms of the compound is $^{15}N$.

In some embodiments, one or more or all of the carbon atoms of one or more or all of the groups $R^{3NA}$, $R^{3NB}$, $R^{7NA}$, $R^{7NB}$, $R^1$, $R^9$, $R^A$ and $R^B$ is $^{11}C$, $^{13}C$, or $^{14}C$.

In some embodiments, one or more or all of the carbon atoms of one or more or all of the groups $R^{3NA}$, $R^{3NB}$, $R^{7NA}$ and $R^{7NB}$ is $^{11}C$, $^{13}C$, or $^{14}C$.

Combinations

All compatible combinations of the embodiments described above are explicitly disclosed herein as if each combination was specifically and individually recited.

In particular, in the compounds of the invention, the groups $R^{3NA}$, $R^{3NB}$, $R^{7NA}$, $R^{7NB}$, $R^1$, $R^9$, $R^A$ and $R^B$ (and $R^{AB}$) are defined as independent variables and it will be recognised by those skilled in the art that any compatible combination of these groups and substituents may be utilised in the compounds and methods of the present invention.

All compatible combinations of these and other defined variables are therefore specifically embraced by the present invention, and are disclosed herein as if each and every combination were individually and explicitly recited.

Some Preferred Embodiments

In some embodiments, the compound of the invention may be selected from the following compounds and pharmaceutically acceptable salts, solvates, and hydrates thereof:

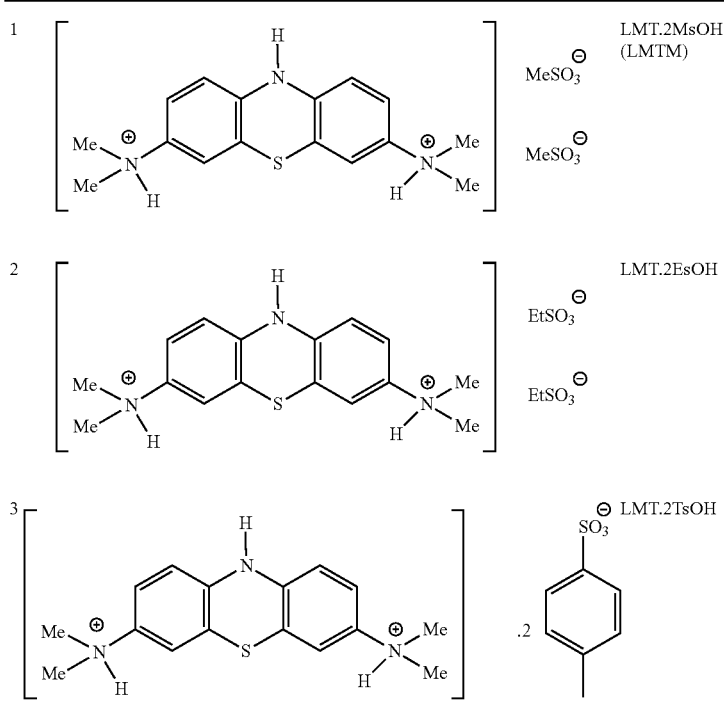

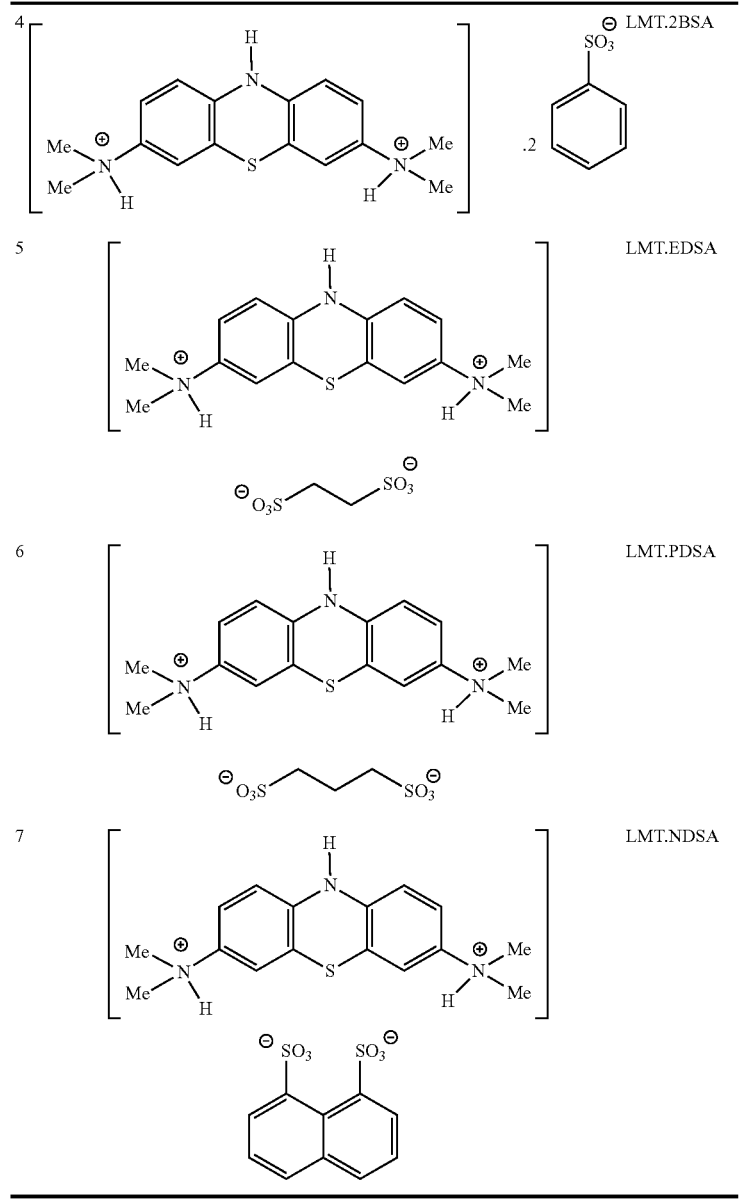

One particular compound of the invention is compound 1:

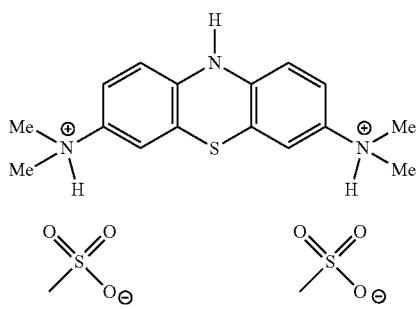

N,N,N',N'-tetramethyl-10H-phenothiazine-3,7-di-aminium bis(methanesulfonate)

This compound may also be referred to as:
N,N,N',N'-tetramethyl-10H-phenothiazine-3,7-diamine bis(hydromethanesulfonate)
Leuco methylthioninium bis(hydromethanesulfonate)
Leuco methylthioninium bis(mesylate)
LMTM
LMT.2MsOH Purity The compounds of the present invention may conveniently be described as being in a "stabilized reduced form". The compounds oxidize (e.g., autoxidize) to give the corresponding oxidized forms. Thus, it is likely, if not inevitable, that compositions comprising the compounds of the present invention will contain, as an impurity, at least some of the corresponding oxidized compound.

Thus, another aspect of the present invention pertains to compounds as described herein, in substantially purified form and/or in a form substantially free from contaminants (e.g., the corresponding oxidized compound, other contaminants).

In some embodiments, the substantially purified form is at least 50% by weight pure, e.g., at least 60% by weight pure, e.g., at least 70% by weight pure, e.g., at least 80% by weight pure, e.g., at least 90% by weight pure, e.g., at least 95% by weight pure, e.g., at least 97% by weight pure, e.g., at least 98% by weight pure, e.g., at least 99% by weight pure.

In some embodiments, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Product-by-Process

In some embodiments, the compound is one which is obtained by, or is obtainable by, a method as described herein.

Chemical Synthesis

Methods for the chemical synthesis of the compounds of the present invention are described herein. These and/or other well known methods may be modified and/or adapted in known ways in order to facilitate the synthesis of additional compounds within the scope of the present invention.

Compounds of Formula (I):

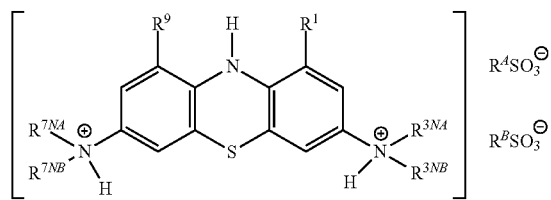

may be prepared from compounds of formula (II):

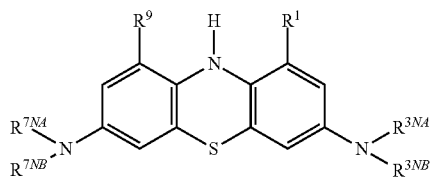

wherein $R^4$, $R^9$, $R^{3NA}$, $R^{3NB}$, $R^{7NA}$, and $R^{7NB}$ are as defined previously.

Compounds of formula (II) may, for example, be prepared from compounds of formula (III):

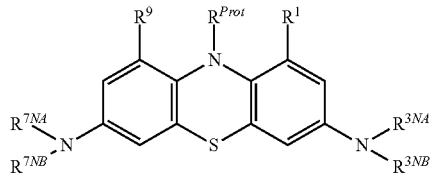

wherein $R^{Prot}$ is an amine protecting group and $R^1$, $R^9$, $R^{3NA}$, $R^{3NB}$, $R^{7NA}$, $R^{7NB}$, $R^A$ and $R^B$ are as defined previously.

By way of non-limiting example, $R^{Prot}$ may be an acyl group, for example an acetyl (—C(=O)Me) or a benzoyl (—C(=O)Ph) group.

The compounds of formula (II) may be prepared e.g. by deprotection of the compounds of formula (III), or by other known methods. Conversely, compounds of formula (II) may be produced by protection of compounds of formula (III).

Compounds of formulae (II) and (III) are known, and may be prepared from known and/or commercially available starting materials, e.g. from corresponding phenothiazine compounds, using known methods.

For example, intermediates of formula (II) and (III) were used in the methods for the synthesis of 3,7-diamino-10H-phenothiazine hydrochloride, hydrobromide, and hydroiodide salts disclosed in WO2007/110627.

As disclosed in that document, a suitable phenothiazine can be converted to the corresponding 3,7-dinitro-phenothiazine, for example using sodium nitrite with acetic acid and chloroform.

The ring amino group may then be protected, for example as the acetate, for example using acetic anhydride and pyridine.

The nitro groups may then be reduced to amino groups, for example using tin (II) chloride with ethanol.

The amino groups may then be substituted, for example disubstituted, for example methyl disubstituted, for example using methyl iodide, sodium hydroxide, DMSO, and tetra-n-butyl ammonium bromide, to provide a N-acetyl protected 3,7-dialkylamino-10H-phenothiazine.

Examples of such a method are illustrated in Schemes 1a and 1b. The use of any one or more of the reagents described herein in the process is of course encompassed by the present invention:

Scheme 1a

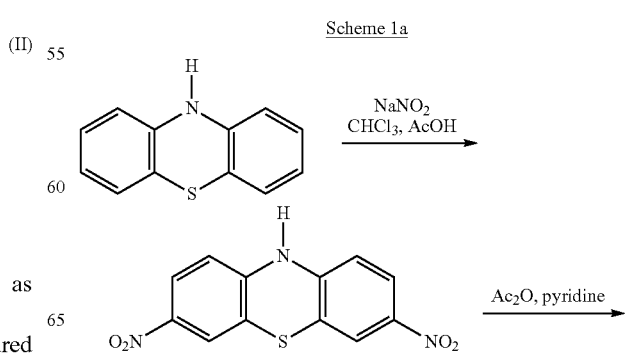

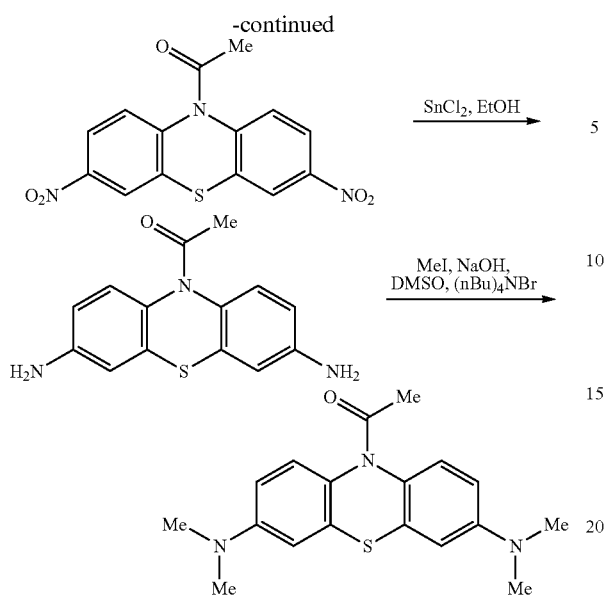

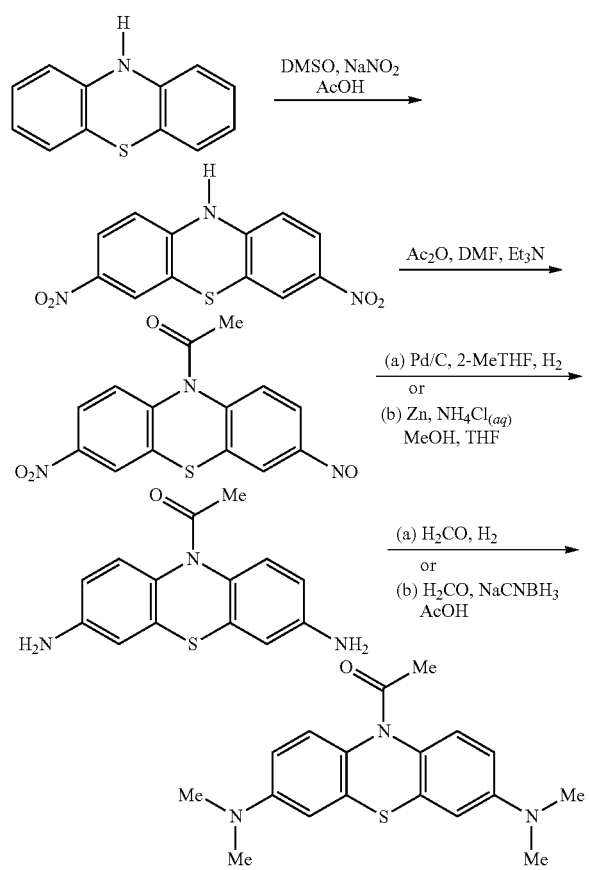

The amino group of this N-acetyl intermediate can then be deprotected, i.e. the N-acetyl group may be removed, for example using aqueous acid.

Compounds of formulae (II) and (Ill) may also be made using the methods disclosed in WO2008/007074. This document discloses compounds of formula (III) and compounds of formula (II) wherein $R^{Prot}$ is an acyl group, for example an acetyl group.

In one approach, an appropriate thioninium chloride (e.g., methyl thioninium chloride, ethyl thioninium chloride, etc) may first be reduced and acetylated to give the corresponding 1-(3,7-bis-dimethylamino-phenothiazin-10-yl)-ethanone, for example, by reaction with hydrazine ($NH_2NH_2$), methyl hydrazine ($MeNHNH_2$), or sodium borohydride ($NaBH_4$); and acetic anhydride (($H_3CCO)_2O$); for example, in the presence of a suitable base, for example, pyridine ($C_5H5N$) or Hünig's base (diisopropylethylamine, $C_8H_{19}N$), for example, in a suitable solvent, for example, ethanol or acetonitrile. The reduced and acetylated compound (of formula (III)) may then be deprotected (by removing the acetyl group), for example by reaction with a suitable acid, to give a compound of formula (II) or may be used directly. Advantageously, this reaction may produce a product with a high degree of purity.

An example is shown in the following scheme.

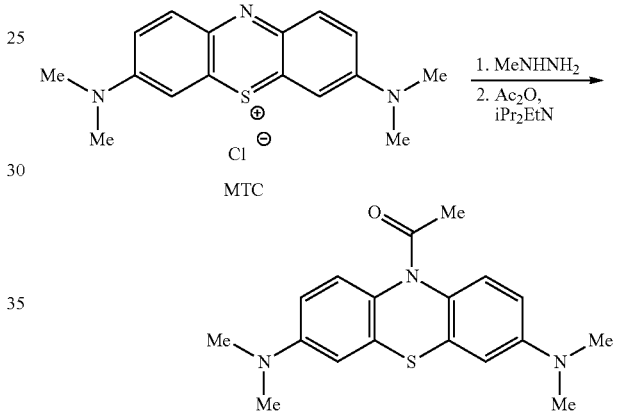

In another approach, an appropriate thioninium salt, for example, ethyl thioninium semi zinc chloride, may be simultaneously reduced and the ring amino group protected, for example, by reaction with a reducing agent phenylhydrazine, ethanol, acetic anhydride, and pyridine.

An example is shown in the following scheme:

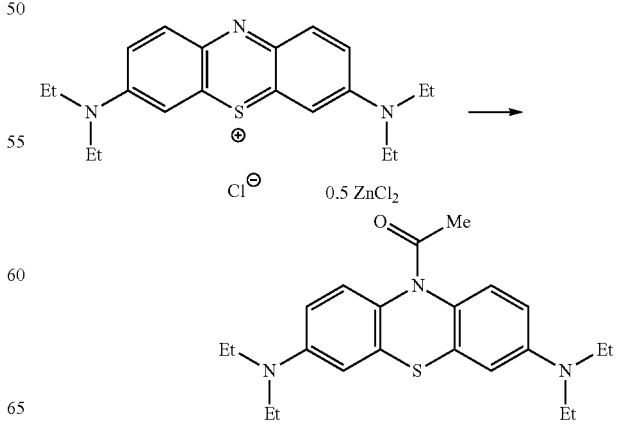

In one aspect, the present invention therefore provides a method of preparing a 3,7-diamino-10H-phenothiazine compound of formula (I):

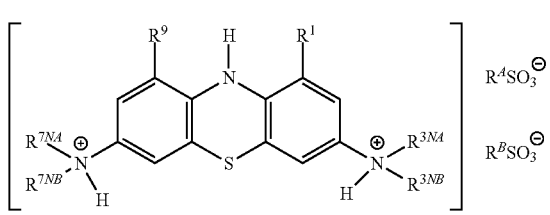
(I)

from a compound of formula (II):

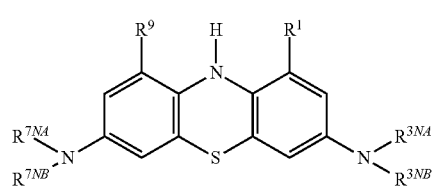
(II)

wherein $R^A$, $R^B$, $R^4$, $R^9$, $R^{3NA}$, $R^{3NB}$, $R^{7NA}$, and $R^{7NB}$ are as previously defined.

In some embodiments, the method comprises the step of: salt formation (SF).

In some embodiments, salt formation (SF) comprises treatment of a compound of formula (II) with an appropriate sulfonic acid.

In some embodiments, salt formation comprises treatment of a solution of a compound of formula (II) with an appropriate sulfonic acid, in an organic solvent.

In a further aspect, the present invention provides a method of preparing a 3,7-diamino-10H-phenothiazine compound of formula (I):

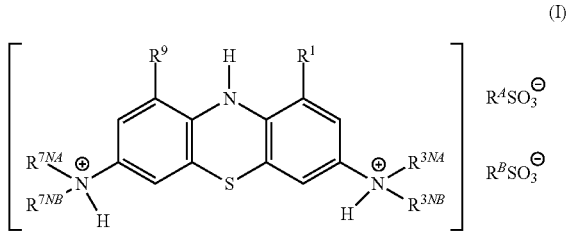
(I)

from a compound of formula (III):

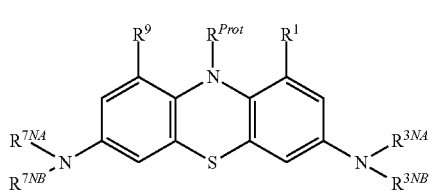
(III)

wherein $R^A$, $R^B$, $R^1$, $R^9$, $R^{3NA}$, $R^{3NB}$, $R^{7NA}$, and $R^{7NB}$ are as previously defined and wherein $R^{Prot}$ is an amine protecting group.

A wide variety of amine protecting groups are widely used and well known in organic synthesis. See, for example, Protective Groups in Organic Synthesis (T. Green and P. Wuts; 4th Edition; John Wiley and Sons, 2006).

In some embodiments, the amine protecting group is an acid-cleavable protecting group.

In some embodiments, the amine protecting group is an acyl group, such as an acetyl group.

In some embodiments, the method comprises the steps of:
ring amino deprotection (DP); and
salt formation (SF).

Ring amino deprotection (DP) comprises removal of the protecting group to convert the N-protected ring amine group (—$NR^{Prot}$—) to a free ring amine group (—NH—). Deprotection of a compound of formula (III) produces the corresponding compound of formula (II).

Methods for the removal of amine protecting groups are known in the art. See, for example, Protective Groups in Organic Synthesis (T. Green and P. Wuts; 4th Edition; John Wiley and Sons, 2006).

In some embodiments, the step of ring amino deprotection (DP) and the step of salt formation (SF) are performed simultaneously (i.e., as one step). For example:

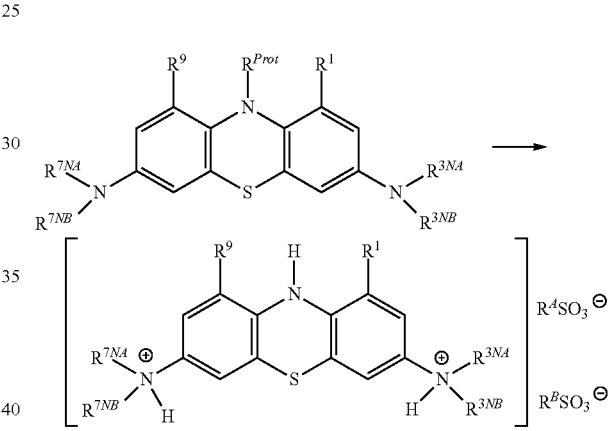

In some embodiments, simultaneous ring amino deprotection (DP) and salt formation (SF) comprises treatment of the compound of formula (III) with an appropriate sulfonic acid, to produce a bis(sulfonate) salt of formula (I).

In some embodiments, simultaneous ring amine deprotection and salt formation may comprise treatment of a solution of a compound of formula (III) in an organic solvent with the sulfonic acid and water.

In some embodiments, the organic solvent is toluene.

In the methods of the invention, the sulfonic acid may be selected from alkylsulfonic acids and arylsulfonic acids. It may be a sulfonic acid of formula $R^A SO_3 H$ or $R^B SO_3 H$, wherein $R^A$ and $R^B$ are as defined herein.

In some embodiments, the sulfonic acid may be a disulfonic acid. i.e. a compound containing two sulfonic acid moieties per molecule. These sulfonic acid moieties may be linked by e.g. an alkylene or arylene group.

In some embodiments the sulfonic acid may be selected from: methanesulfonic acid (MsOH), ethanesulfonic acid (EsOH), benzenesulfonic acid (BSA), naphthalenesulfonic acid (NSA), p-toluenesulfonic acid (TsOH), ethanedisulfonic acid (EDSA), propanedisulfonic acid (PDSA) and naphthalene-1,5-disulfonic acid (NDSA).

In some embodiments, the phenothiazine starting material (i.e. the compound of formula (III) is first heated in said organic solvent until completely dissolved and the resultant solution is filtered before addition of the reagents (i.e. the sulfonic acid and water).

In some embodiments, the compound is heated in said organic solvent at a temperature of about 60-80° C., for example at a temperature of about 70° C.

In some embodiments, the sulfonic acid is added in an amount of at least 2 molar equivalents, for example about 2.2 molar equivalents, relative to the phenothiazine starting material. If a disulfonic acid is used, it will be understood the molar amount of the acid will be at least 1 molar equivalent, for example about 1.1 molar equivalents, so as to achieve the same number of sulfonic acid moieties per molecule of phenothiazine starting material.

It may be desirable to add the sulfonic acid slowly to prevent a temperature increase (exotherm). Therefore, in some embodiments, the sulfonic acid is added gradually.

In some embodiments, the sulfonic acid is added at a temperature of about 15-25° C.

In some embodiments, after addition of the sulfonic acid and water, the reaction is heated to a temperature of about 80-90° C.

In some embodiments, the reaction is maintained at this temperature until judged complete by e.g. chromatographic analysis.

In some embodiments, after reaction, the solution is treated with a counter solvent to precipitate the product. In some embodiments, the counter solvent is an alcohol, for example ethanol.

It may be desirable to 'seed' the reaction mixture with a small amount, for example, about 1 mg per gram of starting material (compound of formula (II), of the desired bis (sulfonate) product. Without wishing to be bound by theory, it is thought that addition of the seed ensures early and efficient precipitation of the desired product, reducing the opportunity for possible side-reactions and by-product formation. The seed is also thought to be of use in controlling the particle size of the precipitated product.

Hence in some embodiments, after reaction, the resultant mixture is seeded with a small amount of the desired bis(sulfonate) salt.

In some embodiments, the seed comprises particles of the desired bis(sulfonate) salt which have been ground.

In some embodiments, the seed comprises particles of the desired bis(sulfonate) salt which have been ground to a size of less than about 100 μm.

In some embodiments, the precipitated product is isolated by filtration.

In some embodiments, after filtration, the product is washed with an organic solvent, for example ethanol or acetonitrile.

Salt formation (SF) produces the bis(sulfonate) salt of formula (I) from the compound of formula (II):

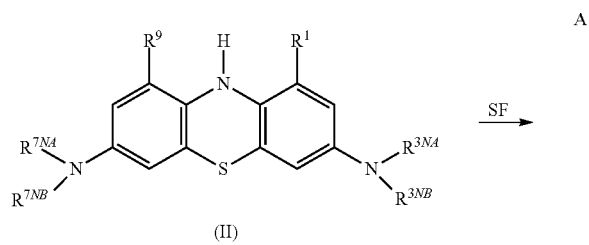

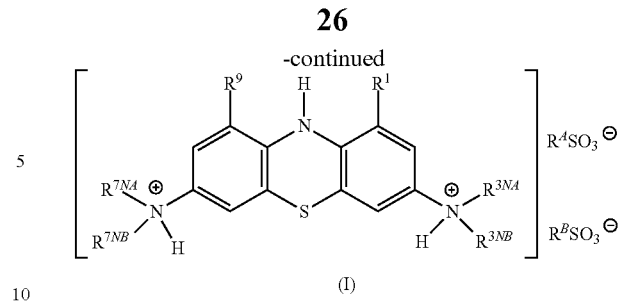

s explained above, the bis(sulfonate) salt may also be prepared directly from a corresponding amino-protected (e.g. N-acetyl) compound of formula (III).

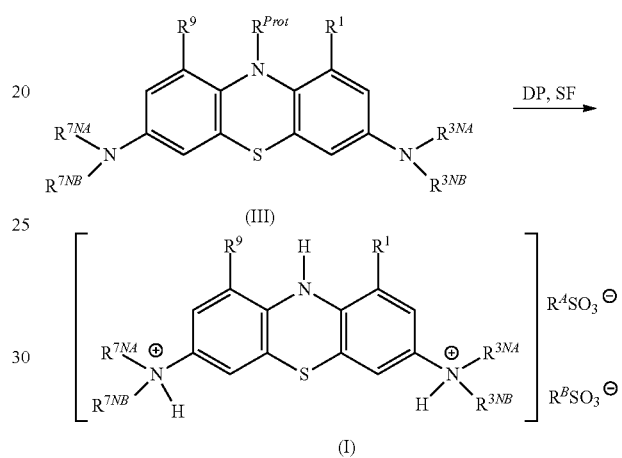

In this case, salt formation may be performed at the same time as deprotection, for example by using the appropriate sulfonic acid, e.g. methanesulfonic acid, for the deprotection step. An example is illustrated in the following scheme:

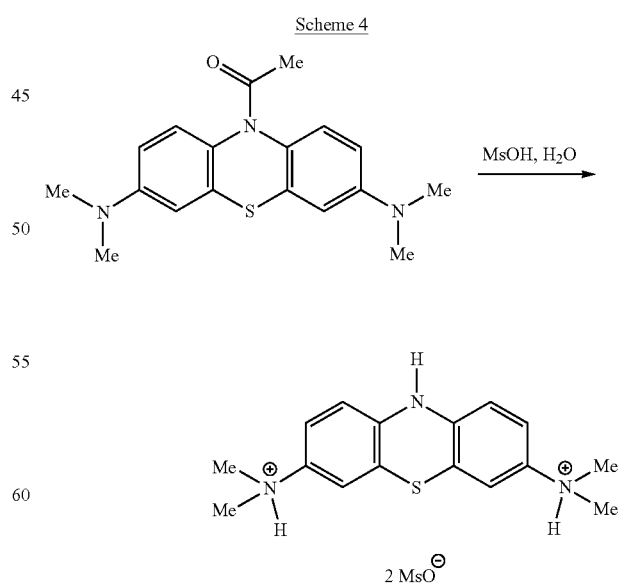

In a further aspect, the present invention provides a method of preparing a compound of formula (I):

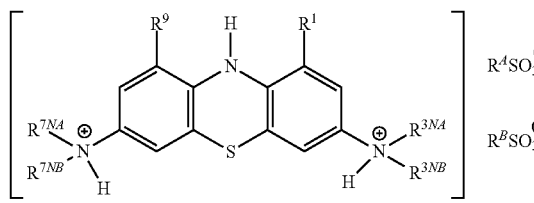

(I)

wherein $R^A$, $R^B$, $R^1$, $R^9$, $R^{3NA}$, $R^{3NB}$, $R^{7NA}$, and $R^{7NB}$ are as previously defined the method comprising:
preparing a compound of formula (II) or (III) as defined herein,
followed by
salt formation (SF) and/or
ring amine deprotection (DP).

The steps of salt formation (SF) and ring amine deprotection (DP) are as described above.

In some embodiments, preparing said compound of formula (II) or (III) comprises a method as disclosed in WO2007/110627.

In some embodiments, preparing said compound of formula (II) or (III) comprises a method as disclosed in WO2008/007074.

In some embodiments, preparing a compound of formula (II) comprises ring amine deprotection (DP) of a compound of formula (III), as set out above.

In some embodiments, preparing a compound of formula (III) comprises one or more steps selected from:
nitration (NO),
ring amino protection (AP),
nitro reduction (NR),
amine substitution (AS).

In some embodiments, preparing a compound of formula (III) comprises the steps of
reduction (RED), and
ring amino protection (AP).

The steps may be performed in any logical order. In some embodiments, the steps are performed in the order listed (i.e., any step in the list is performed at the same time as, or subsequent to, the preceding step in the list).

In some embodiments, nitration (NO) comprises:
nitration (NO), wherein a 10H-phenothiazine is converted to a 3,7-dinitro-10H-phenothiazine, for example:

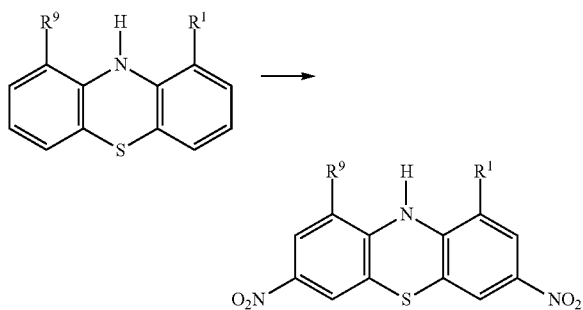

In some embodiments, nitration is performed using a nitrite, for example, sodium nitrite, for example, sodium nitrite with acetic acid, and a solvent such as dimethyl sulfoxide, dimethyl formamide, acetonitrile, tetrahydrofuran, dimethoxyethane, acetone, dichloromethane or chloroform.

In some embodiments, ring amino protection (AP) comprises:
ring amino protection (AP), wherein the ring amino group (—NH—) of a 3,7-dinitro-10H-phenothiazine is converted to a protected ring amino group (—NR$^{prot}$), for example:

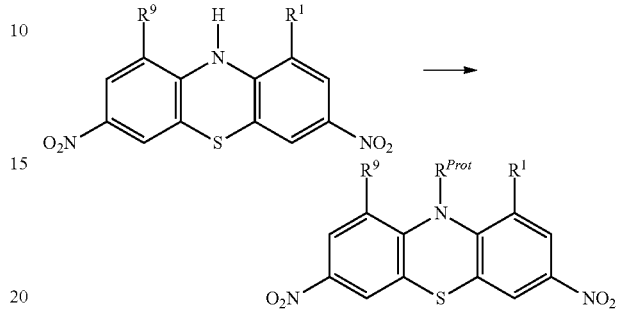

In some embodiments, ring amino protection is achieved as an acetate, for example, using acetic anhydride, for example, using acetic anhydride and a base such as an amine base, for example triethylamine or pyridine.

In some embodiments, nitro reduction (NR) step comprises:
nitro reduction (NR), wherein each of the nitro (—NO$_2$) groups of a protected 3,7-dinitro-10H-phenothiazine is converted to an amino (—NH$_2$) group, for example:

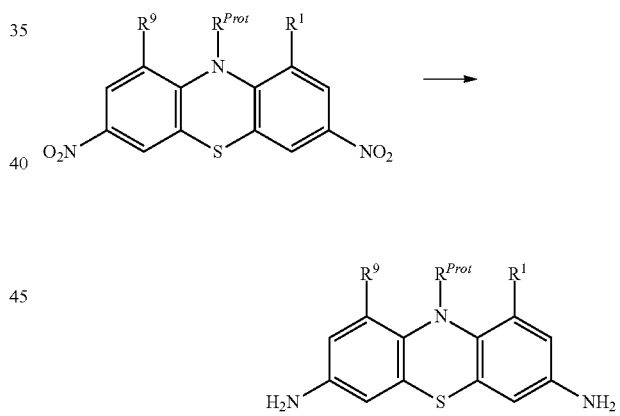

In some embodiments, nitro reduction may be performed using, for example, tin (II) chloride, for example, tin (II) chloride with ethanol.

In some embodiments, nitro reduction may be performed using, for example, palladium on charcoal (Pd/C) and hydrogen in, for example, 2-methyl-tetrahydrofuran.

In some embodiments, nitro reduction may be performed using, for example, zinc and aqueous ammonium chloride in methanol and THE In some embodiments, amine substitution (AS) step comprises:
amine substitution (AS), wherein each of the amino (—NH$_2$) groups of a protected 3,7-diamino-10H-phenothiazine is converted to disubstituted amino group, for example:

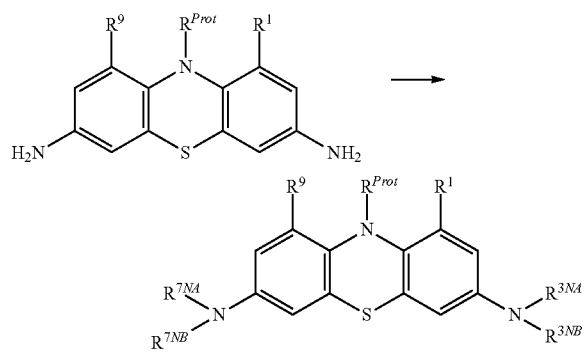

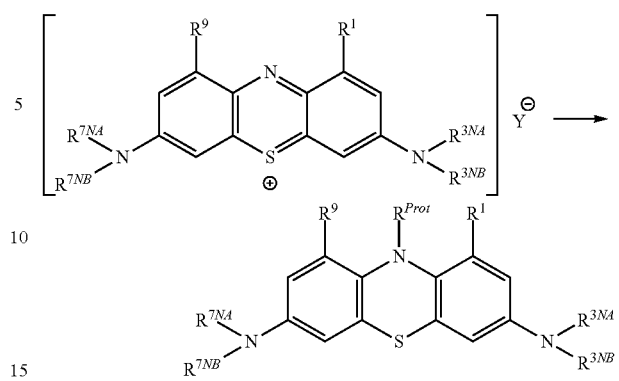

In some embodiments, amine substitution is performed using an alkyl halide, for example, an alkyl iodide, for example, methyl iodide, for example, methyl iodide with sodium hydroxide, DMSO, toluene and tetra-n-butyl ammonium bromide.

In some embodiments, amine substitution comprises treatment with formaldehyde (e.g. paraformaldehyde, formalin) under reducing conditions. For example, treatment with formalin and hydrogen gas, in the presence of a Pd/C catalyst; or treatment with paraformaldehyde in the presence of a reducing agent such as sodium cyanoborohydride and acetic acid.

In some embodiments, the reduction (RED) step is:

reduction (RED), wherein a 3,7-di(disubstituted amino)-thioninium salt is reduced to give the corresponding 3,7-di(disubstituted amino)-10H-phenothiazine, for example by treatment with a reducing agent, such as hydrazine ($NH_2NH_2$), methyl hydrazine ($MeNHNH_2$), or sodium borohydride and a base, such as pyridine, triethylamine, or Hünig's base (diisopropylethylamine).

In some embodiments, the ring amino protection (AP) step is:

ring amino protection (AP), wherein a 3,7-di(disubstituted amino)-10H-phenothiazine is protected, for example by treatment with acetic anhydride, to give the corresponding protected 3,7-di(disubstituted amino)-10H-phenothiazine, for example the corresponding N-acetyl 3,7-di(disubstituted amino)-10H-phenothiazine.

In some embodiments, the steps are performed in the order listed (i.e., any step in the list is performed at the same time as, or subsequent to, the preceding step in the list).

In some embodiments, the step of reduction (RED) and the step of ring amino protection (AP) are performed simultaneously (i.e., as one step).

For example, in some embodiments, the combined reduction (RED) step and ring amino protection (AP) step is:

reduction (RED) and ring amino protection (AP), wherein a 3,7-di(disubstituted amino)-thioninium salt is reduced to give the corresponding 3,7-di(disubstituted amino)-10H-phenothiazine, and the ring amino group (—NH—) of the 3,7-di(disubstituted amino)-10H-phenothiazine is converted to a protected ring amino group (—$R^{Prot}$) to give the corresponding protected 3,7-di(disubstituted amino)-10H-phenothiazine, for example:

wherein Y is a counterion. In some embodiments, Y represents $Cl^-$.

In some embodiments, the 3,7-di(disubstituted amino)-thioninium salt is methylthioninium chloride (MTC).

In some embodiments, the combined reduction (RED) step and ring amino protection (AP) step is achieved using a hydrazine, such as phenylhydrazine, $MeNHNH_2$, or $NH_2NH_2 \cdot H_2O$ and acetic anhydride.

In some embodiments, the step is performed under a nitrogen atmosphere.

In some embodiments the combined reduction (RED) step and ring amino protection (AP) step is performed using, for example, phenylhydrazine, ethanol, acetic anhydride, and pyridine.

In some embodiments, the combined reduction (RED) step and ring amino protection (AP) step is performed using, for example, hydrazine hydrate, acetonitrile, acetic anhydride, and triethylamine, under a nitrogen atmosphere.

In some embodiments, the protected 3,7-di(disubstituted amino)-10H-phenothiazine, for example the N-acetyl 3,7-di(disubstituted amino)-10H-phenothiazine, undergoes a purification step.

In some embodiments, purification comprises addition of an organic solvent, for example toluene, and an acid, for example acetic acid, to dissolve the compound, followed by a washing step.

In some embodiments, washing comprises addition of water and/or aqueous acetic acid to the solution of the compound; agitation and/or heating; and separation of the organic layer.

In some embodiments, washing is repeated, for example up to three times.

In some embodiments, washing is followed by isolation of the purified product.

In some embodiments, isolation of the purified product comprises cooling, precipitation and filtration of the product.

Crystalline Forms

In some embodiments, the compound of the invention is provided in crystalline form.

In some embodiments, the crystalline form is 'Form A' as described herein.

In some embodiments, the crystalline form has the structure depicted in FIG. 17 and\or is characterised by the crystal data shown in an Annex Table 1 and\or the atomic co-ordinates shown in an Annex Table 2 and\or the bond lengths and angles shown in an Annex Table 3 and\or the anisotropic displacement parameters shown in an Annex Table 4 and\or the hydrogen coordinates and isotropic displacement parameters shown in an Annex Table 5.

Reversing and/or Inhibiting the Aggregation of a Protein

One aspect of the invention is the use of a compound or composition as described herein, to regulate (e.g., to reverse and/or inhibit) the aggregation of a protein, for example, aggregation of a protein associated with a neurodegenerative disease and/or clinical dementia. The aggregation may be in vitro, or in vivo, and may be associated with a disease state as discussed below.

Thus, one aspect of the invention pertains to a method of regulating (e.g., reversing and/or inhibiting) the aggregation of a protein, for example, aggregation of a protein associated with a neurodegenerative disease and/or clinical dementia, comprising contacting the protein with an effective amount of a compound or composition as described herein. The method may be performed in vitro, or in vivo.

Similarly, one aspect of the invention pertains to a method of regulating (e.g., reversing and/or inhibiting) the aggregation of a protein in the brain of a mammal, which aggregation is associated with a disease state as described herein, the treatment comprising the step of administering to said mammal in need of said treatment, a prophylactically or therapeutically effective amount of a compound or composition as described herein, that is an inhibitor of said aggregation.

Methods of Treatment

Another aspect of the present invention pertains to a method of treatment comprising administering to a patient in need of treatment a prophylactically or therapeutically effective amount of a compound as described herein, preferably in the form of a pharmaceutical composition.

Use in Methods of Therapy

Another aspect of the present invention pertains to a compound or composition as described herein, for use in a method of treatment (e.g., of a disease condition) of the human or animal body by therapy.

Use in the Manufacture of Medicaments

Another aspect of the present invention pertains to use of a compound or composition as described herein, in the manufacture of a medicament for use in treatment (e.g., of a disease condition).

In some embodiments, the medicament comprises a compound of the invention.

In some embodiments, the medicament is a composition as described hereinbelow.

Disease Conditions Treated—Diseases of Protein Aggregation

The compounds and compositions of the present invention are useful in the treatment or prophylaxis of diseases of protein aggregation.

Thus, in some embodiments, the disease condition is a disease of protein aggregation, and, for example, the treatment is with an amount of a compound or composition as described herein, sufficient to inhibit the aggregation of the protein associated with said disease condition.

In general, the protein aggregation is that which arises from an induced conformational polymerisation interaction, i.e., one in which a conformational change of the protein, or in a fragment thereof, gives rise to templated binding and aggregation of further (precursor) protein molecules in a self-propagating manner. Once nucleation is initiated, an aggregation cascade may ensue which involves the induced conformational polymerisation of further protein molecules, leading to the formation of toxic product fragments in aggregates which are substantially resistant to further proteolysis. The protein aggregates thus formed are thought to be a proximal cause of disease states manifested as neurodegeneration, clinical dementia, and other pathological symptoms.

The following Table lists various disease-associated aggregating proteins and the corresponding diseases of protein aggregation. The use of the compounds and compositions of the invention in respect of these proteins or diseases is encompassed by the present invention.

| Diseases of protein aggregation | | | | |
|---|---|---|---|---|
| Protein | Disease | Aggregating domain and/or mutations | Fibril subunit size (kDa) | Reference |
| Neurodegenerative disorders | | | | |
| Prion protein | Prion diseases | Inherited and sporadic forms | 27 | Prusiner (1998) |
| | (CJD, nvCJD, Fatal familial insomnia, Gerstmann-Straussler-Scheinker syndrome, Kuru) | PrP-27-30; many mutations. | 27 | Prusiner (1998) |
| | | Fibrillogenic domains: 113-120, 178-191, 202-218. | | Gasset et al. (1992) |
| Tau protein | Alzheimer's disease, Down's syndrome, FTDP-17, CBD, post-encephalitic parkinsonism, Pick's disease, parkinsonism with dementia complex of Guam | Inherited and sporadic forms | 10-12 | Wischik et al. (1988) |
| | | Truncated tau (tubulin-binding domain) 297-391. | 10-12 | Wischik et al. (1988) |
| | | Mutations in tau in FTDP-17. | | Hutton et al. (1998) |
| | | Many mutations in presenilin proteins. | | Czech et al. (2000) |

| | | Diseases of protein aggregation | | |
|---|---|---|---|---|
| Protein | Disease | Aggregating domain and/or mutations | Fibril subunit size (kDa) | Reference |
| Amyloid β-protein | Alzheimer's disease, Down's syndrome | Inherited and sporadic forms | 4 | Glenner & Wong, (1984) |
| | | Amyloid β-protein; 1-42(3). Mutations in APP in rare families. | 4 | Glenner & Wong, (1984) Goate et al. (1991) |
| Huntingtin | Huntington's disease | N-termini of protein with expanded glutamine repeats. | 40 | DiFiglia et al. (1997) |
| Ataxins (1, 2, 3, 7) | Spinocerebellar ataxias (SCA1, 2, 3, 7) | Proteins with expanded glutamine repeats. | | Paulson et al. (1999) |
| Atrophin | Dentatorubropallidoluysian atrophy (DRPLA) | Proteins with expanded glutamine repeats. | | Paulson et al. (1999) |
| Androgen receptor | Spinal and bulbar muscular atrophy | Proteins with expanded glutamine repeats. | | Paulson et al. (1999) |
| Neuroserpin | Familial encephalopathy with neuronal inclusion bodies (FENIB) | Neuroserpin; S49P, S52R. | 57 | Davis et al. (1999) |
| α-Synuclein | Parkinson's disease, dementia with Lewy bodies, multiple system atrophy | Inherited and sporadic forms | 19 | Spillantini et al. (1998) also PCT/GB2007/001105 |
| | | A53T, A30P in rare autosomal-dominant PD families. | | Polymeropoulos et al. (1997) |
| TDP-43 | FTLD-TDP | Several TDP-43 mutations | 10-43 | Mackenzie et al. (2010) |
| | Amyotrophic lateral sclerosis | Several TDP-43 mutations | 10-43 | Mackenzie et al. (2010) |
| Cystatin C | Hereditary cerebral angiopathy (Icelandic) | Cystatin C less 10 residues; L68Q. | 12-13 | Abrahamson et al. (1992) |
| Superoxide dismutase 1 | Amyotrophic lateral sclerosis | SOD1 mutations. | 16 | Shibata et al. (1996) |
| | | Non-neurodegenerative disorders | | |
| Haemoglobin | Sickle cell anaemia Inclusion body haemolysis | Haemoglobin beta chain (S). Many mutations. | | Carrell & Gooptu (1998) |
| Serpins | α1-Antitrypsin deficiency (emphysema, cirrhosis) | Mutations | | Lomas et al. (1992) |
| | Antithrombin deficiency (thromboembolic disease) | Mutatons | | Carrell & Gooptu (1998) |
| | C1-inhibitor deficiency (angioedema) | Mutations | | Carrell & Gooptu (1998) |
| Immunoglobulin light chain | Plasma cell dyscrasias (primary systemic AL amyloidosis) | Light chain or fragments. | 0.5-25 | Westermark et al. (1985) |
| Serum amyloid A | Reactive, secondary systemic AA amyloidosis Chronic inflammatory disease | 76-residue fragment (critical residues 2-12). | 4.5-7.5 | Westermark et al. (1985) |
| Transthyretin | Familial amyloid polyneuropathy (systemic; FAP I) | Tetramer dissociated to conformational monomer variant. Many mutations (some not associated with amyloid; several different types of disease). | 10-14 | Gustavsson et al. (1991) |

-continued

Diseases of protein aggregation

| Protein | Disease | Aggregating domain and/or mutations | Fibril subunit size (kDa) | Reference |
|---|---|---|---|---|
| | Senile cardiac amyloidosis | Normal transthyretin | 10-14 | Gustavsson et al. (1991) |
| Gelsolin | Familial amyloidosis - Finnish type (FAP IV) | D187Q leads to truncated 173-225/243 (critical residues 182-192). | 9.5 | Maury & Baumann (1990) |
| β2-Microglobulin | Haemodialysis amyloidosis Prostatic amyloid | β2-Microglobulin | 12-25 | Gorevic et al. (1985) |
| Apolipoprotein AI | Familial amyloid polyneuropathy (systemic; FAP III) | N-terminal 83-93 residues; G26R, W50R, L60R | 9 | Booth et al. (1997) |
| Lysozyme | Familial visceral amyloidosis | Lysozyme or fragments (with or without I56T, D67H) | 14 | Pepys et al. (1993) |
| Amylin (Islet amyloid polypeptide) | Type II diabetes (NIDDM) | Fragments (critical core of 20-29); no mutations | 3.9 | Westermark (1990) |
| Fibrinogen α-chain | Hereditary renal amyloidosis | Fibrinogen fragments | 7-10 | Uemichi et al. (1992) |
| Procalcitonin | Medullary carcinoma of thyroid | Calcitonin fragments | 3.4 | Sletten et al. (1976) |
| Atrial natriuretic factor | Cardiac amyloidosis | ANF, no mutants | 3.5 | Johansson et al. (1987) |
| Insulin | Injection localised amyloidosis | Insulin | | Dische et al. (1988) |
| Multiple proteins | Inclusion body myositis | β-amyloid, tau, ubiquitin, ApoE, and presenilin-1 | | Askenas et al (2009) |
| Other proteins forming amyloid | (in vitro) | Other proteins | | Chiti et al. (1999) |

As described in WO 02/055720, WO2007/110630, and WO2007/110627, diaminophenothiazines have utility in the inhibition of such protein aggregating diseases.

Thus it will be appreciated that, except where context requires otherwise, description of embodiments with respect to tau protein or tau-like proteins (e.g., MAP2; see below), should be taken as applying equally to the other proteins discussed herein (e.g., β-amyloid, synuclein, prion, etc.) or other proteins which may initiate or undergo a similar pathological aggregation by virtue of conformational change in a domain critical for propagation of the aggregation, or which imparts proteolytic stability to the aggregate thus formed (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation, synuclein aggregation, etc. The same applies for "tau proteolytic degradation" etc.

Preferred Aggregating Disease Proteins

Preferred embodiments of the invention are based on tau protein. The term "tau protein," as used herein, refers generally to any protein of the tau protein family. Tau proteins are characterised as being one among a larger number of protein families which co-purify with microtubules during repeated cycles of assembly and disassembly (see, e.g., Shelanski et al., 1973, Proc. Natl. Acad. Sci. USA, Vol. 70, pp. 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (see, e.g., Matus, A., in "Microtubules" [Hyams and Lloyd, Eds.] pp. 155-166, John Wiley and Sons, New York, USA). MAP2 isoforms are almost identical to tau protein in the tandem repeat region, but differ substantially both in the sequence and extent of the N-terminal domain (see, e.g., Kindler and Garner, 1994, Mol. Brain Res., Vol. 26, pp. 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation, and so on.

In some embodiments, the protein is tau protein.

In some embodiments, the protein is a synuclein, e.g., α- or β-synuclein.

In some embodiments, the protein is TDP-43.

TAR DNA-Binding Protein 43 (TDP-43) is a 414 amino acid protein encoded by TARDBP on chromosome 1p36.2. The protein is highly conserved, widely expressed, and predominantly localised to the nucleus but can shuttle between the nucleus and cytoplasm (Mackenzie et al 2010). It is involved in transcription and splicing regulation and may have roles in other processes, such as: microRNA processing, apoptosis, cell division, stabilisation of messenger RNA, regulation of neuronal plasticity and maintenance of dendritic integrity. Furthermore, since 2006 a substantial body of evidence has accumulated in support of the TDP-43 toxic gain of function hypothesis in amyotrophic lateral sclerosis (ALS). TDP-43 is an inherently aggregation-prone protein and aggregates formed in vitro are ultrastructurally similar to the TDP-43 deposits seen in degenerating neurones in ALS patients (Johnson et al 2009). Johnson et al (2008) showed that when TDP-43 is overexpressed in a yeast model only the aggregated form is toxic. Several in vitro studies have also shown that C-terminal fragments of TDP-43 are more likely than full-length TDP-43 to form insoluble cytoplasmic aggregates that become ubiquitinated, and toxic to cells (Arai et al 2010; Igaz et al 2009; Nonaka et al 2009; Zhang et al 2009). Though Nonaka et al (2009) suggested that these cytoplasmic aggregates bind the endogenous full-length protein depleting it from the nucleus, Zhang et al (2009) found retention of normal nuclear expression, suggesting a purely toxic effect for the aggregates. Yang et al (2010) have described the capture of full-length TDP-43 within aggregates of C- and N-terminal fragments of TDP-43 in NSC34 motor neurons in culture. Neurite outgrowth, impaired as a result of the presence of such truncated fragments, could be rescued by overexpression of the full-length protein. Although the role of neurite outgrowth in vivo has not been established, this model would support the suggestion made by Nonaka and colleagues for a role of TDP-43 aggregation in ALS pathogenesis.

Mutant TDP-43 expression in cell cultures has repeatedly been reported to result in increased generation of C-terminal fragments, with even greater cytoplasmic aggregation and toxic effects than the wild-type protein (Kabashi et al 2008; Sreedharan et al 2008; Johnson et al 2009; Nonaka et al 2009; Arai et al 2010; Barmarda et al 2010; Kabashi et al 2010).

Where the protein is tau protein, in some embodiments of the present invention, there is provided a method of inhibiting production of protein aggregates (e.g. in the form of paired helical filaments (PHFs), optionally in neurofibrillary tangles (NFTs) in the brain of a mammal, the treatment being as described above.

Preferred Indications—Diseases of Protein Aggregation

Notably it is not only Alzheimer's disease (AD) in which tau protein (and aberrant function or processing thereof) may play a role. The pathogenesis of neurodegenerative disorders such as Pick's disease and progressive supranuclear palsy (PSP) appears to correlate with an accumulation of pathological truncated tau aggregates in the dentate gyrus and stellate pyramidal cells of the neocortex, respectively. Other dementias include fronto-temporal dementia (FTD); FTD with parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford; especially Table 5.1). All of these diseases, which are characterized primarily or partially by abnormal tau aggregation, are referred to herein as "tauopathies".

Thus, in some embodiments, the disease condition is a tauopathy.

In some embodiments, the disease condition is a neurodegenerative tauopathy.

In some embodiments, the disease condition is selected from Alzheimer's disease (AD), Pick's disease, progressive supranuclear palsy (PSP), fronto temporal dementia (FTD), FTD with parkinsonism linked to chromosome 17 (FTDP 17), frontotemporal lobar degeneration (FTLD) syndromes; disinhibition-dementia-parkinsonism-amyotrophy complex (DDPAC), pallido-ponto-nigral degeneration (PPND), Guam-ALS syndrome, pallido nigro luysian degeneration (PNLD), cortico-basal degeneration (CBD), dementia with argyrophilic grains (AgD), dementia pugilistica (DP) or chronic traumatic encephalopathy (CTE), Down's syndrome (DS), dementia with Lewy bodies (DLB), subacute sclerosing panencephalitis (SSPE), MCI, Niemann-Pick disease, type C (NPC), Sanfilippo syndrome type B (mucopolysaccharidosis III B), or myotonic dystrophies (DM), DM1 or DM2, or chronic traumatic encephalopathy (CTE).

In some embodiments, the disease condition is a lysosomal storage disorder with tau pathology. NPC is caused by mutations in the gene NPC1, which affects cholesterol metabolism (Love et al 1995) and Sanfilippo syndrome type B is caused by a mutation in the gene NAGLU, in which there is lysosomal accumulation of heparin sulphate (Ohmi et al. 2009). In these lysosomal storage disorders, tau pathology is observed and its treatment may decrease the progression of the disease. Other lysosomal storage disorders may also be characterised by accumulation of tau.

Use of phenothiazine diaminium salts in the treatment of Parkinson's Disease and MCI is described in more detail in PCT/GB2007/001105 and PCT/GB2008/002066.

In some embodiments, the disease condition is Parkinson's Disease, MCI, or Alzheimer's disease.

In some embodiments, the disease condition is Huntington's Disease or other polyglutamine disorder such as spinal bulbar muscular atrophy (or Kennedy disease), and dentatorubropallidoluysian atrophy and various spinocerebellar ataxias.

In some embodiments, the disease condition is an FTLD syndrome (which may for example be a tauopathy or TDP-43 proteinopathy, see below).

In some embodiments, the disease condition is PSP or ALS.

In some embodiments, treatment (e.g., treatment of a neurodegenerative tauopathy, e.g., Alzheimer's disease) may optionally be in combination with one or more other agents, for example, one or more cholinesterase inhibitors (such as Donepezil (also known as Aricept™), Rivastigmine (also known as Exelon™), Galantamine (also known as Reminyl™) NMDA receptor antagonists (such as Memantine (also known as Ebixa™, Namenda™) muscarinic receptor agonists, and/or inhibitors of amyloid precursor protein processing that leads to enhanced generation of beta-amyloid.

TDP-43 proteinopathies include amyotrophic lateral sclerosis (ALS; ALS-TDP) and frontotemporal lobar degeneration (FTLD-TDP).

The role of TDP-43 in neurodegeneration in ALS and other neurodegenerative disorders has been reviewed in several recent publications (Chen-Plotkin et al 2010; Gendron et al 2010; Geser et al 2010; Mackenzie et al 2010).

ALS is a neurodegenerative disease, characterised by progressive paralysis and muscle wasting, consequent on the degeneration of both upper and lower motor neurones in the primary motor cortex, brainstem and spinal cord. It is sometimes referred to as motor neuron disease (MND) but there are diseases other than ALS which affect either upper or lower motor neurons. A definite diagnosis requires both upper and lower motor neurone signs in the bulbar, arm and leg musculature with clear evidence of clinical progression that can not be explained by any other disease process (Wijesekera and Leigh 2009).

Although the majority of cases are ALS-TDP, there are other cases where the pathological protein differs from TDP-43. Misfolded SOD1 is the pathological protein in ubiquitin-positive inclusions in ALS with SOD1 mutations (Seetharaman et al 2009) and in a very small subset (approximately 3-4%) of familial ALS, due to mutations in FUS (fused in sarcoma protein), the ubiquitinated pathological protein is FUS (Vance et al 2009; Blair et al 2010). FUS, like TDP-43, appears to be important in nuclear-cytoplasmic shuttling although the ways in which impaired nuclear import of FUS remains unclear. A new molecular classification of ALS, adapted from Mackenzie et al (2010), reflects the distinct underlying pathological mechanisms in the different subtypes (see Table below).

New Molecular Classification of ALS (modified from Mackenzie et al 2010). In the majority of cases, TDP-43 is the pathological ubiquitinated protein found in ALS.

| Ubiquitin-positive inclusions in ALS | | | |
|---|---|---|---|
| Ubiquitinated disease protein | TDP-43 | FUS | SOD1 |
| Clinico-pathologic subtype | ALS-TDP | ALS-FUS | ALS-SOD1 |
| Associated genotype | TARDBP | FUS | SOD1 |
| Frequency of ALS cases | Common | Rare | Rare |

Amyotrophic lateral sclerosis has been recognised as a nosological entity for almost a century and a half and it is recognised in ICD-10 is classified as a subtype of MND in ICD 10 (G12.2). Reliable clinical diagnostic are available for ALS, which differ little from Charcot's original description, and neuropathological criteria, reflecting the underlying molecular pathology, have also been agreed.

While ALS is classified pathologically into three subgroups, ALS-TDP, ALS-SOD1 and ALS-FUS, both latter conditions are rare. The largest study to date showed all sporadic ALS cases to have TDP-43 pathology (Mackenzie et al 2007). Only around 5% of ALS is familial (Byrne et al 2010) and mutations in SOD1, the commonest mutations found in FALS, account for between 12-23% of cases (Andersen et al 2006). SOD1 may also be implicated in 2-7% of SALS. Mutations in FUS appear to be far less common, accounting for only around 3-4% of FALS (Blair et al 2010). So it can be reliably predicted that a clinical case of SALS will have TDP-43 based pathology. Similarly this can be reliably predicted in FALS due to mutations in TDP-43, which account for around 4% of cases (Mackenzie et al 2010). ALS with mutations in: VCP, accounting for 1-2% of FALS (Johnson et al 2010), ANG (Seilhean et al 2009), and CHMP2B (Cox et al 2010) have also been reported to be associated with TDP-43 positive pathology. Although SOD1, FUS and ATXN2 mutations have not been found to be associated with TDP-43 positive aggregates, it has however been reported that TDP-43 is implicated in the pathological processes putatively arising from these mutations (Higashi et al 2010; Ling et al 2010; Elden et al 2010).

It is therefore established that TDP-43 has an important, and potentially central role, in the pathogenesis of the vast majority of SALS cases and may be implicated in the pathogenesis of a significant proportion of FALS. ALS is now widely considered to be a TDP-43 proteinopathy (Neumann et al 2009) and numerous in vitro, and in vivo studies provide support to the hypothesis that toxic gain of function, due to TDP-43 aggregation is responsible for at least some of the neurotoxicity in the disease.

FTLD syndromes are insidious onset, inexorably progressive, neurodegenerative conditions, with peak onset in late middle age. There is often a positive family history of similar disorders in a first degree relative.

Behavioural variant FTD is characterised by early prominent change in social and interpersonal function, often accompanied by repetitive behaviours and changes in eating pattern. In semantic dementia there are prominent word finding problems, despite otherwise fluent speech, with degraded object knowledge and impaired single word comprehension on cognitive assessment. Progressive non-fluent aphasia presents with a combination of motor speech problems and grammatical deficits. The core clinical diagnostic features for these three FTLD syndromes are shown in the Table below and the full criteria in Neary et al (1998).

| Clinical Profile and Core Diagnostic Features of FTLD Syndromes | |
|---|---|
| FTLD Syndrome -Clinical Profile | Core Diagnostic Features |
| Frontotemporal Dementia<br>Character change and disordered social conduct are the dominant features initially and throughout the disease course. Instrumental functions of perception, spatial skills, praxis and memory are intact or relatively well preserved. | 1. Insidious onset and gradual progression<br>2. Early decline in social interpersonal conduct<br>3. Early impairment in regulation of personal conduct<br>4. Early emotional blunting<br>5. Early loss of insight |
| Semantic Dementia<br>Semantic disorder (impaired understanding of word meaning and/or object identity) is the dominant feature initially and throughout the disease course. Other aspects of cognition, including autobiographic memory, are intact or relatively well preserved. | A) Insidious onset and gradual progression<br>B) Language disorder characterised by<br>  1. Progressive, fluent empty speech<br>  2. Loss of word meaning manifest by impaired naming and comprehension<br>  3. Semantic paraphasias and/or<br>  4.<br>Perceptual disorder characterised by<br>  1. Prosopagnosia: impaired recognition of identity of familiar faces and/or |

Clinical Profile and Core Diagnostic Features of FTLD Syndromes

| FTLD Syndrome -Clinical Profile | Core Diagnostic Features |
| --- | --- |
| | 2. Associative agnosia: impaired recognition of object identity<br>C) Preserved perceptual matching and drawing reproduction<br>D) Preserved single word repetition<br>E) Preserved ability to read aloud and write to dictation orthographically regular words |
| Progressive Non-fluent Aphasia<br>Disorder of expressive language is the dominant feature initially and throughout the disease course. Other aspects of cognition are intact or relatively well preserved. | A) Insidious onset and gradual progression<br>B) Non-fluent spontaneous speech with at least one of the following: agrammatism, phonemic paraphasias or anomia |

The discovery that TDP-43-positive inclusions characterize ALS and FTLD-TDP (Neumann et al 2006) was quickly followed by the identification of missense mutations in the TARDBP gene in both familial and sporadic cases of ALS (Gitcho et al 2008; Sreedharan et al., 2008). So far, 38 different TARDBP mutations have been reported in 79 genealogically unrelated families worldwide (Mackenzie et al 2010). TARDBP mutations account for approximately 4% of all familial and around 1.5% of sporadic ALS cases.

As of December 2010, mutations in thirteen genes which are associated with familial and sporadic ALS have been identified. Linkage of ALS to five other chromosome loci has been demonstrated but thus far specific mutations have not been identified.

Methylthioninium (MT) in TDP-43 Proteinopathies

MT has a mode of action which targets and can reduce TDP-43 protein aggregation in cells, which is a pathological feature of the vast majority of both familial and sporadic ALS and is also characteristic of FTLD-P.

In addition laboratory data shows that methylthioninium inhibits the formation of TDP-43 aggregates in SH-SY5Y cells. Following treatment with 0.05 µM MT, the number of TDP-43 aggregates was reduced by 50%. These findings were confirmed by immunoblot analysis (Yamashita et al 2009).

The compounds and compositions of the invention may therefore be useful for the treatment of amyotrophic lateral sclerosis (ALS) and frontotemporal lobar degeneration (FTLD).

Methylthioninium (MT) in Huntington's Disease and Polyglutamine Disorders

MT can reduce polyglutamine protein aggregation in cells, which is a pathological feature of Huntington's disease. Huntington's disease is caused by expansion of a translated CAG repeat located in the N-terminus of huntingtin. Wild-type chromosomes contain 6-34 repeats whereas, in Huntington's disease, chromosomes contain 36-121 repeats. The age of onset of disease correlates inversely with the length of the CAG tracts that code for polyglutamine repeats within the protein.

Laboratory data shows that methylthioninium inhibits the formation of aggregates of a huntingtin derivative containing a polyglutamine stretch of 102 residues in zebrafish (van Bebber et al. 2010). MT, when tested at 0, 10 and 100 µM, prevented the formation of such aggregates in zebrafish in a dose dependent manner.

The compounds and compositions of the invention may therefore be useful for the treatment of Huntington's disease and other polyglutamine disorders such as spinal bulbar muscular atrophy (or Kennedy disease), and dentatorubropallidoluysian atrophy and various spinocerebellar ataxias (Orr & Zoghbi, 2007).

Mitochondrial Diseases and Lafora Disease

The organ most frequently affected in mitochondrial disorders, particularly respiratory chain diseases (RCDs), in addition to the skeletal muscle, is the central nervous system (CNS). CNS manifestations of RCDs comprise stroke-like episodes, epilepsy, migraine, ataxia, spasticity, movement disorders, psychiatric disorders, cognitive decline, or even dementia (mitochondrial dementia). So far mitochondrial dementia has been reported in MELAS, MERRF, LHON, CPEO, KSS, MNGIE, NARP, Leigh syndrome, and Alpers-Huttenlocher disease (Finsterer, 2009). There are four complexes in the mitochondrial respiration chain, involving a series of electron transfers. Abnormal function of any of these complexes can result in mitochondrial diseases secondary to an abnormal electron transport chain and subsequent abnormal mitochondrial respiration. Complex III of the mitochondrial respiration chain acts to transfer electrons to cytochrome c.

Compounds and compositions of the invention may also be used to treat mitochondrial diseases which are associated with a deficient and/or impaired complex III function of the respiration chain. The compounds have the ability to act as effective electron carrier and/or transfer, as the thioninium moiety has a low redox potential converting between the oxidised and reduced form. In the event of an impaired and/or deficient function of Complex III leading to mitochondrial diseases, compounds of the invention are also able to perform the electron transportation and transfer role of complex III because of the ability of the thioninium moiety to shuttle between the oxidised and reduced form, thus acting as an electron carrier in place of sub-optimally functioning complex III, transferring electrons to cytochrome c.

Compounds and compositions of the invention also have the ability to generate an active thioninium moiety that has the ability to divert misfolded protein/amino acid monomers/oligomers away from the Hsp70 ADP-associated protein accumulation and/or refolding pathways, and instead rechannel these abnormal folded protein monomers/oligomers to the pathway that leads directly to the Hsp70 ATP-dependent ubiquitin-proteasome system (UPS), a pathway which removes these misfolded proteins/amino acid monomers/oligomers via the direct route (Jinwal et al. 2009).

Lafora disease (LD) is an autosomal recessive teenage-onset fatal epilepsy associated with a gradual accumulation of poorly branched and insoluble glycogen, termed polyglucosan, in many tissues. In the brain, polyglucosan bodies, or Lafora bodies, form in neurons. Inhibition of Hsp70 ATPase by MT (Jinwal et al. 2009) may upregulate the removal of misfolded proteins. Lafora disease is primarily due to a lysosomal ubiquitin-proteasomal system (UPS) defect because of a mutation in either the Laforin or Malin genes, both located on Chromosome 6, which result in inclusions that may accelerate the aggregation of misfolded tau protein. Secondary mitochondrial damage from the impaired UPS may further result in a suppressed mitochondrial activity and impaired electron transport chain leading to further lipofuscin and initiating the seizures that are characteristic of Lafora disease.

The MT moiety may disaggregate existing tau aggregates, reduce more tau accumulating and enhance lysosomal efficiency by inhibiting Hsp70 ATPase. MT may lead to a reduction in tau tangles by enhancing the ubiquitin proteasomal system removal of tau monomers/oligomers, through its inhibitory action on Hsp70 ATPase.

Thus compounds and compositions of the present invention may have utility in the treatment of Lafora disease.

Disease Conditions Treated—Other Disease Conditions

In some embodiments, the disease condition is skin cancer.

In some embodiments, the disease condition is melanoma.

In some embodiments, the disease condition is a viral, bacterial or protozoal disease condition.

In some embodiments, the (protozoal) disease condition is malaria. Treatment may be in combination with one or more antimicrobial agents, for example, chloroquine and/or atovaquone.

In some embodiments, the (viral) disease condition is caused by Hepatitis C, HIV, or West Nile Virus (WNV).

Other Uses

Another aspect of the present invention pertains to use of a compound as described herein, in a method of inactivating a pathogen in a sample (for example a blood or plasma sample), comprising the steps of introducing the compound into the sample, and exposing the sample to light.

For example, in some embodiments, the method comprises the steps of introducing the compound into the sample, and then exposing the sample to light.

Use as Ligands

The compounds described herein that are capable of inhibiting the aggregation of tau protein will also be capable of acting as ligands or labels of tau protein (or aggregated tau protein). Thus, in some embodiments, the compound of the invention is a ligand of tau protein (or aggregated tau protein).

Such compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic, or therapeutic application.

For example, in some embodiments, the compound is as defined herein, but with the additional limitation that the compound incorporates, is conjugated to, is chelated with, or is otherwise associated with, one or more (e.g., 1, 2, 3, 4, etc.) detectable labels, for example, isotopes, radioisotopes, positron-emitting atoms, magnetic resonance labels, dyes, fluorescent markers, antigenic groups, or therapeutic moieties.

In some embodiments, the compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in some embodiments, the compound is as defined above, but with the additional limitation that the compound incorporates, is conjugated to, is chelated with, or is otherwise associated with, one or more (e.g., 1, 2, 3, 4, etc.) detectable labels.

Labelled compounds (e.g., when ligated to tau protein or aggregated tau protein) may be visualised or detected by any suitable means, and the skilled person will appreciate that any suitable detection means as is known in the art may be used.

For example, the compound (ligand-label) may be suitably detected by incorporating a positron-emitting atom (e.g., $^{11}C$) (e.g., as a carbon atom of one or more alkyl group substituents, e.g., methyl group substituents) and detecting the compound using positron emission tomography (PET) as is known in the art.

Figure 11:
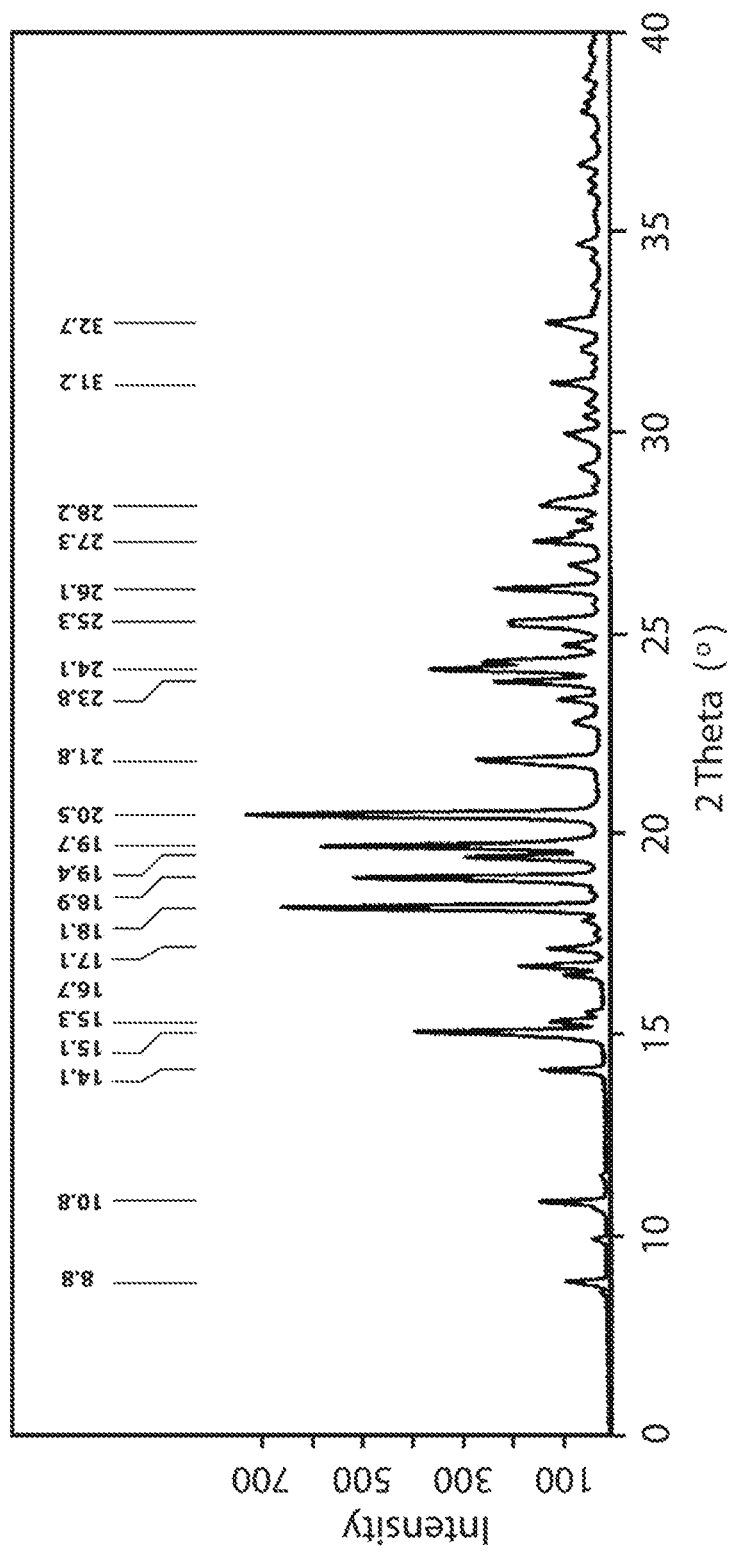
FIG. 11 shows a powder X-ray diffractogram for LMT.2MsOH, measured with Cu Kα radiation.
Figure 12:
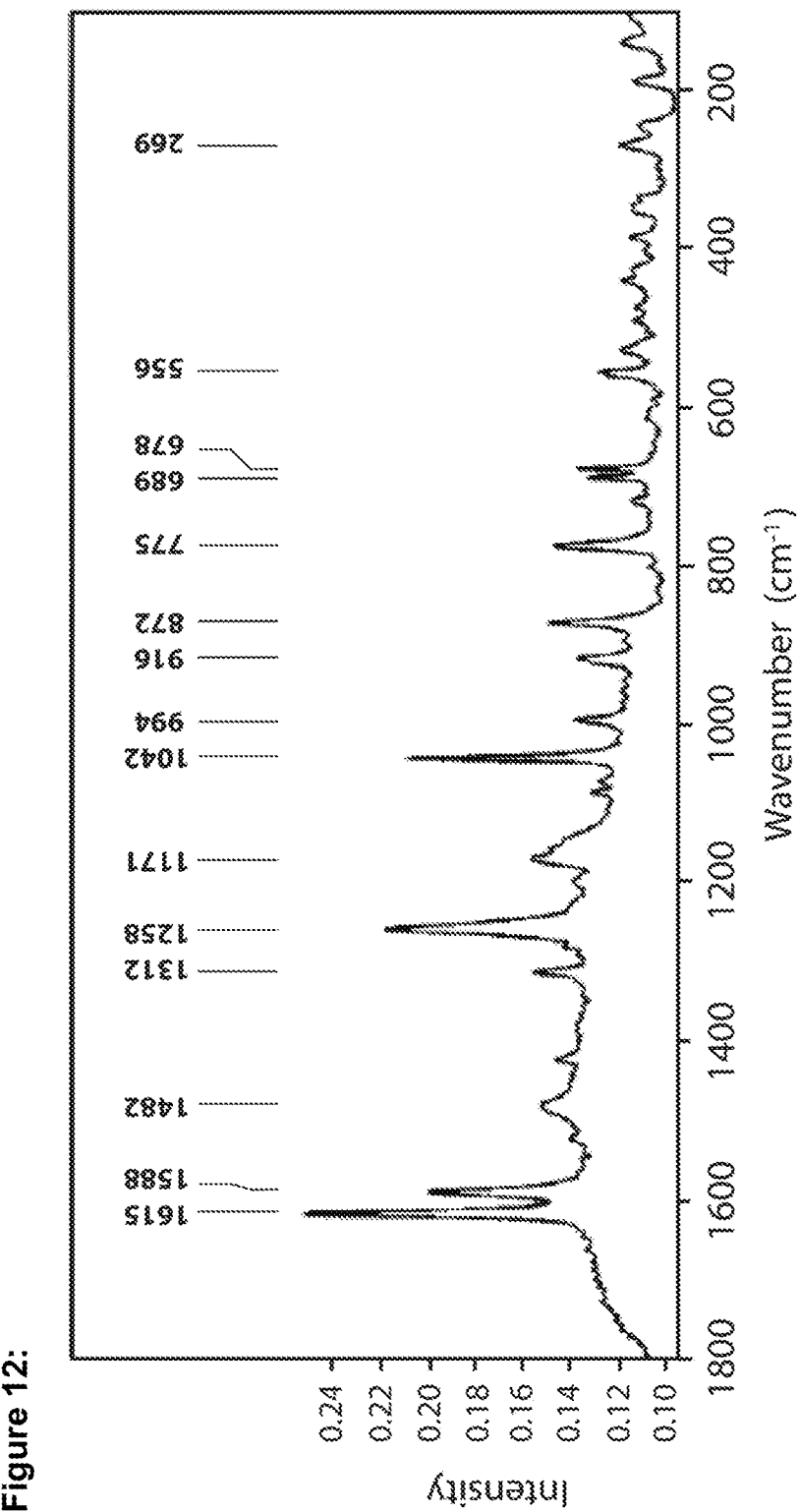
FIG. 12 shows the FT-Raman spectrum for crystalline LMT.2MsOH. The most intense signals are found at 1615 cm$^{-1}$, 1588 cm$^{-1}$ 1258 cm$^{-1}$, and 1042 cm$^{-1}$.
Figure 13:
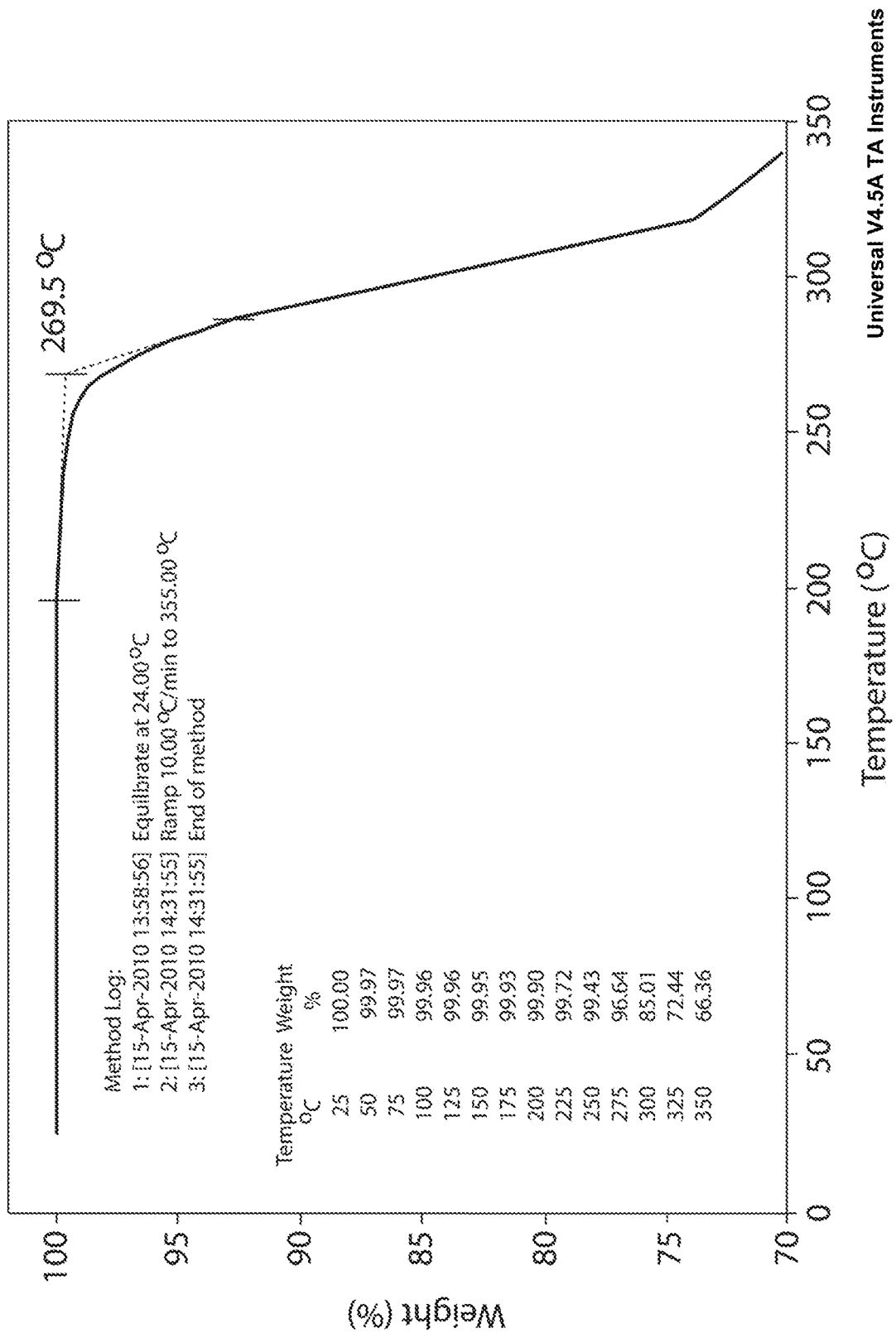
FIG. 13 shows the thermogravimetric profile for crystalline LMT.2MsOH. A constant weight was detected by TG and TG-FTIR up to the beginning of decomposition at 240-270° C.
Figure 14:
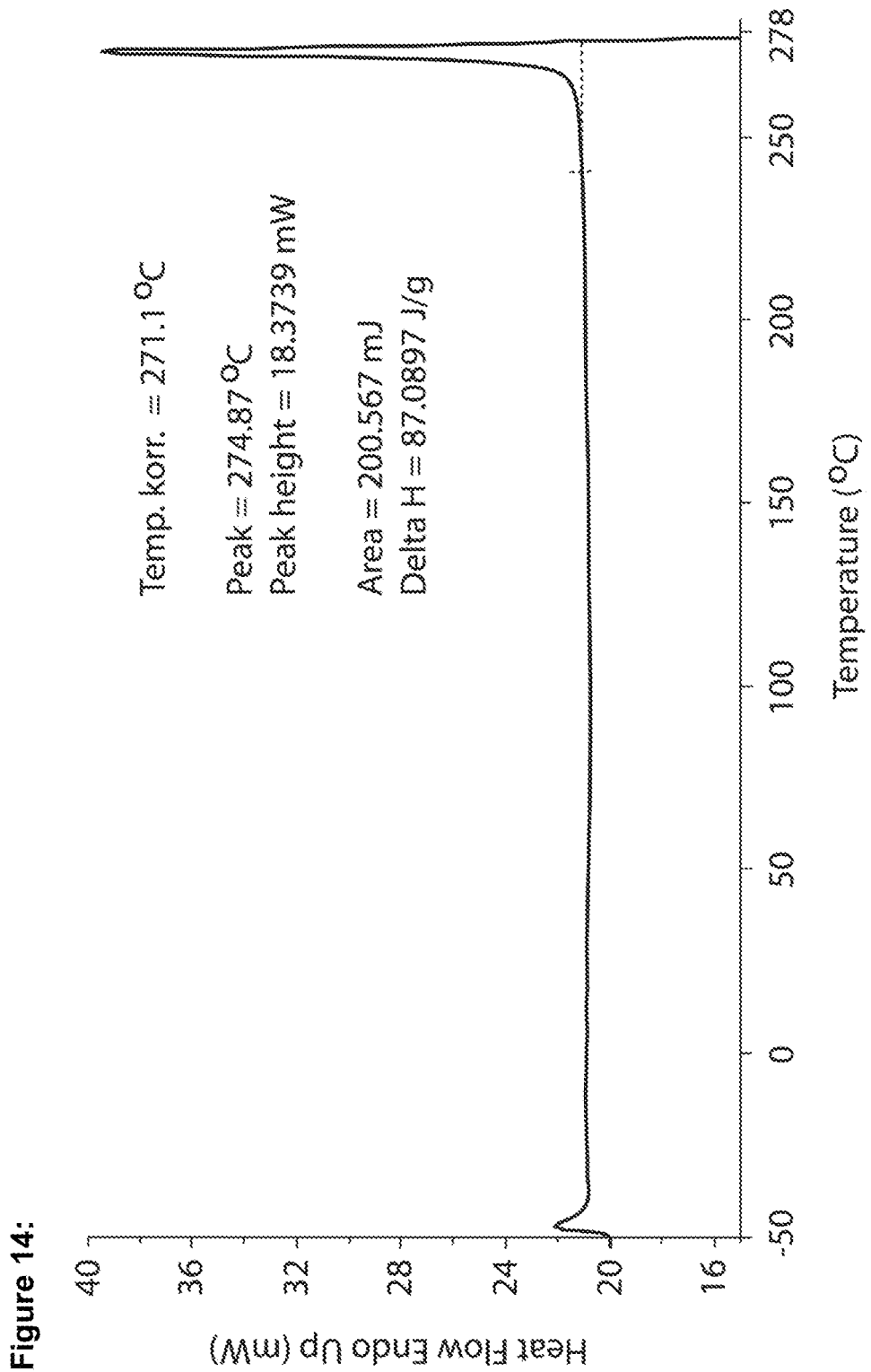
FIG. 14 shows the differential scanning calorimetry analysis for crystalline LMT.2MsOH. A sharp m.p. at 271° C. (ΔH=87 J/g) was immediately followed by decomposition.

Such $^{11}C$ labelled compounds may be prepared by adapting the methods described herein in known ways, for example, in analogy to the methods described in WO 02/075318 (see FIGS. 11a, 11b, 12 therein) and WO 2005/030676.

Thus, another aspect of the present invention pertains to a method of labelling tau protein (or aggregated tau protein) comprising the step of: (i) contacting the tau protein (or aggregated tau protein) with a compound that incorporates, is conjugated to, is chelated with, or is otherwise associated with, one or more (e.g., 1, 2, 3, 4, etc.) detectable labels. The compound may be provided as a composition as described herein.

Another aspect of the present invention pertains to a method of detecting tau protein (or aggregated tau protein) comprising the steps of: (i) contacting the tau protein (or aggregated tau protein) with a compound that incorporates, is conjugated to, is chelated with, or is otherwise associated with, one or more (e.g., 1, 2, 3, 4, etc.) detectable labels, and (ii) detecting the presence and/or amount of said compound bound to tau protein (or aggregated tau protein). The compound may be provided as a composition as described herein. Another aspect of the present invention pertains to a method of diagnosis or prognosis of a tau proteinopathy in a subject believed to suffer from the disease, comprising the steps of: (i) introducing into the subject a compound capable of labelling tau protein or aggregated tau protein, particularly tau protein (e.g., a compound that incorporates, is conjugated to, is chelated with, or is otherwise associated with, one or more (e.g., 1, 2, 3, 4, etc.) detectable labels); (ii) determining the presence and/or amount of said compound bound to tau protein or aggregated tau protein in the brain of the subject; and (iii) correlating the result of the determination made in (ii) with the disease state of the subject. The compound may be provided as a composition as described herein.

Another aspect of the present invention pertains to a compound capable of labelling tau protein or aggregated tau protein (e.g., a compound that incorporates, is conjugated to, is chelated with, or is otherwise associated with, one or more (e.g., 1, 2, 3, 4, etc.) detectable labels), for use in a method of diagnosis or prognosis of a tau proteinopathy. The compound may be provided as a composition as described herein.

Another aspect of the present invention pertains to use of a compound of the invention capable of labelling tau protein or aggregated tau protein, particularly tau protein (e.g., a compound that incorporates, is conjugated to, is chelated with, or is otherwise associated with, one or more (e.g., 1, 2, 3, 4, etc.) detectable labels), in a method of manufacture of a diagnostic or prognostic reagent for use in the diagnosis or prognosis of a tau proteinopathy. The compound may be provided as a composition as described herein.

Those skilled in the art will appreciate that instead of administering ligands/labels directly, they could be administered in a precursor form, for conversion to the active form (e.g., ligating form, labelling form) by an activating agent present in, or administered to, the same subject.

The ligands disclosed herein may be used as part of a method of diagnosis or prognosis. It may be used to select a patient for treatment, or to assess the effectiveness of a treatment or a therapeutic (e.g., an inhibitor of tau protein aggregation) administered to the subject.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of a compound of the invention, or a material, composition or dosage from comprising said compound, which is effective for producing some desired therapeutic effect, commensurate with a reasonable benefit/risk ratio, when administered in accordance with a desired treatment regimen.

Similarly, the term "prophylactically effective amount," as used herein, pertains to that amount of a compound of the invention, or a material, composition or dosage from comprising said compound, which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

For example, it may be beneficial to combine treatment with a compound as described herein with one or more other (e.g., 1, 2, 3, 4) agents or therapies.

The particular combination would be at the discretion of the physician who would select dosages using his/her common general knowledge and dosing regimens known to a skilled practitioner.

The agents (i.e., a compound as described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., a compound as described here, plus one or more other agents) may be formulated together in a single dosage form, or alternatively, the individual agents may be formulated separately and presented together in the form of a kit, optionally with instructions for their use.

Routes of Administration

The compound of the invention, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

Preferred compositions are oral compositions, formulated as described in more detail hereinafter.

The Subject/Patient

The subject/patient may be an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), a monotreme (e.g. platypus), an ape (e.g., gorilla, chimpanzee, orangutang, gibbon), or a human.

Furthermore, the subject/patient may be any of its forms of development, for example, a foetus.

In some embodiments, the subject/patient is a human.

Compositions/Formulations

While it is possible for the compound of the invention to be used (e.g., administered) alone, it is often preferable to present it as a composition or formulation.

Another aspect of the invention therefore provides a composition comprising a compound as described herein, and a pharmaceutically acceptable carrier or diluent.

In some embodiments, the composition is a pharmaceutical composition (e.g., formulation, preparation, medicament) comprising a compound as described herein, and a pharmaceutically acceptable carrier, diluent, or excipient.

In some embodiments, the composition is a pharmaceutical composition comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, New York, USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Some Preferred Formulations

One aspect of the present invention pertains to a dosage unit (e.g., a pharmaceutical tablet or capsule) comprising 20 to 300 mg of a compound as described herein (e.g., obtained by, or obtainable by, a method as described herein; having a purity as described herein; etc.), and a pharmaceutically acceptable carrier, diluent, or excipient.

In some embodiments, the dosage unit is a tablet.

In some embodiments, the dosage unit is a capsule.

In some embodiments, said capsules are gelatine capsules.

In some embodiments, said capsules are HPMC (hydroxypropylmethylcellulose) capsules.

In some embodiments, the amount is 30 to 200 mg.

In some embodiments, the amount is about 30 mg.

In some embodiments, the amount is about 60 mg.

In some embodiments, the amount is about 100 mg.

In some embodiments, the amount is about 150 mg.

In some embodiments, the amount is about 200 mg.

Throughout the present specification dosage amounts, e.g. as set out above, may refer to the amount of the compound itself or may refer to the amount of free base equivalent (i.e. the amount of LMT moiety) contained in the dosage unit. Both these alternatives are expressly disclosed by the present invention.

In some embodiments, the pharmaceutically acceptable carrier, diluent, or excipient is or comprises one or both of a glyceride (e.g., Gelucire 44/14 ®; lauroyl macrogol-32 glycerides PhEur, USP) and colloidal silicon dioxide (e.g., 2% Aerosil 200 ®; Colliodal Silicon Dioxide PhEur, USP).

Novel Formulations—Solid Dosage Forms

Processes generally used for tablet formulation and film coating often require the use of heat accompanied by low humidity during the drying process.

LMTM and the other leuco-methylthionium salts are potentially prone to oxidation to methylthioninium moiety (MT) and to degradation e.g. to L Azure B (LAB) (see Scheme, below):

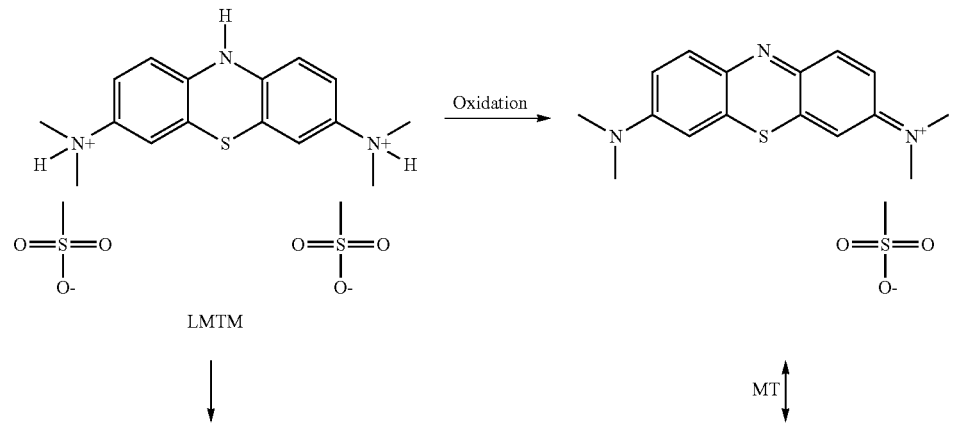

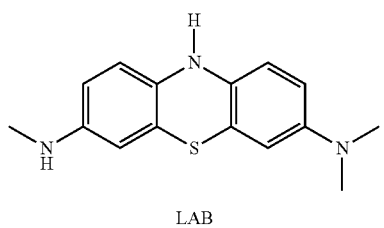

LAB

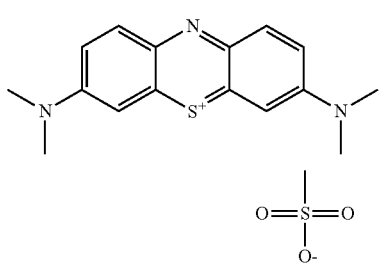

For a material such as e.g. LM™, which is prone to oxidation (as explained above), conventional formulation processes may therefore lead to degradation and hence, potentially, to instability in the performance of the product.

The principle behind the formulations of the present invention is therefore the provision of a method of manufacture of compressed pharmaceutical formulations and capsules containing leuco-methylthionium salts e.g. bis(methanesulfonate) (LM™) as the active substance, by direct tablet compression technology or by other unique tabletting techniques, and by encapsulation, in which the active substance exists substantially in a stable form.

The most commonly used method for the preparation of solid dosage forms is wet granulation (also called moist granulation). This involves adding a granulating fluid to a powder. The granulating fluid may be water or some other solvent that is sufficiently volatile that can subsequently be removed by drying. The granulating fluid may also include a binder. Once the solvent has been removed, the resulting mass is milled.

Wet granulation is often preferred over direct compression because wet granulation is more likely to overcome any problems associated with the physical characteristics of various ingredients in the formulation. Wet granulation provides material which has the required flow and cohesive properties necessary to obtain an acceptable solid dosage form. The content uniformity of the solid dosage form is generally improved with wet granulation because all of the granules usually contain the same amount of drug. Segregation of the drug from excipients is also avoided.

In direct compression, the individual constituents of the composition to be compressed are mixed without previous granulation and then directly compressed. Whilst this appears to be an elegant and simple process, it may be difficult to obtain with it commercially usable tablets which have sufficient strength yet which also disintegrate sufficiently rapidly after administration. Also, many active substances cannot be processed by direct compression since they cannot be compressed without a granulation step.

It has now, surprisingly, been found that compounds of the present invention are stable in a dry compressed solid dosage form such as a tablet, during manufacture and storage, and that the amount of degradation products such as L Azure B (LAB) and methylthioninium (MT) formed can be controlled within the specifications (for example, LAB less than 2% and MT less than 12%).

This is in contrast to the behaviour of e.g. LMTM when processed by conventional wet granulation processes. Without wishing to be bound by theory, in conventional wet granulation processes LM™, for instance, may be very unstable and a substantial amount of LAB and MT may be formed.

Accordingly, one aspect of the present invention provides a pharmaceutical composition comprising a compound of the invention, in solid dosage form. The composition preferably further comprises at least one diluent suitable for dry compression. The pharmaceutical composition is characterised in that the compound exists in a substantially stable form.

Another aspect of the invention provides a free-flowing, cohesive powder, comprising a compound of the invention and at least one diluent suitable for dry compression, and optionally one or more other excipients, said powder being capable of being compressed into a solid dosage form.

These compositions and formulations are initially described herein with respect to the bis(sulfonate) salts of the present invention, in particular LM™. However, the advantages of the present formulation methods are equally applicable to other members of the leuco-methylthionium family of salts For example, the formulations described herein are applicable also to the 3,7-diamino-10H-phenothiazinium salts disclosed in WO2007/110627 (WisTa Laboratories Ltd), which were briefly discussed above. These include leuco-methylthionium bis(hydrobromide) (LMT.2HBr, LMTB) and leuco-methylthionium bis(hydrochloride) (LMT.2HCl, LMTC).

Therefore, in a broader aspect, the present invention provides a pharmaceutical composition comprising a compound of the following formula I:

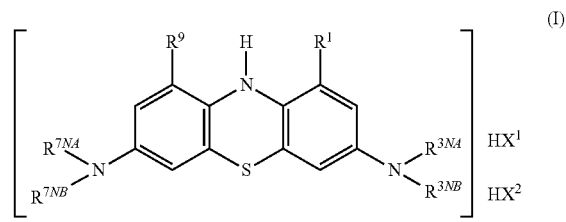

(I)

wherein:

$R^1$, $R^9$, $R^{3NA}$, $R^{3NB}$, $R^{7NA}$ and $R^{7NB}$ are as previously defined;

and wherein each of $HX^1$ and $HX^2$ is independently a protic acid;

or a pharmaceutically acceptable salt, solvate, or hydrate thereof;

in a solid dosage form as described herein.

For completeness, it is noted that, as would be understood by one skilled in the art, the above formula could equally be written as:

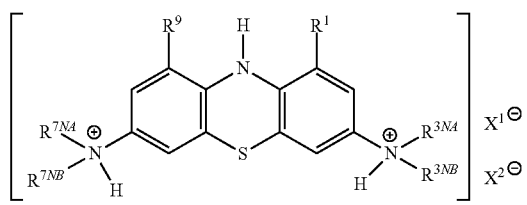

wherein $X^1$ and $X^2$ are the corresponding counterions.

Preferably $X^1$ and $X^2$ are independently sulfonate (such as alkylsulfonate or arylsulfonate, for example $R^A SO_3$ or $R^B SO_3$ as defined above) or halide (ClF, Br, F). In other words, $HX^1$ and $HX^2$ are preferably independently sulfonic acids ($R^A SO_3 H$, $R^B SO_3 H$) or hydrohalides (HCl, HBr, HI).

As used hereafter, the term 'active ingredient' refers to the relevant leuco(methylthioninium) salt. In other words it refers to a compound of formula (I), such as a compound of the invention, for example LM™.

Another aspect of the invention provides a process for the manufacture of said pharmaceutical compositions, by a dry compression method. The process preferably comprises dry compression of an intimate powder mixture of the active compound with at least one diluent suitable for dry compression, and optionally one or more other excipients.

In some embodiments, the process comprises direct compression.

In some embodiments, the process comprises simple direct compression.

In some embodiments, the process comprises dry granulation.

In some embodiments, the process comprises moist granulation of excipients, followed by addition of the active ingredient extra-granularly.

Solid dosage forms according to the invention advantageously exhibit long-term chemical and physical stability of the active ingredient (compound of the invention—e.g. LM™). The pharmaceutical compositions according to the invention also have fast dissolution rates, even after long-term storage.

A "substantially stable" form of the active ingredient means, in the present context, a form which does not react to form impurities such as oxidative impurities or other degradation products to any significant extent during the formulation process, or on storage of the formulated product.

Therefore, in the present context, it may refer to a material which contains, for example, less than 20% w/w, less than 15% w/w, or less than 10% w/w of oxidative impurities or other degradation products. In other words the material contains at least 80% w/w, at least 85% w/w, or at least 90% w/w of the pure active ingredient, in its original (unreacted) form.

In some embodiments, the material containing the active ingredient may contain, for example, less than 20% w/w, less than 15% w/w, less than 12% w/w, or less than 10% w/w of MT. In some embodiments, the material may contain, for example, less than 5% w/w, less than 3% w/w, or less than 2% w/w of LAB.

A "stable" tablet is, in the context of the present invention, a tablet that remains substantially stable after prolonged storage under controlled conditions of temperature and humidity. Stability testing may be carried out with the solid dosage forms directly exposed to the chosen environmental conditions, or with the solid dosage forms contained within packaging.

Content of Active Ingredient

The amount of the active ingredient in the uncoated composition is generally more than about 10% w/w, but can be more than 20%, or more than 30% w/w. The amount of the active ingredient is generally less than about 70% w/w, and usually less than 60% or less than 50% w/w in a tablet formulation. Typically, the amount of the active ingredient in the uncoated tablet core composition is thus from about 10% w/w (or 20% or 30%) to about 70% w/w (or 60% or 50%). Where a coating is applied to the composition, as described below, the overall weight of the composition is increased and thus the percentage of the active ingredient in the overall composition is somewhat reduced.

Diluents

The active ingredient may not be inherently compressible and thus may require addition of suitable diluents to aid compression.

The pharmaceutical compositions of the invention therefore commonly comprise at least 15% w/w, more commonly at least 20%, at least 30%, at least 40% or at least 50% w/w of diluent(s).

Diluents that may be used include one or more of microcrystalline cellulose, lactose, mannitol, calcium salts such as, calcium phosphate dibasic, calcium sulphate and calcium carbonate, and sugars such as lactose, sucrose, dextrose and maltodextrin.

Preferred diluents are microcrystalline cellulose, lactose and mannitol. Spray-dried forms of lactose and mannitol are particularly suitable forms of those compounds for direct compression or dry granulation techniques.

It has unexpectedly been found that when an active ingredient as described herein, for example a compound of the present invention, such as LM™, is formulated with dry compression diluents such as one or more of microcrystalline cellulose, spray dried lactose, anhydrous lactose and mannitol, the resulting solid dosage forms are stable in the sense that the active ingredient remains chemically stable, even after extended storage.

The invention thus provides a method of preparing low, medium- or high-dose tablets, for example low, medium-, or high-dose LMTM tablets, that are stable and have good dissolution profiles, acceptable degrees of hardness and resistance to chipping, as well as a short disintegration time.

Dissolution of Compositions of the Invention

The present inventors have also surprisingly found that the unique solid dosage forms described herein provide a very fast dissolution rate.

As explained hereinbefore, and without wishing to be bound by theory, it is thought that the active methylthioninium (MT) moiety may preferably be absorbed from the stomach and/or the upper GI tract. A fast-disintegrating and fast-dissolving formulation of the leuco(methylthioninium) salts would therefore be advantageous, since this would deliver the maximum possible amount of drug to the intended point of absorption.

The fast dissolution rate of the solid dosage forms described herein means that they are capable of dissolving rapidly in the stomach and/or upper GI tract and hence presenting the active ingredient there effectively, for rapid absorption.

In some embodiments, the formulations of the invention, when evaluated using a standard pharmacopeial method, provide at least 80% dissolution within 30 minutes, preferably at least 80% dissolution within 15 minutes, more preferably at least 80% dissolution within 10 minutes.

In some embodiments, the formulations of the invention, when evaluated using a standard pharmacopeial method, provide at least 90% dissolution within 30 minutes, preferably at least 90% dissolution within 15 minutes, more preferably at least 90% dissolution within 10 minutes.

In some embodiments, the formulations of the invention, when evaluated using a standard pharmacopeial method provide at least 95% dissolution within 30 minutes, preferably at least 95% dissolution within 15 minutes, more preferably at least 95% dissolution within 10 minutes.

Dissolution rates may be measured by standard pharamcopeial methods as described in United States Pharmacopeia (USP) General Chapter <711>. The current USP is USP 34 (2011). For example, dissolution rates for the formulations of the invention may be measured using apparatus according to USP Dissolution Apparatus 2 (Paddle).

In some embodiments, the dissolution rates above are evaluated in 0.1M hydrochloric acid at a working concentration of ~5 µg/ml LMT, with stirring at 50 rpm paddle speed. In some embodiments, the dissolution rates are evaluated by spectrophotometric analysis. In some embodiments, analysis comprises UV/vis spectrophotometry ($\lambda_{max\ LMT}$=255 nm).

As a consequence of their surprisingly high dissolution rate, the formulation methods described herein can provide the active compound with a high degree of bioavailability.

The fast dissolution rate is maintained after prolonged storage, even if storage is under 'stressed' conditions (i.e. increased temperature and humidity). The fast dissolution rate, and hence the good bioavailability, of compositions formulated according to the processes of the present invention is also highly tolerant of variations in the formulation itself.

Other Ingredients

The pharmaceutical composition will generally also include a lubricant. Examples of lubricants include magnesium stearate, calcium stearate, sodium stearyl fumarate, stearic acid, glycerylbehaptate, polyethylene glycol, ethylene oxide polymers (for example, those available under the registered trademark Carbowax from Union Carbide, Inc., Danbury, CT), sodium lauryl sulphate, magnesium lauryl stearate, mixtures of magnesium stearate with sodium lauryl sulphate, and hydrogenated vegetable oil. Preferred lubricants include calcium stearate, magnesium stearate and sodium stearyl fumarate. Most preferred as the lubricant is magnesium stearate. Lubricants generally comprise from about 0.5 to about 5.0% of the total (uncoated) tablet weight. The amount of lubricant employed is generally from about 1.0 to about 2.0%, preferably 0.5 to 2.0% w/w.

In addition to the diluent(s) and lubricant(s), other conventional excipients may also be present in the pharmaceutical compositions of the invention. Such additional excipients include disintegrants, binders, flavouring agents, colours and glidants. Some excipients can serve multiple functions, for example as both binder and tablet disintegrant.

A tablet disintegrant may be present in an amount necessary to achieve rapid dissolution. Disintegrants are excipients which oppose the physical forces of particle bonding in a tablet or capsule when the dosage form is placed in an aqueous environment. Examples of disintegrants include crosslinked polyvinylpyrrolidone (crospovidone), sodium starch glycolate, crosslinked sodium carboxymethyl cellulose (sodium croscarmellose), and pregelatinized starch. Generally the amount of disintegrant can be from 0 to about 25% w/w, more commonly from about 1% to about 15% w/w, and usually less than 10% or less than 5% w/w, of the composition.

Binders are excipients which contribute to particle adhesion in a solid formulation. Examples of binders include cellulose derivatives (carboxymethylcellulose, hydroxypropyl methylcellulose, hydroxypropyl cellulose, hydroxyethylcellulose, ethylcellulose, microcrystalline cellulose) and sugars such as lactose, sucrose, dextrose, glucose, maltodextrin, and mannitol, xylitol, polymethacrylates, polyvinylpyrrolidone, sorbitol, pregelatinized starch, alginic acids, and salts thereof such as sodium alginate, magnesium aluminum silicate, polyethylene glycol, carrageenan and the like. Generally, the amount of binder can vary widely, eg from 0% to 95% w/w of the composition. As noted above, excipients may serve multiple functions. For instance, the tabletting diluent may also serve as a binder.

Glidants are substances added to a powder to improve its flowability. Examples of glidants include magnesium stearate, colloidal silicon dioxide (such as the grades sold as Aerosil), starch and talc. Glidants may be present in the pharmaceutical composition at a level of from 0 to about 5% w/w. Again, however, it should be noted that excipients may serve multiple functions. The lubricant, for example magnesium stearate, may also function as a glidant.

Examples of colours that may be incorporated into the pharmaceutical compositions of the invention include titanium dioxide and/or dyes suitable for food such as those known as FD&C dyes and natural colouring agents. A colouring agent is unlikely to be used in the powder mixture that is compressed in accordance with the aspects of the invention discussed above, but may form part of a coating applied to the composition, as described below, in which case the colouring agent may be present in the film coat in an amount up to about 2.0% w/w.

The tablet is desirably coated with a conventional film coating which imparts toughness, ease of swallowing, and an elegant appearance to the final product. Many polymeric film-coating materials are known in the art. A preferred film-coating material is hydroxypropylmethylcellulose (HPMC) or polyvinyl alcohol-part hydrolysed (PVA). HPMC and PVA may be obtained commercially, for example from Colorcon, in coating formulations containing excipients which serve as coating aids, under the registered trademark Opadry. Opadry formulations may also contain talc, polydextrose, triacetin, polyethyleneglycol, polysorbate 80, titanium dioxide, and one or more dyes or lakes. Other suitable film-forming polymers may also be used, including hydroxypropylcellulose, vinyl copolymers such as polyvinyl pyrollidone and polyvinyl acetate, and acrylatemethacrylate copolymers. Use of a film coating is beneficial for ease of handling and because a blue coloured uncoated core may stain the inside of the mouth during swallowing. Coating also improves light stability of the dosage form.

Coating of the tablets may conveniently be carried out using a conventional coating pan. In preferred embodiments of the process, the coating pan is pre-heated using heated inlet air until the exhaust temperature reaches 35°-55° C., more preferably 40-50° C. This may typically require application of heated inlet air at an inlet temperature of 45-75° C., preferably 50-65° C., for 10-15 minutes. The tablet cores containing the active ingredient (e.g. LMTM) are then added to the coating pan and the aqueous film coat applied. The spray rate is controlled such that the bed temperature is maintained at 38-48° C., more preferably 42-44° C., until the desired weight gain (coating weight) has been achieved.

Dry Compression Methods

'Dry compression', as used herein, refers to compression techniques which do not involve the use of heat or moisture. Dry compression may comprise direct compression of the active ingredient with suitable diluents or it may comprise dry granulation (for example slugging/double compression method or roller compaction).

Direct compression may comprise simple direct compression of the active ingredient with diluents suitable for direct compression. Alternatively it may comprise granulation, for example moist granulation, of the excipients to produce a dry granular excipient mixture which can then be directly compressed with the dry active ingredient (and optionally further dry excipients). This may be referred to as 'extra-granular incorporation' of the active ingredient.

Accordingly, in some embodiments the solid dosage forms of the invention may be produced in a manufacturing process which comprises simple direct compression. In this embodiment, the tablet ingredients, i.e. the active ingredient (e.g. LMTM), diluent(s) and other optional excipients, are blended together in solid particulate form to create an intimate mixture, e.g. in a tumbling blender, and are then compressed using a tablet machine.

In other embodiments, the composition is prepared by a dry granulation process. Dry granulation refers to the process of granulating without the use of granulating fluids. In order for a material to be dry-granulated, at least one of its constituents, either the active ingredient or a diluent, must have cohesive properties. Dry granulation may be performed by a process known as "slugging". In "slugging", the material to be granulated is first made into a large compressed mass or "slug", typically using a tablet press with large flat-faced tooling (an example of a linear press is illustrated in U.S. Pat. No. 4,880,373). A fairly dense slug may be formed by allowing sufficient time for the air to escape from the material to be compacted. Compressed slugs are then milled through a desired mesh screen manually or automatically as, for example, by way of a comminuting mill. Formation of granules by "slugging" is also known as precompression. When tablets are made from the granulated slugged material, the process is referred to as the "double compression method".

Dry granulation may also be performed using a "roller compactor". In a roller compactor, material particles are consolidated and densified by passing the material between two high-pressure rollers. The densified material from a roller compactor is then reduced to a uniform granule size by milling. The uniform granules may then be mixed with other substances, such as a lubricant, to tablet the material (as, for example, by way of a rotary tabletting machine). In addition to pharmaceutical use, roller compaction is used in other industries, such as the food industry, animal feed industry and fertilizer industry.

Dry granulation is nowadays generally understood to mean roller compaction or slugging, and is well known to those skilled in the art (see, for instance, Pharmaceutical Dosage Forms: Tablets (Lieberman, Lachman, and Schwartz (Eds); Marcel Dekker, Inc, 2nd Edition, 1989) and Remington's Pharmaceutical Sciences (A. R. Gennaro (Ed); Mack Publishing Co, Easton, PA, 18th edition, 1990)).

In further embodiments of the invention, tablets are prepared by moist granulation of excipients and incorporation of the active ingredient (e.g. LMTM) extra-granularly. Typically, such a process involves wet massing diluents such as lactose and/or microcrystalline cellulose with water, optionally with the addition of a binder such as polyvinyl pyrrolidone. The wet mass is dried, then passed through a mesh, to form granules. The active ingredient and any remaining excipients, such as a lubricant, are then blended with the dry granules and compressed to form tablets.

Use of Acids in the Compositions of the Invention

Compositions containing leuco(methylthioninium) compounds, including compounds of the invention such as LMTM may, in some embodiments, be stabilised by addition of an appropriate amount of certain acids to the bulk substance prior to formulation. These acids may be used to prevent the formation of further MT, both during formulation and throughout the life of the product, thereby providing a stable pharmaceutical composition for the purposes of obtaining regulatory approval with associated cost savings in packaging.

According to the present invention, therefore, there is also provided a pharmaceutical composition comprising an active ingredient as described herein and a pharmaceutically acceptable carrier, characterised in that said formulation additionally comprises an acid in an amount sufficient to prevent the formation of MT. Without wishing to be bound by theory, it is thought that acids having a pK1 of greater than 1.5 are preferred. In some embodiments, the acid is present in an amount of from 5% to 25% w/w.

Preferably the composition is prepared by a dry compression method as described above.

Preferred acids for the purposes of the invention are maleic acid (pK1 1.9), phosphoric acid (pK1 2.12), ascorbic acid (pK1 4.17), sorbic acid (pK1 4.76), aspartic acid, and sialic acid. The stabilising effect of the added acid may be enhanced by the selection of an appropriate carrier. The carrier is preferably mannitol, a cellulosic material, or a starch, or mixtures thereof. The carrier is typically present in an amount of at least 40% w/w of the formulation.

Particle Size

It has also been found that a significant reduction in the formation of MT can also be achieved by the selection of an appropriate particle size range for the dry powder blend, typically wherein more than 10% of the particles have a size greater than 10 microns. Therefore according to another aspect of the invention, there is provided a pharmaceutical composition comprising an active ingredient as described herein and a pharmaceutically acceptable carrier, additionally characterised in that said composition comprises particles of which more than 10% have a size greater than 10 microns.

Carriers

It has been found that a significant reduction in the formation of MT can also be achieved by the choice of an appropriate carrier, particularly one having a particle shape which is averse to the entry of water. Elcema™, for example, which has long, lamellar particles which are smooth and flat in shape with a non-porous surface, appears to reduce MT formation by limiting the access of water. Ethylcellulose, mannitol and Starch 1500 TM and Microcrystalline cellulose are also particularly suitable for this purpose.

Therefore according to another aspect of the invention, there is provided a pharmaceutical composition comprising a leuco(methylthioninium) compound, for example a compound of the invention such as LMTM, and a pharmaceutically acceptable carrier, characterised in that said carrier is Elcema™, ethylcellulose, mannitol, or Starch 1500 TM.

Encapsulation

Stabilised dry powder blends in accordance with the invention may be formulated, for example, by compressing into tablets or filling into capsules (with or without prior conversion to a granulated powder by means such as described in Formulation Examples 1 to 4) to give pharmaceutical compositions having excellent shelf life.

Capsules according to the invention are typically of gelatin or preferably HPMC. Preferred excipients include lactose, starch, a cellulose, milk sugar and high MW polyethylene glycols.

Conclusions

Pharmaceutical compositions and formulations prepared according to the methods described above are more stable, immediately after completion of manufacture, than formulations produced using conventional aqueous granulation. Furthermore they can demonstrate enhanced stability on storage.

For example, a pharmaceutical formulation thus prepared, with a content of 10 to 50% by weight of LMTM, preferably 15% to 40% by weight of LMTM, makes it possible that in standard stability tests, for example in long term accelerated stability testing, at a temperature of 25° C. and a relative humidity 60±5% the content of L Azure B does not increase by more than 2%, relative to LMTM peak area, within a period of 24 months.

During processing and on storage leuco(methylthioninium) compounds, such as LMTM may also oxidise to produce a small amount of MT (see Scheme, above).

The presence of relatively small concentrations (e.g. less than 12%) of MT in the leuco-formulations of the present invention, although undesirable, is not considered to have adverse clinical significance per se as even if the body is presented with MT in its charged or oxidized form from LMTM and the various other leuco salts, this can then be reduced to the uncharged (reduced) MT form prior to absorption. In addition to the small amount of MT formed during processing such as blending and tabletting, leuco-methylthioninium salts of the present invention may react with oxygen absorbed on the excipients and present within the tablet to give more of the MT particularly in the presence of moisture.

One advantage of the formulations of this invention is to minimise the amount of MT formed in the tablets, e.g. to less than 12% over 2 years when stored at 25° C. at a relative humidity of 60%. This refers to the cumulative amount of MT formed during both processing and storage of the tablets: generally, the formulation methods of the invention result in less than 5% MT formation during processing; a maximum of around 5-7% MT is then formed during storage of the finished pack. This provides a shelf-life of at least 24 months.

This is demonstrated in the Formulation Examples, below.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the compound is in the range of about 100 ng to about 25 mg (more typically about 1 µg to about 10 mg) per kilogram body weight of the subject per day.

In some embodiments, the compound is administered to a human patient according to the following dosage regime: about 100 mg, 3 times daily.

In some embodiments, the compound is administered to a human patient according to the following dosage regime: about 150 mg, 2 times daily.

In some embodiments, the compound is administered to a human patient according to the following dosage regime: about 200 mg, 2 times daily.

EXAMPLES

The following examples are provided solely to illustrate the present invention and are not intended to limit its scope.

Example 1—Synthesis and Characterisation

Laboratory synthesis of 10-Acetyl-N,N,N',N'-tetramethylphenothiazine-3,7-diamine

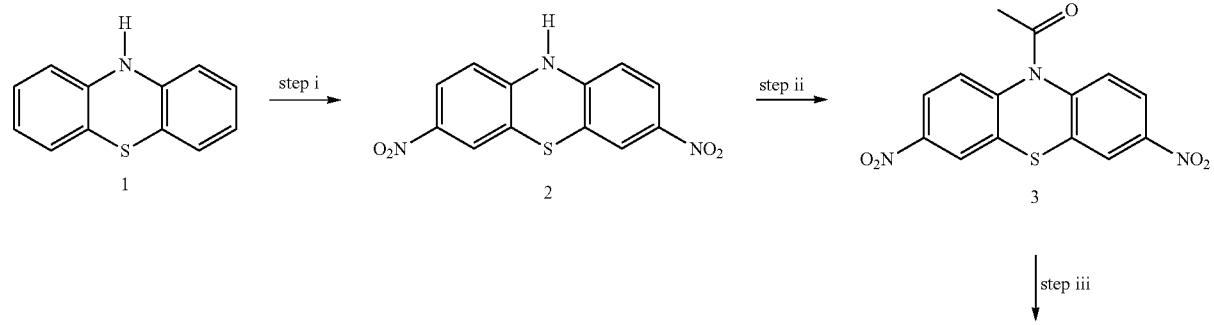

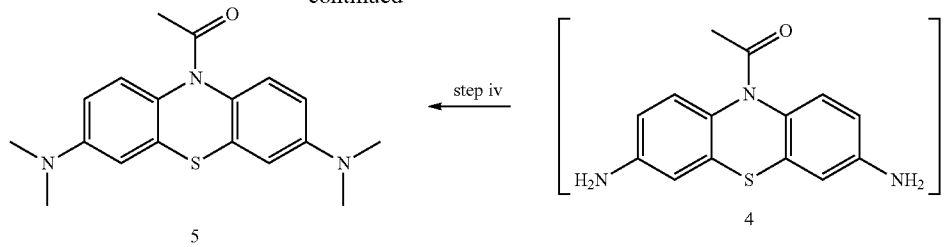

step i; NaNO₂, DMSO, CH₃COOH, step ii; (H₃CCO)O₂, Et₃N, DMF, step iii; Pd/C, 2-MeTHF, H₂ step iv; H₂CO, H₂
or step iii; Zn, (aq) NH₄Cl, MeOH, THF step iv; H₂CO, NaCNBH₃, CH₃COOH Synthesis of 3,7-dinitro-10H-phenothiazine (2)

To a 3 necked 1 litre round bottom flask (RBF) fitted with a thermometer, dropping funnel and a condenser was added phenothiazine (MW 199.28 g/mol, 25.00 g, 125.5 mmol) and dimethylsulfoxide (250 ml) the mixture was stirred for 2 minutes or until the phenothiazine dissolved. The condenser was then connected to a Dreschel bottle half filled with water. Sodium nitrite (MW 69.00 g/mol, 51.94 g, 752.7 mmol) was then added to the RBF and acetic acid (150 ml) was added to the dropping funnel. The acetic acid was then added to the RBF in a drop-wise fashion over a 20 minute period. The light yellow slurry becomes red in colour and a solid precipitated out of solution. Upon completion of the acetic acid addition the mixture was stirred for 2 hours at ambient temperature (36-20° C.) before increasing the temperature to 95° C. and stirring for 17 hours. After this time the mixture was cooled to 50° C. and methanol (100 ml) was added and the mixture cooled further to 22° C. The cooled mixture was then filtered and the cake washed with methanol (3×25 ml). The washed cake was left on the filter with the vacuum applied for 30 minutes before being dried for 15 hours at 50° C. to give the product as a brown solid (MW 289.27 g/mol, 29.45 g, 81%).

Notes

1. The addition of acetic acid produced NOx gases, which was converted to nitric acid by allowing the gas to bubble into a Dreschel bottle half filled with water.
2. The addition of acetic acid is exothermic and the mixture rises from 22° C. to 36° C.
3. Methanol was added to help dissolve any sodium acetate and as an anti-solvent to maximise the product yield.
4. The synthesis was also successful using dimethylformamide (DMF), acetonitrile (MeCN), tetrahydrofuran (THF), acetone or dimethoxyethane (DME) as the reaction solvent.

NMR: The product (5 mg) was dissolved in DMSO-d6 (1.5 ml) and may require to be warmed to completely dissolve the solid.

$\delta_H$(400 MHz; DMSO-d6): 6.72 (2H, d, J 8.8, ArH), 7.77 (2H, d, J 2.8, ArH), 7.87 (2H, dd, J 2.8, 8.8, ArH)

Synthesis of 3,7-dinitro-10-acetylphenothiazine (3)

To a 3 necked 500 ml round bottom flask fitted with a thermometer and a condenser was added 3,7-dinitro-10H-phenothiazine (MW 289.27 g/mol, 29.00 g, 100 mmol), dimethylformamide (58 ml), acetic anhydride (MW 102.09 g/mol, 102.09 g, 1000 mmol) and triethylamine (MW 101.19 g/mol, 40.88 g, 401 mmol). The mixture was heated to 105° C. and stirred at this temperature for 3 hours. The mixture was cooled to ambient temperature (21° C.) before being cooled to 5° C. whereby it was stirred for 1 hour. The product was isolated by filtration and washed with methanol (3×30 ml) to give a light yellow crystalline solid, which was dried at 50° C. for 15 hours (MW 331.31 g/mol, 26.94 g, 81%).

Notes

1. Crystals of the product form during the reaction, after ~1 hour at 105° C.
2. Upon cooling the bulk of the product precipitates at ~70° C.
3. Product was orange in colour before it was washed with methanol.

NMR: The product (10 mg) was dissolved in DMSO-d6 (1.5 ml).

$\delta_H$(400 MHz; DMSO-d6): 2.25 (3H, s, CH₃), 7.92 (2H, d, J 8.8, ArH), 8.28 (2H, dd, J 8.8, 2, ArH), 8.47 (2H, d, J 2, ArH)

Synthesis of 10-Acetyl-N,N,N'N'-tetramethylphenothiazine-3,7-diamine (5)

To a 3 necked 100 ml round bottom flask fitted with a thermometer and a condenser was added 3,7-dinitro-10-acetylphenothiazine (MW 331.31 g/mol, 5 g, 15.09 mmol), palladium on carbon (10%, dry, 0.5 g) and 2-methyltetrahydrofuran (25 ml). The flask was evacuated and purged with hydrogen 5 times before the mixture was heated to 56° C. After 17 hours the reduction was judged to have reached completion (see tlc conditions) giving compound 4, and formalin was added (MW 30.03 g/mol, 14.7 g, 181.1 mmol). The flask was once again evacuated and purged 5 times with hydrogen. After 71 hours from the addition of formalin (total time 88 hours) at 56° C. the tetra-methylation was judged to be complete by tlc. The mixture was filtered at 50° C., the grey catalyst was washed with 2-methyltetrahydrofuran (3×5 ml) and the filtrate and washings were combined. To this solution was added methanol (5 ml) to homogenise the mixture. Cooling to 5° C. resulted in a colourless solid precipitating from solution. A further two volumes of methanol (10 ml) were added and the slurry was stirred for 50 minutes at 5° C. The crude product was isolated by filtration to give a colourless solid, which was washed with methanol (3×5 ml) and dried at 50° C. for 16 hours (MW 327.45 g/mol, 2.26 g, 46%). The filtrate from the isolation process had water added (50 ml), which gave further solid. The suspension was stirred at 5° C. for 2 hours before being collected by filtration, washed with methanol (3×5 ml) and dried at 50° C. for 13 hours. (MW 327.45 g/mol, 0.83 g, 17%). The total yield of product was (3.09 g, 63%).

Notes

1. Normal phase tlc conditions, eluent 75% ethyl acetate, 25% petroleum spirit (40-60° C.), and UV lamp at 254 nm.

2. The retention factor of the dinitro starting material is 0.68 as a yellow spot, the retention factor of the hydrogenation product is 0.25 as a blue spot and the retention factor of the methylation product is 0.67 as a light blue spot.

3. The method for the tlc analysis of the hydrogenation step was direct spotting whereas the analysis of the methylation product had water added to a reaction aliquot which was extracted with ethyl acetate and then spotted.

4. After 17 hours the tlc shows two spots, the major spot was the reduction product the minor spot is unknown.

5. After 88 hours the tlc shows mainly the tetra-methylated product as the major spot.

6. Typically the reduction and methylation would be complete within 72 hours.

7. 1 H NMR spectroscopy of the two samples gave identical spectra, traces of 2-methyltetrahydrofuran were detected along with an unknown signal at 5 ppm.

NMR: The product (10 mg) was dissolved in CDCl$_3$ (1.5 ml).

$\delta_H$(400 MHz; CDCl$_3$): 2.09 (3H, s, CH$_3$), 2.86 (12H, s, NCH$_3$), 6.54 (2H, d, J 8, ArH), 6.64 (2H, s, ArH), 7.19 (2H, brd s, ArH)

Alternative Synthesis of 10-Acetyl-N,N,N'N'-tetramethylphenothiazine-3,7-diamine (5)

To a 50 ml round bottom flask was added 3,7-dinitro-10-acetylphenothiazine (MW 331.31 g/mol, 1 g, 3.02 mmol), zinc dust (MW 65.39 g/mol, 1.38 g, 21.13 mmol), methanol (6 ml) and tetrahydrofuran (2 ml). The mixture was heated to 50° C. after which a warm solution (45-50° C.) of aqueous ammonium chloride (MW 53.49 g/mol, 2.26 g, 42.26 mmol dissolved in 6 ml of water) was added slowly to maintain a gentle reflux. The mixture was then heated to 70° C. and stirred at this temperature for two hours after which it was cooled to ambient temperature (23° C.). The cooled mixture was filtered to remove the zinc salts and the filtrate containing compound 4 was treated with paraformaldehyde (MW 30.03 g/mol, 1.09 g, 36.22 mmol), sodium cyanoborohydride (MW 62.84 g/mol, 1.14 g, 18.11 mmol) and acetic acid (2 ml). The mixture was heated to 50° C. and stirred at this temperature for 3 hours. After cooling to ambient temperature (23° C.), water (2×10 ml) was added and the colourless slurry was stirred for 16 hours. The solid was then collected by filtration and washed with methanol (3×2 ml) to give the title compound (MW 327.45 g/mol, 0.91 g, 92%) as an off-white solid.

Notes

1. Reduction reaction using zinc and aqueous ammonium chloride was fast and clean taking only 2 hours to reach completion with no other spots recorded by tlc analysis.

2. The reductive methylation using sodium cyanoborohydride, paraformaldehyde and acetic acid was fast and clean, taking only 3 hours to reach completion.

NMR: The product (10 mg) was dissolved in CDCl$_3$ (1.5 ml).

$\delta_H$(400 MHz; CDCl$_3$): 2.17 (3H, s, CH$_3$), 2.94 (12H, s, NCH$_3$), 6.61 (2H, d, J 8, ArH), 6.71 (2H, s, ArH), 7.26 (2H, brd s, ArH)

Synthesis 1: Synthesis of N,N,N',N'-tetramethyl-10H-phenothiazine-3,7-diaminium bis(methanesulphonate) (LMT.2MsOH)

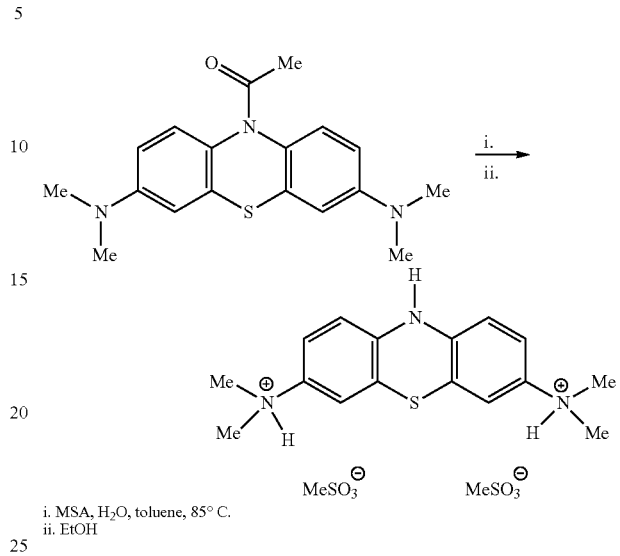

i. MSA, H$_2$O, toluene, 85° C.
ii. EtOH

10-Acetyl-N,N,N'N'-tetramethyl-10H-phenothiazine-3,7-diamine (AcMT) (150 g) was added to a 3-neck round bottomed flask. Toluene (1.8 l) was added and the mixture heated to reflux for 30 min. The solution was allowed to cool to 70° C. before being passed through an in-line 5μ filter to a jacketed vessel fitted with distillation apparatus.[1] Toluene (150 ml) was added to the round bottom flask. This was used to rinse the transfer line and filter. Approximately 1.4 l. of toluene was distilled off under reduced pressure.[2] The temperature was lowered to 18° C. before water (42 ml) was added.[3] This was followed by the addition of methanesulphonic acid (MSA) (65.5 ml, 99%, 2.2 equiv.) over a 5 min. period.[4] A second portion of water (18 ml) was added. The mixture was heated to 85° C. for 3 h by which time the reaction was judged complete by tlc analysis. The biphasic solution was allowed to cool to 50° C. before absolute EtOH (150 ml) was added over 20 min.[5] The mixture was seeded using 150 mg of N,N,N',N'-tetramethyl-10H-phenothiazine-3,7-diaminium bis(methanesulphonate).[6-8] A second portion of EtOH (600 ml) was added over 90 min.[9] and the reaction allowed to cool to 20° C. over 1 h.[10] It was stirred at this temperature for 1 h. before the solid was collected by filtration. The cake was washed with 3×300 ml of MeCN,[11] sucked dry for 5 min. and placed under vacuum overnight to give the product as a yellow crystalline solid (85-90% yield).

$\nu_{max}$ (KBr)/cm$^{-1}$; 3430 (NH), 3014 (=CH), 2649 (C—H), 1614 (C=C), 1487 (C—C), 1318 (S=O), 1199 (SO2-O), 1059 (S=O), 823 (ArC=—H)

$\delta_H$(600 MHz; CD$_3$OD); 2.71 (6H, s, SCH$_3$), 3.21 (12H, s, NCH$_3$), 6.75 (2H, d, J 8.8 Hz, ArH), 7.22 (4H, d J 2.9 Hz, ArH), 7.24 (4H, dd J 2.9, 8.8 Hz, ArH), $\delta_C$(100 MHz; CD$_3$OD); 38.2 (SCH$_3$), 45.9 (NCH$_3$), 115.0 (CH), 118.2 (CH), 118.7 (QC), 119.9 (OH), 137.1 (CH), 142.8 (QC)

MP: 271° C.

m/z (EI+): Calculated 285.129970; Observed 285.131292 (100%, [M-2MSA]+).

m/z (ES−): Calculated 95; Observed 95 (100%, [M-LMT]$^-$).

Elemental analysis % (C$_{18}$H27N3O6S3): Calculated C (45.26), N (8.80), S (20.14), H (5.70);

Observed C (45.19), N (8.76), S (19.84), H (5.53)

Notes

1. Heating to reflux ensures complete dissolution of AcMT for transfer through 5 filter. Toluene is a good solvent and a 70° C. target is a compromise between ensuring the material stays in solution and minimising potential damage to plastic transfer hoses and filter.

2. 500 ml of remaining toluene ensures reaction volume meets minimum stir depth of reactor.

3. Volume of water is controlled to ensure product crystallises out as a free flowing precipitate. Seeding the reaction reduces the impact of small variations in water volume.

4. 2.2 equivalents of MSA are used to effect the hydrolysis and form the salt whilst leaving a sufficient quantity of excess acid (0.2 equiv.) to ensure the stability of the product in solution. Addition of MSA causes a slight exotherm, hence the 5 minute addition time.

5. EtOH is used as counter solvent to precipitate the product. A portion is added before the seed to ensure the seed does not dissolve. An extended addition time ensures controlled crystallisation of the product (see notes 7 and 8).

6. It is possible to carry out the reaction without the use of a seed, however its incorporation ensures the early precipitation of LMT.2MsOH which in turn prevents formation of by-products (such as the alcohol ester EMS a potential genotoxic by-product—not detected in the synthetic process) and encapsulation of EtOH.

7. The seed is also useful as a means of controlling the particle size of the product. When the seed material was used which has been ground in a mortar and pestle to <100 m a significant reduction in the average particle size of the product is observed. When <100 seed which had not been ground was used no such effect was observed. Therefore, without wishing to be bound by theory, it appears that the ability of the seed to control the particle size is not a function of the seed particle size, it is linked to the proportion of internal or 'new' crystal faces that the crushing of the seed has exposed.

8. Finally, when the seed material was relatively large and uncrushed a considerable amount of product (skin) may adhere to the side of the reactor vessel during the EtOH addition. This may be reduced by introducing a heat/cool cycle into the process after the EtOH addition. However, an unexpected bonus of the utilisation of the crushed seed was that the level of skinned material present after EtOH addition was reduced by ~90%. Therefore it was no longer necessary to carry out the heat/cool cycle. It seems that this is linked to the small seed size rather than new faces because when the reaction was carried out using uncrushed <100 seed the same reduction in skinning was observed.

9. The rate of EtOH addition has an effect on particle size and EtOH inclusion. Fast addition (<1 h) reduces particle size however EtOH inclusion increases. A slow addition (2 h) has the opposite effect hence a balance must be struck.

10. Rate of cooling has a similar although reduced effect. Fast cool down (<1 h) leads to reduction in particle size with a concomitant increase in EtOH levels. A slow cool has the opposite effect.

11. EtOH is equally effective as MeCN at removing the related substances, however its use is accompanied by a slight increase in the level of retained EtOH.

Characterisation of N,N,N',N'-tetramethyl-10H-phenothiazine-3,7-diaminium bis(methanesulphonate) (LMT.2MsOH)

Elemental Analysis (Microanalysis)

The analysis has good correlation between the theoretical values and the analysis values for carbon, nitrogen, hydrogen and sulphur.

Results of the elemental analysis:

| | Molecular Formula $C_{18}H_{27}N_3O_6S_3$ | |
|---|---|---|
| Element | % Theoretical | % Found |
| C | 45.26 | 45.19 |
| H | 5.70 | 5.53 |
| N | 8.80 | 8.76 |
| S | 20.14 | 19.84 |

1H—Nuclear Magnetic Resonance (NMR) Spectroscopy

Figure 1:
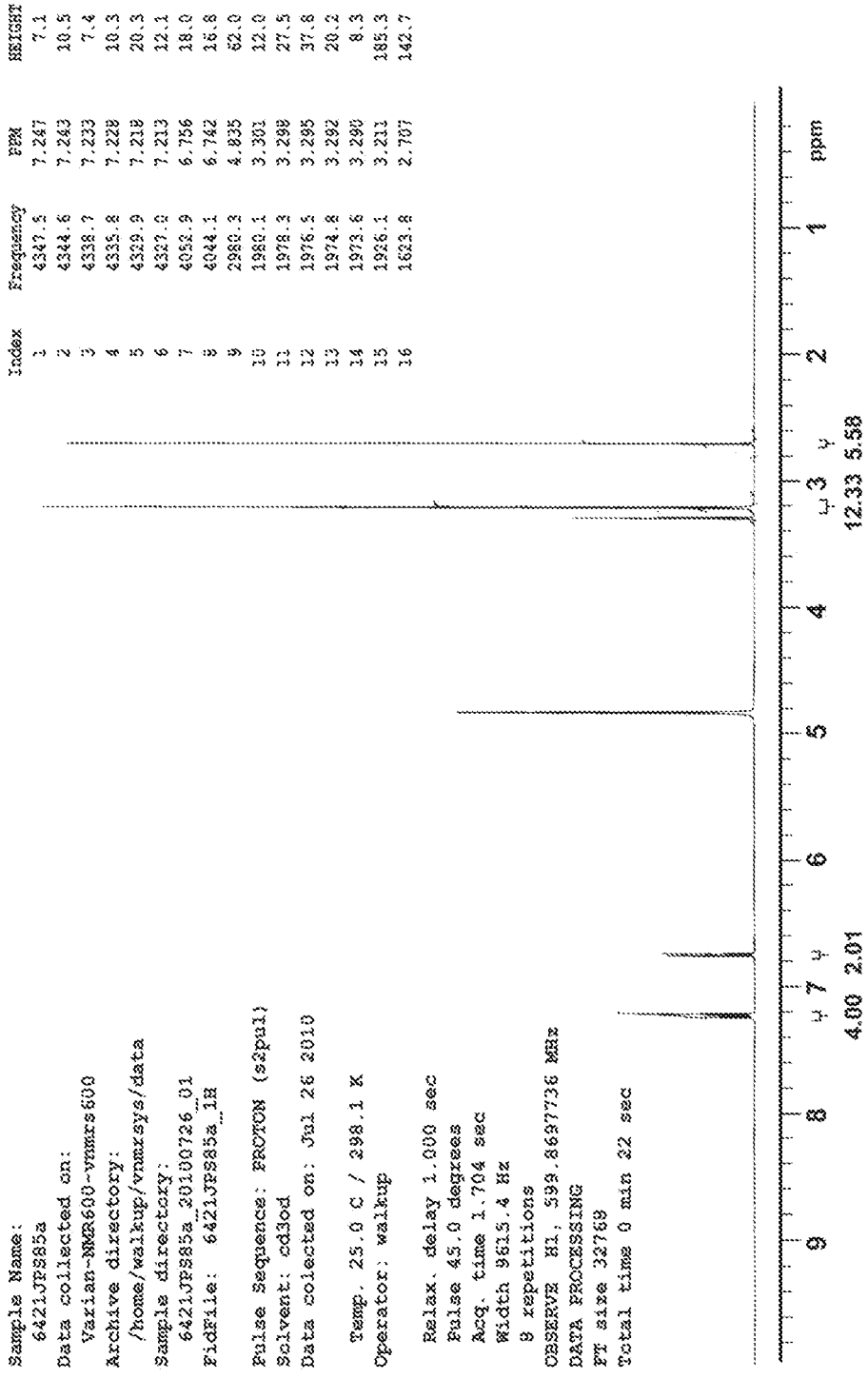
FIG. 1 shows the $^1$H NMR spectrum of an exemplary compound of the invention (LMT.2MsOH) in deuterated methanol (CD$_3$OD) at 600 MHz.

The $^1$H NMR spectrum was obtained in deuterated methanol $CD_3OD$, on a Varian 600 MHZ instrument and is shown in FIG. 1.

Assignment of the $^1$H NMR spectrum is below:

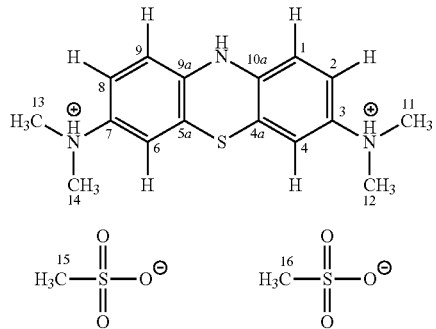

| Assignment | Chemical shift (PPM) | Protons | Group |
|---|---|---|---|
| 15/16 | 2.71 | 6H, s | 2 × $SCH_3$ |
| 11/12/13/14 | 3.21 | 12H, s | 2 × $N(CH_3)_2$ |
| 1/9 | 6.75 | 2H, d, 8.8 Hz | 2 × C—H (Aromatic) |
| 4/6 | 7.22 | 2H, d, 2.9 Hz | 2 × C—H (Aromatic) |
| 2/8 | 7.24 | 2H, dd, 8.8 and 2.9 Hz | 2 × C—H (Aromatic) |

$^{13}$C—Nuclear Magnetic Resonance (NMR) Spectroscopy

Figure 2:
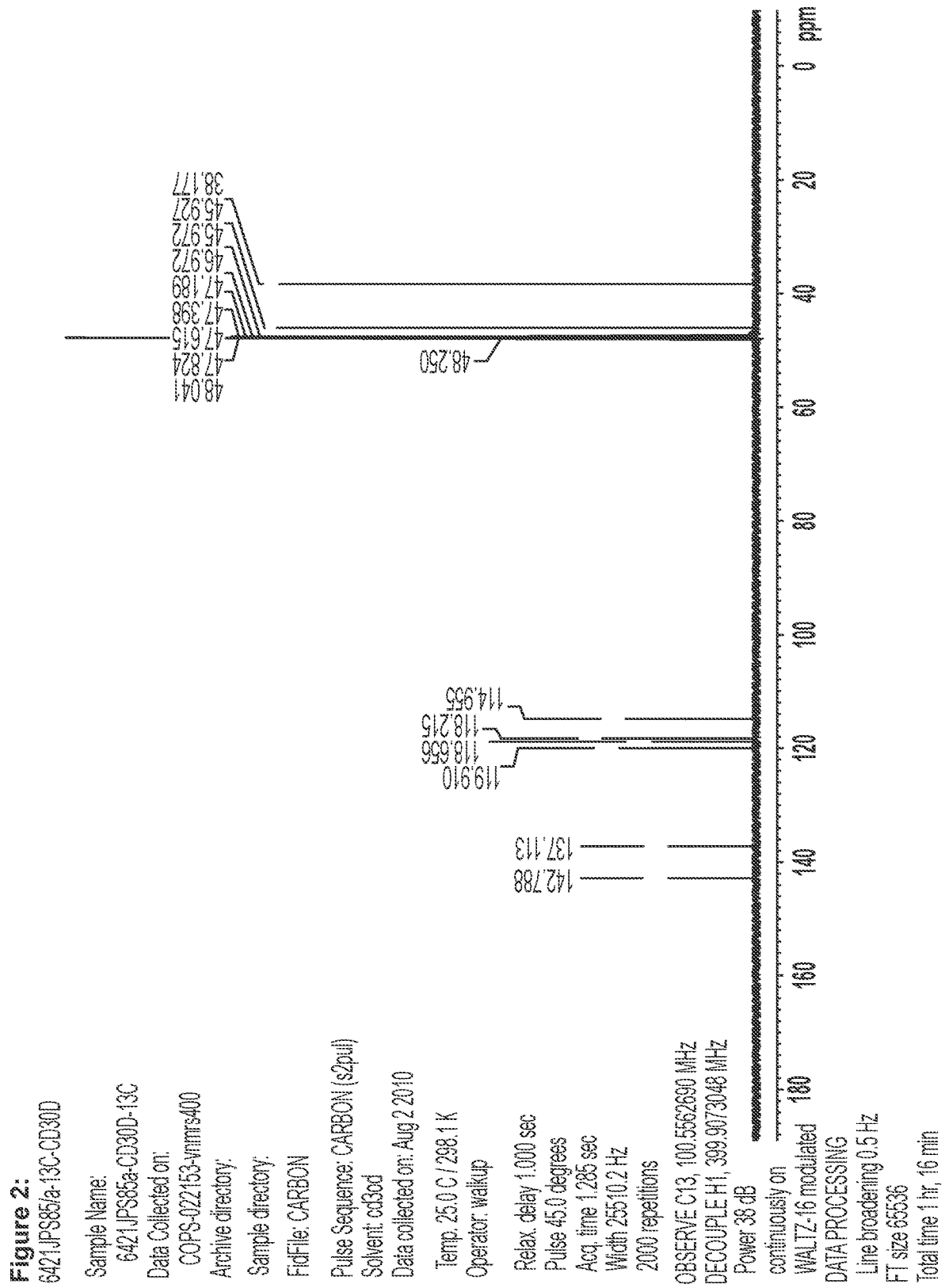
FIG. 2 shows the $^{13}$C NMR spectrum of LMT.2MsOH in CD$_3$OD at a frequency of 100.56 MHz.

The $^{13}$C NMR spectrum was obtained on a Varian 400 MHz NMR instrument at a frequency of 100.56 MHz in deuterated methanol $CD_3OD$ and is shown in FIG. 2.

The initial assignment of the $^{13}$C-NMR spectrum was based on correlation with charts of known chemical shifts, (Literature Reference: Structure Determination of Organic Compounds: Tables of Spectral Data, Pretsch E., et al., Springer, London, p 122).

Figure 3:
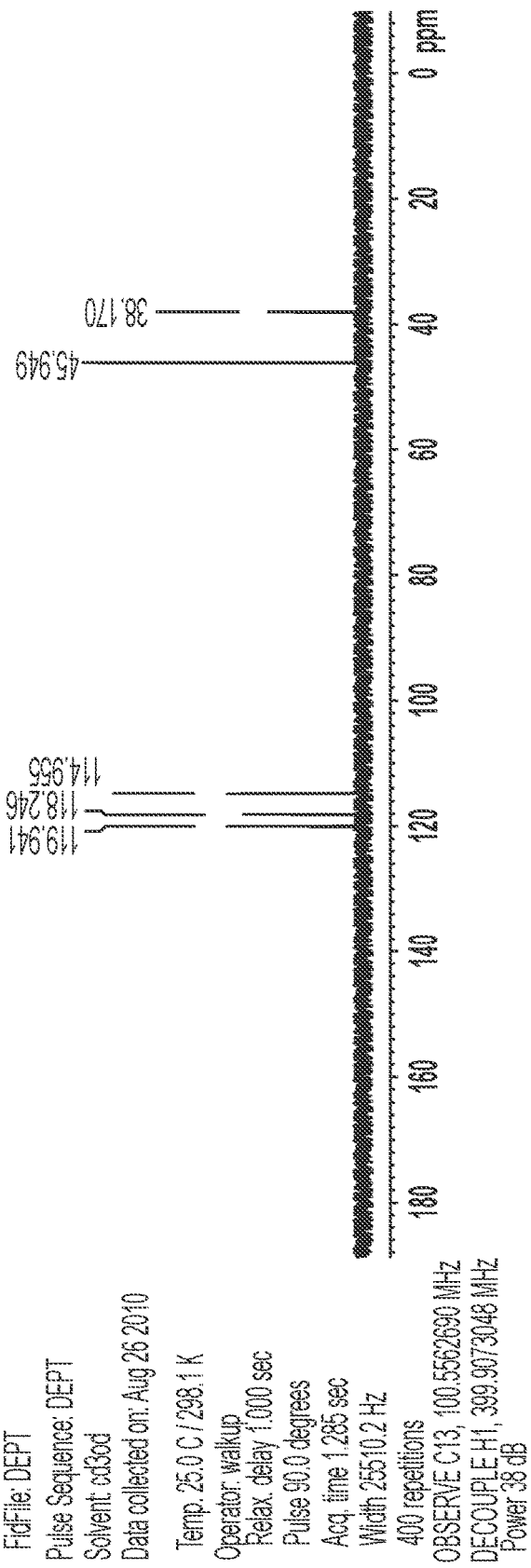
FIG. 3 shows the DEPT-135 spectrum of LMT.2MsOH in CD$_3$OD at a frequency of 100.56 MHz.
Figure 4:
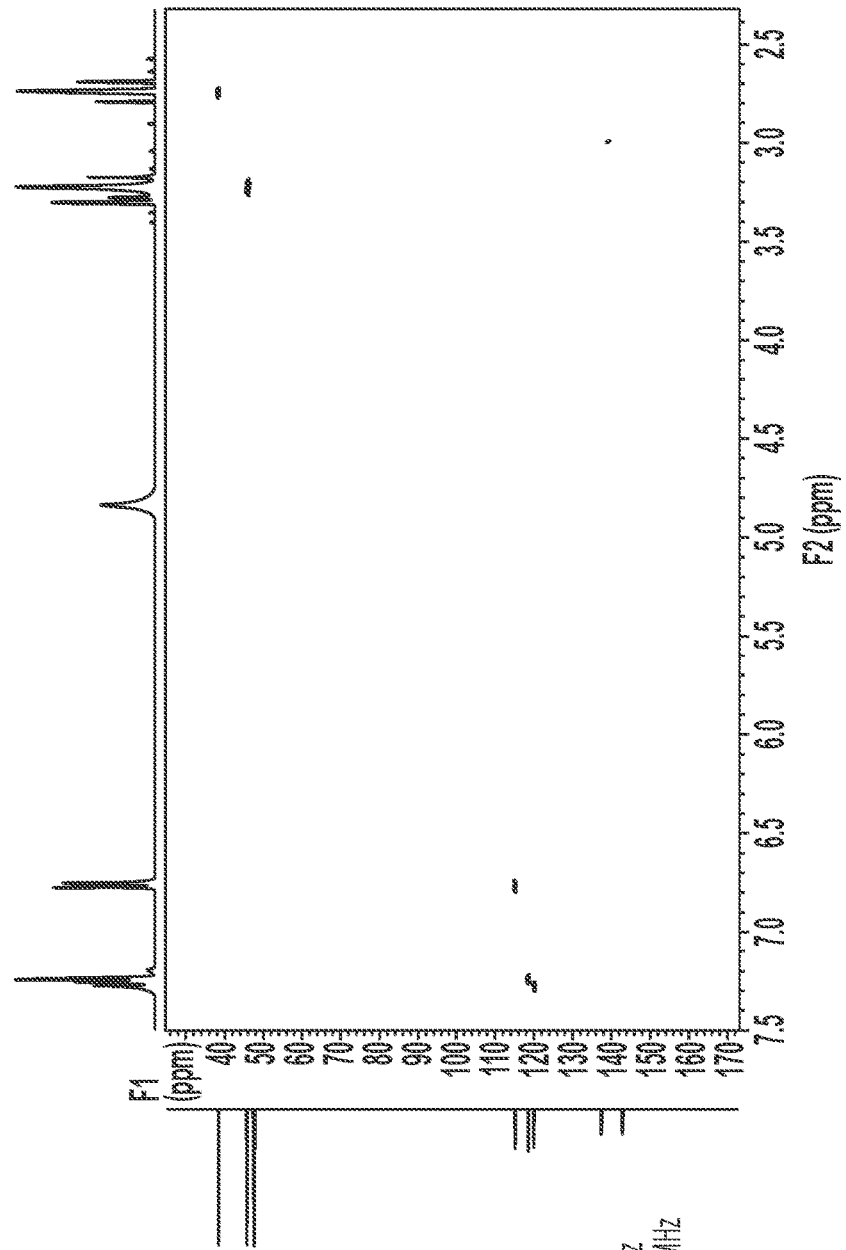
FIG. 4 shows the HSQC spectrum of LMT.2MsOH in CD$_3$OD at a frequency of 100.56 MHz.
Figure 5:
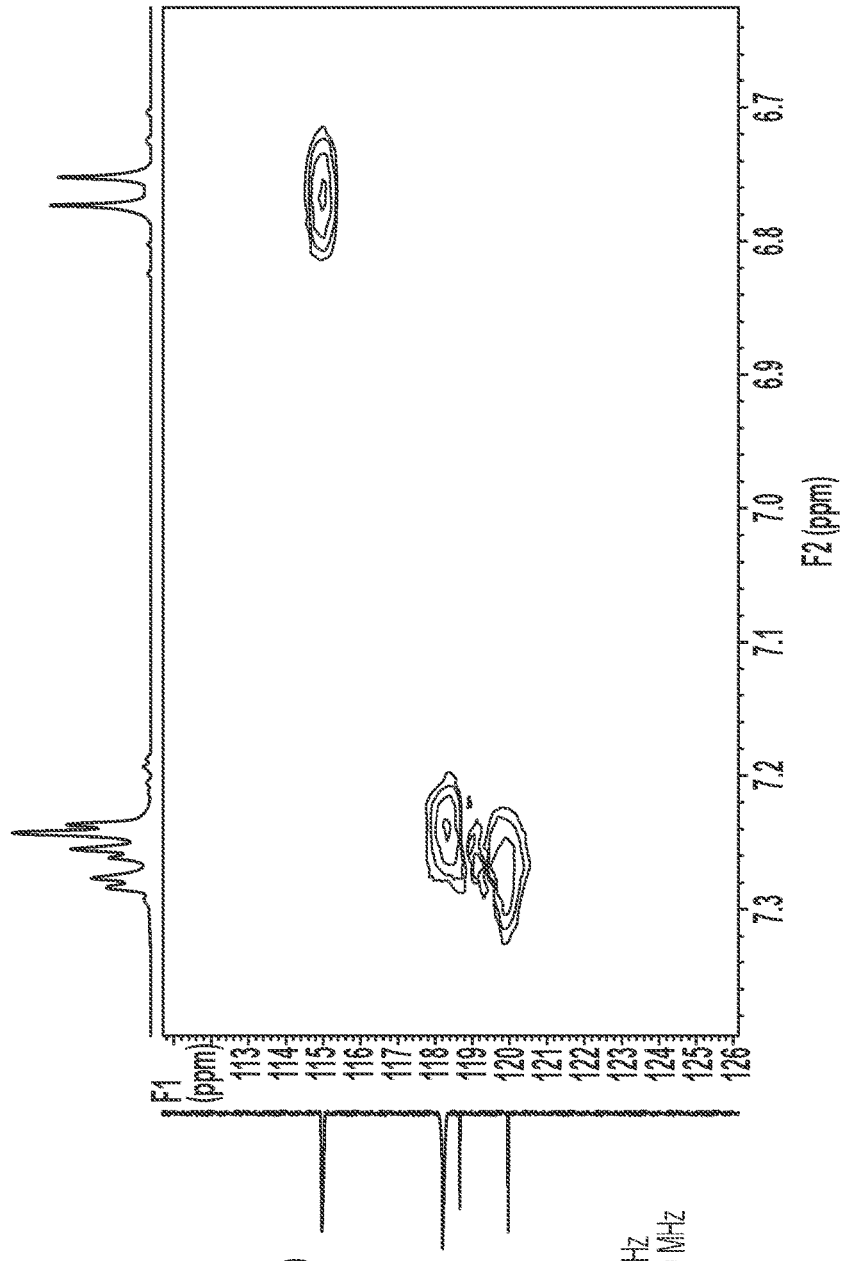
FIG. 5 shows the an expanded section of the HSQC spectrum of LMT.2MsOH in CD$_3$OD at a frequency of 100.56 MHz.

Further assignments utilised DEPT-135, HSQC and HMBC experiments to unambiguously confirm the assignments. DEPT-135 (Distortionless Enhancement by Polarisation Transfer), HSQC (Heteronuclear Single Quantum Coherence) and HMBC (Heteronuclear Multiple Bond Correlation) spectra were obtained on a Varian 400 MHz NMR instrument at a frequency of 100.56 MHz (see FIGS. 3-5).

| Assignment | Chemical shift (PPM) | NMR Region | DEPT-135 |
| --- | --- | --- | --- |
| 15/16 | 38.2 | Alkyl | $CH_3$ |
| 11/12/13/14 | 45.9 | Alkyl | $CH_3$ |
| 1/9 | 115.0 | Aromatic-C | CH |
| 4/6 | 118.2 | Aromatic-C | CH |
| 4a/5a | 118.7 | Aromatic-C | C |
| 2/8 | 119.9 | Aromatic-C | C |
| 3/7 | 137.1 | Aromatic-C | CH |
| 9a/10a | 142.8 | Aromatic-C | C |

Infrared Spectroscopy (IR)

Figure 6:
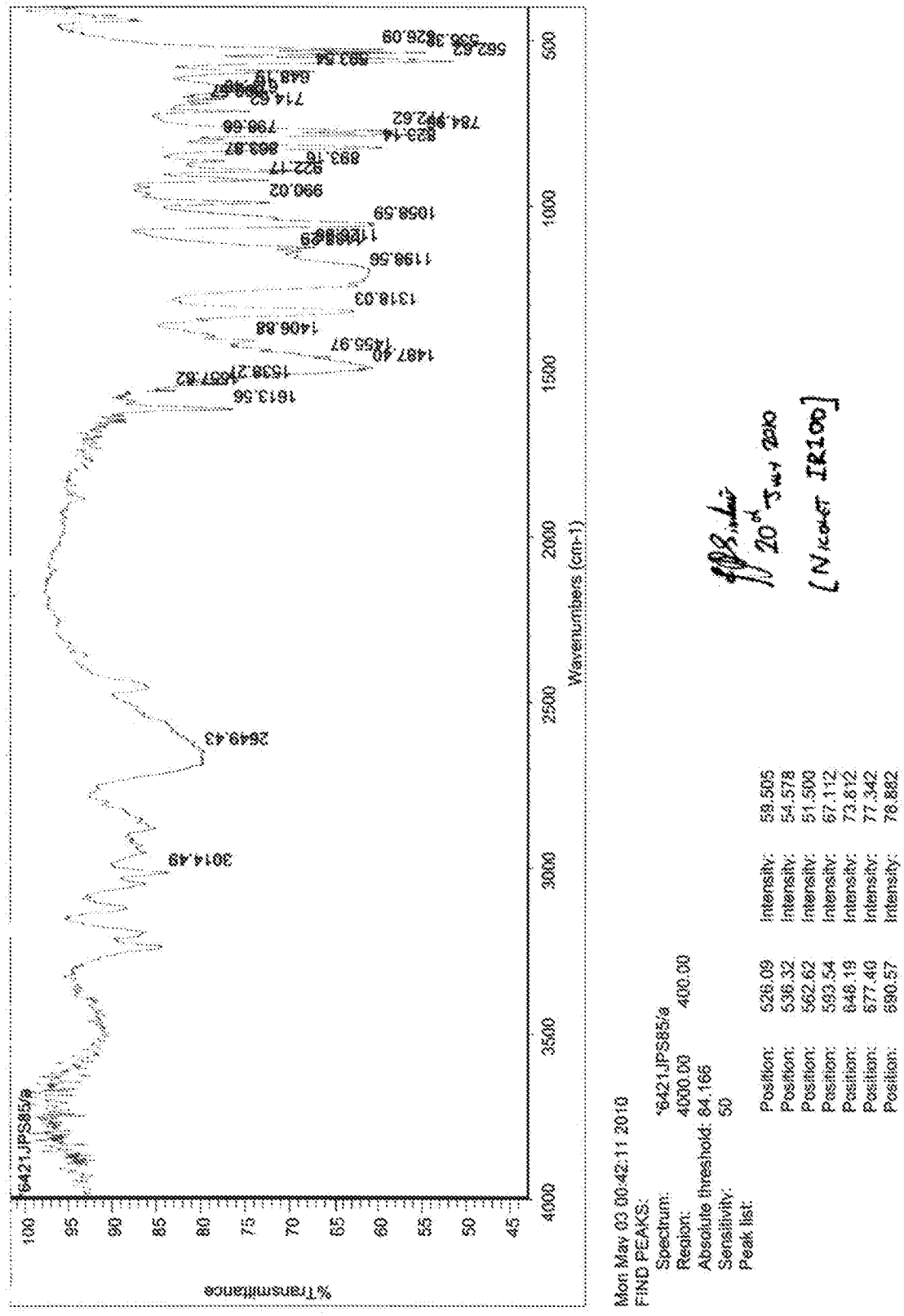
FIG. 6 shows the infrared (FT-IR) spectrum of LMT.2MsOH (KBr).

A sample was thoroughly mixed and ground in a mortar and pestle with 200 mg of anhydrous KBr. This mixture was then pressed into a disc, using a die at a pressure of 1500 psi. The IR spectrum was then obtained on a Nicolet Avatar 320 FT-IR spectrometer. The spectrum is shown in FIG. 6.

Assignment of the infrared spectrum:

| Peak Wavenumber ($cm^{-1}$) | Peak Type | Assignment |
| --- | --- | --- |
| ~3430 | broad | N—H stretch |
| 3014 | medium | =C—H stretch |
| 2649 | medium | C—H stretch |
| 1614 | medium | C=C stretch |
| 1487 | strong | C—C stretch |
| 1318 | strong | S=O stretch |
| 1199 | strong | $SO_2$—O stretch |
| 1059 | strong | S=O stretch |
| 823 | strong | Aromatic C—H stretch |

Mass Spectrometry (MS)

Mass spectroscopic analysis was carried out using a Waters, LCT Premier XE mass spectrometer. A flow rate of 1 ml/hr was adopted. The source used for the analysis of the active component was electron impact ionisation in the positive mode. The source used for the analysis of the methanesulphonate counter ion was electrospray ionisation in the positive mode.

Figure 7:
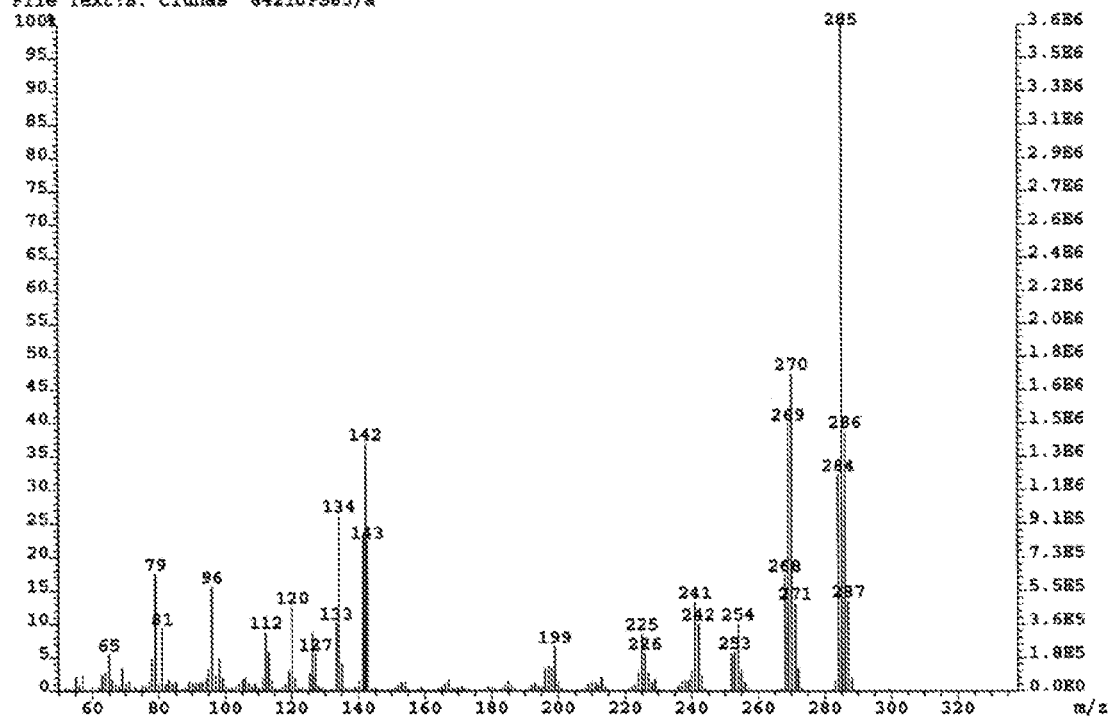
FIG. 7 shows the electron impact (EI) mass spectrum of LMT.2MsOH.

Using electron impact ionisation a major peak is observed at 285 (see FIG. 7). This corresponds to the molecular ion $C_{16}H_{19}N_3S$. A comparison of the exact mass measured and the theoretical value is provided below:

| Theoretical | Peak m/z | Abundance (%) | Assignment |
| --- | --- | --- | --- |
| 285.129970 | 285.131292 | 100 | $C_{16}H_{19}N_3S$ |

The measured accurate mass is in good agreement with the calculated mass for $C_{16}H_{19}N_3S$.

Figure 8:
FIG. 8 shows the electrospray ionisation (ESI) mass spectrum of LMT.2MsOH.

Using electrospray ionisation a major peak is observed at 95 (see FIG. 8). This corresponds to the molecular ion of the counter ion $CH_3O_3S$:

| Peak m/z | Abundance (%) | Assignment |
| --- | --- | --- |
| 95 | 100 | $CH_3O_3S$ |

Ultraviolet-Visible Spectroscopy (UV-Vis)

Figure 9:
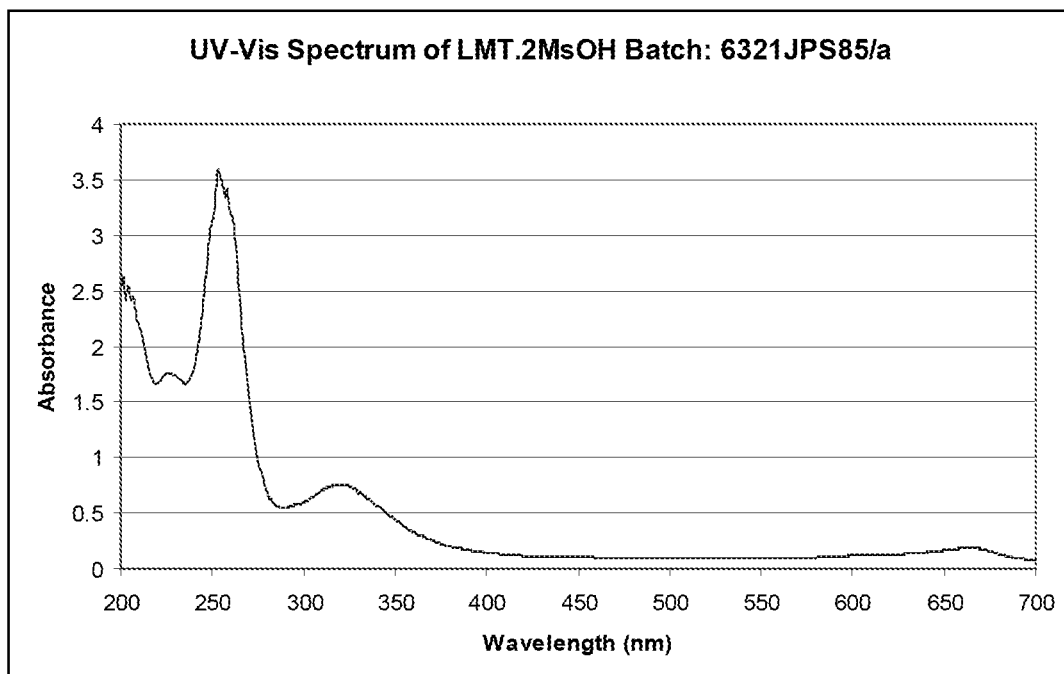
FIG. 9 shows the UV/Vis spectrum of LMT.2MsOH in de-ionised water.

A 5 mg sample was dissolved in de-ionised water, and made up to 100 ml in a volumetric flask. The analysis was carried out using quartz curvets in a Perkin Elmer Lambda 25 UV/Vis spectrometer. The UV-Vis spectrum is shown in FIG. 9.

Assignment of the UV-Vis Spectrum:

| $\lambda_{max}$ (nm) | Absorbance |
| --- | --- |
| 226 | 1.7615 |
| 255 | 3.5860 |
| 332 | 0.7527 |
| 664 | 0.1845 |

The extinction coefficient E for the lambda max at 255 nm was 34254.64. This was calculated according to the Beer-Lambert Law:

$$\varepsilon = \frac{A}{C \times l}$$

where A=Absorbance Log ($I_0/I$) 3.5860; C=Concentration Mol/L; l=path length 1 cm High Performance Liquid Chromatography (HPLC)

A 100 mg sample was submitted for HPLC analysis. The analysis was carried out on an Agilent 1200 series with VWD Detector or PDA for identity, according to the method summarised in the table below.

HPLC Method:

| Parameters | Conditions |
| --- | --- |
| Column | Zorbax SB-CN, 50 × 4.6 mm, 3.5 μm. |
| Column temperature | 283 K |
| Mobile phase | A: 0.1% v/v Formic acid in water |
| | B: 100% acetonitrile |
| Flow rate | 1 ml/min |
| Injection volume | 5 μl |
| Stop time | 22 min. |
| Wavelength | UV at 255 nm Bandwidth at 4 nm. |
| | Reference wavelength set at off. |
| | PDA scan 190 nm to 800 nm (Identity only) |
| Auto sampler temperature | 278 K Protected from light. |

| | Time (min.) | Mobile Phase A (%) | Mobile Phase B (%) |
| --- | --- | --- | --- |
| Mobile Phase Gradient | | | |
| | 0.0 | 100 | 0 |
| | 10.0 | 90 | 10 |
| | 17.0 | 50 | 50 |
| | 18.0 | 50 | 50 |
| | 18.1 | 100 | 0 |
| | 22.0 | 100 | 0 |

Figure 10:
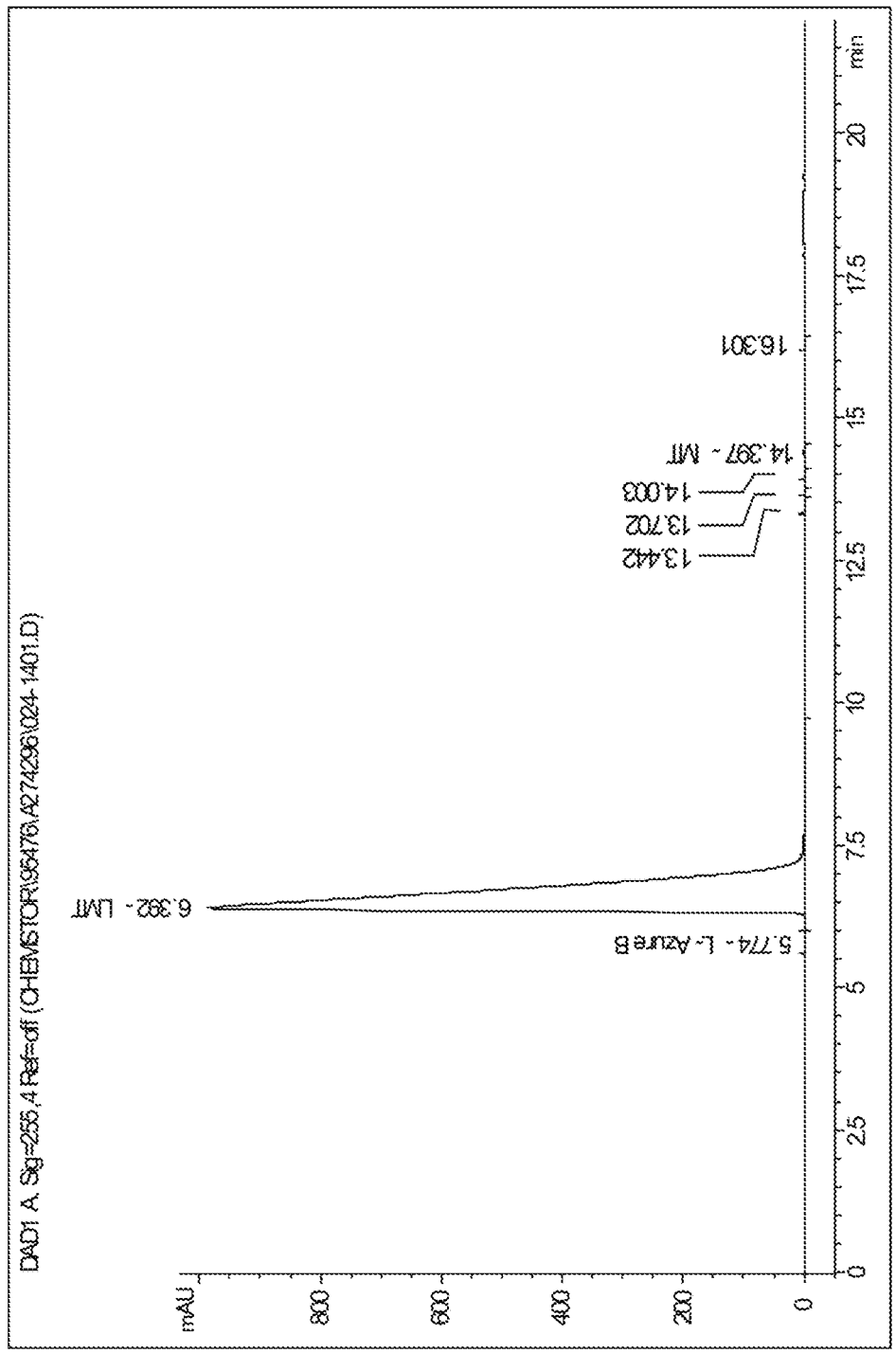
FIG. 10 shows the HPLC trace for LMT.2MsOH.

The HPLC trace is shown in FIG. 10. The organic purity was found to be 99.45% w/w.

| HPLC Analysis (% Purity) including retention times | | |
| --- | --- | --- |
| LMT | $MT^+$ | Leuco Azure B |
| 6.39 min. | 14.38 min. | 5.77 min. |
| 99.45 | 0.55 | <0.05 |

Crystalline Form

In the above-described method, LMT.2MsOH is produced in crystalline form. The crystalline form of LMT.2MsOH is illustrated by the X-ray powder diffraction spectrum shown in FIG. 11. The XRPD exhibits sharp signals, indicative of a high degree of crystalline order. Variations in relative peak intensity may be observed, which are attributable to orientation effects in combination with differences in particle size.

Only slight variations in relative peak intensity (less than 50%) are observed as a function of sample thickness (0.1 mm vs. 1.0 mm).

The crystal form is further characterised by FT-Raman, thermogravimetric (TG), differential scanning calorimetric (DSC), dynamic vapour sorption (DVS) analysis, and microscopy (FIGS. 12-16). This form may conveniently be referred to as 'Form A'.

Crystals for single crystal X-ray analysis were obtained from ethanol, methanesulfonic acid and water. See FIG. 17c.

Instrumental Details

X-Ray Powder Diffraction: Bruker 08 Advance, Cu Kα radiation (λ=1.54180 Å), 40 kV/40 mA, LynxEye detector, 0.02° step size in 2θ, 37 s per step, 2.5°-50° 2θ scanning range. The samples were prepared on silicon single crystal sample holders with 0.1 or 1.0 mm depth without any special treatment other than the application of slight pressure to get a flat surface. All samples were rotated during the measurement.

Differential Scanning Calorimetry: Perkin Elmer DSC 7. Gold crucibles closed under $N_2$, heating rate 20° C./min, scan from −50° C. to 280° C.

Dynamic Vapor Sorption: Projekt Messtechnik SPS 11-100n water vapor sorption analyzer. The samples were placed in aluminum crucibles on top of a microbalance and were equilibrated at 25° C. and 50% r.h. before starting a pre-defined humidity program at 25° C. (50-0-95-50% r.h., scanning with Δ r.h.=5% h$^{-1}$ and with 'isohumid' equilibration periods at the extreme values).

FT-Raman Spectroscopy: Bruker RFS100. Nd:YAG 1064 nm excitation, 50 mW laser power, Ge-detector, 128 scans, range 50-3500 cm$^{-1}$, 2 cm$^{-1}$ resolution. Aluminum sample holder.

Polarizing Light Microscopy: Leitz Orthoplan microscope with Leica OFC280 CCO camera.

TG: TA Instruments TGA Q5000. Open aluminum crucible, $N_2$ atmosphere, heating rate 10° C. min$^{-1}$, range 25-300° C.

TG-FTIR: Netzsch Thermo-Microbalance TG 209 with Bruker FT-IR Spectrometer Vector 22. Aluminum crucible with micro-hole, N2 atmosphere, heating rate 10° C. min$^{-1}$, range 25-250° C.

Without wishing to be bound by theory, it is suggested that this form represents the only stable polymorphic form of LMT.2MsOH. Polymorphism studies have shown that Form A is reproduced in nearly all crystallisation systems (studies were performed using de-gassed solvents, under an inert atmosphere).

Amorphous LMT.2MsOH can be prepared by evaporation of an aqueous solution of LMT.2MsOH, however the amorphous material recrystallises to Form A upon further drying.

Industrial Scale Synthesis of AcMT and LMT.2MsOH

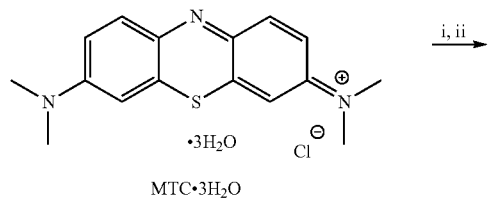

MTC·3H₂O

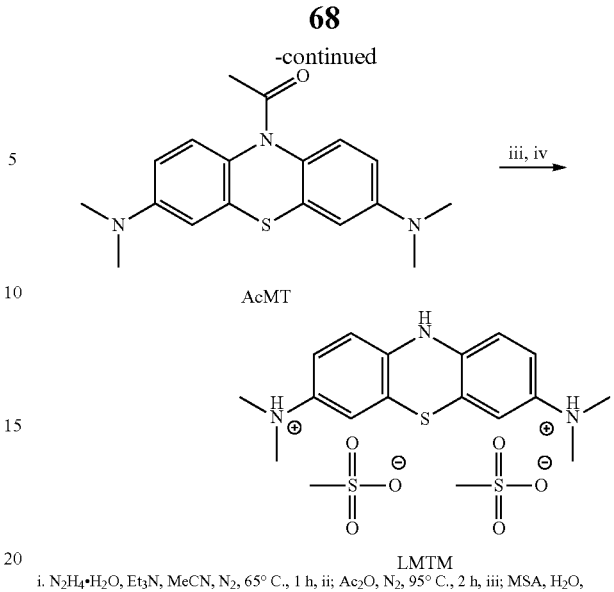

i. N₂H₄·H₂O, Et₃N, MeCN, N₂, 65° C., 1 h, ii; Ac₂O, N₂, 95° C., 2 h, iii; MSA, H₂O, Toluene, N₂, 85° C., iv; EtOH.

Large Scale Synthesis of 10-acetyl-N,N,N'N'-tetramethyl-10H-phenothiazine-3,7-diamine (AcMT)

Acetonitrile (MeCN) (300 l) was added to reactor 1 (R1) and cooled to −5-0° C. Methylthioninium chloride trihydrate (MTC.3H₂O) (150 kg) was added and the temperature increased to 15-25° C. Triethylamine (Et₃N) (100 l) was added followed by MeCN rinse (20 l). Hydrazine hydrate (N₂H4. H₂O) (12 l) was added over 30 min. The reaction temperature was increased to 60-70° C. over 1 h and then maintained at this temperature for 1 h before being reduced to 40-50° C. Acetic anhydride (Ac₂O) (240 l) was added over 1 h followed by MeCN (20 l) rinse. Batch temperature was increased to 90-100° C. for 2 h. Temperature was reduced to 55-65° C. and water (340 l) was added over 2 h whilst maintaining the temperature. The batch temperature was then reduced to −5-5° C. over 2 h. and held there for 6 h. The solid was collected by filtration. The cake was fully de-liquored before water (400 l) was added to R1. The temperature in R1 was allowed to rise to 15-25° C. before the water was used in portions to wash the filter cake. The product was dried under a stream of nitrogen for 6 h. before being offloaded (Yield: 90-110 kg).

Large Scale Purification of 10-acetyl-N,N,N'N'-tetramethyl-10H-phenothiazine-3,7-diamine (AcMT)

Water (300 l) was added to R1, followed by 10-Acetyl-N,N,N'N'-tetramethyl-10H-phenothiazine-3,7-diamine (AcMT) (100 kg). Toluene (400 l) and 80% aqueous acetic acid (40 l) were added, followed by a water rinse (50 l). The batch temperature was increased to 75-85° C. for 1 h. The agitator was stopped and the layers allowed to settle for 30 min. The lower aqueous layer is removed and fresh water (300 l), 80% aqueous acetic acid (40 l) followed by water rinse (50 l) were then added. The mixture was stirred at 75-85° C. for 1 h before the agitator was stopped and the layers allowed to settle over 30 min. The lower aqueous layer was removed and fresh water (300 l), 80% aqueous acetic acid (40 l) followed by water rinse (50 l) were then added. The mixture was stirred at 75-85° C. for 1 h before the agitator was stopped. The layers were allowed to settle

Large Scale Synthesis of N,N,N',N'-tetramethyl-10H-phenothiazine-3,7-diaminium bis(methanesulphonate) (LMT.2MsOH)

AcMT (18-22 kg) was added to R1. Toluene (volume (1)=16×AcMT weight) was added and the mixture heated to 90-100° C. The solution was allowed to cool to 60-80° C. before being passed through an in-line 5μ filter to reactor 2 (R2). Toluene (50 l) was added to reactor 1 (still at ~70° C.) and stirred for 30 min. This was used to rinse the transfer line and filter. The above process was repeated once more. The process of removing the excess toluene from R2 by distillation under reduced pressure was then started. The capacity of R2 permitting, two more portions of AcMT (18-22 kg each) were transferred from R1 to R2 following the method described above. The distillation was complete when the batch volume in R2 was reduced to ~340 l. The temperature was increased to 95-105° C. for 15-30 min. before being cooled to 15-25° C. Water (20 l) was added to R2. This was followed by the addition of methanesulphonic acid (MSA) (33 l, 99%, 2.2 equiv.) whilst keeping the batch temperature at 15-30° C. A second portion of water (10 l) was added and the mixture stirred at this temperature for 2 h. The mixture was heated to 80-90° C. for 3-4 h. The biphasic solution was allowed to cool to 48-58° C. before absolute EtOH (75 l) was added over 15-30 min. The stirrer was stopped and the mixture was seeded using 150 g of crushed (<100μ) N,N,N',N'tetramethyl-10H-phenothiazine-3,7-diaminium bis(methanesulphonate). A second portion of EtOH (300 l) was added over 80-110 min. Jacket temperature was set to 10° C. and when the temperature reached 25° C. the jacket temperature was reset to 20° C. It was stirred at 15-25° C. for 2 h. before the solid was collected by filtration. The cake was thoroughly de-liquored. MeCN (300 l) was added to R2 and stirred for 15 min before being used portion-wise to wash the filter cake. A second 300 l of MeCN was added to R2 and the wash process repeated. The product was dried on the filter until loss on drying <0.2% before being offloaded (80-90% yield).

Synthesis 2: Synthesis and analysis of N,N,N',N'-Tetramethyl-10H-phenothiazine-3,7-diaminium bis(ethanesulfonate) (LMT.2EsOH)

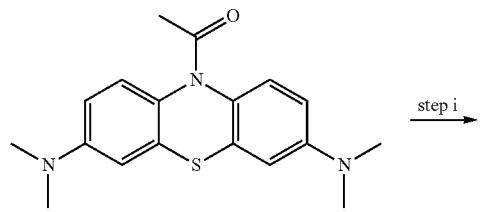

step i

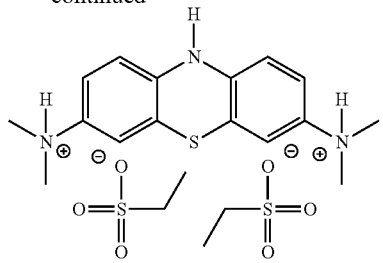

step i: H$_2$O, MeOH, EsOH, IPA, Acetone

Synthetic Method for LMT.2EsOH

The synthesis of LMT.2EsOH was carried out by acid hydrolysis of 10-Acetyl-N,N,N',N'-tetramethyl-10H-phenothiazine-3,7-diamine. The acid used was ethanesulfonic acid and the solvent combination was aqueous methanol.

Experimental Details

To a 100 ml round bottom flask was added 10-Acetyl-N,N,N',N'-tetramethyl-10H-phenothiazine-3,7-diamine (5 g, 15.27 mmol, MW 327.45 g/mol), (70%, aq) ethanesulfonic acid (7.21 g, 45.81 mmol, MW 110.13 g/mol) and methanol (25 ml). The mixture was heated to 75° C. and stirred at this temperature 4 hours before the mixture was cooled over ice water. No solid formed and the methanol was removed under vacuum to give a viscous green oil. To this oil was added isopropanol (25 ml) and the mixture was heated to reflux to ensure a homogenous solution. Once cooled acetone was added until a precipitate formed. The suspension was cooled over ice water for 1 hour before being filtered to give the crude product as a yellow solid, which turned green upon exposure to air. The crude was washed with acetone (3×5 ml) and air dried for 3 days to give the crude product (3.35 g, 43%, MW 505.68 g/mol) as a light green solid.

$v_{max}$ (KBr)/cm$^{-1}$; 3448 (NH), 3263 (=CH), 3030 (=CH), 2987 (CH), 2938 (CH), 2582 (SO$_3$), 2452 (SO$_3$H), 1487 (C—C), 1211 (O=S=O), 1188 (O=S=O), 1145 (O=S=O), 1026.

$\delta_H$(400 MHz; D$_2$O): 1.07 (6H, t, J 7.6, CH$_3$), 2.72 (4H, q, J 7.6, SCH$_2$), 3.02 (12H, s, N CH$_3$), 6.54 (2H, d, J 9.2, ArH), 7.02 (4H, brd s, ArH);

$\delta_C$(100 MHz; D$_2$O): 142.3 (QC), 136.6 (QC), 119.9 (CH), 118.4 (QC), 118.2 (CH), 115.2 (CH), 46.2 (NCH$_3$), 45.3 (SCH$_2$), 8.3 (CH$_3$).

MP: 208-210° C. (IPA/Acetone)

m/z (EI+): Calculated mass 285.129970; Observed 285.129761 (100%, [M-2EsOH]+).

m/z (ES-): Calculated mass 109; Observed 109 (100%, [M-LMT]−).

Crystallography

A 1 g sample of LMT.2EsOH was dissolved in acetic acid (~0.1 g) and ethyl acetate was layered on top and allowed to slowly diffuse over 3 days in the dark. Crystals developed and were collected and analysed by X-ray diffraction and confirmed the product as the bis(ethanesulfonate). See FIG. 17a.

Synthesis 3: Synthesis and Analysis of N,N,N',N'-Tetramethyl-10H-phenothiazine-3,7-diaminium bis(p-toluenesulfonate) (LMT.2TsOH)

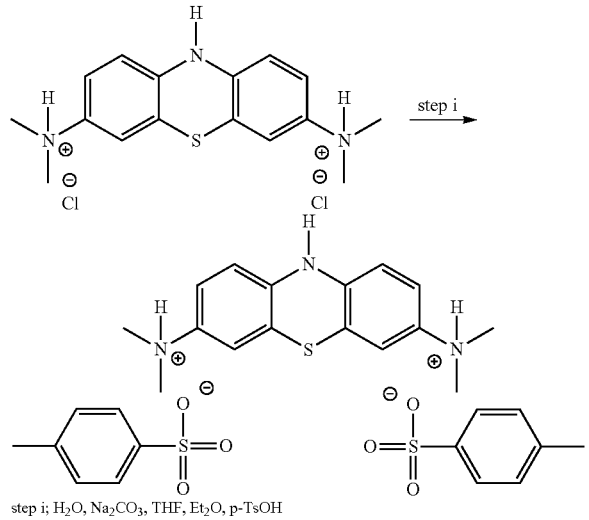

step i; H₂O, Na₂CO₃, THF, Et₂O, p-TsOH

Synthetic Method for LMT.2TsOH

The synthesis of LMT.2TsOH was carried out by neutralising N,N,N',N'-tetramethyl-10H-phenothiazine-3,7-diaminium dichloride with sodium carbonate and extracting the neutral species into organic solvent. The extract was treated with p-toluenesulphonic acid and the mixture concentrated to dryness.

Experimental Details

To a 50 ml beaker was added sodium carbonate (0.59 g, 5.58 mmol, MW 105.99 g/mol) and water (10 ml), the mixture was stirred until the solid had dissolved. To a 100 ml separating funnel was added N,N,N',N'-Tetramethyl-10H-phenothiazine-3,7-diaminium dichloride (1 g, 2.79 mmol, MW 358.33 g/mol), tetrahydrofuran (35 ml) and diethylether (5 ml) then the aqueous solution of sodium carbonate. The neutral species was extracted into the organic solvent layer and separated from the aqueous layer. To the organic extract was added p-toluenesulphonic acid monohydrate (1.06 g, 5.58 mmol, MW 190.20 g/mol) pre-dissolved in tetrahydrofuran (5 ml) and the mixture was concentrated to dryness to give the product (MW 629.8216 g/mol) as a crunchy green amorphous foam.

$v_{max}$ (KBr)/cm⁻¹; 3440 (NH), 3270 (=CH), 3032 (=CH), 2628 (SO₃H), 1484 (C—C), 1194 (O=S=O), 1122 (O=S=O), 1032.

$\delta_H$(400 MHz; D₂O); 2.24 (6H, s, CH₃), 3.09 (12H, s, NCH₃), 6.62 (2H, d, J 8.4, ArH), 7.10 (4H, s, ArH), 7.13 (4H, d, J 8.4, Ts-H), 7.61 (4H, d, J 8.4, Ts-H)

$\delta_C$(100 MHz; D₂O); 19.9 (CH₃), 45.9 (NCH₃), 115.0 (CH), 118.2 (CH), 118.6 (QC), 119.9 (CH), 125.5 (CH), 128.5 (CH), 137.0 (QC), 140.5 (QC), 141.9 (QC), 142.8 (QC).

Mp: 108° C. (THF/Et₂O)

m/z (EI+): Calculated mass 285.129970; Observed 285.129398 (100%, [M-2TsOH]+).

m/z (ES−): Calculated mass 171.0116; Observed 171.0121 (100%, [M-LMT]⁻).

Synthesis 4: Synthesis and analysis of N,N,N',N'-Tetramethyl-10H-phenothiazine-3,7-diaminium ethanedisulfonate (LMT.EDSA)

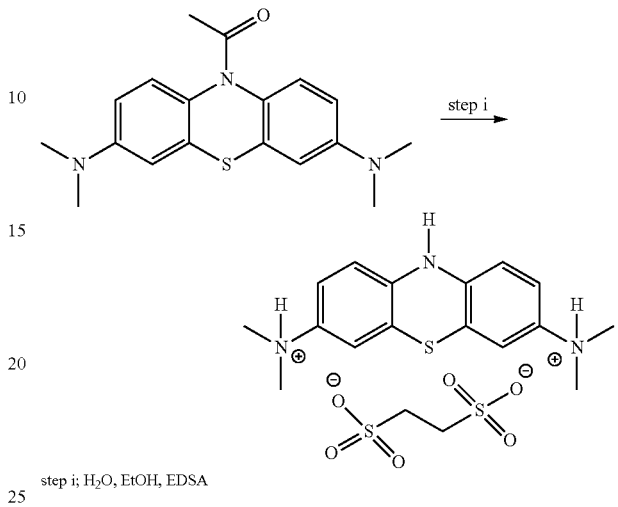

step i; H₂O, EtOH, EDSA

The synthesis of LMT.EDSA was carried out by acid hydrolysis of 10-acetyl-N,N,N',N'-tetramethyl-10H-phenothiazine-3,7-diamine. The acid used was 1,2-ethanedisulfonic acid and the solvent combination was aqueous ethanol.

Experimental Details

To a 25 ml round bottom flask was added 10-acetyl-N,N,N',N'-tetramethyl-10H-phenothiazine-3,7-diamine (1 g, 3.05 mmol, MW 327.45 g/mol), 1,2-ethanedisulfonic acid monohydrate (0.95 g, 4.58 mmol, MW 208.21 g/mol), water (1 ml) and ethanol (5 ml). The mixture was heated to 85° C. and stirred at this temperature for 2.5 hours where a yellow green solid precipitated from solution. The slurry was cooled over ice water for 30 min before filtering to give the crude product as a green yellow solid. The crude was washed with ethanol (3×3 ml) and air dried for 15 min before being oven dried for 3.5 hours at 70° C. to give the crude product (1.33 g, 91%, MW 475.61 g/mol) as a yellow solid.

Purification of LMT.EDSA

To a 50 ml conical flask was added crude LMT.EDSA (1 g, 2.10 mmol, MW 475.61 g/mol) and water (10 ml). The slurry was heated to 95° C. and stirred at this temperature until the solid dissolved. The solution was then allowed to cool to 25° C. where a light green crystalline solid formed. The slurry was then cooled over ice water for 30 min before filtering. The solid collected was washed with methanol (3×3 ml) and air dried for 18 hours to give the purified product (0.88 g, 88%, MW 475.61 g/mol) as a crystalline light green solid.

$v_{max}$ (KBr)/cm⁻¹; 3408 (NH), 3280 (=CH), 3221 (C—H), 3036 (=CH), 2574 (SO₃H), 2480 (SO₃H), 1484 (C—C), 1226 (O=S=O)

$\delta_H$(400 MHz; D₂O); 2.98 (12H, s, NCH₃), 3.06 (4H, s, SCH₂), 6.45 (2H, d, J 6, ArH), 6.95 (4H, d J 4, ArH)

$\delta_C$(100 MHz; D₂O); 46.2 (NCH₃), 46.4 (SCH₂), 115.1 (CH), 118.1 (CH), 118.4 (QC), 119.8 (CH), 136.5 (QC), 142.1 (QC)

MP: decomposes at 268° C. (H₂O)

m/z (EI+): Calculated 285.129970; Observed 285.130948 (100%, [M-EDSA]+).

m/z (ES−): Calculated 188.9528; Observed 188.9535 (100%, [M-LMT]−).

Crystallography

A 40 mg sample of LMT.EDSA was dissolved in hot deuterated water (~1 ml) and allowed to slowly cool in the dark. Crystals developed which were collected and analysed by X-ray diffraction and confirmed the product as the monohydrate of the 1:1 LMT to EDSA adduct. See FIG. 17b.

Synthesis 5: Synthesis and analysis of N,N,N',N'-Tetramethyl-10H-phenothiazine-3,7-diaminium naphthalenedisulfonate (LMT.NDSA)

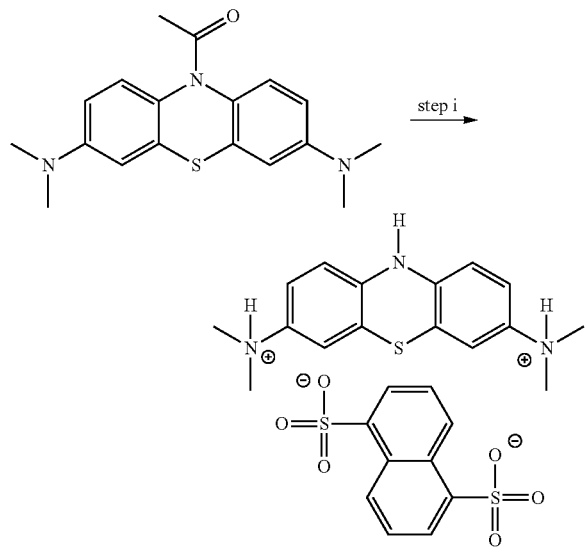

step i; H$_2$O, EtOH, NDSA

Synthetic Method for LMT.NDSA

The synthesis of LMT.NDSA was carried out by acid hydrolysis of 10-acetyl-N,N,N',N'-tetramethyl-10H-phenothiazine-3,7-diamine. The acid used was 1,5-naphthalenedisulfonic acid and the solvent combination was aqueous ethanol.

Experimental Details

To a 25 ml round bottom flask was added 10-Acetyl-N,N,N',N'-tetramethyl-10H-phenothiazine-3,7-diamine (1 g, 3.05 mmol, MW 327.45 g/mol), 1,5-naphthalenedisulfonic acid tetrahydrate (1.65 g, 4.58 mmol, MW 360.36 g/mol), water (1 ml) and ethanol (5 ml). The mixture was heated to 85° C. and stirred at this temperature for 30 minutes where the mixture was still insoluble. To the hot mixture was added water (4 ml) and the reaction heated to 95° C. and stirred at this temperature for 8 hours. The suspension was cooled over ice water for 10 minutes before being filtered to give the crude product as a light green solid. The crude was washed with ethanol (3×5 ml) and air dried for 3 days to give the crude product (1.75 g, 100%, MW 573.71 g/mol) as a light green blue solid.

$\nu_{max}$ (KBr)/cm$^{-1}$; 3382 (NH), 3302 (=CH), 3040 (=CH), 2525 (SO$_3$H), 1478 (C—C), 1238 (O=S=O), 1219 (O=S=O), 1179, 1158, 1030.

$\delta_H$(400 MHz; D$_2$O); 3.06 (12H, s, NCH$_3$), 6.70 (2H, brd, ArH), 7.14 (4H, brd, ArH), 7.43 (2H, t, J 8.0, 7.6, Naph-H), 7.94 (2H, d, J 7.2, Naph-H), 8.87 (2H, d, J 78.4, Naph-H), 9.10 (1H, s, NH)

$\delta_C$(100 MHz; D$_2$O); 46.0 (NCH$_3$), 115.3 (CH), 117.5 (QC), 118.7 (CH), 120.4 (CH), 124.6 (CH), 124.7 (CH), 129.6 (CH), 129.9 (QC), 138.3 (QC), 141.7 (QC), 143.8 (QC).

MP; decomposes at 256° C. (MeCN)

m/z (EI+): Calculated mass 285.129970; Observed 285.130367 (100%, [M-NDSA]+).

m/z (ES−): Calculated mass 286.9684; Observed 286.9697 (100%, [M-LMT]−).

Example 2—Solubility Studies i) Solubility of N,N,N',N'-tetramethyl-10H-phenothiazine-3,7-diaminium dibromide, dichloride and bis(methanesulphonate) (LMT.2HBr, LMT.2HCl and LMT.2MsOH) salts Two aqueous solutions (pH 2.00 and 3.01 at 21.4° C.) were prepared by carefully adding HCl (5 M) to deionised water.

In each experiment a 5 ml aliquot of one of the aforementioned solutions was heated to 37° C. A portion of the appropriate salt (LMT.2MsOH, LMT.2HCl or LMT.2HBr) was added and the mixture stirred for a few moments to allow for complete dissolution of the solid. This step was repeated until no further dissolution took place.

The results are shown in the Table:

| Salt | pH (21.4° C.) | g/5 ml* (37° C.) |
|---|---|---|
| LMT•2HBr | 3.01 | 4.726-5.236 |
| LMT•2HBr | 2.00 | 4.822-5.096 |
| LMT•2HCl | 3.01 | 4.978-6.029 |
| LMT•2HCl | 2.00 | 4.404-4.961 |
| LMT•2MsOH | 2.00 | 8.825-9.943 |

*Lower limit of range corresponds to total weight at which complete dissolution was observed. Upper limit is total weight added before saturation was achieved As can be seen LMT.2MsOH has a good aqueous solubility.

ii) pH Dependence of LMT.2MsOH Salt

In related experiments three buffered stock solutions were prepared (pH 2, pH 3, and pH 7) as follows:

pH 2 Buffered Aqueous Solution

A solution of (0.2 M) potassium chloride (KCl) (0.745 g in 50 mL of deionised water) was initially prepared. From this solution 50 mL was taken and diluted with approximately 80 mL of deionised water. A (0.2 M) hydrochloric acid (HCl) solution was then used to adjust the pH to 2, before further dilution with deionised water to make up to 200 mL. A final pH of 2.00 at 21.6° C. was recorded.

pH 3 Buffered Aqueous Solution

A solution of (0.1 M) potassium hydrogen phthalate (2.042 g in 100 mL of deionised water) was initially prepared. From this solution 100 mL was taken and diluted with approximately 50 mL of deionised water. A 0.2 M HCl solution was then used to adjust the pH to 3, before further dilution with deionised water to make up to 200 mL. A final pH of 2.99 at 21.7° C. was recorded.

pH 7 Buffered Aqueous Solution

A solution of (0.1 M) potassium phosphate monobasic (KH$_2$PO$_4$) (1.370 g in 100 mL of deionised water) was initially prepared. From this solution 100 mL was taken and diluted with approximately 80 mL of deionised water. A 0.5 M sodium hydroxide (NaOH) solution was then used to adjust the pH to 7, before further dilution with deionised water to make up to 200 mL. A final pH of 7.07 at 22° C. was recorded.

Method

A 5 mL aliquot of an aqueous buffered solution was added to a vial which contained a micro-flea. This vial was placed into a water bath set at 25° C. To the solution was added LMT.2MsOH in 1-1.5 g portions. After each addition, a 10 minutes stir time was allowed to ensure maximum opportunity for dissolution. The homogeneity of the mixture was judged by eye. If solid was still present, after the stir time, as judged by visual inspection, the saturation point was judged to have been reached.

Results

The viscosity of the resulting mixtures precluded adequate isolation of the excess solid, therefore it was not possible to determine exact solubility values. Consequently each of the results are reported as a range in which the total mass of LMT.2MsOH added prior to the saturation point constitutes the lower limit and the total mass of LMT.2MsOH added, post saturation point, provides the upper limit.

The results from each of the three experiments are shown below:

| pH   | Solubility (g/mL) |
|------|-------------------|
| 2.00 | 1.600–1.773       |
| 2.99 | 1.981–2.092       |
| 7.07 | 2.033–2.114       |

As can be seen, the solubility tailed off slightly as the pH was reduced, however LMT.2MsOH performed well in each of the three aqueous systems.

In conclusion LMT.2MsOH has better aqueous solubility than MTC (not shown) and enhanced solubility compared to the corresponding chloride and bromide salts. This suggests an increased utility in respect of the treatment and uses described herein.

Example 3—Inhibition of Aggregation and Toxicity

Methods: Solid Phase Assay for Tau Aggregation

The tau-tau aggregation assay uses purified recombinant tau fragments in a solid-phase immunoassay. Methods are described in detail in e.g. WO 96/30766. Briefly, the assay measures the binding of truncated tau (amino acids 297-391) in solution to solid-phase bound truncated tau (residues 297-390). Binding of the former is detected with the antibody mAb 423, which specifically recognises peptides containing a C-terminal Glu-391 residue. The Tau complex formed in vitro is similar to the aggregated complex that forms in Alzheimer's disease as a consequence of the stability of the pathological Tau-Tau binding interaction through a 94/95-amino acid repeat domain (residues 297-390), found in the proteolytically stable core of the paired helical filament.

The $B_{50}$ value (expressed as mean±SE) is determined as the concentration of compound at which tau-tau binding is decreased by 50%.

Methods: Cell-Based Tau Aggregation Assay

The assay is based on 3T6 mouse cells that have been engineered to express both full-length human tau protein (htau40) under the control of an inducible promoter (pOP-RSVI), and to express low levels of truncated tau (295-390, dGA) under the control of a constitutive promoter (pcDNA3.1). Expression of large quantities of htau40 is induced by the addition of IPTG (10-50 µM), which in turn leads to the production of additional truncated tau by a process in which aggregation and processing of the full length-tau occurs in the presence of dGA tau which acts as template. Addition of tau-tau aggregation inhibitors to the assay blocks this process. Methods are described in more detail in WO 02/055720.

Results are expressed as the concentration at which there is a 50% inhibition of generation of the 12 kD fragment. This is referred to as the $EC_{50}$ value.

Cells (4A and clones thereof) are grown to ~80% confluency in a 10-cm dish, before splitting to two 24-well plates and allowed to grow for 24 hrs. Test item is added at various concentrations and, after 24 hrs, IPTG is added. After overnight incubation the medium is removed, the wells are washed with PBS and cells are collected by the addition of Laemmli buffer. Samples were stored at −20° C. for subsequent gel electrophoresis, Western blotting and antibody labelling. Samples are separated by SDS PAGE, transferred to PVDF membrane and the tau labelled with 7/51 antibody detected by ECL on a Kodak Image Station. Compound was typically tested at four concentrations in triplicate over a range of concentrations with all the samples being run on one gel. The ratio of the intensities of the dGA to htau40 bands, normalised to control samples in which there had been no drug, was plotted against drug concentration and the $EC_{50}$ value was determined graphically from the concentration at which the ratio falls to 0.5.

The method is summarised in Table 1 immediately below. MTC (TRx0014.047) was run as a control in all experiments and the $EC_{50}$ value was normalised to MTC having an $EC_{50}$=0.59 µM.

TABLE 1 summary of assay procedure for measuring $EC_{50}$

| Timing | Action |
|--------|--------|
| Day 1 | Split cells to 24-well plates |
| Day 2 | Add drug at various concentrations |
| Day 3 | Late afternoon, add IPTG |
| Day 4 | Morning, collect in Laemmli buffer, store −20° C. before further processing |
| Processing Day | Run samples on SDS Page gels, transfer to PVDF membrane, labeled with 7/51 anti tau antibody. Blots are quantified using the Kodak 1D software and data is transferred to the Systat statistics package for graphing. |

Methods: Cellular Toxicity Assay

Cells (3T6 mouse fibroblast) are grown to ~80% confluency in a 10-cm dish, before splitting to 96 well plates, 10% of the 10-cm dish per 96-well plate, 50 µl per well. One column of 8 wells is left empty (to be a reagent blank in the assay). The cells were allowed to grow overnight before drug was added to four wells at the starting concentration (typically 200 µM for MTC or LMT.2HBr) and in subsequent wells using a 1:2 dilution series with the final four wells of cells being used as a control without drug. This allows two drugs to be tested per 96-well plate. The cells were left in the presence of drug for 48 hrs, after which medium was removed and cells washed with PBS. Cell number was determined using a Cytotox 96 well kit (Promega) which is based on the lactate dehydrogenase (LDH) assay. The assay quantitatively measures LDH, a stable cytosolic enzyme released on cell lysis. Released LDH is measured with an enzymatic assay which results in the conversion of a tetrazolium salt into a red formazan product. The amount of colour formed is proportional to the number of cells lysed.

Briefly, cells are lysed with 50 µl/well 1× lysis buffer for 45-60 minutes, followed by 50 µl/well LDH assay reagent for 30 minutes and the reaction stopped with 50 µl/well stop buffer. The absorbance is read at 490 nm. The absorbance relative to untreated wells (untreated cells=1.0) was plotted against drug concentration. The $LD_{50}$ was determined graphically from the concentration at which the absorbance is decreased by 50%. MTC (TRx0014.047) was run as a control in all experiments when testing LMT.2HBr and the $LD_{50}$ value was corrected to MTC with an $LD_{50}$=65 µM.

Results:

Various bis(sulfonate) salts according to the invention were tested and compared with bis(halide) salts N,N,N',N'-tetramethyl-10H-phenothiazine-3,7-diaminium dichloride (LMTC, LMT.2HCl) and N,N,N',N'-tetramethyl-10H-phenothiazine-3,7-diaminium di(bromide) LMT.2HBr and with methylthioninium chloride (MTC).

In vitro data for the different methylthioninium salt forms are summarised in Table 2 immediately below:

TABLE 2

Summary of the in vitro data.

| Compound | $LD_{50}$ (µM) | $EC_{50}$ (µM) | THx | $B_{50}$ (µM) |
|---|---|---|---|---|
| MTC | 65 ± 5 | 0.59 ± 0.04 | 110 | 195.6 ± 16.1 (n = 10) |
| LMT•2HBr | 61 ± 4 (n = 20) | 0.66 ± 0.15 (n = 8) | 92 | 472.4 ± 27.6 (n = 3) |
| LMT•2MsOH | 34 ± 4 (n = 8) | 0.19 ± 0.04 (n = 8) | 179 | 238.2 ± 74.2 (n = 3) |
| LMT•2HCl | 64 ± 8 (n = 10) | 0.63 ± 0.10 (n = 7) | 102 | 360.8 ± 38.2 (n = 3) |
| LMT•2TsOH | 87 ± 10 (n = 8) | 0.62 ± 0.34 (n = 2) | 140 | 296.0 ± 37.9 (n = 3) |
| LMT•NDSA | 77 ± 15 (n = 8) | 0.71 ± 0.34 (n = 4) | 108 | 333.7 ± 63.2 (n = 2) |
| LMT•EDSA | 78 ± 6 (n = 8) | 0.68 ± 0.32 (n = 4) | 115 | 399.9 ± 17.6 (n = 2) |
| LMT•2EsOH | 52 ± 3 (n = 8) | 0.52 ± 0.13 (n = 3) | 100 | 297.0 ± 75.1 (n = 3) |
| MSA* | — | NE (20) | — | >500 |
| EDSA* | — | NE (20) | — | >500 |

THx, therapeutic index (THx = $LD_{50}/EC_{50}$)
Values expressed as mean ± SE.
NE = not effective (at max dose tested)
*MSA = methansulfonic acid; EDSA = ethanedisulfonic acid Comments The EC50 values (mean±SE) for LMT.2MsOH and LMT.2HCl are 0.19±0.04 µM and 0.63 25±0.10 µM, respectively, with corresponding therapeutic indices of 179 and 102.

The relative potency of compounds in the cell-based model of tau-tau aggregation is LMT.2MsOH>MTC, LMT.2HBr, LMT.2HCl. The therapeutic index is 63% greater for LMT.2MsOH compared with MTC.

The order of potency in the cell-based assay is MTC, LMT.2MsOH>LMT.2HCl>LMT.2HBr. The B50 values for LMT.2MsOH and LMT.2HCl are 238.2±74.2 µM and 360.8±38.2 µM, respectively. The order of relative potency in the cell-free assay is LMT.2MsOH>MTC, LMT.2HCl, LMT.2HBr.

Example 4—Toxicology, Impurities and Effect on the Hemopoietic System

LMT.2HBr, LMT.2HCl, LMT.2MsOH or MTC were administered daily for 14 days to female Wistar rats; the doses were 95 mg MT/kg/day from Days 1 to 10 and 60 mg MT/kg/day from Days 11 to 14. Clinical signs of raised body posture, subdued behaviour and general weakness were seen in all treated groups. Treatment-related deaths occurred in the LMT.2HBr— and MTC-treated groups.

Changes in red blood cell parameters were seen in the blood and bone marrow of all treated groups that were indicative of a regenerative anaemia. These included: decreased numbers of red blood cells, low haemoglobin concentration and increased numbers of reticulocytes in blood and an increase in the numbers of red cell precursors in bone marrow. This was corroborated histologically by increased levels of erythropoiesis in the spleen.

A decrease in the numbers of neutrophilic granulocytes was seen in the bone marrow of all treated animals though the magnitude of this effect was considerably greater in the LMT.2HBr-treated group than in the other groups. This difference was also noted in the severity of the neutropaenia observed in prepared blood smears where there was a marked depletion of mature neutrophils in LMT.2HBr-treated animals, a modest decrease with MTC and no decrease in the LMT.2HCl or LMT.2MsOH groups. The results of this study suggest that, in rats at least, LMT.2HBr has a higher propensity to cause neutrophil depletion than LMT.2HCl, LMT.2MsOH or MTC. Decreased numbers of mature neutrophils and granulocytes were also observed in the bone marrow at the high dose (45 mg MT/kg/day) in a 6-month study of LMT-2HBr in the rat. The decreased neutrophils or neutropaenia observed after LMT.2HBr although reversible would make patients more susceptible to bacterial infections as their primary role is in destruction of bacteria.

Thus LMT.2MsOH shows improved properties compared with LMT.2HBr in rats in terms of both tolerability (dose-related deaths) and in neutrophil response.

Table: Neutrophil response in rats following 14 day oral administration of different salt forms of LMT. Total neutrophils are recorded as a percentage of total white cells (approximately 100 white blood cells (range 100 to 107) were examined from each slide; frequency in the presence of immature neutrophils was recorded per animal group; dose-related deaths recorded as animal numbers per group of 8 rats.

| Compound | Neutrophils | Early neutrophils | Dose-related deaths |
|---|---|---|---|
| Vehicle control | 15.50% | 0/8 | 0/8 |
| LMT•2HBr | 3.00% * | 8/8 | 2/8 |
| LMT•2HCl | 19.90% | 2/8 | 0/8 |
| LMT•2MsOH | 18.30% | 1/8 | 0/8 |

* $P < 0.001$ compared with control

Although LMT.2HCl and LMT.2MsOH are comparable in the above analysis, there is a distinction in the impurities found in the two salt forms. For LMT.2HCl, the presence of methyl chloride was detected during synthesis and trapped within the product in such a way that it was difficult to remove entirely. By contrast impurities such as ethyl and methyl methanesulfonate (EMS, MMS) could be controlled to much lower levels in the LMT.2MsOH synthetic process Studies on the hemopoietic system were performed in rat, monkey and minipig.

The lowest doses at which methemoglobinemia was observed were 15 mg MT/kg/day in rats (MTC and LMT.2HBr) or 30 mg MT/kg/day (LMT.2MsOH), 5.3 mg MT/kg/day in primates (MTC), and 10 mg MT/kg/day (LMT.2MsOH and LMT.2HBr) in minipigs.

After the first 28-days of dosing in the 9-month LMT.2MsOH study in minipigs, there are no indications of methemoglobinemia at 3 mg MT/kg/day.

However, as would be expected, as dose levels of MTC, LMT.2HBr or LMT.2MsOH increased, signs of oxidative stress to RBCs emerged in a dose-related fashion, evidenced by increasing levels of methemoglobin and ultimately at doses that were not tolerated, Heinz body (aggregates of denatured, precipitated hemoglobin within red cells) formation.

Example 5—Pharmacokinetics

FIG. 18 shows a comparison of the plasma concentration in pig of the MT moiety over time following dosing of LMT.2HBr, LMT.2HCl and LMT.2MsOH at (two oral doses, 2 and 15 mg/kg).

As can be seen the $C_{max}$ (at $T_{max}$ of 1 hour) for LMT.2MsOH was more than 2-fold greater than that for LMT.2HCl or LMT.2HBr. Thus LMT.2MsOH can provide a more effective exposure to MT than LMT.2HCl or LMT.2HBr.

Example 6—Gastric Irritation Studies

Study (28-day rat with MTC or LMT.2HBr): Incidence and severity of selected microscopic findings in stomach from terminal animals Incidence and severity of selected findings in sternum, femur, liver and spleen: terminal kill

| Tissue and finding | Level (mg/kg/day) | Male 1M MTC | 2M MTC | 3M MTC | 4M MTC | 5M LMT•2HBr | 6M LMT•2HBr | 7M LMT•2HBr | Female 1F MTC | 2F MTC | 3F MTC | 4F MTC | 5F LMT•2HBr | 6F LMT•2HBr | 7F LMT•2HBr |
|---|---|---|---|---|---|---|---|---|---|---|---|---|---|---|---|
|  |  | 0 | 5 | 30 | 90 | 5 | 30 | 90 | 0 | 5 | 30 | 90 | 5 | 30 | 90 |
| Stomach (non glandular) | No. examined: | 5 | 0 | 0 | 5 | 0 | 0 | 5 | 5 | 0 | 0 | 5 | 0 | 0 | 5 |
| Gastritis | 1 | — | — | — | — | — | — | 1 | — | — | — | — | — | — | — |
|  | 2 | — | — | — | 1 | — | — | — | — | — | — | — | — | — | 1 |
|  | 3 | — | — | — | — | — | — | 1 | — | — | — | 1 | — | — | 1 |
| Inflammatory cell infiltration | 1 | — | — | — | 1 | — | — | — | — | — | — | — | — | — | — |

Key: "—" = finding not present, 1 = minimal, 2 = slight, 3 = moderate, 4 = moderately severe, 5 = severe From the above the following can be predicted with 10 per group Incidence and severity of selected findings in sternum, femur, liver and spleen: terminal kill

| Tissue and finding | Level (mg/kg/day) | Male 1M MTC | 2M MTC | 3M MTC | 4M MTC | 5M LMT•2HBr | 6M LMT•2HBr | 7M LMT•2HBr | Female 1F MTC | 2F MTC | 3F MTC | 4F MTC | 5F LMT•2HBr | 6F LMT•2HBr | 7F LMT•2HBr |
|---|---|---|---|---|---|---|---|---|---|---|---|---|---|---|---|
|  |  | 0 | 5 | 30 | 90 | 5 | 30 | 90 | 0 | 5 | 30 | 90 | 5 | 30 | 90 |
| Stomach (non glandular) | No. examined: | 10 | 0 | 0 | 10 | 0 | 0 | 10 | 10 | 0 | 0 | 10 | 0 | 0 | 10 |
| Gastritis | 1 | — | — | — | — | — | — | 2 | — | — | — | — | — | — | — |
|  | 2 | — | — | — | 2 | — | — | — | — | — | — | — | — | — | 2 |
|  | 3 | — | — | — | — | — | — | 2 | — | — | — | 2 | — | — | 2 |
| total |  |  |  |  | 2 |  |  | 4 |  |  |  | 2 |  |  | 4 |

Study (28-day rat study with LMT.2MsOH): Incidence and severity of selected microscopic findings in sternum, liver, spleen and stomach from terminal animals Incidence and severity of selected findings in sternum, liver and spleen: terminal kill

|  |  | Males | | | | Females | | | |
| --- | --- | --- | --- | --- | --- | --- | --- | --- | --- |
| Tissue and finding | Level (mg/kg/day) | 1M 0 | 2M 5 | 3M 30 | 4M 90 | 1F 0 | 2F 5 | 3F 30 | 4F 90 |
| | No. examined: | 10 | 0 | 0 | 10 | 10 | 0 | 0 | 10 |
| | Grade * — | | | | | | | | |
| Stomach (non glandular) | | | | | | | | | |
| Gastritis | 1 | — | | | — | — | | | — |
| | 2 | — | | | 2 | — | | | 2 |
| | 3 | — | | | — | — | | | 1 |
| total | | | | | 2 | | | | 3 |
| Inflammatory cell infiltration | 1 | — | | | 4 | — | | | 4 |
| | 2 | — | | | — | — | | | 1 |

* Key: "—" = finding not present, 1 = minimal, 2 = slight, 3 = moderate, 4 = moderately severe, 5 = severe These results show that LMT.2MsOH causes less gastric irritation that LMT.2HBr.

Example 7—Formulations

Formulation Example 1: Preparation of LMTM Tablets Using Direct Compression

Tablets having the following compositions were prepared by a direct compression method

| | Tablet strength (LMT mg/tablet) | | | | |
| --- | --- | --- | --- | --- | --- |
| | 50 | 75 | 100 | 125 | 150 |
| Ingredient | (mg/tablet) | | | | |
| LMTM | 84.43 | 126.65 | 168.86 | 211.08 | 253.29 |
| Spray-dried mannitol | 344.57 | 302.35 | 290.14 | 392.92 | 425.71 |
| Microcrystalline cellulose (Avicel PH 102 or PH 112) | 50.00 | 75.00 | 95.00 | 125.00 | 150.00 |
| Crospovidone (crosslinked polyvinylpyrrolidone) | 15.00 | 15.00 | 15.00 | 15.00 | 15.00 |
| Magnesium stearate | 6.00 | 6.00 | 6.00 | 6.00 | 6.00 |
| Total tablet core weight | 500.00 | 525.00 | 575.00 | 750.00 | 850.00 |

The LMTM, spray-dried mannitol, microcrystalline cellulose, crospovidone and magnesium stearate were blended in a tumbling blender, and then compressed using a tabletting machine.

The tablet cores were then film coated with an aqueous suspension of Opadry* blue (*registered trademark of Colorcon for a range of film coating materials).

Formulation Example 2: Preparation of LMTM Tablets Using Dry Granulation (Roller Compaction)

Tablets having the following compositions were prepared by a dry granulation method:

| | Tablet strength (LMT mg/tablet) | | | | |
| --- | --- | --- | --- | --- | --- |
| | 50 | 75 | 100 | 125 | 150 |
| Ingredient | (mg/tablet) | | | | |
| LMTM | 84.43 | 126.65 | 168.86 | 211.08 | 253.29 |
| Spray-dried mannitol | 344.57 | 302.35 | 290.14 | 392.92 | 425.71 |
| Microcrystalline cellulose (Avicel PH 102 or PH 112) | 50.00 | 75.00 | 95.00 | 125.00 | 150.00 |
| Crospovidone (crosslinked polyvinylpyrrolidone) | 15.00 | 15.00 | 15.00 | 15.00 | 15.00 |
| Magnesium stearate | 6.00 | 6.00 | 6.00 | 6.00 | 6.00 |
| Total tablet core weight | 500.00 | 525.00 | 575.00 | 750.00 | 850.00 |

The LMTM, spray-dried mannitol, microcrystalline cellulose, crospovidone and magnesium stearate were blended in a tumbling blender. The mix was then dry granulated using a roller compactor and then milled with an oscillating granulator using a suitable screen. In this case, half of magnesium stearate was used prior to roller compaction and half of the magnesium stearate was then added to the granulation and blended prior to compression on a conventional tabletting machine.

The tablet cores were then film coated with an aqueous suspension of Opadry* blue (*registered trademark of Colorcon for a range of film coating materials).

Formulation Example 3: Preparation of LMTM Tablets by Dry Granulation (Slugging)

Tablets having the following compositions were prepared by a further dry granulation method.

| | Tablet strength (LMT mg/tablet) | | | | |
| --- | --- | --- | --- | --- | --- |
| | 50 | 75 | 100 | 125 | 150 |
| Ingredient | (mg/tablet) | | | | |
| LMTM | 84.43 | 126.65 | 168.86 | 211.08 | 253.29 |
| Spray-dried mannitol | 344.57 | 302.35 | 290.14 | 392.92 | 425.71 |
| Microcrystalline cellulose (Avicel PH 102 or PH 112) | 50.00 | 75.00 | 95.00 | 125.00 | 150.00 |
| Crospovidone (crosslinked polyvinylpyrrolidone) | 15.00 | 15.00 | 15.00 | 15.00 | 15.00 |
| Magnesium stearate | 6.00 | 6.00 | 6.00 | 6.00 | 6.00 |
| Total tablet core weight | 500.00 | 525.00 | 575.00 | 750.00 | 850.00 |

The LMTM and excipients were blended in a tumbling blender, and then compressed to produce slugs (plain, flat faced tablets) using a tabletting machine.

The slugs were then milled using an oscillating granulator fitted with a 20 mesh screen.

In this example, half of magnesium stearate was used prior to slugging and then half of the magnesium stearate added to the granulation and blended prior to compression on a conventional tabletting machine.

The tablet cores were then film coated with an aqueous suspension of Opadry* blue (*registered trademark of Colorcon for a range of film coating materials).

Formulation Example 4: Preparation of LMTM Tablets by Wet Granulation of Excipients and Incorporation of LMTM Extra-Granularly Tablets having the following compositions were prepared by a wet granulation method:

|  | Tablet strength (LMT mg/tablet) | | | | |
| --- | --- | --- | --- | --- | --- |
|  | 50 | 75 | 100 | 125 | 150 |
| Ingredient |  |  | (mg/tablet) |  |  |
| LMTM | 84.43 | 126.65 | 168.86 | 211.08 | 253.29 |
| Mannitol | 334.57 | 292.35 | 280.14 | 380.92 | 413.71 |
| Microcrystalline cellulose (Avicel PH 102) | 50.00 | 75.00 | 95.00 | 125.00 | 150.00 |
| Crospovidone (crosslinked polyvinylpyrrolidone) | 15.00 | 15.00 | 15.00 | 15.00 | 15.00 |
| Polyvinylpyrrolidone | 10.00 | 10.00 | 10.00 | 12.00 | 12.00 |
| Magnesium stearate | 6.00 | 6.00 | 6.00 | 6.00 | 6.00 |
| Total tablet core weight | 500.00 | 525.00 | 575.00 | 750.00 | 850.00 |

The mannitol, crospovidone (a third of the total) and microcrystalline cellulose were blended in a tumbling blender. The blended material was then granulated using a solution of PVP in water. The wet mass was dried in a fluid bed dryer and then milled using an oscillating granulator fitted with a suitable screen.

The milled material was then blended with the remainder of the crospovidone and magnesium stearate, and the LMTM, prior to compression on a conventional tablet machine. The tablet cores were then film coated with an aqueous suspension of Opadry* blue (*registered trademark of Colorcon for a range of film coating materials).

Formulation Example 5: Preparation of LMTM Capsules

Capsules having the following compositions were prepared.

|  | Capsule strength (LMT mg/capsule) | | | | | |
| --- | --- | --- | --- | --- | --- | --- |
|  | 50 | 75 | 100 | 125 | 150 | 200 |
| Ingredient |  |  | mg/capsule |  |  |  |
| LMTM | 84.43 | 126.65 | 168.86 | 211.08 | 253.29 | 337.72 |
| Spray-dried mannitol | 191.07 | 148.85 | 116.64 | 79.42 | 42.21 | 37.78 |
| Crospovidone (crosslinked polyvinylpyrrolidone) | 3.00 | 3.00 | 3.00 | 3.00 | 3.00 | 3.00 |
| Magnesium stearate | 1.50 | 1.50 | 1.50 | 1.50 | 1.50 | 1.50 |
| Total capsule fill weight | 280.00 | 280.00 | 290.00 | 295.00 | 300.00 | 380.00 |

The LMTM and the excipients were blended in a tumbling blender. The resulting drug blends were filled into capsules (50, 75, 100, 125 and 150 mg formulations into size 1 capsules and the 200 mg formulation into size 0 capsules) using a capsule filling machine. Both gelatine capsules and HPMC capsules were prepared.

Formulation Example 6: Results of Stability Testing LMTM 75 mg Film Coated Tablets

|  | Time Point | Storage Location | |
| --- | --- | --- | --- |
| Test | (months) | 25° C./60% RH | 40° C./75% RH |
| Assay as % LMT free base | 0 | 102.2 | 102.2 |
|  | 1 | 101.5 | 94.8 |
|  | 3 | 100.0 | 94.2 |
|  | 6 | 96.4 | not done |
|  | 9 | 95.6 | not done |
|  | 12 | 96.0 | not done |

Formulation Example 7: Results of Stability Testing LMTM 100 mg Film Coated Tablets

|  | Time Point | Storage Location | |
| --- | --- | --- | --- |
| Test | (months) | 25° C./60% RH | 40° C./75% RH |
| Assay as % LMT free base | 0 | 101.0 | 101.0 |
|  | 1 | 96.7 | 93.7 |
|  | 3 | 95.9 | 92.8 |
|  | 6 | 96.0 | 94.2 |
|  | 9 | 97.1 | not done |
|  | 12 | 96.8 | not done |

Formulation Example 8: Results of Stability Testing LMTM 75 mg Film Coated Tablets

|  | Time Point | Storage Location | |
| --- | --- | --- | --- |
| Test | (months) | 25° C./60% RH | 40° C./75% RH |
| % MT formed | 0 | 2.16 | 2.06 |
|  | 1 | 2.05 | 3.79 |
|  | 3 | 2.19 | 4.51 |

-continued

| Test | Time Point (months) | Storage Location | |
|---|---|---|---|
| | | 25° C./60% RH | 40° C./75% RH |
| | 6 | 2.83 | 5.71 |
| | 9 | 3.53 | not done |
| | 12 | 3.28 | not done |

Formulation Example 9: Results of Stability Testing LMTM 100 mg Film Coated Tablets

| Test | Time Point (months) | Storage Location | |
|---|---|---|---|
| | | 25° C./60% RH | 40° C./75% RH |
| % MT formed | 0 | 2.07 | 2.07 |
| | 1 | 1.78 | 3.27 |
| | 3 | 1.81 | 4.92 |
| | 6 | 2.51 | 5.07 |
| | 9 | 2.72 | |
| | 12 | 2.88 | |

Formulation Example 10: LMTB 100 mg Film-Coated Tablets

| Material | mg/tablet (as LMT) | mg/tablet (as LMTM) | % (core only) |
|---|---|---|---|
| Tablet Core | | | |
| LMTB (batch number 0802100070) | 100.00 | 163.03 | 32.61 |
| Spray Dried Mannitol (Pearlitol 200 SD) | 329.00 | 265.97 | 53.19 |
| Microcrystalline cellulose | 50.00 | 50.00 | 10.00 |
| Crospovidone | 15.00 | 15.00 | 3.00 |
| Magnesium Stearate | 6.00 | 6.00 | 1.20 |
| Tablet Core Total | 500.00 | 500.00 | 100.00 |
| Film Coat | | | |
| Polyvinyl Alcohol (part hydrolysed) | 8.80 | 8.80 | |
| Talc | 4.00 | 4.00 | |
| Titanium Dioxide | 3.10 | 3.10 | |
| Macrogol PEG 3350 | 2.47 | 2.47 | |
| Lecithin (soya) | 0.70 | 0.70 | |
| Iron Oxide Yellow | 0.47 | 0.47 | |
| Indigo Carmine Aluminium Lake | 0.45 | 0.45 | |
| Total Film Coated Tablet | 520.00 | 520.00 | |
| Manufacturer | Piramal, Morpeth, UK | | |
| Tablet Core Batch Number | A02581 | | |
| Date of Manufacture | 15$^{TH}$ Oct. 2009 | | |

Tablets having the above formulation were prepared by a direct compression method as described above and then film coated (see Formulation Example 1).

Formulation Example 11: LMTM 75 mg Film-Coated Tablets

| Material | mg/tablet (theoretical) | mg/tablet (actual) | % (core only) |
|---|---|---|---|
| Tablet Core | | | |
| LMTM (batch numbers 800225510 & 80224450) | 75.00 | 126.80 | 24.15 |
| Spray Dried Mannitol (Pearlitol 200 SD) | 354.00 | 302.20 | 57.56 |
| Microcrystalline cellulose | 75.00 | 75.00 | 14.29 |
| Crospovidone | 15.00 | 15.00 | 2.86 |
| Magnesium stearate | 6.00 | 6.00 | 1.14 |
| Tablet core total | 525.00 | 525.00 | 100.00 |
| Film Coat | | | |
| Polyvinyl Alcohol (part hydrolysed) | 13.86 | 13.86 | |
| Talc | 6.30 | 6.30 | |
| Titanium Dioxide | 4.89 | 4.89 | |
| Macrogol PEG 3350 | 3.89 | 3.89 | |
| Lecithin (soya) | 1.10 | 1.10 | |
| Iron Oxide Yellow | 0.75 | 0.75 | |
| Indigo Carmine Aluminium Lake | 0.71 | 0.71 | |
| Total Film Coated Tablet | 556.5 | 556.5 | |
| Manufacturer | Piramal, Morpeth, UK | | |
| Tablet Core Batch Number | A04827 | | |
| Date of Manufacture | 5$^{th}$ Aug. 2010 | | |

Tablets having the above formulation were prepared by a direct compression method as described above and then film coated (see Formulation Example 1).

Formulation Example 12—Dissolution Studies

LMTB film-coated tablets (3×100 mg) and LMTM tablets (4×75 mg), prepared as in Formulation Examples 10 and 11, were stirred (see FIG. 19) at a paddle speed of 50 rpm and the dissolution rate was assessed, using a standard pharmacopeial method (USP 34) and the conditions specified below.

Instrumental Conditions

| Parameter | Condition |
|---|---|
| Media | 0.1M HCl (Degassed with He purging) |
| Media Volume | 1000 ml, 6 vessels |
| Dissolved Oxygen | <3.00 ppm |
| Bath Temperature | 37° C. ± 0.5° C. |
| Paddles | Teflon Coated |
| Paddle Speed | 50 rpm |
| Pull Volume | 10 ml - no media replacement |
| Filter | HDPE 10 μm |
| Time points | 10, 15, 30 and 45 min |
| Vessels | 6 (protected from light) |
| $\lambda_{max\ LMT}$ | 255 nm |

| Parameter | Condition |
|---|---|
| Sample Working Concentration (μg/ml) | ca 5 μg/ml (as free base) LMT |
| Standard Working Concentration (μg/ml) | ca 5 μg/ml (as free base) LMT |

(Q=75% at 45 mins. For S1, 6 of 6 tablets not less than 80% dissolution at 45 minutes).
Results are shown in the following tables.
LMTM (4×75 mg; Batch No: A04827)
Dissolution (% dissolved):

| Vessel | T = 10 min | T = 15 min | T = 30 min | T = 45 min |
|---|---|---|---|---|
| 1 | 94 | 95 | 97 | 99 |
| 2 | 90 | 91 | 94 | 95 |
| 3 | 94 | 94 | 97 | 97 |
| 4 | 95 | 94 | 97 | 97 |
| 5 | 92 | 92 | 94 | 94 |
| 6 | 93 | 92 | 96 | 97 |
| Mean | 93 | 93 | 96 | 97 |

LMTB (3×100 mg; Batch No: A02581)
Dissolution (% dissolved):

| Vessel | T ° 10 min | T ° 15 min | T ° 30 min | T ° 45 min |
|---|---|---|---|---|
| 1 | 91 | 95 | 96 | 96 |
| 2 | 96 | 100 | 99 | 99 |
| 3 | 95 | 98 | 98 | 99 |
| 4 | 93 | 95 | 96 | 96 |
| 5 | 96 | 98 | 99 | 100 |
| 6 | 98 | 102 | 102 | 102 |
| Mean | 95 | 98 | 98 | 99 |

Tablets which had been stored for varying periods of time, under normal (25° C./60% RH) or 'stressed' conditions (40° C./75% RH), were also tested using the same method.
Results are shown in the tables below.
LMTM (4×75 mg; Batch No: A04827)—stored at 25° C./60% RH
Dissolution (% dissolved):

| Storage Time | Vessel | T = 10 min | T = 15 min | T = 30 min | T = 45 min |
|---|---|---|---|---|---|
| 1 month | 1 | 97 | 97 | 97 | 99 |
| | 2 | 96 | 98 | 101 | 101 |
| | 3 | 98 | 99 | 102 | 102 |
| | 4 | 95 | 97 | 98 | 100 |
| | 5 | 97 | 98 | 101 | 101 |
| | 6 | 98 | 98 | 100 | 101 |
| | Mean | 97 | 98 | 100 | 101 |
| 3 months | 1 | 91 | 93 | 95 | 97 |
| | 2 | 92 | 95 | 96 | 96 |
| | 3 | 93 | 94 | 95 | 97 |
| | 4 | 92 | 93 | 96 | 96 |
| | 5 | 93 | 94 | 95 | 96 |
| | 6 | 90 | 91 | 94 | 95 |
| | Mean | 92 | 93 | 95 | 96 |
| 6 months | 1 | 89 | 89 | 90 | 91 |
| | 2 | 91 | 90 | 93 | 94 |
| | 3 | 98 | 97 | 98 | 98 |
| | 4 | 97 | 97 | 99 | 99 |
| | 5 | 94 | 94 | 96 | 96 |
| | 6 | 88 | 90 | 93 | 93 |
| | Mean | 93 | 93 | 95 | 95 |
| 9 months | 1 | 92 | 93 | 92 | 94 |
| | 2 | 90 | 94 | 95 | 97 |
| | 3 | 86 | 91 | 90 | 93 |
| | 4 | 85 | 91 | 96 | 94 |
| | 5 | 90 | 85 | 94 | 94 |
| | 6 | 92 | 96 | 94 | 96 |
| | Mean | 89 | 92 | 93 | 94 |

LMTM (4×75 mg; Batch No: A04827)—stored at 40° C./75% RH
Dissolution (% dissolved):

| Storage Time | Vessel | T ° 10 min | T ° 15 min | T ° 30 min | T ° 45 min |
|---|---|---|---|---|---|
| 1 month | 1 | 94 | 95 | 97 | 98 |
| | 2 | 94 | 96 | 96 | 97 |
| | 3 | 94 | 96 | 94 | 96 |
| | 4 | 94 | 95 | 95 | 95 |
| | 5 | 100 | 102 | 103 | 101 |
| | 6 | 93 | 94 | 96 | 97 |
| | Mean | 95 | 96 | 97 | 97 |
| 3 months | 1 | 92 | 93 | 95 | 96 |
| | 2 | 93 | 94 | 95 | 97 |
| | 3 | 89 | 91 | 92 | 92 |
| | 4 | 89 | 89 | 89 | 91 |
| | 5 | 93 | 95 | 96 | 97 |
| | 6 | 93 | 95 | 98 | 97 |
| | Mean | 91 | 93 | 94 | 95 |
| 6 months | 1 | 69 | 84 | 92 | 94 |
| | 2 | 93 | 94 | 97 | 91 |
| | 3 | 64 | 85 | 92 | 94 |
| | 4 | 74 | 89 | 92 | 94 |
| | 5 | 91 | 95 | 95 | 96 |
| | 6 | 73 | 90 | 93 | 94 |
| | Mean | 77 | 89 | 94 | 94 |

LMTB (3×100 mg; Batch No: A02581)—stored at 25° C./60% RH
Dissolution (% dissolved):

| Storage Time | Vessel | T ° 10 min | T ° 15 min | T ° 30 min | T ° 45 min |
|---|---|---|---|---|---|
| 3 weeks | 1 | 96 | 98 | 98 | 98 |
| | 2 | 94 | 97 | 97 | 98 |
| | 3 | 94 | 97 | 97 | 97 |
| | 4 | 98 | 100 | 101 | 101 |
| | 5 | 92 | 94 | 95 | 95 |
| | 6 | 92 | 95 | 97 | 97 |
| | Mean | 94 | 97 | 98 | 98 |
| 3 months | 1 | 89 | 92 | 92 | 92 |
| | 2 | 89 | 92 | 93 | 92 |
| | 3 | 93 | 96 | 96 | 96 |
| | 4 | 95 | 98 | 99 | 98 |
| | 5 | 95 | 96 | 96 | 96 |
| | 6 | 96 | 99 | 98 | 97 |
| | Mean | 93 | 96 | 96 | 95 |
| 6 months | 1 | 96 | 97 | 96 | 97 |
| | 2 | 95 | 101 | 100 | 101 |
| | 3 | 95 | 97 | 96 | 97 |
| | 4 | 95 | 95 | 95 | 96 |
| | 5 | 96 | 98 | 99 | 99 |
| | 6 | 95 | 94 | 94 | 96 |

-continued

| Storage Time | Vessel | T° 10 min | T° 15 min | T° 30 min | T° 45 min |
|---|---|---|---|---|---|
| 9 months | Mean | 95 | 97 | 97 | 98 |
| | 1 | 87 | 91 | 93 | 91 |
| | 2 | 88 | 92 | 94 | 92 |
| | 3 | 90 | 93 | 91 | 92 |
| | 4 | 91 | 95 | 93 | 94 |
| | 5 | 91 | 93 | 93 | 92 |
| | 6 | 94 | 95 | 95 | 93 |
| | Mean | 90 | 93 | 93 | 92 |
| 12 months | 1 | 92 | 97 | 98 | 97 |
| | 2 | 91 | 92 | 92 | 92 |
| | 3 | 95 | 96 | 95 | 96 |
| | 4 | 94 | 95 | 95 | 95 |
| | 5 | 89 | 89 | 89 | 89 |
| | 6 | 97 | 98 | 98 | 98 |
| | Mean | 93 | 94 | 95 | 94 |

LMTB (3×100 mg; Batch No: A02581)—stored at 40° C./75% RH

Dissolution (% dissolved):

| Storage Time | Vessel | T° 10 min | T° 15 min | T° 30 min | T° 45 min |
|---|---|---|---|---|---|
| 3 weeks | 1 | 94 | 98 | 99 | 98 |
| | 2 | 96 | 100 | 100 | 101 |
| | 3 | 94 | 97 | 96 | 97 |
| | 4 | 94 | 98 | 98 | 98 |
| | 5 | 95 | 97 | 98 | 98 |
| | 6 | 95 | 97 | 98 | 97 |
| | Mean | 95 | 98 | 98 | 98 |
| 3 months | 1 | 92 | 93 | 94 | 93 |
| | 2 | 93 | 97 | 97 | 97 |
| | 3 | 90 | 92 | 92 | 92 |
| | 4 | 84 | 89 | 94 | 94 |
| | 5 | 84 | 97 | 97 | 97 |
| | 6 | 93 | 94 | 93 | 94 |
| | Mean | 89 | 94 | 95 | 95 |
| 6 months | 1 | 8 | 72 | 96 | 96 |
| | 2 | 48 | 82 | 95 | 96 |
| | 3 | 91 | 93 | 94 | 94 |
| | 4 | 94 | 98 | 98 | 99 |
| | 5 | 13 | 71 | 93 | 93 |
| | 6 | 74 | 87 | 92 | 93 |
| | Mean | 55 | 84 | 95 | 95 |

Annex—Crystallographic Data

Crystallographic Data for LMT.EDSA (FIG. 17a):

TABLE 1

Crystal data and structure refinement for LMT•EDSA.

| | |
|---|---|
| Identification code | 6408CM136 |
| Empirical formula | $C_{18} H_{27} N_3 O_7 S_3$ |
| Formula weight | 493.62 |
| Temperature | 100(2) K |
| Wavelength | 0.71073 Å |
| Crystal system | Monoclinic |
| Space group | C2/c |
| Unit cell dimensions | a = 18.2832(3) Å  α = 90°. |
| | b = 11.8667(3) Å  β = 114.1990(10)°. |
| | c = 10.9539(2) Å  γ = 90°. |
| Volume | 2167.74(8) Å$^3$ |
| Z | 4 |
| Density (calculated) | 1.519 Mg/m$^3$ |
| Absorption coefficient | 0.389 mm$^{-1}$ |
| F(000) | 1048 |

TABLE 1-continued

Crystal data and structure refinement for LMT•EDSA.

| | |
|---|---|
| Crystal size | 0.28 × 0.21 × 0.18 mm$^3$ |
| Theta range for data collection | 2.11 to 27.51°. |
| Index ranges | −23 <= h <= 23, −15 <= k <= 15, −14 <= l <= 14 |
| Reflections collected | 25214 |
| Independent reflections | 2487 [R(int) = 0.0486] |
| Completeness to theta = 25.00° | 99.9% |
| Absorption correction | Semi-empirical from equivalents |
| Max. and min. transmission | 0.9333 and 0.8989 |
| Refinement method | Full-matrix least-squares on F$^2$ |
| Data/restraints/parameters | 2487/0/144 |
| Goodness-of-fit on F$^2$ | 1.080 |
| Final R indices [I > 2sigma(I)] | R1 = 0.0315, wR2 = 0.0906 |
| R indices (all data) | R1 = 0.0336, wR2 = 0.0925 |
| Largest diff. peak and hole | 0.333 and −0.654 e · Å$^{-3}$ |

TABLE 2

Atomic coordinates (×10$^4$) and equivalent isotropic displacement parameters (Å$^2$ × 10$^3$) for LMT•EDSA. U(eq) is defined as one third of the trace of the orthogonalized U$^{ij}$ tensor.

| | x | y | z | U(eq) |
|---|---|---|---|---|
| S(1) | 10000 | 2270(1) | 12500 | 19(1) |
| S(2) | 3802(1) | 204(1) | 9934(1) | 11(1) |
| N(1) | 10000 | −370(1) | 12500 | 18(1) |
| N(2) | 7750(1) | 1619(1) | 7782(1) | 12(1) |
| O(1) | 3943(1) | −435(1) | 11137(1) | 18(1) |
| O(2) | 3830(1) | 1425(1) | 10131(1) | 17(1) |
| O(3) | 3063(1) | −144(1) | 8793(1) | 15(1) |
| C(1) | 9411(1) | 1332(1) | 11218(1) | 13(1) |
| C(2) | 9493(1) | 154(1) | 11332(1) | 14(1) |
| C(3) | 9040(1) | −512(1) | 10228(1) | 16(1) |
| C(4) | 8481(1) | −30(1) | 9061(1) | 16(1) |
| C(5) | 8383(1) | 1126(1) | 8996(1) | 13(1) |
| C(6) | 8852(1) | 1814(1) | 10051(1) | 13(1) |
| C(8) | 7127(1) | 2225(1) | 8087(1) | 16(1) |
| C(9) | 8070(1) | 2352(1) | 7003(1) | 17(1) |
| C(10) | 4593(1) | −141(1) | 9448(1) | 13(1) |
| O(1S) | 5000 | 2293(1) | 2500 | 24(1) |

TABLE 3

Bond lengths [Å] and angles [°] for LMT•EDSA.

| | |
|---|---|
| S(1)—C(1) | 1.7696(13) |
| S(1)—C(1)#1 | 1.7696(13) |
| S(2)—O(1) | 1.4488(10) |
| S(2)—O(2) | 1.4629(10) |
| S(2)—O(3) | 1.4747(10) |
| S(2)—C(10) | 1.7802(13) |
| N(1)—C(2) | 1.3826(15) |
| N(1)—C(2)#1 | 1.3826(15) |
| N(1)—H(1) | 0.8800 |
| N(2)—C(5) | 1.4785(16) |
| N(2)—C(9) | 1.4959(17) |
| N(2)—C(8) | 1.4970(17) |
| N(2)—H(2) | 0.9300 |
| C(1)—C(6) | 1.3913(17) |
| C(1)—C(2) | 1.4049(18) |
| C(2)—C(3) | 1.3972(19) |
| C(3)—C(4) | 1.3908(19) |
| C(3)—H(3) | 0.9500 |
| C(4)—C(5) | 1.3804(19) |
| C(4)—H(4) | 0.9500 |
| C(5)—C(6) | 1.3881(18) |
| C(6)—H(6) | 0.9500 |
| C(8)—H(8A) | 0.9800 |
| C(8)—H(8B) | 0.9800 |
| C(8)—H(8C) | 0.9800 |
| C(9)—H(9A) | 0.9800 |
| C(9)—H(9B) | 0.9800 |

TABLE 3-continued

Bond lengths [Å] and angles [°] for LMT•EDSA.

| | |
|---|---|
| C(9)—H(9C) | 0.9800 |
| C(10)—C(10)#2 | 1.522(2) |
| C(10)—H(10A) | 0.9900 |
| C(10)—H(10B) | 0.9900 |
| O(1S)—H(1O1) | 0.7486 |
| O(1S)—H(2O1) | 0.9717 |
| C(1)—S(1)—C(1)#1 | 102.05(9) |
| O(1)—S(2)—O(2) | 113.66(6) |
| O(1)—S(2)—O(3) | 112.60(6) |
| O(2)—S(2)—O(3) | 111.52(6) |
| O(1)—S(2)—C(10) | 106.77(6) |
| O(2)—S(2)—C(10) | 106.71(6) |
| O(3)—S(2)—C(10) | 104.89(6) |
| C(2)—N(1)—C(2)#1 | 126.50(17) |
| C(2)—N(1)—H(1) | 116.7 |
| C(2)#1—N(1)—H(1) | 116.7 |
| C(5)—N(2)—C(9) | 113.51(10) |
| C(5)—N(2)—C(8) | 112.13(10) |
| C(9)—N(2)—C(8) | 111.06(11) |
| C(5)—N(2)—H(2) | 106.5 |
| C(9)—N(2)—H(2) | 106.5 |
| C(8)—N(2)—H(2) | 106.5 |
| C(6)—C(1)—C(2) | 120.17(12) |
| C(6)—C(1)—S(1) | 116.69(10) |
| C(2)—C(1)—S(1) | 123.14(10) |
| N(1)—C(2)—C(3) | 118.76(13) |
| N(1)—C(2)—C(1) | 122.44(13) |
| C(3)—C(2)—C(1) | 118.79(12) |
| C(4)—C(3)—C(2) | 120.95(13) |
| C(4)—C(3)—H(3) | 119.5 |
| C(2)—C(3)—H(3) | 119.5 |
| C(5)—C(4)—C(3) | 119.15(13) |
| C(5)—C(4)—H(4) | 120.4 |
| C(3)—C(4)—H(4) | 120.4 |
| C(4)—C(5)—C(6) | 121.24(12) |
| C(4)—C(5)—N(2) | 118.50(12) |
| C(6)—C(5)—N(2) | 120.25(12) |
| C(5)—C(6)—C(1) | 119.54(12) |
| C(5)—C(6)—H(6) | 120.2 |
| C(1)—C(6)—H(6) | 120.2 |
| N(2)—C(8)—H(8A) | 109.5 |
| N(2)—C(8)—H(8B) | 109.5 |
| H(8A)—C(8)—H(8B) | 109.5 |
| N(2)—C(8)—H(8C) | 109.5 |
| H(8A)—C(8)—H(8C) | 109.5 |
| H(8B)—C(8)—H(8C) | 109.5 |
| N(2)—C(9)—H(9A) | 109.5 |
| N(2)—C(9)—H(9B) | 109.5 |
| H(9A)—C(9)—H(9B) | 109.5 |
| N(2)—C(9)—H(9C) | 109.5 |
| H(9A)—C(9)—H(9C) | 109.5 |
| H(9B)—C(9)—H(9C) | 109.5 |
| C(10)#2—C(10)—S(2) | 111.21(12) |
| C(10)#2—C(10)—H(10A) | 109.4 |
| S(2)—C(10)—H(10A) | 109.4 |
| C(10)#2—C(10)—H(10B) | 109.4 |
| S(2)—C(10)—H(10B) | 109.4 |
| H(10A)—C(10)—H(10B) | 108.0 |
| H(1O1)—O(1S)—H(2O1) | 100.8 |

Symmetry transformations used to generate equivalent atoms:
1 −x + 2, y, −z + 5/2
2 −x + 1, −y, −z + 2

TABLE 4

Anisotropic displacement parameters (Å$^2$ × 10$^3$) for LMT•EDSA. The anisotropic displacement factor exponent takes the form: $-2p^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| S(1) | 20(1) | 10(1) | 14(1) | 0 | −6(1) | 0 |
| S(2) | 10(1) | 12(1) | 9(1) | 0(1) | 2(1) | 0(1) |
| N(1) | 22(1) | 9(1) | 14(1) | 0 | −3(1) | 0 |
| N(2) | 12(1) | 13(1) | 9(1) | 0(1) | 2(1) | −1(1) |
| O(1) | 16(1) | 22(1) | 13(1) | 5(1) | 5(1) | 0(1) |
| O(2) | 17(1) | 13(1) | 17(1) | −2(1) | 4(1) | 0(1) |
| O(3) | 11(1) | 16(1) | 13(1) | −1(1) | 0(1) | −1(1) |
| C(1) | 12(1) | 13(1) | 11(1) | −1(1) | 2(1) | −2(1) |
| C(2) | 12(1) | 13(1) | 13(1) | 0(1) | 2(1) | 0(1) |
| C(3) | 19(1) | 11(1) | 14(1) | −2(1) | 3(1) | −1(1) |
| C(4) | 16(1) | 15(1) | 12(1) | −2(1) | 2(1) | −1(1) |
| C(5) | 12(1) | 15(1) | 10(1) | 1(1) | 2(1) | 0(1) |
| C(6) | 13(1) | 12(1) | 12(1) | 0(1) | 4(1) | 0(1) |
| C(8) | 13(1) | 18(1) | 15(1) | 1(1) | 5(1) | 1(1) |
| C(9) | 18(1) | 22(1) | 12(1) | 2(1) | 6(1) | −2(1) |
| C(10) | 11(1) | 17(1) | 10(1) | −2(1) | 3(1) | −1(1) |
| O(1S) | 25(1) | 14(1) | 18(1) | 0 | −7(1) | 0 |

TABLE 5

Hydrogen coordinates (×10$^4$) and isotropic displacement parameters (Å$^2$ × 10$^3$) for LMT•EDSA.

| | x | y | z | U(eq) |
|---|---|---|---|---|
| H(1) | 10000 | −1111 | 12500 | 22 |
| H(2) | 7492 | 1019 | 7227 | 15 |
| H(3) | 9114 | −1305 | 10275 | 19 |
| H(4) | 8171 | −489 | 8319 | 19 |
| H(6) | 8791 | 2610 | 9978 | 15 |
| H(8A) | 6937 | 1734 | 8616 | 23 |
| H(8B) | 6675 | 2426 | 7248 | 23 |
| H(8C) | 7359 | 2911 | 8596 | 23 |
| H(9A) | 8321 | 3023 | 7531 | 26 |
| H(9B) | 7629 | 2582 | 6164 | 26 |
| H(9C) | 8469 | 1933 | 6802 | 26 |
| H(10A) | 4571 | −955 | 9239 | 16 |
| H(10B) | 4521 | 284 | 8628 | 16 |
| H(1O1) | 5146 | 2050 | 3190 | 29 |
| H(2O1) | 4556 | 1790 | 2015 | 29 |

Crystallographic Data for LMT.2EsOH (FIG. 17b)

TABLE 1

Crystal data and structure refinement for LMT•2EsOH.

| | |
|---|---|
| Identification code | 6408cm173c_0m |
| Empirical formula | $C_{20}H_{31}N_3O_6S_3$ |
| Formula weight | 505.66 |
| Temperature | 100(2) K |
| Wavelength | 0.71073 Å |
| Crystal system | Monoclinic |
| Space group | C2/c |
| Unit cell dimensions | a = 40.8384(12) Å  α = 90°. |
| | b = 25.2658(7) Å  β = 115.4540(10)° |
| | c = 20.3833(6) Å  γ = 90°. |
| Volume | 18990.2(9) Å$^3$ |
| Z | 32 |
| Density (calculated) | 1.415 Mg/m$^3$ |
| Absorption coefficient | 0.354 mm$^{-1}$ |
| F(000) | 8576 |
| Crystal size | 0.32 × 0.24 × 0.18 mm$^3$ |
| Theta range for data collection | 0.98 to 25.00°. |
| Index ranges | −48 <= h <= 48, −29 <= k <= 30, −24 <= l <= 23 |
| Reflections collected | 108984 |
| Independent reflections | 16707 [R(int) = 0.0912] |
| Completeness to theta = 25.00° | 99.9% |

TABLE 1-continued

Crystal data and structure refinement for LMT•2EsOH.

| | |
|---|---|
| Absorption correction | Semi-empirical from equivalents |
| Max. and min. transmission | 0.9391 and 0.8952 |
| Refinement method | Full-matrix least-squares on $F^2$ |
| Data/restraints/parameters | 16707/25/1205 |
| Goodness-of-fit on $F^2$ | 1.085 |
| Final R indices [I > 2sigma(I)] | R1 = 0.0628, wR2 = 0.1638 |
| R indices (all data) | R1 = 0.0986, wR2 = 0.1918 |
| Largest diff. peak and hole | 2.683 and −0.811 e · Å$^{-3}$ |

TABLE 2

Atomic coordinates (×10$^4$) and equivalent isotropic displacement parameters (Å$^2$ × 10$^3$) for LMT•2EsOH. U(eq) is defined as one third of the trace of the orthogonalized U$^{ij}$ tensor.

| | x | y | z | U(eq) |
|---|---|---|---|---|
| S(1A) | 256(1) | 3950(1) | 1866(1) | 69(1) |
| N(1A) | −401(1) | 3176(1) | 1220(2) | 29(1) |
| N(2A) | 980(1) | 2230(1) | 2700(2) | 25(1) |
| N(3A) | −743(1) | 5348(1) | 744(2) | 25(1) |
| C(1A) | −207(1) | 4102(2) | 1408(3) | 33(1) |
| C(2A) | −297(1) | 4633(2) | 1295(3) | 32(1) |
| C(3A) | −652(1) | 4786(2) | 916(2) | 24(1) |
| C(4A) | −926(1) | 4413(2) | 664(2) | 27(1) |
| C(5A) | −836(1) | 3880(2) | 784(3) | 28(1) |
| C(6A) | −479(1) | 3714(2) | 1142(2) | 25(1) |
| C(7A) | −60(1) | 2948(2) | 1584(2) | 25(1) |
| C(8A) | −27(1) | 2402(2) | 1631(2) | 24(1) |
| C(9A) | 308(1) | 2154(2) | 1988(2) | 25(1) |
| C(10A) | 614(1) | 2468(2) | 2318(2) | 24(1) |
| C(11A) | 588(1) | 3011(2) | 2281(2) | 29(1) |
| C(12A) | 254(1) | 3255(2) | 1917(3) | 32(1) |
| C(13A) | 1017(1) | 1896(2) | 3334(3) | 36(1) |
| C(14A) | 1092(1) | 1933(2) | 2196(3) | 41(1) |
| C(15A) | −662(2) | 5526(2) | 130(3) | 50(1) |
| C(16A) | −570(1) | 5712(2) | 1375(3) | 33(1) |
| S(1B) | 2816(1) | 1091(1) | 1548(1) | 26(1) |
| N(1B) | 2213(1) | 258(1) | 1144(2) | 21(1) |
| N(2B) | 3639(1) | −517(1) | 2667(2) | 27(1) |
| N(3B) | 1743(1) | 2378(1) | 956(2) | 22(1) |
| C(1B) | 2355(1) | 1198(2) | 1329(2) | 19(1) |
| C(2B) | 2237(1) | 1719(2) | 1291(2) | 22(1) |
| C(3B) | 1873(1) | 1825(2) | 1032(2) | 21(1) |
| C(4B) | 1620(1) | 1417(2) | 832(2) | 22(1) |
| C(5B) | 1738(1) | 896(2) | 890(2) | 21(1) |
| C(6B) | 2104(1) | 778(2) | 1128(2) | 21(1) |
| C(7B) | 2566(1) | 73(2) | 1537(2) | 22(1) |
| C(8B) | 2628(1) | −468(2) | 1684(2) | 23(1) |
| C(9B) | 2974(1) | −666(2) | 2055(2) | 24(1) |
| C(10B) | 3263(1) | −320(2) | 2304(2) | 24(1) |
| C(11B) | 3213(1) | 220(2) | 2178(2) | 23(1) |
| C(12B) | 2866(1) | 417(2) | 1788(2) | 22(1) |
| C(13B) | 3693(2) | −973(2) | 3183(3) | 38(1) |
| C(14B) | 3785(1) | −651(2) | 2126(2) | 29(1) |
| C(15B) | 1835(1) | 2684(2) | 426(3) | 34(1) |
| C(16B) | 1872(1) | 2660(2) | 1668(3) | 35(1) |
| S(1C) | 5390(1) | 3672(1) | 1826(1) | 25(1) |
| N(1C) | 4792(1) | 2826(1) | 1436(2) | 25(1) |
| N(2C) | 6224(1) | 2099(1) | 3029(2) | 20(1) |
| N(3C) | 4310(1) | 4945(1) | 1101(2) | 26(1) |
| C(1C) | 4925(1) | 3774(2) | 1581(2) | 20(1) |
| C(2C) | 4803(1) | 4289(2) | 1510(2) | 21(1) |
| C(3C) | 4436(1) | 4388(2) | 1235(2) | 21(1) |
| C(4C) | 4184(1) | 3984(2) | 1037(2) | 25(1) |
| C(5C) | 4307(1) | 3464(2) | 1126(2) | 23(1) |
| C(6C) | 4676(1) | 3350(2) | 1388(2) | 21(1) |
| C(7C) | 5145(1) | 2651(2) | 1833(2) | 22(1) |
| C(8C) | 5213(1) | 2113(2) | 1990(2) | 22(1) |
| C(9C) | 5559(1) | 1925(2) | 2384(2) | 21(1) |
| C(10C) | 5847(1) | 2278(2) | 2639(2) | 20(1) |
| C(11C) | 5788(1) | 2813(2) | 2493(2) | 21(1) |
| C(12C) | 5443(1) | 3002(2) | 2087(2) | 20(1) |
| C(13C) | 6374(1) | 1945(2) | 2499(2) | 26(1) |
| C(14C) | 6284(1) | 1670(2) | 3576(2) | 24(1) |
| C(15C) | 4375(2) | 5182(2) | 496(3) | 47(1) |
| C(16C) | 4468(2) | 5280(2) | 1771(2) | 47(2) |
| S(1D) | 7907(1) | 1349(1) | 2060(1) | 32(1) |
| N(1D) | 7269(1) | 547(1) | 1633(2) | 29(1) |
| N(2D) | 8670(1) | −331(2) | 2894(2) | 28(1) |
| N(3D) | 6848(1) | 2694(1) | 1136(2) | 27(1) |
| C(1D) | 7440(1) | 1484(2) | 1723(2) | 25(1) |
| C(2D) | 7333(1) | 2011(2) | 1602(2) | 27(1) |
| C(3D) | 6969(1) | 2136(2) | 1304(2) | 26(1) |
| C(4D) | 6709(1) | 1744(2) | 1117(3) | 32(1) |
| C(5D) | 6818(1) | 1220(2) | 1238(3) | 32(1) |
| C(6D) | 7179(1) | 1080(2) | 1536(2) | 24(1) |
| C(7D) | 7614(1) | 338(2) | 1971(2) | 22(1) |
| C(8D) | 7660(1) | −209(2) | 2063(2) | 24(1) |
| C(9D) | 8001(1) | −439(2) | 2370(2) | 25(1) |
| C(10D) | 8302(1) | −111(2) | 2608(2) | 24(1) |
| C(11D) | 8268(1) | 437(2) | 2537(2) | 26(1) |
| C(12D) | 7925(1) | 662(2) | 2212(2) | 23(1) |
| C(13D) | 8743(1) | −762(2) | 3435(3) | 43(1) |
| C(14D) | 8764(1) | −504(2) | 2294(3) | 31(1) |
| C(15D) | 6807(2) | 2848(2) | 397(3) | 41(1) |
| C(16D) | 7078(2) | 3086(2) | 1700(3) | 36(1) |
| S(2) | 525(1) | 500(1) | 1331(1) | 35(1) |
| S(3) | 827(1) | 2850(1) | 152(1) | 25(1) |
| S(4) | 1743(1) | 4426(1) | 389(1) | 29(1) |
| S(5) | 3048(1) | 3051(1) | 1414(1) | 30(1) |
| S(6) | 5663(1) | 497(1) | 1723(1) | 33(1) |
| S(7) | 5874(1) | 2562(1) | 455(1) | 34(1) |
| S(8) | 8160(1) | 2896(1) | 1391(1) | 23(1) |
| S(9) | 8481(1) | 615(1) | 291(1) | 26(1) |
| O(1) | 619(4) | 884(5) | 1948(7) | 56(2) |
| O(2) | 392(10) | 52(10) | 1452(19) | 70(6) |
| O(3) | 886(4) | 594(6) | 1706(8) | 55(2) |
| O(1') | 342(2) | 769(3) | 1689(4) | 61(2) |
| O(2') | 419(6) | −77(6) | 1226(11) | 70(5) |
| O(3') | 893(2) | 480(4) | 1357(5) | 58(2) |
| O(4) | 1009(1) | 2335(2) | 358(2) | 35(1) |
| O(5) | 1031(1) | 3269(1) | 635(2) | 41(1) |
| O(6) | 718(1) | 2970(1) | −613(2) | 27(1) |
| O(7) | 1911(1) | 3966(1) | 826(2) | 45(1) |
| O(8) | 1422(1) | 4299(1) | −282(2) | 45(1) |
| O(9) | 1667(1) | 4851(1) | 790(2) | 30(1) |
| O(10) | 3321(1) | 2861(2) | 1185(2) | 41(1) |
| O(11) | 2835(1) | 2637(2) | 1525(3) | 68(1) |
| O(12) | 3217(1) | 3392(1) | 2047(2) | 46(1) |
| O(13) | 5318(1) | 542(2) | 1772(2) | 56(1) |
| O(14) | 5728(1) | −26(1) | 1506(2) | 60(1) |
| O(15) | 5964(1) | 678(1) | 2388(2) | 42(1) |
| O(16) | 5932(1) | 2520(1) | −212(2) | 32(1) |
| O(17) | 5774(1) | 2071(2) | 681(2) | 57(1) |
| O(18) | 6182(1) | 2836(1) | 1038(2) | 39(1) |
| O(19) | 8126(1) | 2360(1) | 1113(2) | 31(1) |
| O(20) | 8540(1) | 3032(1) | 1876(2) | 35(1) |
| O(21) | 7918(1) | 3019(1) | 1720(2) | 31(1) |
| O(22) | 8264(1) | 640(1) | −494(2) | 26(1) |
| O(23) | 8590(1) | 62(1) | 534(2) | 31(1) |
| O(24) | 8786(1) | 983(1) | 553(2) | 33(1) |
| C(1S) | 298(2) | 782(2) | 463(4) | 62(2) |
| C(2S) | 387(2) | 1337(2) | 396(3) | 45(2) |
| C(3S) | 2064(1) | 4682(2) | 95(3) | 30(1) |
| C(4S) | 1928(1) | 5196(2) | −337(3) | 39(1) |
| C(5S) | 2748(1) | 3452(2) | 689(3) | 37(1) |
| C(6S) | 2934(1) | 3925(2) | 551(3) | 32(1) |
| C(7S) | 5504(1) | 2984(2) | 239(3) | 39(1) |
| C(8S) | 5570(1) | 3516(2) | −63(4) | 54(2) |
| C(9S) | 5626(2) | 921(2) | 1016(3) | 38(1) |
| C(10S) | 5990(3) | 881(4) | 989(5) | 100(3) |
| C(11S) | 8047(1) | 3340(2) | 650(3) | 28(1) |
| C(12S) | 7648(1) | 3320(2) | 118(3) | 38(1) |

TABLE 2-continued

Atomic coordinates (×10⁴) and equivalent isotropic displacement parameters ($Å^2 \times 10^3$) for LMT•2EsOH. U(eq) is defined as one third of the trace of the orthogonalized $U^{ij}$ tensor.

|       | x       | y       | z      | U(eq) |
|-------|---------|---------|--------|-------|
| C(13S)| 8200(1) | 808(2)  | 708(3) | 27(1) |
| C(14S)| 7876(1) | 454(2)  | 490(3) | 34(1) |
| C(15S)| 414(1)  | 2769(2) | 254(3) | 36(1) |
| C(16S)| 186(2)  | 3261(2) | 66(3)  | 49(2) |

TABLE 3

Bond lengths [Å] and angles [°] for LMT•2EsOH.

| | |
|---|---|
| S(1A)—C(1A) | 1.756(5) |
| S(1A)—C(12A) | 1.759(5) |
| N(1A)—C(7A) | 1.390(6) |
| N(1A)—C(6A) | 1.389(6) |
| N(1A)—H(1AA) | 0.8800 |
| N(2A)—C(10A) | 1.485(5) |
| N(2A)—C(14A) | 1.492(6) |
| N(2A)—C(13A) | 1.495(6) |
| N(2A)—H(2AA) | 0.9300 |
| N(3A)—C(3A) | 1.474(5) |
| N(3A)—C(16A) | 1.489(6) |
| N(3A)—C(15A) | 1.494(6) |
| N(3A)—H(3A) | 0.9300 |
| C(1A)—C(2A) | 1.384(6) |
| C(1A)—C(6A) | 1.404(6) |
| C(2A)—C(3A) | 1.371(6) |
| C(2A)—H(2A) | 0.9500 |
| C(3A)—C(4A) | 1.384(6) |
| C(4A)—C(5A) | 1.389(6) |
| C(4A)—H(4A) | 0.9500 |
| C(5A)—C(6A) | 1.384(6) |
| C(5A)—H(5A) | 0.9500 |
| C(7A)—C(8A) | 1.387(6) |
| C(7A)—C(12A) | 1.399(6) |
| C(8A)—C(9A) | 1.391(6) |
| C(8A)—H(8A) | 0.9500 |
| C(9A)—C(10A) | 1.384(6) |
| C(9A)—H(9A) | 0.9500 |
| C(10A)—C(11A) | 1.376(6) |
| C(11A)—C(12A) | 1.388(6) |
| C(11A)—H(11A) | 0.9500 |
| C(13A)—H(13A) | 0.9800 |
| C(13A)—H(13B) | 0.9800 |
| C(13A)—H(13C) | 0.9800 |
| C(14A)—H(14A) | 0.9800 |
| C(14A)—H(14B) | 0.9800 |
| C(14A)—H(14C) | 0.9800 |
| C(15A)—H(15A) | 0.9800 |
| C(15A)—H(15B) | 0.9800 |
| C(15A)—H(15C) | 0.9800 |
| C(16A)—H(16A) | 0.9800 |
| C(16A)—H(16B) | 0.9800 |
| C(16A)—H(16C) | 0.9800 |
| S(1B)—C(12B) | 1.761(4) |
| S(1B)—C(1B) | 1.762(4) |
| N(1B)—C(6B) | 1.385(5) |
| N(1B)—C(7B) | 1.392(6) |
| N(1B)—H(1B) | 0.8800 |
| N(2B)—C(10B) | 1.474(6) |
| N(2B)—C(14B) | 1.502(6) |
| N(2B)—C(13B) | 1.512(6) |
| N(2B)—H(2BB) | 0.9300 |
| N(3B)—C(3B) | 1.479(5) |
| N(3B)—C(16B) | 1.496(6) |
| N(3B)—C(15B) | 1.501(6) |
| N(3B)—H(3B) | 0.9300 |
| C(1B)—C(2B) | 1.392(6) |
| C(1B)—C(6B) | 1.410(6) |
| C(2B)—C(3B) | 1.372(6) |
| C(2B)—H(2B) | 0.9500 |
| C(3B)—C(4B) | 1.391(6) |
| C(4B)—C(5B) | 1.391(6) |
| C(4B)—H(4B) | 0.9500 |
| C(5B)—C(6B) | 1.389(6) |
| C(5B)—H(5B) | 0.9500 |
| C(7B)—C(8B) | 1.399(6) |
| C(7B)—C(12B) | 1.406(6) |
| C(8B)—C(9B) | 1.377(6) |
| C(8B)—H(8B) | 0.9500 |
| C(9B)—C(10B) | 1.381(6) |
| C(9B)—H(9B) | 0.9500 |
| C(10B)—C(11B) | 1.384(6) |
| C(11B)—C(12B) | 1.388(6) |
| C(11B)—H(11B) | 0.9500 |
| C(13B)—H(13D) | 0.9800 |
| C(13B)—H(13E) | 0.9800 |
| C(13B)—H(13F) | 0.9800 |
| C(14B)—H(14D) | 0.9800 |
| C(14B)—H(14E) | 0.9800 |
| C(14B)—H(14F) | 0.9800 |
| C(15B)—H(15D) | 0.9800 |
| C(15B)—H(15E) | 0.9800 |
| C(15B)—H(15F) | 0.9800 |
| C(16B)—H(16D) | 0.9800 |
| C(16B)—H(16E) | 0.9800 |
| C(16B)—H(16F) | 0.9800 |
| S(1C)—C(12C) | 1.760(4) |
| S(1C)—C(1C) | 1.765(4) |
| N(1C)—C(7C) | 1.387(5) |
| N(1C)—C(6C) | 1.395(5) |
| N(1C)—H(1C) | 0.8800 |
| N(2C)—C(10C) | 1.469(5) |
| N(2C)—C(14C) | 1.498(5) |
| N(2C)—C(13C) | 1.503(5) |
| N(2C)—H(2CC) | 0.9300 |
| N(3C)—C(3C) | 1.482(5) |
| N(3C)—C(15C) | 1.494(6) |
| N(3C)—C(16C) | 1.497(6) |
| N(3C)—H(3C) | 0.9300 |
| C(1C)—C(2C) | 1.377(6) |
| C(1C)—C(6C) | 1.411(6) |
| C(2C)—C(3C) | 1.380(6) |
| C(2C)—H(2C) | 0.9500 |
| C(3C)—C(4C) | 1.381(6) |
| C(4C)—C(5C) | 1.390(6) |
| C(4C)—H(4C) | 0.9500 |
| C(5C)—C(6C) | 1.397(6) |
| C(5C)—H(5C) | 0.9500 |
| C(7C)—C(8C) | 1.397(6) |
| C(7C)—C(12C) | 1.413(6) |
| C(8C)—C(9C) | 1.378(6) |
| C(8C)—H(8C) | 0.9500 |
| C(9C)—C(10C) | 1.386(6) |
| C(9C)—H(9C) | 0.9500 |
| C(10C)—C(11C) | 1.384(6) |
| C(11C)—C(12C) | 1.377(6) |
| C(11C)—H(11C) | 0.9500 |
| C(13C)—H(13G) | 0.9800 |
| C(13C)—H(13H) | 0.9800 |
| C(13C)—H(13I) | 0.9800 |
| C(14C)—H(14G) | 0.9800 |
| C(14C)—H(14H) | 0.9800 |
| C(14C)—H(14I) | 0.9800 |
| C(15C)—H(15G) | 0.9800 |
| C(15C)—H(15H) | 0.9800 |
| C(15C)—H(15I) | 0.9800 |
| C(16C)—H(16G) | 0.9800 |
| C(16C)—H(16H) | 0.9800 |
| C(16C)—H(16I) | 0.9800 |
| S(1D)—C(12D) | 1.760(4) |
| S(1D)—C(1D) | 1.761(5) |
| N(1D)—C(7D) | 1.381(6) |
| N(1D)—C(6D) | 1.389(6) |
| N(1D)—H(1D) | 0.8800 |
| N(2D)—C(10D) | 1.471(6) |
| N(2D)—C(13D) | 1.486(6) |
| N(2D)—C(14D) | 1.495(6) |
| N(2D)—H(2D) | 0.9300 |
| N(3D)—C(3D) | 1.483(6) |
| N(3D)—C(15D) | 1.495(6) |

TABLE 3-continued

Bond lengths [Å] and angles [°] for LMT•2EsOH.

| | |
|---|---|
| N(3D)—C(16D) | 1.504(6) |
| N(3D)—H(3D) | 0.9300 |
| C(1D)—C(2D) | 1.389(6) |
| C(1D)—C(6D) | 1.405(6) |
| C(2D)—C(3D) | 1.379(6) |
| C(2D)—H(2DD) | 0.9500 |
| C(3D)—C(4D) | 1.381(6) |
| C(4D)—C(5D) | 1.385(7) |
| C(4D)—H(4D) | 0.9500 |
| C(5D)—C(6D) | 1.377(6) |
| C(5D)—H(5D) | 0.9500 |
| C(7D)—C(8D) | 1.394(6) |
| C(7D)—C(12D) | 1.409(6) |
| C(8D)—C(9D) | 1.385(6) |
| C(8D)—H(8D) | 0.9500 |
| C(9D)—C(10D) | 1.384(6) |
| C(9D)—H(9D) | 0.9500 |
| C(10D)—C(11D) | 1.391(6) |
| C(11D)—C(12D) | 1.388(6) |
| C(11D)—H(11D) | 0.9500 |
| C(13D)—H(13J) | 0.9800 |
| C(13D)—H(13K) | 0.9800 |
| C(13D)—H(13L) | 0.9800 |
| C(14D)—H(14J) | 0.9800 |
| C(14D)—H(14K) | 0.9800 |
| C(14D)—H(14L) | 0.9800 |
| C(15D)—H(15J) | 0.9800 |
| C(15D)—H(15K) | 0.9800 |
| C(15D)—H(15L) | 0.9800 |
| C(16D)—H(16J) | 0.9800 |
| C(16D)—H(16K) | 0.9800 |
| C(16D)—H(16L) | 0.9800 |
| S(2)—O(2) | 1.32(3) |
| S(2)—O(3) | 1.359(16) |
| S(2)—O(1') | 1.423(7) |
| S(2)—O(3') | 1.481(8) |
| S(2)—O(2') | 1.510(16) |
| S(2)—O(1) | 1.503(13) |
| S(2)—C(1S) | 1.756(6) |
| S(3)—O(5) | 1.442(3) |
| S(3)—O(6) | 1.459(3) |
| S(3)—O(4) | 1.469(3) |
| S(3)—C(15S) | 1.795(5) |
| S(4)—O(7) | 1.446(4) |
| S(4)—O(9) | 1.461(3) |
| S(4)—O(8) | 1.466(3) |
| S(4)—C(3S) | 1.779(5) |
| S(5)—O(11) | 1.438(4) |
| S(5)—O(12) | 1.456(4) |
| S(5)—O(10) | 1.463(3) |
| S(5)—C(5S) | 1.775(5) |
| S(6)—O(14) | 1.453(4) |
| S(6)—O(15) | 1.456(4) |
| S(6)—O(13) | 1.458(4) |
| S(6)—C(9S) | 1.749(5) |
| S(7)—O(17) | 1.442(4) |
| S(7)—O(18) | 1.479(4) |
| S(7)—O(16) | 1.482(3) |
| S(7)—C(7S) | 1.744(5) |
| S(8)—O(21) | 1.447(3) |
| S(8)—O(19) | 1.452(3) |
| S(8)—O(20) | 1.479(3) |
| S(8)—C(11S) | 1.776(4) |
| S(9)—O(24) | 1.458(3) |
| S(9)—O(22) | 1.458(3) |
| S(9)—O(23) | 1.486(3) |
| S(9)—C(13S) | 1.765(5) |
| O(1)—O(3) | 1.56(2) |
| C(1S)—C(2S) | 1.470(8) |
| C(1S)—H(1S1) | 0.9900 |
| C(1S)—H(1S2) | 0.9900 |
| C(2S)—H(2S1) | 0.9800 |
| C(2S)—H(2S2) | 0.9800 |
| C(2S)—H(2S3) | 0.9800 |
| C(3S)—C(4S) | 1.534(7) |
| C(3S)—H(3S1) | 0.9900 |
| C(3S)—H(3S2) | 0.9900 |
| C(4S)—H(4S1) | 0.9800 |
| C(4S)—H(4S2) | 0.9800 |
| C(4S)—H(4S3) | 0.9800 |
| C(5S)—C(6S) | 1.506(7) |
| C(5S)—H(5S1) | 0.9900 |
| C(5S)—H(5S2) | 0.9900 |
| C(6S)—H(6S1) | 0.9800 |
| C(6S)—H(6S2) | 0.9800 |
| C(6S)—H(6S3) | 0.9800 |
| C(7S)—C(8S) | 1.550(7) |
| C(7S)—H(7S1) | 0.9900 |
| C(7S)—H(7S2) | 0.9900 |
| C(8S)—H(8S1) | 0.9800 |
| C(8S)—H(8S2) | 0.9800 |
| C(8S)—H(8S3) | 0.9800 |
| C(9S)—C(10S) | 1.511(10) |
| C(9S)—H(9S1) | 0.9900 |
| C(9S)—H(9S2) | 0.9900 |
| C(10S)—H(10A) | 0.9800 |
| C(10S)—H(10B) | 0.9800 |
| C(10S)—H(10C) | 0.9800 |
| C(11S)—C(12S) | 1.522(7) |
| C(11S)—H(11E) | 0.9900 |
| C(11S)—H(11F) | 0.9900 |
| C(12S)—H(12A) | 0.9800 |
| C(12S)—H(12B) | 0.9800 |
| C(12S)—H(12C) | 0.9800 |
| C(13S)—C(14S) | 1.498(6) |
| C(13S)—H(13M) | 0.9900 |
| C(13S)—H(13N) | 0.9900 |
| C(14S)—H(14M) | 0.9800 |
| C(14S)—H(14N) | 0.9800 |
| C(14S)—H(14O) | 0.9800 |
| C(15S)—C(16S) | 1.500(7) |
| C(15S)—H(15M) | 0.9900 |
| C(15S)—H(15N) | 0.9900 |
| C(16S)—H(16M) | 0.9800 |
| C(16S)—H(16N) | 0.9800 |
| C(16S)—H(16O) | 0.9800 |
| C(1A)—S(1A)—C(12A) | 102.6(2) |
| C(7A)—N(1A)—C(6A) | 126.5(4) |
| C(7A)—N(1A)—H(1AA) | 116.8 |
| C(6A)—N(1A)—H(1AA) | 116.8 |
| C(10A)—N(2A)—C(14A) | 112.3(4) |
| C(10A)—N(2A)—C(13A) | 112.8(4) |
| C(14A)—N(2A)—C(13A) | 111.3(4) |
| C(10A)—N(2A)—H(2AA) | 106.7 |
| C(14A)—N(2A)—H(2AA) | 106.7 |
| C(13A)—N(2A)—H(2AA) | 106.7 |
| C(3A)—N(3A)—C(16A) | 114.4(3) |
| C(3A)—N(3A)—C(15A) | 111.3(4) |
| C(16A)—N(3A)—C(15A) | 110.1(4) |
| C(3A)—N(3A)—H(3A) | 106.8 |
| C(16A)—N(3A)—H(3A) | 106.8 |
| C(15A)—N(3A)—H(3A) | 106.8 |
| C(2A)—C(1A)—C(6A) | 120.3(4) |
| C(2A)—C(1A)—S(1A) | 116.7(3) |
| C(6A)—C(1A)—S(1A) | 123.0(3) |
| C(3A)—C(2A)—C(1A) | 120.4(4) |
| C(3A)—C(2A)—H(2A) | 119.8 |
| C(1A)—C(2A)—H(2A) | 119.8 |
| C(2A)—C(3A)—C(4A) | 120.6(4) |
| C(2A)—C(3A)—N(3A) | 120.2(4) |
| C(4A)—C(3A)—N(3A) | 119.1(4) |
| C(3A)—C(4A)—C(5A) | 118.8(4) |
| C(3A)—C(4A)—H(4A) | 120.6 |
| C(5A)—C(4A)—H(4A) | 120.6 |
| C(6A)—C(5A)—C(4A) | 121.8(4) |
| C(6A)—C(5A)—H(5A) | 119.1 |
| C(4A)—C(5A)—H(5A) | 119.1 |
| C(5A)—C(6A)—N(1A) | 119.7(4) |
| C(5A)—C(6A)—C(1A) | 118.0(4) |
| N(1A)—C(6A)—C(1A) | 122.3(4) |
| C(8A)—C(7A)—N(1A) | 119.7(4) |
| C(8A)—C(7A)—C(12A) | 118.4(4) |
| N(1A)—C(7A)—C(12A) | 121.9(4) |
| C(7A)—C(8A)—C(9A) | 121.9(4) |
| C(7A)—C(8A)—H(8A) | 119.0 |
| C(9A)—C(8A)—H(8A) | 119.0 |

TABLE 3-continued

Bond lengths [Å] and angles [°] for LMT•2EsOH.

| | |
|---|---|
| C(10A)—C(9A)—C(8A) | 118.4(4) |
| C(10A)—C(9A)—H(9A) | 120.8 |
| C(8A)—C(9A)—H(9A) | 120.8 |
| C(11A)—C(10A)—C(9A) | 120.9(4) |
| C(11A)—C(10A)—N(2A) | 117.9(4) |
| C(9A)—C(10A)—N(2A) | 121.2(4) |
| C(10A)—C(11A)—C(12A) | 120.4(4) |
| C(10A)—C(11A)—H(11A) | 119.8 |
| C(12A)—C(11A)—H(11A) | 119.8 |
| C(11A)—C(12A)—C(7A) | 119.9(4) |
| C(11A)—C(12A)—S(1A) | 116.5(3) |
| C(7A)—C(12A)—S(1A) | 123.5(3) |
| N(2A)—C(13A)—H(13A) | 109.5 |
| N(2A)—C(13A)—H(13B) | 109.5 |
| H(13A)—C(13A)—H(13B) | 109.5 |
| N(2A)—C(13A)—H(13C) | 109.5 |
| H(13A)—C(13A)—H(13C) | 109.5 |
| H(13B)—C(13A)—H(13C) | 109.5 |
| N(2A)—C(14A)—H(14A) | 109.5 |
| N(2A)—C(14A)—H(14B) | 109.5 |
| H(14A)—C(14A)—H(14B) | 109.5 |
| N(2A)—C(14A)—H(14C) | 109.5 |
| H(14A)—C(14A)—H(14C) | 109.5 |
| H(14B)—C(14A)—H(14C) | 109.5 |
| N(3A)—C(15A)—H(15A) | 109.5 |
| N(3A)—C(15A)—H(15B) | 109.5 |
| H(15A)—C(15A)—H(15B) | 109.5 |
| N(3A)—C(15A)—H(15C) | 109.5 |
| H(15A)—C(15A)—H(15C) | 109.5 |
| H(15B)—C(15A)—H(15C) | 109.5 |
| N(3A)—C(16A)—H(16A) | 109.5 |
| N(3A)—C(16A)—H(16B) | 109.5 |
| H(16A)—C(16A)—H(16B) | 109.5 |
| N(3A)—C(16A)—H(16C) | 109.5 |
| H(16A)—C(16A)—H(16C) | 109.5 |
| H(16B)—C(16A)—H(16C) | 109.5 |
| C(12B)—S(1B)—C(1B) | 101.6(2) |
| C(6B)—N(1B)—C(7B) | 125.1(4) |
| C(6B)—N(1B)—H(1B) | 117.4 |
| C(7B)—N(1B)—H(1B) | 117.4 |
| C(10B)—N(2B)—C(14B) | 111.3(3) |
| C(10B)—N(2B)—C(13B) | 114.6(4) |
| C(14B)—N(2B)—C(13B) | 110.7(4) |
| C(10B)—N(2B)—H(2BB) | 106.5 |
| C(14B)—N(2B)—H(2BB) | 106.5 |
| C(13B)—N(2B)—H(2BB) | 106.5 |
| C(3B)—N(3B)—C(16B) | 113.0(3) |
| C(3B)—N(3B)—C(15B) | 111.8(3) |
| C(16B)—N(3B)—C(15B) | 111.1(4) |
| C(3B)—N(3B)—H(3B) | 106.9 |
| C(16B)—N(3B)—H(3B) | 106.9 |
| C(15B)—N(3B)—H(3B) | 106.9 |
| C(2B)—C(1B)—C(6B) | 120.4(4) |
| C(2B)—C(1B)—S(1B) | 117.8(3) |
| C(6B)—C(1B)—S(1B) | 121.5(3) |
| C(3B)—C(2B)—C(1B) | 119.7(4) |
| C(3B)—C(2B)—H(2B) | 120.2 |
| C(1B)—C(2B)—H(2B) | 120.2 |
| C(2B)—C(3B)—C(4B) | 121.1(4) |
| C(2B)—C(3B)—N(3B) | 120.3(4) |
| C(4B)—C(3B)—N(3B) | 118.7(4) |
| C(5B)—C(4B)—C(3B) | 119.2(4) |
| C(5B)—C(4B)—H(4B) | 120.4 |
| C(3B)—C(4B)—H(4B) | 120.4 |
| C(4B)—C(5B)—C(6B) | 121.1(4) |
| C(4B)—C(5B)—H(5B) | 119.5 |
| C(6B)—C(5B)—H(5B) | 119.5 |
| N(1B)—C(6B)—C(5B) | 120.1(4) |
| N(1B)—C(6B)—C(1B) | 121.4(4) |
| C(5B)—C(6B)—C(1B) | 118.5(4) |
| N(1B)—C(7B)—C(8B) | 119.9(4) |
| N(1B)—C(7B)—C(12B) | 121.8(4) |
| C(8B)—C(7B)—C(12B) | 118.3(4) |
| C(9B)—C(8B)—C(7B) | 121.6(4) |
| C(9B)—C(8B)—H(8B) | 119.2 |
| C(7B)—C(8B)—H(8B) | 119.2 |
| C(8B)—C(9B)—C(10B) | 119.0(4) |
| C(8B)—C(9B)—H(9B) | 120.5 |
| C(10B)—C(9B)—H(9B) | 120.5 |
| C(9B)—C(10B)—C(11B) | 121.4(4) |
| C(9B)—C(10B)—N(2B) | 120.8(4) |
| C(11B)—C(10B)—N(2B) | 117.6(4) |
| C(10B)—C(11B)—C(12B) | 119.5(4) |
| C(10B)—C(11B)—H(11B) | 120.3 |
| C(12B)—C(11B)—H(11B) | 120.3 |
| C(11B)—C(12B)—C(7B) | 120.3(4) |
| C(11B)—C(12B)—S(1B) | 118.2(3) |
| C(7B)—C(12B)—S(1B) | 121.2(3) |
| N(2B)—C(13B)—H(13D) | 109.5 |
| N(2B)—C(13B)—H(13E) | 109.5 |
| H(13D)—C(13B)—H(13E) | 109.5 |
| N(2B)—C(13B)—H(13F) | 109.5 |
| H(13D)—C(13B)—H(13F) | 109.5 |
| H(13E)—C(13B)—H(13F) | 109.5 |
| N(2B)—C(14B)—H(14D) | 109.5 |
| N(2B)—C(14B)—H(14E) | 109.5 |
| H(14D)—C(14B)—H(14E) | 109.5 |
| N(2B)—C(14B)—H(14F) | 109.5 |
| H(14D)—C(14B)—H(14F) | 109.5 |
| H(14E)—C(14B)—H(14F) | 109.5 |
| N(3B)—C(15B)—H(15D) | 109.5 |
| N(3B)—C(15B)—H(15E) | 109.5 |
| H(15D)—C(15B)—H(15E) | 109.5 |
| N(3B)—C(15B)—H(15F) | 109.5 |
| H(15D)—C(15B)—H(15F) | 109.5 |
| H(15E)—C(15B)—H(15F) | 109.5 |
| N(3B)—C(16B)—H(16D) | 109.5 |
| N(3B)—C(16B)—H(16E) | 109.5 |
| H(16D)—C(16B)—H(16E) | 109.5 |
| N(3B)—C(16B)—H(16F) | 109.5 |
| H(16D)—C(16B)—H(16F) | 109.5 |
| H(16E)—C(16B)—H(16F) | 109.5 |
| C(12C)—S(1C)—C(1C) | 101.7(2) |
| C(7C)—N(1C)—C(6C) | 125.4(4) |
| C(7C)—N(1C)—H(1C) | 117.3 |
| C(6C)—N(1C)—H(1C) | 117.3 |
| C(10C)—N(2C)—C(14C) | 114.9(3) |
| C(10C)—N(2C)—C(13C) | 110.2(3) |
| C(14C)—N(2C)—C(13C) | 111.2(3) |
| C(10C)—N(2C)—H(2CC) | 106.7 |
| C(14C)—N(2C)—H(2CC) | 106.7 |
| C(13C)—N(2C)—H(2CC) | 106.7 |
| C(3C)—N(3C)—C(15C) | 111.2(4) |
| C(3C)—N(3C)—C(16C) | 112.9(4) |
| C(15C)—N(3C)—C(16C) | 111.5(4) |
| C(3C)—N(3C)—H(3C) | 106.9 |
| C(15C)—N(3C)—H(3C) | 106.9 |
| C(16C)—N(3C)—H(3C) | 106.9 |
| C(2C)—C(1C)—C(6C) | 120.3(4) |
| C(2C)—C(1C)—S(1C) | 117.7(3) |
| C(6C)—C(1C)—S(1C) | 121.8(3) |
| C(1C)—C(2C)—C(3C) | 119.7(4) |
| C(1C)—C(2C)—H(2C) | 120.2 |
| C(3C)—C(2C)—H(2C) | 120.2 |
| C(2C)—C(3C)—C(4C) | 121.8(4) |
| C(2C)—C(3C)—N(3C) | 118.6(4) |
| C(4C)—C(3C)—N(3C) | 119.5(4) |
| C(3C)—C(4C)—C(5C) | 118.7(4) |
| C(3C)—C(4C)—H(4C) | 120.7 |
| C(5C)—C(4C)—H(4C) | 120.7 |
| C(4C)—C(5C)—C(6C) | 120.9(4) |
| C(4C)—C(5C)—H(5C) | 119.5 |
| C(6C)—C(5C)—H(5C) | 119.5 |
| N(1C)—C(6C)—C(5C) | 119.9(4) |
| N(1C)—C(6C)—C(1C) | 121.3(4) |
| C(5C)—C(6C)—C(1C) | 118.7(4) |
| N(1C)—C(7C)—C(8C) | 119.9(4) |
| N(1C)—C(7C)—C(12C) | 122.0(4) |
| C(8C)—C(7C)—C(12C) | 118.1(4) |
| C(9C)—C(8C)—C(7C) | 121.5(4) |
| C(9C)—C(8C)—H(8C) | 119.2 |
| C(7C)—C(8C)—H(8C) | 119.2 |
| C(8C)—C(9C)—C(10C) | 119.3(4) |
| C(8C)—C(9C)—H(9C) | 120.3 |
| C(10C)—C(9C)—H(9C) | 120.3 |
| C(11C)—C(10C)—C(9C) | 120.5(4) |

TABLE 3-continued

Bond lengths [Å] and angles [°] for LMT•2EsOH.

| | |
|---|---|
| C(11C)—C(10C)—N(2C) | 117.5(4) |
| C(9C)—C(10C)—N(2C) | 121.9(4) |
| C(12C)—C(11C)—C(10C) | 120.4(4) |
| C(12C)—C(11C)—H(11C) | 119.8 |
| C(10C)—C(11C)—H(11C) | 119.8 |
| C(11C)—C(12C)—C(7C) | 120.1(4) |
| C(11C)—C(12C)—S(1C) | 118.4(3) |
| C(7C)—C(12C)—S(1C) | 121.3(3) |
| N(2C)—C(13C)—H(13G) | 109.5 |
| N(2C)—C(13C)—H(13H) | 109.5 |
| H(13G)—C(13C)—H(13H) | 109.5 |
| N(2C)—C(13C)—H(13I) | 109.5 |
| H(13G)—C(13C)—H(13I) | 109.5 |
| H(13H)—C(13C)—H(13I) | 109.5 |
| N(2C)—C(14C)—H(14G) | 109.5 |
| N(2C)—C(14C)—H(14H) | 109.5 |
| H(14G)—C(14C)—H(14H) | 109.5 |
| N(2C)—C(14C)—H(14I) | 109.5 |
| H(14G)—C(14C)—H(14I) | 109.5 |
| H(14H)—C(14C)—H(14I) | 109.5 |
| N(3C)—C(15C)—H(15G) | 109.5 |
| N(3C)—C(15C)—H(15H) | 109.5 |
| H(15G)—C(15C)—H(15H) | 109.5 |
| N(3C)—C(15C)—H(15I) | 109.5 |
| H(15G)—C(15C)—H(15I) | 109.5 |
| H(15H)—C(15C)—H(15I) | 109.5 |
| N(3C)—C(16C)—H(16G) | 109.5 |
| N(3C)—C(16C)—H(16H) | 109.5 |
| H(16G)—C(16C)—H(16H) | 109.5 |
| N(3C)—C(16C)—H(16I) | 109.5 |
| H(16G)—C(16C)—H(16I) | 109.5 |
| H(16H)—C(16C)—H(16I) | 109.5 |
| C(12D)—S(1D)—C(1D) | 102.4(2) |
| C(7D)—N(1D)—C(6D) | 126.5(4) |
| C(7D)—N(1D)—H(1D) | 116.7 |
| C(6D)—N(1D)—H(1D) | 116.7 |
| C(10D)—N(2D)—C(13D) | 114.5(4) |
| C(10D)—N(2D)—C(14D) | 111.3(3) |
| C(13D)—N(2D)—C(14D) | 110.7(4) |
| C(10D)—N(2D)—H(2D) | 106.6 |
| C(13D)—N(2D)—H(2D) | 106.6 |
| C(14D)—N(2D)—H(2D) | 106.6 |
| C(3D)—N(3D)—C(15D) | 111.2(4) |
| C(3D)—N(3D)—C(16D) | 114.3(4) |
| C(15D)—N(3D)—C(16D) | 111.2(4) |
| C(3D)—N(3D)—H(3D) | 106.5 |
| C(15D)—N(3D)—H(3D) | 106.5 |
| C(16D)—N(3D)—H(3D) | 106.5 |
| C(2D)—C(1D)—C(6D) | 120.2(4) |
| C(2D)—C(1D)—S(1D) | 117.4(3) |
| C(6D)—C(1D)—S(1D) | 122.4(3) |
| C(3D)—C(2D)—C(1D) | 119.7(4) |
| C(3D)—C(2D)—H(2DD) | 120.1 |
| C(1D)—C(2D)—H(2DD) | 120.1 |
| C(2D)—C(3D)—C(4D) | 120.7(4) |
| C(2D)—C(3D)—N(3D) | 120.7(4) |
| C(4D)—C(3D)—N(3D) | 118.4(4) |
| C(3D)—C(4D)—C(5D) | 119.2(5) |
| C(3D)—C(4D)—H(4D) | 120.4 |
| C(5D)—C(4D)—H(4D) | 120.4 |
| C(6D)—C(5D)—C(4D) | 121.5(4) |
| C(6D)—C(5D)—H(5D) | 119.2 |
| C(4D)—C(5D)—H(5D) | 119.2 |
| C(5D)—C(6D)—N(1D) | 118.7(4) |
| C(5D)—C(6D)—C(1D) | 118.6(4) |
| N(1D)—C(6D)—C(1D) | 122.7(4) |
| N(1D)—C(7D)—C(8D) | 119.7(4) |
| N(1D)—C(7D)—C(12D) | 121.5(4) |
| C(8D)—C(7D)—C(12D) | 118.7(4) |
| C(9D)—C(8D)—C(7D) | 121.8(4) |
| C(9D)—C(8D)—H(8D) | 119.1 |
| C(7D)—C(8D)—H(8D) | 119.1 |
| C(10D)—C(9D)—C(8D) | 118.3(4) |
| C(10D)—C(9D)—H(9D) | 120.9 |
| C(8D)—C(9D)—H(9D) | 120.9 |
| C(9D)—C(10D)—C(11D) | 121.7(4) |
| C(9D)—C(10D)—N(2D) | 121.0(4) |
| C(11D)—C(10D)—N(2D) | 117.1(4) |

TABLE 3-continued

Bond lengths [Å] and angles [°] for LMT•2EsOH.

| | |
|---|---|
| C(12D)—C(11D)—C(10D) | 119.5(4) |
| C(12D)—C(11D)—H(11D) | 120.3 |
| C(10D)—C(11D)—H(11D) | 120.3 |
| C(11D)—C(12D)—C(7D) | 120.0(4) |
| C(11D)—C(12D)—S(1D) | 116.4(3) |
| C(7D)—C(12D)—S(1D) | 123.4(3) |
| N(2D)—C(13D)—H(13J) | 109.5 |
| N(2D)—C(13D)—H(13K) | 109.5 |
| H(13J)—C(13D)—H(13K) | 109.5 |
| N(2D)—C(13D)—H(13L) | 109.5 |
| H(13J)—C(13D)—H(13L) | 109.5 |
| H(13K)—C(13D)—H(13L) | 109.5 |
| N(2D)—C(14D)—H(14J) | 109.5 |
| N(2D)—C(14D)—H(14K) | 109.5 |
| H(14J)—C(14D)—H(14K) | 109.5 |
| N(2D)—C(14D)—H(14L) | 109.5 |
| H(14J)—C(14D)—H(14L) | 109.5 |
| H(14K)—C(14D)—H(14L) | 109.5 |
| N(3D)—C(15D)—H(15J) | 109.5 |
| N(3D)—C(15D)—H(15K) | 109.5 |
| H(15J)—C(15D)—H(15K) | 109.5 |
| N(3D)—C(15D)—H(15L) | 109.5 |
| H(15J)—C(15D)—H(15L) | 109.5 |
| H(15K)—C(15D)—H(15L) | 109.5 |
| N(3D)—C(16D)—H(16J) | 109.5 |
| N(3D)—C(16D)—H(16K) | 109.5 |
| H(16J)—C(16D)—H(16K) | 109.5 |
| N(3D)—C(16D)—H(16L) | 109.5 |
| H(16J)—C(16D)—H(16L) | 109.5 |
| H(16K)—C(16D)—H(16L) | 109.5 |
| O(2)—S(2)—O(3) | 118.5(17) |
| O(2)—S(2)—O(1') | 87.9(12) |
| O(3)—S(2)—O(1') | 108.0(8) |
| O(2)—S(2)—O(3') | 117.2(14) |
| O(3)—S(2)—O(3') | 31.5(6) |
| O(1')—S(2)—O(3') | 138.3(6) |
| O(2)—S(2)—O(2') | 23.8(18) |
| O(3)—S(2)—O(2') | 115.1(10) |
| O(1')—S(2)—O(2') | 110.6(8) |
| O(3')—S(2)—O(2') | 101.4(8) |
| O(2)—S(2)—O(1) | 111.9(14) |
| O(3)—S(2)—O(1) | 65.7(9) |
| O(1')—S(2)—O(1) | 42.6(5) |
| O(3')—S(2)—O(1) | 95.8(7) |
| O(2')—S(2)—O(1) | 134.1(9) |
| O(2)—S(2)—C(1S) | 117.0(16) |
| O(3)—S(2)—C(1S) | 118.1(6) |
| O(1')—S(2)—C(1S) | 99.1(4) |
| O(3')—S(2)—C(1S) | 97.8(4) |
| O(2')—S(2)—C(1S) | 104.8(8) |
| O(1)—S(2)—C(1S) | 114.6(5) |
| O(5)—S(3)—O(6) | 113.5(2) |
| O(5)—S(3)—O(4) | 112.5(2) |
| O(6)—S(3)—O(4) | 111.9(2) |
| O(5)—S(3)—C(15S) | 107.5(2) |
| O(6)—S(3)—C(15S) | 106.2(2) |
| O(4)—S(3)—C(15S) | 104.6(2) |
| O(7)—S(4)—O(9) | 113.8(2) |
| O(7)—S(4)—O(8) | 113.4(2) |
| O(9)—S(4)—O(8) | 111.3(2) |
| O(7)—S(4)—C(3S) | 106.0(2) |
| O(9)—S(4)—C(3S) | 106.6(2) |
| O(8)—S(4)—C(3S) | 104.9(2) |
| O(11)—S(5)—O(12) | 112.3(3) |
| O(11)—S(5)—O(10) | 114.1(3) |
| O(12)—S(5)—O(10) | 109.9(2) |
| O(11)—S(5)—C(5S) | 107.4(2) |
| O(12)—S(5)—C(5S) | 107.2(2) |
| O(10)—S(5)—C(5S) | 105.5(2) |
| O(14)—S(6)—O(15) | 112.2(2) |
| O(14)—S(6)—O(13) | 113.4(3) |
| O(15)—S(6)—O(13) | 111.4(2) |
| O(14)—S(6)—C(9S) | 105.6(2) |
| O(15)—S(6)—C(9S) | 108.3(2) |
| O(13)—S(6)—C(9S) | 105.4(3) |
| O(17)—S(7)—O(18) | 114.0(2) |
| O(17)—S(7)—O(16) | 114.2(2) |
| O(18)—S(7)—O(16) | 110.7(2) |

TABLE 3-continued

Bond lengths [Å] and angles [°] for LMT•2EsOH.

| | |
|---|---|
| O(17)—S(7)—C(7S) | 105.8(3) |
| O(18)—S(7)—C(7S) | 105.3(2) |
| O(16)—S(7)—C(7S) | 106.0(2) |
| O(21)—S(8)—O(19) | 114.3(2) |
| O(21)—S(8)—O(20) | 111.7(2) |
| O(19)—S(8)—O(20) | 111.95(19) |
| O(21)—S(8)—C(11S) | 106.3(2) |
| O(19)—S(8)—C(11S) | 108.1(2) |
| O(20)—S(8)—C(11S) | 103.7(2) |
| O(24)—S(9)—O(22) | 113.23(19) |
| O(24)—S(9)—O(23) | 112.94(19) |
| O(22)—S(9)—O(23) | 111.07(18) |
| O(24)—S(9)—C(13S) | 106.1(2) |
| O(22)—S(9)—C(13S) | 107.7(2) |
| O(23)—S(9)—C(13S) | 105.3(2) |
| S(2)—O(1)—O(3) | 52.7(7) |
| S(2)—O(3)—O(1) | 61.6(8) |
| C(2S)—C(1S)—S(2) | 115.9(5) |
| C(2S)—C(1S)—H(1S1) | 108.3 |
| S(2)—C(1S)—H(1S1) | 108.3 |
| C(2S)—C(1S)—H(1S2) | 108.3 |
| S(2)—C(1S)—H(1S2) | 108.3 |
| H(1S1)—C(1S)—H(1S2) | 107.4 |
| C(1S)—C(2S)—H(2S1) | 109.5 |
| C(1S)—C(2S)—H(2S2) | 109.5 |
| H(2S1)—C(2S)—H(2S2) | 109.5 |
| C(1S)—C(2S)—H(2S3) | 109.5 |
| H(2S1)—C(2S)—H(2S3) | 109.5 |
| H(2S2)—C(2S)—H(2S3) | 109.5 |
| C(4S)—C(3S)—S(4) | 111.3(3) |
| C(4S)—C(3S)—H(3S1) | 109.4 |
| S(4)—C(3S)—H(3S1) | 109.4 |
| C(4S)—C(3S)—H(3S2) | 109.4 |
| S(4)—C(3S)—H(3S2) | 109.4 |
| H(3S1)—C(3S)—H(3S2) | 108.0 |
| C(3S)—C(4S)—H(4S1) | 109.5 |
| C(3S)—C(4S)—H(4S2) | 109.5 |
| H(4S1)—C(4S)—H(4S2) | 109.5 |
| C(3S)—C(4S)—H(4S3) | 109.5 |
| H(4S1)—C(4S)—H(4S3) | 109.5 |
| H(4S2)—C(4S)—H(4S3) | 109.5 |
| C(6S)—C(5S)—S(5) | 112.7(3) |
| C(6S)—C(5S)—H(5S1) | 109.0 |
| S(5)—C(5S)—H(5S1) | 109.0 |
| C(6S)—C(5S)—H(5S2) | 109.0 |
| S(5)—C(5S)—H(5S2) | 109.0 |
| H(5S1)—C(5S)—H(5S2) | 107.8 |
| C(5S)—C(6S)—H(6S1) | 109.5 |
| C(5S)—C(6S)—H(6S2) | 109.5 |
| H(6S1)—C(6S)—H(6S2) | 109.5 |
| C(5S)—C(6S)—H(6S3) | 109.5 |
| H(6S1)—C(6S)—H(6S3) | 109.5 |
| H(6S2)—C(6S)—H(6S3) | 109.5 |
| C(8S)—C(7S)—S(7) | 110.6(4) |
| C(8S)—C(7S)—H(7S1) | 109.5 |
| S(7)—C(7S)—H(7S1) | 109.5 |
| C(8S)—C(7S)—H(7S2) | 109.5 |
| S(7)—C(7S)—H(7S2) | 109.5 |
| H(7S1)—C(7S)—H(7S2) | 108.1 |
| C(7S)—C(8S)—H(8S1) | 109.5 |
| C(7S)—C(8S)—H(8S2) | 109.5 |
| H(8S1)—C(8S)—H(8S2) | 109.5 |
| C(7S)—C(8S)—H(8S3) | 109.5 |
| H(8S1)—C(8S)—H(8S3) | 109.5 |
| H(8S2)—C(8S)—H(8S3) | 109.5 |
| C(10S)—C(9S)—S(6) | 104.5(5) |
| C(10S)—C(9S)—H(9S1) | 110.8 |
| S(6)—C(9S)—H(9S1) | 110.8 |
| C(10S)—C(9S)—H(9S2) | 110.8 |
| S(6)—C(9S)—H(9S2) | 110.8 |
| H(9S1)—C(9S)—H(9S2) | 108.9 |
| C(9S)—C(10S)—H(10A) | 109.5 |
| C(9S)—C(10S)—H(10B) | 109.5 |
| H(10A)—C(10S)—H(10B) | 109.5 |
| C(9S)—C(10S)—H(10C) | 109.5 |
| H(10A)—C(10S)—H(10C) | 109.5 |
| H(10B)—C(10S)—H(10C) | 109.5 |
| C(12S)—C(11S)—S(8) | 113.0(3) |
| C(12S)—C(11S)—H(11E) | 109.0 |
| S(8)—C(11S)—H(11E) | 109.0 |
| C(12S)—C(11S)—H(11F) | 109.0 |
| S(8)—C(11S)—H(11F) | 109.0 |
| H(11E)—C(11S)—H(11F) | 107.8 |
| C(11S)—C(12S)—H(12A) | 109.5 |
| C(11S)—C(12S)—H(12B) | 109.5 |
| H(12A)—C(12S)—H(12B) | 109.5 |
| C(11S)—C(12S)—H(12C) | 109.5 |
| H(12A)—C(12S)—H(12C) | 109.5 |
| H(12B)—C(12S)—H(12C) | 109.5 |
| C(14S)—C(13S)—S(9) | 111.6(3) |
| C(14S)—C(13S)—H(13M) | 109.3 |
| S(9)—C(13S)—H(13M) | 109.3 |
| C(14S)—C(13S)—H(13N) | 109.3 |
| S(9)—C(13S)—H(13N) | 109.3 |
| H(13M)—C(13S)—H(13N) | 108.0 |
| C(13S)—C(14S)—H(14M) | 109.5 |
| C(13S)—C(14S)—H(14N) | 109.5 |
| H(14M)—C(14S)—H(14N) | 109.5 |
| C(13S)—C(14S)—H(14O) | 109.5 |
| H(14M)—C(14S)—H(14O) | 109.5 |
| H(14N)—C(14S)—H(14O) | 109.5 |
| C(16S)—C(15S)—S(3) | 112.7(4) |
| C(16S)—C(15S)—H(15M) | 109.0 |
| S(3)—C(15S)—H(15M) | 109.0 |
| C(16S)—C(15S)—H(15N) | 109.0 |
| S(3)—C(15S)—H(15N) | 109.0 |
| H(15M)—C(15S)—H(15N) | 107.8 |
| C(15S)—C(16S)—H(16M) | 109.5 |
| C(15S)—C(16S)—H(16N) | 109.5 |
| H(16M)—C(16S)—H(16N) | 109.5 |
| C(15S)—C(16S)—H(16O) | 109.5 |
| H(16M)—C(16S)—H(16O) | 109.5 |
| H(16N)—C(16S)—H(16O) | 109.5 |

Symmetry transformations used to generate equivalent atoms:

TABLE 4

Anisotropic displacement parameters (Å$^2$ × 10$^3$) for LMT•2EsOH. The anisotropic displacement factor exponent takes the form: $-2\pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| S(1A) | 18(1) | 21(1) | 121(2) | 12(1) | −15(1) | −2(1) |
| N(1A) | 15(2) | 24(2) | 36(2) | 1(2) | 0(2) | −3(2) |
| N(2A) | 19(2) | 20(2) | 27(2) | 5(2) | 1(2) | 0(2) |
| N(3A) | 17(2) | 23(2) | 27(2) | −1(2) | 3(2) | 1(2) |
| C(1A) | 20(3) | 22(2) | 39(3) | 3(2) | −4(2) | −1(2) |
| C(2A) | 17(2) | 24(2) | 39(3) | 2(2) | −4(2) | −1(2) |
| C(3A) | 22(2) | 22(2) | 25(2) | −1(2) | 7(2) | −2(2) |
| C(4A) | 17(2) | 29(2) | 31(3) | −5(2) | 7(2) | 2(2) |
| C(5A) | 15(2) | 28(2) | 37(3) | −6(2) | 9(2) | −6(2) |
| C(6A) | 18(2) | 23(2) | 26(2) | −2(2) | 3(2) | −3(2) |
| C(7A) | 22(2) | 23(2) | 25(2) | 0(2) | 5(2) | −2(2) |
| C(8A) | 21(2) | 25(2) | 21(2) | −3(2) | 6(2) | −7(2) |
| C(9A) | 25(2) | 22(2) | 24(2) | 2(2) | 7(2) | −3(2) |
| C(10A) | 19(2) | 24(2) | 22(2) | 3(2) | 4(2) | 2(2) |
| C(11A) | 19(2) | 23(2) | 33(3) | 2(2) | 1(2) | −8(2) |
| C(12A) | 20(3) | 22(2) | 42(2) | 6(2) | 2(2) | −1(2) |
| C(13A) | 28(3) | 39(3) | 30(3) | 15(2) | 0(2) | −2(2) |
| C(14A) | 34(3) | 44(3) | 37(3) | 1(2) | 7(2) | 13(2) |
| C(15A) | 96(5) | 26(3) | 36(3) | 3(2) | 37(3) | 2(3) |
| C(16A) | 32(3) | 26(2) | 30(3) | −9(2) | 4(2) | 6(2) |
| S(1B) | 17(1) | 18(1) | 39(1) | 3(1) | 7(1) | −1(1) |
| N(1B) | 21(2) | 16(2) | 25(2) | −2(2) | 8(2) | −3(2) |
| N(2B) | 29(2) | 24(2) | 20(2) | 4(2) | 1(2) | 6(2) |
| N(3B) | 21(2) | 19(2) | 21(2) | −2(2) | 3(2) | 2(2) |
| C(1B) | 17(2) | 20(2) | 18(2) | 0(2) | 5(2) | 0(2) |
| C(2B) | 21(2) | 23(2) | 16(2) | −3(2) | 3(2) | −4(2) |
| C(3B) | 22(2) | 18(2) | 18(2) | −2(2) | 6(2) | 1(2) |
| C(4B) | 16(2) | 23(2) | 20(2) | −1(2) | 3(2) | 0(2) |
| C(5B) | 16(2) | 21(2) | 21(2) | −1(2) | 5(2) | −4(2) |

TABLE 4-continued

Anisotropic displacement parameters (Å² × 10³) for LMT•2EsOH. The anisotropic displacement factor exponent takes the form: −2π²[h² a*²U¹¹ + ... + 2 h k a* b* U¹²]

| | $U^{11}$ | $U^{22}$ | $U^{33}$ | $U^{23}$ | $U^{13}$ | $U^{12}$ |
|---|---|---|---|---|---|---|
| C(6B) | 25(2) | 20(2) | 17(2) | 0(2) | 9(2) | 1(2) |
| C(7B) | 22(2) | 24(2) | 20(2) | −3(2) | 9(2) | 0(2) |
| C(8B) | 29(3) | 19(2) | 27(2) | 0(2) | 17(2) | −2(2) |
| C(9B) | 32(3) | 20(2) | 25(2) | 3(2) | 16(2) | 4(2) |
| C(10B) | 31(3) | 24(2) | 14(2) | 1(2) | 7(2) | 9(2) |
| C(11B) | 24(2) | 23(2) | 19(2) | −2(2) | 6(2) | −1(2) |
| C(12B) | 28(3) | 18(2) | 20(2) | 0(2) | 9(2) | 2(2) |
| C(13B) | 53(3) | 30(3) | 26(3) | 14(2) | 11(2) | 17(2) |
| C(14B) | 22(2) | 30(2) | 27(3) | 1(2) | 4(2) | 6(2) |
| C(15B) | 42(3) | 22(2) | 35(3) | 3(2) | 15(2) | 3(2) |
| C(16B) | 39(3) | 30(3) | 25(3) | −8(2) | 2(2) | 10(2) |
| S(1C) | 16(1) | 21(1) | 34(1) | 2(1) | 6(1) | 0(1) |
| N(1C) | 15(2) | 22(2) | 31(2) | −8(2) | 4(2) | −5(2) |
| N(2C) | 16(2) | 19(2) | 23(2) | 0(2) | 6(2) | 0(1) |
| N(3C) | 21(2) | 28(2) | 27(2) | 1(2) | 7(2) | 5(2) |
| C(1C) | 16(2) | 25(2) | 15(2) | −1(2) | 2(2) | 0(2) |
| C(2C) | 20(2) | 24(2) | 17(2) | −2(2) | 6(2) | −1(2) |
| C(3C) | 21(2) | 20(2) | 19(2) | 1(2) | 6(2) | 5(2) |
| C(4C) | 20(2) | 34(2) | 20(2) | −2(2) | 7(2) | 4(2) |
| C(5C) | 20(2) | 26(2) | 20(2) | −1(2) | 6(2) | −1(2) |
| C(6C) | 22(2) | 24(2) | 15(2) | −4(2) | 7(2) | −1(2) |
| C(7C) | 18(2) | 29(2) | 17(2) | −4(2) | 6(2) | 2(2) |
| C(8C) | 17(2) | 22(2) | 27(2) | −8(2) | 9(2) | −6(2) |
| C(9C) | 21(2) | 20(2) | 22(2) | −3(2) | 10(2) | −2(2) |
| C(10C) | 14(2) | 25(2) | 18(2) | −3(2) | 5(2) | 1(2) |
| C(11C) | 15(2) | 24(2) | 21(2) | −5(2) | 6(2) | −7(2) |
| C(12C) | 18(2) | 19(2) | 21(2) | −4(2) | 7(2) | 2(2) |
| C(13C) | 17(2) | 30(2) | 29(2) | 2(2) | 9(2) | 3(2) |
| C(14C) | 23(2) | 23(2) | 23(2) | 2(2) | 7(2) | −2(2) |
| C(15C) | 46(3) | 45(3) | 56(4) | 22(3) | 29(3) | 11(3) |
| C(16C) | 38(3) | 33(3) | 46(3) | −18(2) | −4(3) | 8(2) |
| S(1D) | 25(1) | 23(1) | 46(1) | −3(1) | 13(1) | −4(1) |
| N(1D) | 26(2) | 23(2) | 36(2) | −4(2) | 11(2) | −4(2) |
| N(2D) | 22(2) | 35(2) | 23(2) | 2(2) | 7(2) | 2(2) |
| N(3D) | 27(2) | 24(2) | 34(2) | 0(2) | 16(2) | 2(2) |
| C(1D) | 28(2) | 28(2) | 20(2) | −3(2) | 10(2) | 0(2) |
| C(2D) | 30(3) | 29(2) | 23(2) | −5(2) | 13(2) | −4(2) |
| C(3D) | 33(3) | 24(2) | 24(2) | −1(2) | 13(2) | 1(2) |
| C(4D) | 27(3) | 31(3) | 33(3) | 0(2) | 10(2) | −1(2) |
| C(5D) | 26(3) | 29(3) | 36(3) | −6(2) | 8(2) | −6(2) |
| C(6D) | 29(3) | 24(2) | 19(2) | −3(2) | 10(2) | 0(2) |
| C(7D) | 23(2) | 27(2) | 16(2) | 0(2) | 9(2) | −1(2) |
| C(8D) | 30(3) | 27(2) | 19(2) | 0(2) | 15(2) | −3(2) |
| C(9D) | 29(3) | 29(2) | 16(2) | 3(2) | 9(2) | −2(2) |
| C(10D) | 24(2) | 30(2) | 17(2) | −2(2) | 8(2) | 0(2) |
| C(11D) | 26(3) | 32(2) | 17(2) | −6(2) | 7(2) | −6(2) |
| C(12D) | 28(3) | 24(2) | 18(2) | −5(2) | 11(2) | −1(2) |
| C(13D) | 33(3) | 60(4) | 33(3) | 19(3) | 11(2) | 10(3) |
| C(14D) | 30(3) | 33(3) | 32(3) | 3(2) | 16(2) | 5(2) |
| C(15D) | 51(3) | 34(3) | 41(3) | 6(2) | 23(3) | 10(2) |
| C(16D) | 35(3) | 26(2) | 47(3) | −12(2) | 19(3) | −3(2) |
| S(2) | 36(1) | 27(1) | 45(1) | 9(1) | 18(1) | 2(1) |
| S(3) | 23(1) | 22(1) | 24(1) | −3(2) | 4(1) | −1(1) |
| S(4) | 16(1) | 23(1) | 40(1) | −4(1) | 4(1) | −1(1) |
| S(5) | 23(1) | 24(1) | 41(1) | 8(1) | 12(1) | 4(1) |
| S(6) | 42(1) | 19(1) | 29(1) | 0(1) | 9(1) | −2(1) |
| S(7) | 31(1) | 28(1) | 39(1) | 4(1) | 12(1) | 1(1) |
| S(8) | 20(1) | 19(1) | 24(1) | 0(1) | 4(1) | −1(1) |
| S(9) | 23(1) | 23(1) | 27(1) | −1(1) | 7(1) | 4(1) |
| O(1) | 67(4) | 53(4) | 52(5) | 19(4) | 29(4) | 10(4) |
| O(2) | 56(6) | 25(9) | 107(14) | 17(8) | 13(8) | −20(7) |
| O(3) | 55(4) | 54(4) | 57(5) | 23(4) | 25(4) | 8(3) |
| O(1') | 79(5) | 68(4) | 48(4) | 25(3) | 39(4) | 31(4) |
| O(2') | 53(4) | 20(7) | 109(13) | 14(6) | 9(7) | −4(5) |
| O(3') | 35(3) | 71(5) | 68(5) | 41(4) | 21(4) | 9(3) |
| O(4) | 26(2) | 26(2) | 44(2) | 3(2) | 7(2) | 2(1) |
| O(5) | 40(2) | 33(2) | 35(2) | −10(2) | 0(2) | −8(2) |
| O(6) | 23(2) | 31(2) | 26(2) | −2(1) | 9(1) | −6(1) |
| O(7) | 27(2) | 27(2) | 72(3) | 11(2) | 11(2) | 0(2) |
| O(8) | 16(2) | 42(2) | 57(2) | −18(2) | −3(2) | −2(2) |
| O(9) | 24(2) | 29(2) | 38(2) | −2(2) | 14(2) | −3(2) |
| O(10) | 43(2) | 49(2) | 33(2) | 12(2) | 18(2) | 30(2) |
| O(11) | 37(2) | 48(2) | 95(4) | 34(2) | 4(2) | −11(2) |
| O(12) | 78(3) | 30(2) | 34(2) | −2(2) | 28(2) | 3(2) |
| O(13) | 52(3) | 72(3) | 56(3) | −16(2) | 35(2) | −33(2) |
| O(14) | 94(4) | 25(2) | 35(2) | −2(2) | 3(2) | 13(2) |
| O(15) | 37(2) | 40(2) | 35(2) | −9(2) | 1(2) | 5(2) |
| O(16) | 23(2) | 37(2) | 36(2) | −16(2) | 13(2) | −8(1) |
| O(17) | 59(3) | 36(2) | 68(3) | 23(2) | 21(2) | −5(2) |
| O(18) | 28(2) | 52(2) | 32(2) | −9(2) | 9(2) | 0(2) |
| O(19) | 33(2) | 19(2) | 34(2) | −1(1) | 7(2) | −2(1) |
| O(20) | 20(2) | 24(2) | 45(2) | −4(2) | −1(2) | −2(1) |
| O(21) | 32(2) | 34(2) | 28(2) | 3(1) | 14(2) | 2(1) |
| O(22) | 26(2) | 27(2) | 24(2) | −2(1) | 9(1) | −2(1) |
| O(23) | 26(2) | 23(2) | 39(2) | 3(1) | 9(2) | 8(1) |
| O(24) | 26(2) | 25(2) | 42(2) | −5(2) | 8(2) | −4(1) |
| C(1S) | 60(4) | 50(4) | 56(4) | 14(3) | 5(3) | 6(3) |
| C(2S) | 48(3) | 52(3) | 36(3) | 10(3) | 19(3) | −2(3) |
| C(3S) | 20(2) | 37(3) | 30(3) | −4(2) | 6(2) | 5(2) |
| C(4S) | 32(3) | 57(3) | 28(3) | 14(2) | 12(2) | 8(2) |
| C(5S) | 23(3) | 31(3) | 50(3) | 11(2) | 9(2) | 8(2) |
| C(6S) | 37(3) | 32(3) | 26(3) | 6(2) | 13(2) | 3(2) |
| C(7S) | 32(3) | 47(3) | 38(3) | −2(2) | 14(2) | 1(2) |
| C(8S) | 48(4) | 22(3) | 73(4) | 9(3) | 8(3) | −3(2) |
| C(9S) | 45(3) | 31(3) | 43(3) | 11(2) | 24(3) | 7(2) |
| C(10S) | 118(8) | 88(6) | 104(7) | −11(5) | 58(6) | −22(6) |
| C(11S) | 30(3) | 25(2) | 30(3) | 3(2) | 14(2) | −2(2) |
| C(12S) | 40(3) | 40(3) | 30(3) | 3(2) | 11(2) | 2(2) |
| C(13S) | 29(3) | 25(2) | 26(2) | 0(2) | 11(2) | 1(2) |
| C(14S) | 35(3) | 32(3) | 37(3) | −2(2) | 18(2) | −2(2) |
| C(15S) | 38(3) | 39(3) | 35(3) | 2(2) | 19(2) | −2(2) |
| C(16S) | 51(4) | 50(3) | 63(4) | 5(3) | 40(3) | 4(3) |

TABLE 5

Hydrogen coordinates (×10⁴) and isotropic displacement parameters (Å² × 10³) for LMT•2EsOH.

| | x | y | z | U(eq) |
|---|---|---|---|---|
| H(1AA) | −585 | 2958 | 1019 | 35 |
| H(2AA) | 1142 | 2510 | 2886 | 30 |
| H(3A) | −993 | 5379 | 587 | 30 |
| H(2A) | −112 | 4894 | 1482 | 38 |
| H(4A) | −1173 | 4519 | 414 | 32 |
| H(5A) | −1024 | 3623 | 616 | 33 |
| H(8A) | −239 | 2190 | 1412 | 29 |
| H(9A) | 327 | 1779 | 2005 | 30 |
| H(11A) | 801 | 3220 | 2506 | 34 |
| H(13A) | 956 | 2107 | 3668 | 55 |
| H(13B) | 1268 | 1770 | 3586 | 55 |
| H(13C) | 853 | 1592 | 3162 | 55 |
| H(14A) | 950 | 1606 | 2041 | 62 |
| H(14B) | 1350 | 1846 | 2447 | 62 |
| H(14C) | 1048 | 2153 | 1770 | 62 |
| H(15A) | −399 | 5529 | 288 | 75 |
| H(15B) | −759 | 5883 | −21 | 75 |
| H(15C) | −775 | 5281 | −280 | 75 |
| H(16A) | −638 | 5607 | 1762 | 49 |
| H(16B) | −652 | 6075 | 1222 | 49 |
| H(16C) | −306 | 5694 | 1555 | 49 |
| H(1B) | 2048 | 25 | 885 | 25 |
| H(2BB) | 3779 | −238 | 2945 | 33 |
| H(3B) | 1492 | 2364 | 765 | 27 |
| H(2B) | 2408 | 2001 | 1444 | 26 |
| H(4B) | 1368 | 1494 | 658 | 26 |
| H(5B) | 1566 | 616 | 765 | 25 |
| H(8B) | 2428 | −704 | 1523 | 28 |
| H(9B) | 3012 | −1036 | 2140 | 29 |
| H(11B) | 3416 | 453 | 2358 | 28 |
| H(13D) | 3579 | −889 | 3507 | 57 |
| H(13E) | 3953 | −1033 | 3472 | 57 |
| H(13F) | 3582 | −1293 | 2905 | 57 |
| H(14D) | 3650 | −952 | 1829 | 43 |
| H(14E) | 4042 | −744 | 2383 | 43 |

TABLE 5-continued

Hydrogen coordinates (×10⁴) and isotropic displacement parameters ($Å^2 \times 10^3$) for LMT•2EsOH.

| | x | y | z | U(eq) |
|---|---|---|---|---|
| H(14F) | 3758 | −345 | 1811 | 43 |
| H(15D) | 2099 | 2713 | 612 | 50 |
| H(15E) | 1729 | 3039 | 363 | 50 |
| H(15F) | 1737 | 2500 | −42 | 50 |
| H(16D) | 1800 | 2460 | 1997 | 53 |
| H(16E) | 1763 | 3014 | 1591 | 53 |
| H(16F) | 2137 | 2692 | 1883 | 53 |
| H(1C) | 4627 | 2587 | 1195 | 30 |
| H(2CC) | 6358 | 2390 | 3285 | 24 |
| H(3C) | 4060 | 4939 | 950 | 32 |
| H(2C) | 4971 | 4574 | 1649 | 25 |
| H(4C) | 3932 | 4060 | 845 | 30 |
| H(5C) | 4137 | 3182 | 1006 | 27 |
| H(8C) | 5015 | 1871 | 1821 | 26 |
| H(9C) | 5601 | 1557 | 2480 | 25 |
| H(11C) | 5987 | 3052 | 2673 | 25 |
| H(13G) | 6256 | 1619 | 2248 | 39 |
| H(13H) | 6636 | 1887 | 2761 | 39 |
| H(13I) | 6327 | 2230 | 2142 | 39 |
| H(14G) | 6168 | 1769 | 3891 | 36 |
| H(14H) | 6544 | 1621 | 3871 | 36 |
| H(14I) | 6177 | 1339 | 3323 | 36 |
| H(15G) | 4636 | 5189 | 631 | 70 |
| H(15H) | 4280 | 5544 | 406 | 70 |
| H(15I) | 4252 | 4970 | 55 | 70 |
| H(16G) | 4450 | 5092 | 2174 | 70 |
| H(16H) | 4333 | 5614 | 1683 | 70 |
| H(16I) | 4723 | 5354 | 1894 | 70 |
| H(1D) | 7088 | 320 | 1462 | 34 |
| H(2D) | 8828 | −56 | 3133 | 33 |
| H(3D) | 6618 | 2711 | 1123 | 32 |
| H(2DD) | 7510 | 2283 | 1724 | 32 |
| H(4D) | 6459 | 1833 | 909 | 38 |
| H(5D) | 6639 | 950 | 1112 | 38 |
| H(8D) | 7452 | −429 | 1911 | 28 |
| H(9D) | 8028 | −812 | 2416 | 30 |
| H(11D) | 8478 | 655 | 2709 | 31 |
| H(13J) | 8654 | −656 | 3792 | 65 |
| H(13K) | 9004 | −828 | 3683 | 65 |
| H(13L) | 8618 | −1085 | 3187 | 65 |
| H(14J) | 8622 | −820 | 2060 | 46 |
| H(14K) | 9023 | −587 | 2493 | 46 |
| H(14L) | 8707 | −220 | 1935 | 46 |
| H(15J) | 7042 | 2819 | 377 | 61 |
| H(15K) | 6720 | 3214 | 295 | 61 |
| H(15L) | 6632 | 2612 | 33 | 61 |
| H(16J) | 7101 | 2976 | 2179 | 54 |
| H(16K) | 6965 | 3437 | 1582 | 54 |
| H(16L) | 7320 | 3101 | 1708 | 54 |
| H(1S1) | 354 | 568 | 117 | 74 |
| H(1S2) | 34 | 756 | 315 | 74 |
| H(2S1) | 348 | 1552 | 757 | 67 |
| H(2S2) | 230 | 1466 | −93 | 67 |
| H(2S3) | 641 | 1363 | 479 | 67 |
| H(3S1) | 2296 | 4750 | 523 | 36 |
| H(3S2) | 2109 | 4415 | −213 | 36 |
| H(4S1) | 1692 | 5133 | −749 | 59 |
| H(4S2) | 2102 | 5315 | −517 | 59 |
| H(4S3) | 1901 | 5469 | −21 | 59 |
| H(5S1) | 2641 | 3235 | 241 | 44 |
| H(5S2) | 2548 | 3575 | 803 | 44 |
| H(6S1) | 3029 | 4152 | 984 | 48 |
| H(6S2) | 2760 | 4126 | 137 | 48 |
| H(6S3) | 3134 | 3806 | 444 | 48 |
| H(7S1) | 5283 | 2814 | −129 | 47 |
| H(7S2) | 5465 | 3051 | 679 | 47 |
| H(8S1) | 5796 | 3675 | 290 | 81 |
| H(8S2) | 5368 | 3758 | −148 | 81 |
| H(8S3) | 5587 | 3453 | −521 | 81 |
| H(9S1) | 5428 | 806 | 551 | 46 |
| H(9S2) | 5579 | 1289 | 1119 | 46 |
| H(10A) | 6182 | 981 | 1462 | 150 |
| H(10B) | 5993 | 1119 | 613 | 150 |
| H(10C) | 6028 | 516 | 875 | 150 |
| H(11E) | 8109 | 3705 | 840 | 33 |
| H(11F) | 8195 | 3253 | 387 | 33 |
| H(12A) | 7581 | 2956 | −55 | 57 |
| H(12B) | 7605 | 3553 | −295 | 57 |
| H(12C) | 7500 | 3438 | 363 | 57 |
| H(13M) | 8341 | 797 | 1242 | 33 |
| H(13N) | 8118 | 1177 | 569 | 33 |
| H(14M) | 7744 | 447 | −41 | 52 |
| H(14N) | 7716 | 589 | 698 | 52 |
| H(14O) | 7955 | 95 | 671 | 52 |
| H(15M) | 272 | 2476 | −63 | 44 |
| H(15N) | 475 | 2669 | 763 | 44 |
| H(16M) | 317 | 3544 | 407 | 74 |
| H(16N) | −43 | 3188 | 97 | 74 |
| H(16O) | 135 | 3371 | −430 | 74 |

Crystallographic Data for LMT.2MsOH (FIG. 17c)

TABLE 1

Crystal data and structure refinement for LMT•2MsOH.

| | |
|---|---|
| Identification code | 64412SC171 |
| Empirical formula | C18 H27 N3 O6 S3 |
| Formula weight | 477.61 |
| Temperature | 150(2) K |
| Wavelength | 0.71073 Å |
| Crystal system | Triclinic |
| Space group | P-1 |
| Unit cell dimensions | a = 11.6401(6) Å  α = 104.682(2)°. |
| | b = 12.0744(6) Å  β = 92.386(2)°. |
| | c = 18.4846(9) Å  γ = 116.151(2)°. |
| Volume | 2220.42(19) $Å^3$ |
| Z | 4 |
| Density (calculated) | 1.429 $Mg/m^3$ |
| Absorption coefficient | 0.374 $mm^{-1}$ |
| F(000) | 1008 |
| Crystal size | 0.30 × 0.18 × 0.04 $mm^3$ |
| Theta range for data collection | 1.16 to 27.57°. |
| Index ranges | −15 <= h <= 15, −15 <= k <= 15, −24 <= l <= 24 |
| Reflections collected | 42564 |
| Independent reflections | 10184 [R(int) = 0.0662] |
| Completeness to theta = 25.00° | 99.6% |
| Absorption correction | Semi-empirical from equivalents |
| Max. and min. transmission | 0.9852 and 0.8962 |
| Refinement method | Full-matrix least-squares on $F^2$ |
| Data/restraints/parameters | 10184/198/552 |
| Goodness-of-fit on $F^2$ | 1.071 |
| Final R indices [I > 2sigma(I)] | R1 = 0.0593, wR2 = 0.1399 |
| R indices (all data) | R1 = 0.0909, wR2 = 0.1566 |
| Largest diff. peak and hole | 1.192 and −0.905 e · $Å^{-3}$ |

TABLE 2

Atomic coordinates (×10⁴) and equivalent isotropic displacement parameters ($Å^2 \times 10^3$) for eul1_0m. U(eq) is defined as one third of the trace of the orthogonalized $U^{ij}$ tensor.

| | x | y | z | U(eq) |
|---|---|---|---|---|
| C(1A) | 2847(3) | 7453(4) | 3069(2) | 28(1) |
| C(2A) | 2545(3) | 8117(3) | 2643(2) | 27(1) |
| C(3A) | 3528(3) | 9173(4) | 2496(2) | 29(1) |
| C(4A) | 4823(3) | 9566(4) | 2760(2) | 37(1) |
| C(5A) | 5121(3) | 8863(4) | 3154(2) | 39(1) |
| C(6A) | 4156(3) | 7809(4) | 3317(2) | 34(1) |
| C(7A) | 3630(5) | 5911(5) | 3768(2) | 48(1) |
| C(8A) | 4139(5) | 5179(5) | 4015(2) | 55(1) |
| C(9A) | 3314(5) | 4011(5) | 4119(2) | 58(1) |
| C(10A) | 1978(5) | 3531(5) | 3953(2) | 52(1) |
| C(11A) | 1451(5) | 4217(4) | 3678(2) | 45(1) |

TABLE 2-continued

Atomic coordinates (×10⁴) and equivalent isotropic displacement parameters (Å² × 10³) for eul1_0m. U(eq) is defined as one third of the trace of the orthogonalized $U^{ij}$ tensor.

| | x | y | z | U(eq) |
|---|---|---|---|---|
| C(12A) | 2292(4) | 5408(4) | 3601(2) | 42(1) |
| C(13A) | 3947(4) | 10426(4) | 1555(2) | 39(1) |
| C(14A) | 3035(4) | 10981(4) | 2698(2) | 36(1) |
| C(15A) | 479(5) | 2617(4) | 4788(2) | 56(1) |
| C(16A) | 422(9) | 1431(7) | 3338(3) | 21(2) |
| C(16') | −175(7) | 1295(6) | 3509(4) | 38(2) |
| C(1B) | 1734(3) | 3733(3) | 1573(2) | 20(1) |
| C(2B) | 467(3) | 2802(3) | 1532(2) | 20(1) |
| C(3B) | −556(3) | 2949(3) | 1228(2) | 20(1) |
| C(4B) | −328(3) | 4011(3) | 986(2) | 21(1) |
| C(5B) | 938(3) | 4959(3) | 1054(2) | 22(1) |
| C(6B) | 1992(3) | 4819(3) | 1335(2) | 21(1) |
| C(7B) | 4382(3) | 5861(3) | 1707(2) | 21(1) |
| C(8B) | 5559(3) | 6955(3) | 1766(2) | 22(1) |
| C(9B) | 6724(3) | 7111(3) | 2126(2) | 22(1) |
| C(10B) | 6691(3) | 6167(3) | 2435(2) | 20(1) |
| C(11B) | 5535(3) | 5073(3) | 2382(2) | 20(1) |
| C(12B) | 4385(3) | 4907(3) | 2011(2) | 20(1) |
| C(13B) | −2276(3) | 1245(3) | 1673(2) | 27(1) |
| C(14B) | −2081(3) | 892(3) | 317(2) | 27(1) |
| C(15B) | 8932(3) | 7573(3) | 3209(2) | 26(1) |
| C(16B) | 8431(3) | 5579(3) | 2180(2) | 29(1) |
| C(1S) | 3536(4) | 59(4) | 4695(2) | 38(1) |
| C(2S) | 8797(4) | 7948(3) | 434(2) | 33(1) |
| C(3S) | 5403(4) | 3853(4) | 327(2) | 40(1) |
| C(4S) | 6718(6) | 3037(5) | 4356(2) | 67(2) |
| N(1A) | 4480(3) | 7134(4) | 3726(2) | 46(1) |
| N(2A) | 3126(3) | 9915(3) | 2118(2) | 29(1) |
| N(3A) | 1056(5) | 2317(4) | 4117(2) | 68(1) |
| N(1B) | 3245(2) | 5734(3) | 1338(2) | 24(1) |
| N(2B) | −1895(2) | 1871(3) | 1060(1) | 21(1) |
| N(3B) | 7903(2) | 6237(2) | 2774(2) | 21(1) |
| O(1S) | 1876(5) | 153(5) | 5602(3) | 31(1) |
| O(2S) | 1457(5) | 367(5) | 4352(3) | 27(1) |
| O(3S) | 3166(4) | 2156(4) | 5329(3) | 28(1) |
| O(2S') | 3198(4) | 1901(4) | 4683(3) | 26(1) |
| O(1S') | 2515(5) | 924(5) | 5683(3) | 25(1) |
| O(3S') | 1291(5) | −191(6) | 4380(3) | 27(1) |
| O(4S) | 10898(2) | 10147(2) | 1042(1) | 34(1) |
| O(5S) | 9224(3) | 9462(3) | 1796(2) | 40(1) |
| O(6S) | 10527(2) | 8353(2) | 1521(2) | 39(1) |
| O(7S) | 6954(2) | 2997(3) | 257(1) | 34(1) |
| O(8S) | 6130(2) | 2435(2) | 845(1) | 31(1) |
| O(9S) | 4703(3) | 1484(2) | 383(2) | 44(1) |
| O(10S) | 7552(3) | 4905(3) | 3786(2) | 53(1) |
| O(11S) | 8403(4) | 3384(4) | 3483(2) | 73(1) |
| O(12S) | 6252(3) | 2791(3) | 2924(2) | 57(1) |
| S(1) | 2478(1) | 713(1) | 4948(1) | 30(1) |
| S(2) | 9944(1) | 9074(1) | 1257(1) | 23(1) |
| S(3) | 5818(1) | 2588(1) | 111(1) | 22(1) |
| S(4) | 7286(1) | 3562(1) | 3574(1) | 26(1) |
| S(1A) | 1567(1) | 6322(1) | 3376(1) | 32(1) |
| S(1B) | 2994(1) | 3393(1) | 1838(1) | 26(1) |

TABLE 3

Bond lengths [Å] and angles [°] for eul1_0m.

| | |
|---|---|
| C(1A)—C(2A) | 1.390(5) |
| C(1A)—C(6A) | 1.408(4) |
| C(1A)—S(1A) | 1.753(4) |
| C(2A)—C(3A) | 1.388(5) |
| C(2A)—H(2A) | 0.9500 |
| C(3A)—C(4A) | 1.388(5) |
| C(3A)—N(2A) | 1.472(5) |
| C(4A)—C(5A) | 1.387(6) |
| C(4A)—H(4A) | 0.9500 |
| C(5A)—C(6A) | 1.390(6) |
| C(5A)—H(5A) | 0.9500 |
| C(6A)—N(1A) | 1.393(5) |
| C(7A)—C(12A) | 1.386(6) |

TABLE 3-continued

Bond lengths [Å] and angles [°] for eul1_0m.

| | |
|---|---|
| C(7A)—N(1A) | 1.394(6) |
| C(7A)—C(8A) | 1.409(5) |
| C(8A)—C(9A) | 1.380(7) |
| C(8A)—H(8A) | 0.9500 |
| C(9A)—C(10A) | 1.387(7) |
| C(9A)—H(9A) | 0.9500 |
| C(10A)—C(11A) | 1.399(5) |
| C(10A)—N(3A) | 1.502(7) |
| C(11A)—C(12A) | 1.386(7) |
| C(11A)—H(11A) | 0.9500 |
| C(12A)—S(1A) | 1.768(5) |
| C(13A)—N(2A) | 1.506(4) |
| C(13A)—H(13A) | 0.9800 |
| C(13A)—H(13B) | 0.9800 |
| C(13A)—H(13C) | 0.9800 |
| C(14A)—N(2A) | 1.499(5) |
| C(14A)—H(14A) | 0.9800 |
| C(14A)—H(14B) | 0.9800 |
| C(14A)—H(14C) | 0.9800 |
| C(15A)—N(3A) | 1.477(6) |
| C(15A)—H(15A) | 0.9800 |
| C(15A)—H(15B) | 0.9800 |
| C(15A)—H(15C) | 0.9800 |
| C(16A)—N(3A) | 1.482(6) |
| C(16A)—H(16H) | 0.9800 |
| C(16A)—H(16I) | 0.9800 |
| C(16A)—H(16J) | 0.9800 |
| C(16')—N(3A) | 1.563(6) |
| C(16')—H(16K) | 0.9800 |
| C(16')—H(16L) | 0.9800 |
| C(16')—H(16M) | 0.9800 |
| C(1B)—C(2B) | 1.390(4) |
| C(1B)—C(6B) | 1.398(4) |
| C(1B)—S(1B) | 1.770(3) |
| C(2B)—C(3B) | 1.394(4) |
| C(2B)—H(2B) | 0.9500 |
| C(3B)—C(4B) | 1.384(4) |
| C(3B)—N(2B) | 1.479(4) |
| C(4B)—C(5B) | 1.386(4) |
| C(4B)—H(4B) | 0.9500 |
| C(5B)—C(6B) | 1.407(4) |
| C(5B)—H(5B) | 0.9500 |
| C(6B)—N(1B) | 1.387(4) |
| C(7B)—N(1B) | 1.391(4) |
| C(7B)—C(8B) | 1.397(4) |
| C(7B)—C(12B) | 1.405(4) |
| C(8B)—C(9B) | 1.398(4) |
| C(8B)—H(8B) | 0.9500 |
| C(9B)—C(10B) | 1.385(4) |
| C(9B)—H(9B) | 0.9500 |
| C(10B)—C(11B) | 1.387(4) |
| C(10B)—N(3B) | 1.478(4) |
| C(11B)—C(12B) | 1.386(4) |
| C(11B)—H(11B) | 0.9500 |
| C(12B)—S(1B) | 1.766(3) |
| C(13B)—N(2B) | 1.494(4) |
| C(13B)—H(13D) | 0.9800 |
| C(13B)—H(13E) | 0.9800 |
| C(13B)—H(13F) | 0.9800 |
| C(14B)—N(2B) | 1.503(4) |
| C(14B)—H(14D) | 0.9800 |
| C(14B)—H(14E) | 0.9800 |
| C(14B)—H(14F) | 0.9800 |
| C(15B)—N(3B) | 1.497(4) |
| C(15B)—H(15D) | 0.9800 |
| C(15B)—H(15E) | 0.9800 |
| C(15B)—H(15F) | 0.9800 |
| C(16B)—N(3B) | 1.503(4) |
| C(16B)—H(16A) | 0.9800 |
| C(16B)—H(16B) | 0.9800 |
| C(16B)—H(16C) | 0.9800 |
| C(1S)—S(1) | 1.755(4) |
| C(1S)—H(1S1) | 0.9800 |
| C(1S)—H(1S2) | 0.9800 |
| C(1S)—H(1S3) | 0.9800 |
| C(2S)—S(2) | 1.768(3) |
| C(2S)—H(2S1) | 0.9800 |
| C(2S)—H(2S2) | 0.9800 |

TABLE 3-continued

Bond lengths [Å] and angles [°] for eul1_0m.

| Bond/Angle | Value |
|---|---|
| C(2S)—H(2S3) | 0.9800 |
| C(3S)—S(3) | 1.755(4) |
| C(3S)—H(3S1) | 0.9800 |
| C(3S)—H(3S2) | 0.9800 |
| C(3S)—H(3S3) | 0.9800 |
| C(4S)—S(4) | 1.762(4) |
| C(4S)—H(4S1) | 0.9800 |
| C(4S)—H(4S2) | 0.9800 |
| C(4S)—H(4S3) | 0.9800 |
| N(1A)—H(1A) | 0.8800 |
| N(2A)—H(2A1) | 0.9300 |
| N(3A)—H(3A) | 0.9300 |
| N(1B)—H(1B) | 0.8800 |
| N(2B)—H(2B1) | 0.9300 |
| N(3B)—H(3B) | 0.9300 |
| O(1S)—S(1) | 1.573(5) |
| O(2S)—S(1) | 1.422(5) |
| O(3S)—S(1) | 1.508(5) |
| O(2S')—S(1) | 1.528(5) |
| O(1S')—S(1) | 1.312(5) |
| O(3S')—S(1) | 1.473(5) |
| O(4S)—S(2) | 1.449(2) |
| O(5S)—S(2) | 1.447(3) |
| O(6S)—S(2) | 1.472(2) |
| O(7S)—S(3) | 1.458(2) |
| O(8S)—S(3) | 1.467(2) |
| O(9S)—S(3) | 1.433(3) |
| O(10S)—S(4) | 1.451(3) |
| O(11S)—S(4) | 1.417(3) |
| O(12S)—S(4) | 1.443(3) |
| C(2A)—C(1A)—C(6A) | 119.8(3) |
| C(2A)—C(1A)—S(1A) | 117.7(2) |
| C(6A)—C(1A)—S(1A) | 122.0(3) |
| C(3A)—C(2A)—C(1A) | 120.3(3) |
| C(3A)—C(2A)—H(2A) | 119.9 |
| C(1A)—C(2A)—H(2A) | 119.9 |
| C(2A)—C(3A)—C(4A) | 120.5(4) |
| C(2A)—C(3A)—N(2A) | 116.9(3) |
| C(4A)—C(3A)—N(2A) | 122.3(3) |
| C(5A)—C(4A)—C(3A) | 118.9(4) |
| C(5A)—C(4A)—H(4A) | 120.5 |
| C(3A)—C(4A)—H(4A) | 120.5 |
| C(4A)—C(5A)—C(6A) | 121.7(3) |
| C(4A)—C(5A)—H(5A) | 119.1 |
| C(6A)—C(5A)—H(5A) | 119.1 |
| C(5A)—C(6A)—N(1A) | 120.6(3) |
| C(5A)—C(6A)—C(1A) | 118.6(4) |
| N(1A)—C(6A)—C(1A) | 120.8(4) |
| C(12A)—C(7A)—N(1A) | 122.0(3) |
| C(12A)—C(7A)—C(8A) | 118.7(5) |
| N(1A)—C(7A)—C(8A) | 119.3(4) |
| C(9A)—C(8A)—C(7A) | 120.2(5) |
| C(9A)—C(8A)—H(8A) | 119.9 |
| C(7A)—C(8A)—H(8A) | 119.9 |
| C(8A)—C(9A)—C(10A) | 120.1(4) |
| C(8A)—C(9A)—H(9A) | 120.0 |
| C(10A)—C(9A)—H(9A) | 120.0 |
| C(9A)—C(10A)—C(11A) | 120.6(5) |
| C(9A)—C(10A)—N(3A) | 121.4(4) |
| C(11A)—C(10A)—N(3A) | 117.8(4) |
| C(12A)—C(11A)—C(10A) | 118.5(4) |
| C(12A)—C(11A)—H(11A) | 120.7 |
| C(10A)—C(11A)—H(11A) | 120.7 |
| C(7A)—C(12A)—C(11A) | 121.8(4) |
| C(7A)—C(12A)—S(1A) | 121.7(4) |
| C(11A)—C(12A)—S(1A) | 116.2(3) |
| N(2A)—C(13A)—H(13A) | 109.5 |
| N(2A)—C(13A)—H(13B) | 109.5 |
| H(13A)—C(13A)—H(13B) | 109.5 |
| N(2A)—C(13A)—H(13C) | 109.5 |
| H(13A)—C(13A)—H(13C) | 109.5 |
| H(13B)—C(13A)—H(13C) | 109.5 |
| N(2A)—C(14A)—H(14A) | 109.5 |
| N(2A)—C(14A)—H(14B) | 109.5 |
| H(14A)—C(14A)—H(14B) | 109.5 |
| N(2A)—C(14A)—H(14C) | 109.5 |
| H(14A)—C(14A)—H(14C) | 109.5 |
| H(14B)—C(14A)—H(14C) | 109.5 |
| N(3A)—C(15A)—H(15A) | 109.5 |
| N(3A)—C(15A)—H(15B) | 109.5 |
| H(15A)—C(15A)—H(15B) | 109.5 |
| N(3A)—C(15A)—H(15C) | 109.5 |
| H(15A)—C(15A)—H(15C) | 109.5 |
| H(15B)—C(15A)—H(15C) | 109.5 |
| N(3A)—C(16A)—H(16H) | 109.5 |
| N(3A)—C(16A)—H(16I) | 109.5 |
| N(3A)—C(16A)—H(16J) | 109.5 |
| N(3A)—C(16')—H(16K) | 109.5 |
| N(3A)—C(16')—H(16L) | 109.5 |
| H(16K)—C(16')—H(16L) | 109.5 |
| N(3A)—C(16')—H(16M) | 109.5 |
| H(16K)—C(16')—H(16M) | 109.5 |
| H(16L)—C(16')—H(16M) | 109.5 |
| C(2B)—C(1B)—C(6B) | 121.3(3) |
| C(2B)—C(1B)—S(1B) | 116.9(2) |
| C(6B)—C(1B)—S(1B) | 121.5(2) |
| C(1B)—C(2B)—C(3B) | 118.7(3) |
| C(1B)—C(2B)—H(2B) | 120.7 |
| C(3B)—C(2B)—H(2B) | 120.7 |
| C(4B)—C(3B)—C(2B) | 121.2(3) |
| C(4B)—C(3B)—N(2B) | 118.7(3) |
| C(2B)—C(3B)—N(2B) | 119.5(3) |
| C(3B)—C(4B)—C(5B) | 119.7(3) |
| C(3B)—C(4B)—H(4B) | 120.1 |
| C(5B)—C(4B)—H(4B) | 120.1 |
| C(4B)—C(5B)—C(6B) | 120.4(3) |
| C(4B)—C(5B)—H(5B) | 119.8 |
| C(6B)—C(5B)—H(5B) | 119.8 |
| N(1B)—C(6B)—C(1B) | 122.5(3) |
| N(1B)—C(6B)—C(5B) | 118.7(3) |
| C(1B)—C(6B)—C(5B) | 118.7(3) |
| N(1B)—C(7B)—C(8B) | 119.3(3) |
| N(1B)—C(7B)—C(12B) | 121.7(3) |
| C(8B)—C(7B)—C(12B) | 119.0(3) |
| C(7B)—C(8B)—C(9B) | 120.9(3) |
| C(7B)—C(8B)—H(8B) | 119.5 |
| C(9B)—C(8B)—H(8B) | 119.5 |
| C(10B)—C(9B)—C(8B) | 118.7(3) |
| C(10B)—C(9B)—H(9B) | 120.6 |
| C(8B)—C(9B)—H(9B) | 120.6 |
| C(9B)—C(10B)—C(11B) | 121.4(3) |
| C(9B)—C(10B)—N(3B) | 121.0(3) |
| C(11B)—C(10B)—N(3B) | 117.4(3) |
| C(12B)—C(11B)—C(10B) | 119.7(3) |
| C(12B)—C(11B)—H(11B) | 120.1 |
| C(10B)—C(11B)—H(11B) | 120.1 |
| C(11B)—C(12B)—C(7B) | 120.2(3) |
| C(11B)—C(12B)—S(1B) | 117.6(2) |
| C(7B)—C(12B)—S(1B) | 121.8(2) |
| N(2B)—C(13B)—H(13D) | 109.5 |
| N(2B)—C(13B)—H(13E) | 109.5 |
| H(13D)—C(13B)—H(13E) | 109.5 |
| N(2B)—C(13B)—H(13F) | 109.5 |
| H(13D)—C(13B)—H(13F) | 109.5 |
| H(13E)—C(13B)—H(13F) | 109.5 |
| N(2B)—C(14B)—H(14D) | 109.5 |
| N(2B)—C(14B)—H(14E) | 109.5 |
| H(14D)—C(14B)—H(14E) | 109.5 |
| N(2B)—C(14B)—H(14F) | 109.5 |
| H(14D)—C(14B)—H(14F) | 109.5 |
| H(14E)—C(14B)—H(14F) | 109.5 |
| N(3B)—C(15B)—H(15D) | 109.5 |
| N(3B)—C(15B)—H(15E) | 109.5 |
| H(15D)—C(15B)—H(15E) | 109.5 |
| N(3B)—C(15B)—H(15F) | 109.5 |
| H(15D)—C(15B)—H(15F) | 109.5 |
| H(15E)—C(15B)—H(15F) | 109.5 |
| N(3B)—C(16B)—H(16A) | 109.5 |
| N(3B)—C(16B)—H(16B) | 109.5 |
| H(16A)—C(16B)—H(16B) | 109.5 |
| N(3B)—C(16B)—H(16C) | 109.5 |
| H(16A)—C(16B)—H(16C) | 109.5 |
| H(16B)—C(16B)—H(16C) | 109.5 |
| S(1)—C(1S)—H(1S1) | 109.5 |
| S(1)—C(1S)—H(1S2) | 109.5 |
| H(1S1)—C(1S)—H(1S2) | 109.5 |

TABLE 3-continued

Bond lengths [Å] and angles [°] for eul1_0m.

| | |
|---|---|
| S(1)—C(1S)—H(1S3) | 109.5 |
| H(1S1)—C(1S)—H(1S3) | 109.5 |
| H(1S2)—C(1S)—H(1S3) | 109.5 |
| S(2)—C(2S)—H(2S1) | 109.5 |
| S(2)—C(2S)—H(2S2) | 109.5 |
| H(2S1)—C(2S)—H(2S2) | 109.5 |
| S(2)—C(2S)—H(2S3) | 109.5 |
| H(2S1)—C(2S)—H(2S3) | 109.5 |
| H(2S2)—C(2S)—H(2S3) | 109.5 |
| S(3)—C(3S)—H(3S1) | 109.5 |
| S(3)—C(3S)—H(3S2) | 109.5 |
| H(3S1)—C(3S)—H(3S2) | 109.5 |
| S(3)—C(3S)—H(3S3) | 109.5 |
| H(3S1)—C(3S)—H(3S3) | 109.5 |
| H(3S2)—C(3S)—H(3S3) | 109.5 |
| S(4)—C(4S)—H(4S1) | 109.5 |
| S(4)—C(4S)—H(4S2) | 109.5 |
| H(4S1)—C(4S)—H(4S2) | 109.5 |
| S(4)—C(4S)—H(4S3) | 109.5 |
| H(4S1)—C(4S)—H(4S3) | 109.5 |
| H(4S2)—C(4S)—H(4S3) | 109.5 |
| C(6A)—N(1A)—C(7A) | 124.8(3) |
| C(6A)—N(1A)—H(1A) | 117.6 |
| C(7A)—N(1A)—H(1A) | 117.6 |
| C(3A)—N(2A)—C(14A) | 110.2(3) |
| C(3A)—N(2A)—C(13A) | 114.9(3) |
| C(14A)—N(2A)—C(13A) | 111.1(3) |
| C(3A)—N(2A)—H(2A1) | 106.7 |
| C(14A)—N(2A)—H(2A1) | 106.7 |
| C(13A)—N(2A)—H(2A1) | 106.7 |
| C(15A)—N(3A)—C(10A) | 111.1(3) |
| C(15A)—N(3A)—C(16A) | 130.2(6) |
| C(10A)—N(3A)—C(16A) | 101.3(4) |
| C(15A)—N(3A)—C(16') | 102.0(5) |
| C(10A)—N(3A)—C(16') | 119.1(4) |
| C(16A)—N(3A)—C(16') | 28.2(3) |
| C(15A)—N(3A)—H(3A) | 103.9 |
| C(10A)—N(3A)—H(3A) | 103.9 |
| C(16A)—N(3A)—H(3A) | 103.9 |
| C(16')—N(3A)—H(3A) | 116.0 |
| C(6B)—N(1B)—C(7B) | 125.8(3) |
| C(6B)—N(1B)—H(1B) | 117.1 |
| C(7B)—N(1B)—H(1B) | 117.1 |
| C(3B)—N(2B)—C(13B) | 114.9(2) |
| C(3B)—N(2B)—C(14B) | 109.1(2) |
| C(13B)—N(2B)—C(14B) | 111.1(3) |
| C(3B)—N(2B)—H(2B1) | 107.1 |
| C(13B)—N(2B)—H(2B1) | 107.1 |
| C(14B)—N(2B)—H(2B1) | 107.1 |
| C(10B)—N(3B)—C(15B) | 114.9(2) |
| C(10B)—N(3B)—C(16B) | 110.6(2) |
| C(15B)—N(3B)—C(16B) | 110.8(2) |
| C(10B)—N(3B)—H(3B) | 106.7 |
| C(15B)—N(3B)—H(3B) | 106.7 |
| C(16B)—N(3B)—H(3B) | 106.7 |
| O(1S')—S(1)—O(2S) | 131.2(3) |
| O(1S')—S(1)—O(3S') | 123.5(3) |
| O(2S)—S(1)—O(3S') | 25.1(2) |
| O(1S')—S(1)—O(3S) | 71.7(3) |
| O(2S)—S(1)—O(3S) | 110.8(3) |
| O(3S')—S(1)—O(3S) | 134.9(3) |
| O(1S')—S(1)—O(2S') | 116.5(3) |
| O(2S)—S(1)—O(2S') | 84.3(3) |
| O(3S')—S(1)—O(2S') | 107.5(3) |
| O(3S)—S(1)—O(2S') | 45.0(2) |
| O(1S')—S(1)—O(1S) | 33.5(2) |
| O(2S)—S(1)—O(1S) | 109.1(3) |
| O(3S')—S(1)—O(1S) | 93.0(3) |
| O(3S)—S(1)—O(1S) | 103.3(3) |
| O(2S')—S(1)—O(1S) | 148.0(3) |
| O(1S')—S(1)—C(1S) | 107.0(2) |
| O(2S)—S(1)—C(1S) | 114.7(2) |
| O(3S')—S(1)—C(1S) | 102.3(2) |
| O(3S)—S(1)—C(1S) | 113.6(2) |
| O(2S')—S(1)—C(1S) | 95.2(2) |
| O(1S)—S(1)—C(1S) | 104.4(2) |
| O(4S)—S(2)—O(5S) | 112.76(15) |
| O(4S)—S(2)—O(6S) | 111.68(16) |
| O(5S)—S(2)—O(6S) | 112.07(17) |
| O(4S)—S(2)—C(2S) | 108.24(17) |
| O(5S)—S(2)—C(2S) | 106.71(17) |
| O(6S)—S(2)—C(2S) | 104.86(16) |
| O(9S)—S(3)—O(7S) | 112.41(17) |
| O(9S)—S(3)—O(8S) | 113.91(16) |
| O(7S)—S(3)—O(8S) | 111.12(14) |
| O(9S)—S(3)—C(3S) | 105.99(19) |
| O(7S)—S(3)—C(3S) | 107.38(18) |
| O(8S)—S(3)—C(3S) | 105.42(16) |
| O(11S)—S(4)—O(12S) | 112.8(2) |
| O(11S)—S(4)—O(10S) | 114.1(2) |
| O(12S)—S(4)—O(10S) | 110.8(2) |
| O(11S)—S(4)—C(4S) | 106.2(3) |
| O(12S)—S(4)—C(4S) | 107.6(2) |
| O(10S)—S(4)—C(4S) | 104.6(2) |
| C(1A)—S(1A)—C(12A) | 100.76(19) |
| C(12B)—S(1B)—C(1B) | 101.93(14) |

Symmetry transformations used to generate equivalent atoms:

TABLE 4

Anisotropic displacement parameters (Å² × 10³) for eul1_0m. The anisotropic displacement factor exponent takes the form: $-2\pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(1A) | 22(1) | 45(2) | 19(1) | 2(1) | 1(1) | 21(1) |
| C(2A) | 17(1) | 41(2) | 20(1) | 4(1) | 0(1) | 14(1) |
| C(3A) | 19(1) | 46(2) | 15(1) | 2(1) | 1(1) | 12(1) |
| C(4A) | 19(1) | 57(2) | 19(1) | −4(1) | 2(1) | 12(1) |
| C(5A) | 19(1) | 66(2) | 20(1) | −6(1) | −2(1) | 21(1) |
| C(6A) | 23(1) | 59(2) | 17(1) | −4(1) | −2(1) | 26(1) |
| C(7A) | 75(2) | 90(2) | 15(1) | 8(2) | 5(1) | 73(2) |
| C(8A) | 86(2) | 98(2) | 19(1) | 6(2) | 0(1) | 83(2) |
| C(9A) | 101(2) | 92(2) | 20(2) | 6(2) | −2(2) | 86(2) |
| C(10A) | 100(2) | 76(2) | 18(1) | 9(1) | 3(2) | 78(2) |
| C(11A) | 86(2) | 71(2) | 16(1) | 14(1) | 7(1) | 69(2) |
| C(12A) | 75(2) | 75(2) | 15(1) | 15(1) | 8(1) | 67(2) |
| C(13A) | 27(1) | 44(2) | 20(2) | 8(2) | 4(2) | −3(2) |
| C(14A) | 39(2) | 30(2) | 25(2) | 7(2) | 10(2) | 5(2) |
| C(15A) | 104(4) | 34(2) | 28(2) | 4(2) | −10(2) | 34(3) |
| C(1B) | 17(1) | 22(1) | 18(1) | 4(1) | 3(1) | 10(1) |
| C(2B) | 21(1) | 22(1) | 18(1) | 6(1) | 4(1) | 10(1) |
| C(3B) | 19(1) | 23(1) | 19(1) | 5(1) | 4(1) | 10(1) |
| C(4B) | 20(1) | 23(1) | 22(1) | 6(1) | 3(1) | 12(1) |
| C(5B) | 22(1) | 21(1) | 24(1) | 7(1) | 4(1) | 11(1) |
| C(6B) | 18(1) | 22(1) | 23(1) | 5(1) | 6(1) | 10(1) |
| C(7B) | 21(1) | 20(1) | 23(1) | 6(1) | 6(1) | 11(1) |
| C(8B) | 23(1) | 19(1) | 26(1) | 6(1) | 6(1) | 11(1) |
| C(9B) | 21(1) | 19(1) | 26(1) | 5(1) | 7(1) | 9(1) |
| C(10B) | 19(1) | 21(1) | 19(1) | 3(1) | 4(1) | 10(1) |
| C(11B) | 20(1) | 21(1) | 20(1) | 5(1) | 5(1) | 10(1) |
| C(12B) | 18(1) | 20(1) | 20(1) | 6(1) | 5(1) | 8(1) |
| C(13B) | 21(2) | 30(2) | 24(2) | 10(2) | 4(1) | 7(1) |
| C(14B) | 24(2) | 26(2) | 21(2) | 0(1) | 0(1) | 6(1) |
| C(15B) | 24(2) | 22(2) | 25(2) | 0(1) | 0(1) | 8(1) |
| C(16B) | 27(2) | 31(2) | 27(2) | 0(2) | 2(1) | 18(2) |
| C(1S) | 33(2) | 49(2) | 28(2) | 7(2) | 0(2) | 20(2) |
| C(2S) | 35(2) | 29(2) | 26(2) | 2(2) | −6(2) | 12(2) |
| C(3S) | 62(3) | 44(2) | 31(2) | 12(2) | 9(2) | 40(2) |
| C(4S) | 95(4) | 51(3) | 30(2) | 16(2) | 22(2) | 11(3) |
| N(1A) | 42(2) | 88(3) | 23(2) | 2(2) | −6(1) | 52(2) |
| N(2A) | 20(1) | 32(2) | 19(1) | 5(1) | 2(1) | 0(1) |
| N(3A) | 159(4) | 58(2) | 17(2) | 1(2) | −12(2) | 84(3) |
| N(1B) | 18(1) | 25(1) | 34(2) | 17(1) | 7(1) | 9(1) |
| N(2B) | 17(1) | 25(1) | 21(1) | 6(1) | 2(1) | 10(1) |
| N(3B) | 18(1) | 20(1) | 21(1) | 2(1) | 1(1) | 8(1) |
| O(4S) | 39(2) | 25(1) | 33(1) | 10(1) | 12(1) | 9(1) |
| O(5S) | 37(2) | 35(1) | 34(1) | 0(1) | 14(1) | 10(1) |
| O(6S) | 30(1) | 27(1) | 54(2) | 14(1) | −11(1) | 8(1) |
| O(7S) | 27(1) | 48(2) | 42(2) | 28(1) | 16(1) | 22(1) |
| O(8S) | 33(1) | 42(1) | 34(1) | 23(1) | 13(1) | 25(1) |

TABLE 4-continued

Anisotropic displacement parameters (Å² × 10³) for eu11_0m. The anisotropic displacement factor exponent takes the form: $-2\pi^2[h^2 a^{*2}U^{11} + \ldots + 2 h k a^* b^* U^{12}]$

|  | $U^{11}$ | $U^{22}$ | $U^{33}$ | $U^{23}$ | $U^{13}$ | $U^{12}$ |
|---|---|---|---|---|---|---|
| O(9S) | 33(2) | 28(1) | 53(2) | 7(1) | −5(1) | 3(1) |
| O(10S) | 96(2) | 27(1) | 26(1) | 4(1) | −11(2) | 24(2) |
| O(11S) | 84(3) | 128(3) | 45(2) | 25(2) | 15(2) | 82(3) |
| O(12S) | 43(2) | 54(2) | 28(2) | 2(1) | −5(1) | −11(1) |
| S(1) | 21(1) | 19(1) | 45(1) | 13(1) | −12(1) | 5(1) |
| S(2) | 23(1) | 22(1) | 20(1) | 5(1) | 3(1) | 9(1) |
| S(3) | 19(1) | 22(1) | 28(1) | 10(1) | 6(1) | 11(1) |
| S(4) | 29(1) | 22(1) | 18(1) | 6(1) | 2(1) | 4(1) |
| S(1A) | 29(1) | 43(1) | 39(1) | 19(1) | 5(1) | 26(1) |
| S(1B) | 17(1) | 22(1) | 39(1) | 15(1) | 1(1) | 7(1) |

TABLE 5

Hydrogen coordinates (×10⁴) and isotropic displacement parameters (Å² × 10³) for eu11_0m.

|  | x | y | z | U(eq) |
|---|---|---|---|---|
| H(2A) | 1662 | 7847 | 2452 | 32 |
| H(4A) | 5495 | 10304 | 2671 | 45 |
| H(5A) | 6007 | 9108 | 3318 | 47 |
| H(8A) | 5053 | 5489 | 4110 | 66 |
| H(9A) | 3662 | 3536 | 4304 | 69 |
| H(11A) | 536 | 3874 | 3547 | 54 |
| H(13A) | 4800 | 11131 | 1827 | 58 |
| H(13B) | 3517 | 10752 | 1260 | 58 |
| H(13C) | 4057 | 9728 | 1211 | 58 |
| H(14A) | 2513 | 10627 | 3064 | 54 |
| H(14B) | 2623 | 11370 | 2445 | 54 |
| H(14C) | 3910 | 11643 | 2966 | 54 |
| H(15A) | 1173 | 3266 | 5213 | 84 |
| H(15B) | −13 | 1828 | 4928 | 84 |
| H(15C) | −105 | 2958 | 4669 | 84 |
| H(16H) | −60 | 541 | 3357 | 32 |
| H(16I) | 1086 | 1487 | 3019 | 32 |
| H(16J) | −179 | 1679 | 3122 | 32 |
| H(16K) | −683 | 569 | 3701 | 56 |
| H(16L) | 94 | 977 | 3039 | 56 |
| H(16M) | −708 | 1698 | 3407 | 56 |
| H(2B) | 301 | 2081 | 1708 | 24 |
| H(4B) | −1035 | 4090 | 775 | 25 |
| H(5B) | 1095 | 5709 | 911 | 26 |
| H(8B) | 5567 | 7602 | 1559 | 27 |
| H(9B) | 7524 | 7850 | 2158 | 27 |
| H(11B) | 5531 | 4439 | 2601 | 24 |
| H(13D) | −1727 | 843 | 1744 | 41 |
| H(13E) | −3189 | 582 | 1529 | 41 |
| H(13F) | −2161 | 1901 | 2148 | 41 |
| H(14D) | −1922 | 1307 | −87 | 41 |
| H(14E) | −2973 | 184 | 197 | 41 |
| H(14F) | −1468 | 547 | 355 | 41 |
| H(15D) | 9282 | 8071 | 2855 | 39 |
| H(15E) | 9634 | 7519 | 3485 | 39 |
| H(15F) | 8555 | 8004 | 3570 | 39 |
| H(16A) | 7739 | 4713 | 1898 | 43 |
| H(16B) | 9145 | 5506 | 2426 | 43 |
| H(16C) | 8752 | 6089 | 1829 | 43 |
| H(1S1) | 4324 | 513 | 5083 | 56 |
| H(1S2) | 3770 | 163 | 4204 | 56 |
| H(1S3) | 3106 | −863 | 4655 | 56 |
| H(2S1) | 8396 | 8376 | 210 | 50 |
| H(2S2) | 8124 | 7229 | 571 | 50 |
| H(2S3) | 9237 | 7616 | 64 | 50 |
| H(3S1) | 5170 | 3997 | −144 | 60 |
| H(3S2) | 6146 | 4646 | 652 | 60 |
| H(3S3) | 4661 | 3623 | 594 | 60 |
| H(4S1) | 6520 | 2129 | 4255 | 100 |
| H(4S2) | 5930 | 3121 | 4436 | 100 |
| H(4S3) | 7389 | 3569 | 4811 | 100 |
| H(1A) | 5282 | 7506 | 3975 | 55 |
| H(2A1) | 2289 | 9350 | 1848 | 35 |

TABLE 5-continued

Hydrogen coordinates (×10⁴) and isotropic displacement parameters (Å² × 10³) for eu11_0m.

|  | x | y | z | U(eq) |
|---|---|---|---|---|
| H(3A) | 1596 | 2011 | 4279 | 82 |
| H(1B) | 3327 | 6282 | 1083 | 29 |
| H(2B1) | −2456 | 2212 | 994 | 26 |
| H(3B) | 7679 | 5766 | 3119 | 25 |

REFERENCES

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Andersen, P. (2006) Amyotrophic lateral sclerosis associated with mutations in the CuZn superoxide dismutase gene. Current Neurology and Neuroscience Reports 6, 37-46.

Arai, T., Hasegawa, M., Nonoka, T., Kametani, F., Yamashita, M., Hosokawa, M., Niizato, K., Tsuchiya, K., Kobayashi, Z., Ikeda, K., Yoshida, M., Onaya, M., Fujishiro, H. & Akiyama, H. (2010) Phosphorylated and cleaved TDP-43 in ALS, FTLD and other neurodegenerative disorders and in cellular models of TDP-43 proteinopathy. Neuropathology 30, 170-181.

Askanas, V., Engel, W. K. & Nogalska, A. (2009) Inclusion body myositis: a degenerative muscle disease associated with intra-muscle fiber multi-protein aggregates, proteasome inhibition, endoplasmic reticulum stress and decreased lysosomal degradation. Brain Pathology 19, 493-506.

Barmada, S. J., Skibinski, G., Korb, E., Rao, E. J., Wu, J. Y. & Finkbeiner, S. (2010) Cytoplasmic mislocalization of TDP-43 is toxic to neurons and enhanced by a mutation associated with familial amyotrophic lateral sclerosis. Journal of Neuroscience 30, 639-649.

Blair, I. P., Williams, K. L., Warraich, S. T., Durnall, J. C., Thoeng, A. D., Manavis, J., Blumbergs, P. C., Vucic, S., Kiernan, M. C. & Nicholson, G. A. (2010) FUS mutations in amyotrophic lateral sclerosis: clinical, pathological, neurophysiological and genetic analysis. Journal of Neurology Neurosurgery and Psychiatry 81, 639-645.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. *Nature* 385, 787-793.

Byrne, S., Walsh, C., Lynch, C., Bede, P., Elamin, M., Kenna, K., McLaughlin, R. & Hardiman, O. (2011) Rate of familial amyotrophic lateral sclerosis: a systematic review and meta-analysis. Journal of Neurology, Neurosurgery & Psychiatry 82, 623-627.

Carrell, R. W. & Gooptu, B. (1998) Conformational changes and disease—serpins, prions and Alzheimer's. *Current Opinion in Structural Biology* 8, 799-809.

Chen-Plotkin, A. S., Lee, V. M. Y. & Trojanowski, J. Q. (2010) TAR DNA-binding protein 43 in neurodegenerative disease. Nature Reviews Neurology 6, 211-220.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Cox, L. E., Ferraiuolo, L., Goodall, E. F., Heath, P. R., Higginbottom, A., Mortiboys, H., Hollinger, H. C., Hartley, J. A., Brockington, A., Burness, C. E., Morrison, K. E., Wharton, S. B., Grierson, A. J., Ince, P. G., Kirby, J. & Shaw, P. J. (2010) Mutations in CHMP2B in lower motor neuron predominant amyotrophic lateral sclerosis (ALS). PLOS One 5, e9872.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Elden, A. C., Kim, H.-J., Hart, M. P., Chen-Plotkin, A. S., Johnson, B. S., Fang, X., Armakola, M., Geser, F., Greene, R., Lu, M. M., Padmanabhan, A., Clay-Falcone, D., McCluskey, L., Elman, L., Juhr, D., Gruber, P. J., Rub, U., Auburger, G., Trojanowski, J. Q., Lee, V. M. Y., Van Deerlin, V. M., Bonini, N. M. & Gitler, A. D. (2010) Ataxin-2 intermediate-length polyglutamine expansions are associated with increased risk for ALS. Nature 466, 1069-1075.

Finsterer, J (2009) Mitochondrial disorders, cognitive impairment and dementia. *J. Neurol. Sci.* 283:143-148

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Gendron, T. F., Josephs, K. A. & Petrucelli, L. (2010) Review: Transactive response DNA-binding protein 43 (TDP-43): mechanisms of neurodegeneration. Neuropathology and Applied Neurobiology 36, 97-112.

Geser, F., Lee, V. M.-Y. & Trojanowski, J. Q. (2010) Amyotrophic lateral sclerosis and frontotemporal lobar degeneration: A spectrum of TDP-43 proteinopathies. Neuropathology 30, 103-112.

Gitcho, M. A., Baloh, R. H., Chakraverty, S., Mayo, K., Norton, J. B., Levitch, D., Hatanpaa, K. J., White, C. L., III, Bigio, E. H., Caselli, R., Baker, M., Al-Lozi, M. T., Morris, J. C., Pestronk, A., Rademakers, R., Goate, A. M. & Cairns, N.J. (2008) TDP-43 A315T mutation in familial motor neuron disease. Annals of Neurology 63, 535-538.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustavsson, A., Engström, U. & Westermark, P. (1991) Normal transthyretin and synthetic transthyretin fragments form amyloid-like fibrils in vitro. *Biochemical and Biophysical Research Communications* 175, 1159-1164.

Higashi, S., Tsuchiya, Y., Araki, T., Wada, K. & Kabuta, T. (2010) TDP-43 physically interacts with amyotrophic lateral sclerosis-linked mutant CuZn superoxide dismutase. Neurochemistry International 57, 906-913.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Igaz, L. M., Kwong, L. K., Chen-Plotkin, A., Winton, M. J., Unger, T. L., Xu, Y., Neumann, M., Trojanowski, J. Q. & Lee, V. M. Y. (2009) Expression of TDP-43 C-terminal fragments in vitro recapitulates pathological features of TDP-43 proteinopathies. Journal of Biological Chemistry 284, 8516-8524.

Jinwal, U K, Miyata, Y, Koren, J, III, Jones, J R, Trotter, J H et al. (2009) Chemical manipulation of Hsp70 ATPase activity regulates tau stability. *J. Neurosci.* 29:12079-12088

Johansson, B., Wernstedt, C. & Westermark, P. (1987) Atrial natriuretic peptide deposited as atrial amyloid fibrils. Biochemical and *Biophysical Research Communications* 148, 1087-1092.

Johnson, B. S., McCaffery, J. M., Lindquist, S. & Gitler, A. D. (2008) A yeast TDP-43 proteinopathy model: Exploring the molecular determinants of TDP-43 aggregation and cellular toxicity. Proceedings of the National Academy of Sciences 105, 6439-6444.

Johnson, B. S., Snead, D., Lee, J. J., McCaffery, J. M., Shorter, J. & Gitler, A. D. (2009) TDP-43 is intrinsically aggregation-prone, and amyotrophic lateral sclerosis-linked mutations accelerate aggregation and increase toxicity. Journal of Biological Chemistry 284, 20329-20339.

Johnson, J. O., Mandrioli, J., Benatar, M., Abramzon, Y., Van Deerlin, V. M., Trojanowski, J. Q., Gibbs, J. R., Brunetti, M., Gronka, S., Wuu, J., Ding, J., McCluskey, L., Martinez-Lage, M., Falcone, D., Hernandez, D. G., Arepalli, S., Chong, S., Schymick, J. C., Rothstein, J., Landi, F., Wang, Y.-D., Calvo, A., Mora, G., Sabatelli, M., Monsurrò, M. R., Battistini, S., Salvi, F., Spataro, R., Sola, P., Borghero, G., Galassi, G., Scholz, S. W., Taylor, J. P., Restagno, G., Chió, A. & Traynor, B. J. (2010) Exome sequencing reveals VCP mutations as a cause of familial ALS. Neuron 68, 857-864.

Kabashi, E., Lin, L., Tradewell, M. L., Dion, P. A., Bercier, V., Bourgouin, P., Rochefort, D., Bel Hadj, S., Durham, H. D., Velde, C. V., Rouleau, G. A. & Drapeau, P. (2010) Gain and loss of function of ALS-related mutations of TARDBP (TDP-43) cause motor deficits in vivo. Human Molecular Genetics 19, 671-683.

Kabashi, E., Valdmanis, P. N., Dion, P., Spiegelman, D., McConkey, B. J., Velde, C. V., Bouchard, J.-P., Lacomblez, L., Pochigaeva, K., Salachas, F., Pradat, P.-F., Camu, W., Meininger, V., Dupre, N. & Rouleau, G. A. (2008) TARDBP mutations in individuals with sporadic and familial amyotrophic lateral sclerosis. Nature Genetics 40, 572-574.

Ling, S.-C., Albuquerque, C. P., Han, J. S., Lagier-Tourenne, C., Tokunaga, S., Zhou, H. & Cleveland, D. W. (2010) ALS-associated mutations in TDP-43 increase its stability and promote TDP-43 complexes with FUS/TLS. Proceedings of the National Academy of Sciences 107, 13318-13323.

Lomas, D. A., Evans, D. L., Finch, J. T. & Carrell, R. W. (1992) The mechanism of Z a1-antitrypsin accumulation in the liver. Nature 357, 605-607.

Love, S., Bridges, L. R. & Case, C. P. (1995) Neurofibrillary tangles in Niemann-Pick disease type C. Brain 118, 119-129.

Mackenzie, I. R. A., Bigio, E. H., Ince, P. G., Geser, F., Neumann, M., Cairns, N.J., Kwong, L. K., Forman, M. S., Ravits, J., Stewart, H., Eisen, A., McClusky, L., Kretzschmar, H. A., Monoranu, C. M., Highley, J. R., Kirby, J., Siddique, T., Shaw, P. J., Lee, V. M. Y. & Trojanowski, J. Q. (2007) Pathological TDP-43 distinguishes sporadic amyotrophic lateral sclerosis from amyotrophic lateral sclerosis with SOD1 mutations. Annals of Neurology 61, 427-434.

Mackenzie, I. R. A., Rademakers, R. & Neumann, M. (2010) TDP-43 and FUS in amyotrophic lateral sclerosis and frontotemporal dementia. The Lancet Neurology 9, 995-1007.

Maury, C. P. & Baumann, M. (1990) Isolation and characterization of cardiac amyloid in familial amyloid polyneuropathy type IV (Finnish): relation of the amyloid protein to variant gelsolin. Biochimica et Biophysica Acta 1096, 84-86.

Neary, D., Snowden, J. S., Gustafson, L., Passant, U., Stuss, D., Black, S., Freedman, M., Kertesz, A., Robert, P. H., Albert, M., Boone, K., Miller, B. L., Cummings, J. & Benson, D. F. (1998) Frontotemporal lobar degeneration: a consensus on clinical diagnostic criteria. Neurology 51, 1546-1554.

Neumann, M. (2009) Molecular neuropathology of TDP-43 proteinopathies. International Journal of Molecular Sciences 10, 232-246.

Neumann, M., Sampathu, D. M., Kwong, L. K., Truax, A. C., Micsenyi, M. C., Chou, T. T., Bruce, J., Schuck, T., Grossman, M., Clark, C. M., McCluskey, L. F., Miller, B. L., Masliah, E., Mackenzie, I. R., Feldman, H., Feiden, W., Kretzschmar, H. A., Trojanowski, J. Q. & Lee, V. M. Y. (2006) Ubiquitinated TDP-43 in frontotemporal lobar degeneration and amyotrophic lateral sclerosis. Science 314, 130-133.

Nonaka, T., Kametani, F., Arai, T., Akiyama, H. & Hasegawa, M. (2009) Truncation and pathogenic mutations facilitate the formation of intracellular aggregates of TDP-43. Human Molecular Genetics 18, 3353-3364.

Ohmi, K., Kudo, L. C., Ryazantsev, S., Zhao, H.-Z., Karsten, S. L. & Neufeld, E. F. (2009) Sanfilippo syndrome type B, a lysosomal storage disease, is also a tauopathy. Proceedings of the National Academy of Sciences 106, 8332-8337.

Orr, H. T. & Zoghbi, H. Y. (2007) Trinucleotide repeat disorders. Annual Review of Neuroscience 30, 575-621.

Paulson, H. L. (1999) Human genetics '99: trinucleotide repeats. American Journal of Human Genetics 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. Nature 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. Science 276, 2045-2047.

Prusiner, S. B., Scott, M. R., DeArmond, S. J. & Cohen, F. E. (1998) Prion protein biology. Cell 93, 337-348.

Seetharaman, S. V., Prudencio, M., Karch, C., Holloway, S. P., Borchelt, D. R. & Hart, P. J. (2009) Immature copper-zinc superoxide dismutase and familial amyotrophic lateral sclerosis. Experimental Biology and Medicine 234, 1140-1154.

Seilhean, D., Cazeneuve, C., Thuries, V., Russaouen, O., Millecamps, S., Salachas, F., Meininger, V., LeGuern, E. & Duyckaerts, C. (2009) Accumulation of TDP-43 and α-actin in an amyotrophic lateral sclerosis patient with the K171 ANG mutation Acta Neuropathologica 118, 561-573.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. Journal of Neuropathology and Experimental Neurology 55, 481-490.

Sletten, K., Westermark, P. & Natvig, J. B. (1976) Characterization of amyloid fibril proteins from medullary carcinoma of the thyroid. Journal of Experimental Medicine 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. Proceedings of the National Academy of Sciences, USA 95, 6469-6473.

Sreedharan, J., Blair, I. P., Tripathi, V. B., Hu, X., Vance, C., Rogelj, B., Ackerley, S., Durnall, J. C., Williams, K. L., Buratti, E., Baralle, F., de Belleroche, J., Mitchell, J. D., Leigh, P. N., Al-Chalabi, A., Miller, C. C., Nicholson, G. & Shaw, C. E. (2008) TDP-43 mutations in familial and sporadic amyotrophic lateral sclerosis. Science 319, 1668-1672.

Uemichi, T., Liuepnicks, J. j. & Benson, M. D. (1994) Hereditary renal amyloidosis with a novel variant fibrinogen. Journal of Clinical Investigation 93, 731-736.

van Bebber, F., Paquet, D., Hruscha, A., Schmid, B. & Haass, C. (2010) Methylene blue fails to inhibit Tau and polyglutamine protein dependent toxicity in zebrafish. Neurobiology of Disease 39, 265-271.

Vance, C., Rogelj, B., Hortobagyi, T., De Vos, K. J., Nishimura, A. L., Sreedharan, J., Hu, X., Smith, B., Ruddy, D., Wright, P., Ganesalingam, J., Williams, K. L., Tripathi, V., Al-Saraj, S., AI-Chalabi, A., Leigh, P. N., Blair, I. P., Nicholson, G., de Belleroche, J., Gallo, J.-M., Miller, C. C. & Shaw, C. E. (2009) Mutations in FUS, an RNA processing protein, cause familial amyotrophic lateral sclerosis type 6. Science 323, 1208-1211.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H. & Pitkanen, P. (1985) Systemic amyloidosis: A review with emphasis on pathogenesis. *Applied Physiology* 3, 55-68.

Westermark, P., Johnson, K. H., O'Brien, T. D. & Betsholtz, C. (1992) Islet amyloid polypeptide—a novel controversy in diabetes research. *Diabetologia* 35, 297-303.

Wijesekera, L. & Leigh, P. N. (2009) Amyotrophic lateral sclerosis. Orphanet Journal of Rare Diseases 4, 3.

Wischik, C. M., Novak, M., Thogersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

Yamashita, M., Nonaka, T., Arai, T., Kametani, F., Buchman, V. L., Ninkina, N., Bachurin, S. O., Akiyama, H., Goedert, M. & Hasegawa, M. (2009) Methylene blue and dimebon inhibit aggregation of TDP-43 in cellular models. FEBS Letters 583, 2419-2424.

Zhang, Y.-J., Xu, Y.-F., Cook, C., Gendron, T. F., Roettges, P., Link, C. D., Lin, W.-L., Tong, J., Castanedes-Casey, M., Ash, P., Gass, J., Rangachari, V., Buratti, E., Baralle, F., Golde, T. E., Dickson, D. W. & Petrucelli, L. (2009) Aberrant cleavage of TDP-43 enhances aggregation and cellular toxicity. Proceedings of the National Academy of Sciences 106, 7607-7612.

The invention claimed is:

1. A dosage unit comprising 20 to 300 mg of a compound of the following formula:

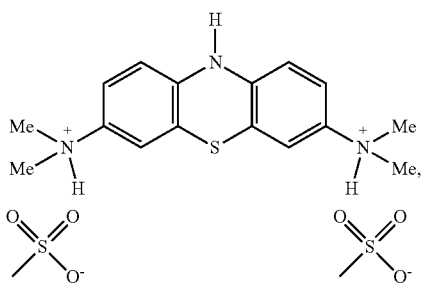

or comprising 20 to 300 mg of a free base equivalent of said compound, and further comprising a pharmaceutically acceptable carrier, diluent, or excipient.

2. The dosage unit according to claim 1, which is a tablet comprising 20 to 300 mg of the compound.

3. The dosage unit according to claim 1, which is a capsule comprising 20 to 300 mg of the compound.

4. The dosage unit according to claim 1, which comprises 30 to 200 mg of the compound.

5. The dosage unit according to claim 1, which comprises about 30 mg of the compound.

6. The dosage unit according to claim 1, in which less than 12% of said compound is converted to methylthionium:

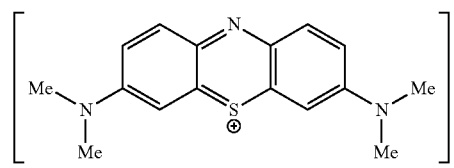

over 2 years when stored at 25° C. at a relative humidity of 60%.

7. The dosage unit according to claim 1, which comprises about 60 mg of the compound.

8. The dosage unit according to claim 1, which comprises about 100 mg of the compound.

9. The dosage unit according to claim 1, which comprises about 150 mg of the compound.

10. The dosage unit according to claim 1, which comprises about 200 mg of the compound.

11. The dosage unit according to claim 1, which is a tablet comprising 20 to 300 mg of the free base equivalent of the compound.

12. The dosage unit according to claim 1, which is a capsule comprising 20 to 300 mg of the free base equivalent of the compound.

13. The dosage unit according to claim 1, which comprises 30 to 200 mg of the free base equivalent of the compound.

14. The dosage unit according to claim 1, which comprises about 30 mg of the free base equivalent of the compound.

15. The dosage unit according to claim 1, which comprises about 60 mg of the free base equivalent of the compound.

16. The dosage unit according to claim 1, which comprises about 100 mg of the free base equivalent of the compound.

17. The dosage unit according to claim 1, which comprises about 150 mg of the free base equivalent of the compound.

18. The dosage unit according to claim 1, which comprises about 200 mg of the free base equivalent of the compound.

* * * * *